US012780865B2

(12) United States Patent
Salam et al.

(10) Patent No.: US 12,780,865 B2
(45) Date of Patent: Nov. 3, 2026

(54) CLEAVABLE CYCLIC LOOP NUCLEOTIDES FOR NANOPORE SEQUENCING

(71) Applicant: Illumina, Inc., San Diego, CA (US)

(72) Inventors: Abdul Sadeer Abd Salam, Singapore (SG); Xiangyuan Yang, Singapore (SG); Hassan Zakiruddin Bohra, Singapore (SG); Yin Nah Teo, Singapore (SG); Min Yen Lee, Singapore (SG); Ramesh Neelakandan, Singapore (SG); Jeffrey G. Mandell, San Deigo, CA (US); Erin Garcia, San Deigo, CA (US); Sharyuen Soh, Singapore (SG); Daniel Hartoyo Lukamto, Singapore (SG); Eric Murtfeldt, San Diego, CA (US); Michael Howard, Santee, CA (US); Seth McDonald, San Diego, CA (US); Tsz Ying Yuen, Singapore (SG); Jean-Alexandre Richard, Singapore (SG); Shi Yuan Jeow, Singapore (SG); Jin Yong Neo, Singapore (SG); Xi Liew, Singapore (SG)

(73) Assignee: Illumina, Inc., San Diego, CA (US)

( * ) Notice: Subject to any disclaimer, the term of this patent is extended or adjusted under 35 U.S.C. 154(b) by 460 days.

(21) Appl. No.: 18/311,876

(22) Filed: May 3, 2023

(65) Prior Publication Data

US 2023/0357307 A1 Nov. 9, 2023

Related U.S. Application Data

(60) Provisional application No. 63/338,401, filed on May 4, 2022.

(51) Int. Cl.

| | |
|---|---|
| ***C07H 21/00*** | (2006.01) |
| ***C07H 19/10*** | (2006.01) |
| ***C12Q 1/6869*** | (2018.01) |

(52) U.S. Cl.

CPC ............ *C07H 21/00* (2013.01); *C07H 19/10* (2013.01); *C12Q 1/6869* (2013.01)

(58) Field of Classification Search

CPC ...... C07H 21/00; C07H 19/10; C12Q 1/6869; C12Q 1/6809; C12Q 1/6806

See application file for complete search history.

(56) References Cited

U.S. PATENT DOCUMENTS

| | | | |
|---|---|---|---|
| 6,723,513 | B2 | 4/2004 | Lexow |
| 8,324,360 | B2 | 12/2012 | Kokoris et al. |
| 9,588,079 | B2 | 3/2017 | Gundlach et al. |
| 10,301,345 | B2 | 5/2019 | Kokoris et al. |
| 10,745,685 | B2 | 8/2020 | Kokoris et al. |
| 11,034,996 | B2 | 6/2021 | Gates et al. |

FOREIGN PATENT DOCUMENTS

| | | | |
|---|---|---|---|
| WO | WO 2008/128686 | 10/2008 | |
| WO | WO 2008/157696 | 12/2008 | |
| WO | WO 2009/055617 | 5/2009 | |
| WO | WO-2020236526 A1 * | 11/2020 | ............ C07H 19/14 |

OTHER PUBLICATIONS

Alguero et al., May 30, 2007,. Incorporation of two modified nucleosides allows selective platination of an oligonucleotide making it suitable for duplex cross-linking, Journal of Biological Inorganic Chemistry, 12(6):901-911.

Barragan et al., Sep. 7, 2011, Photocontrolled DNA Binding of a Receptor-Targeted Organometallic Ruthenium(II) Complex, Journal of the American Chemical Society, 133(35):14098-14108.

Prestinari et al., Jan. 2011, Intrastrand locks increase duplex stability and base pairing selectivity, Chemical Communications, 47(38):10824-10826.

Schneider et al., Jun. 8, 2010, Translesion Synthesis of 1,3-GTG Cisplatin DNA Lesions, Chembiochem, 11(11):1521-1524.

Wolna et al., Nov. 4, 2013, Single-molecule detection of a guanine(C8)-thymine(N3) cross-link using ion channel recording, Journal of Physical Organic Chemistry., 27(4):247-251.

* cited by examiner

*Primary Examiner* — Jezia Riley

(74) *Attorney, Agent, or Firm* — Knobbe, Martens, Olson & Bear, LLP

(57) ABSTRACT

In one aspect, the disclosed technology relates to nanopore sequencing with a polynucleotide comprising a plurality of nucleotides, wherein each nucleotide comprises a linker construct between two positions of the nucleotide, wherein the linker construct optionally comprises a reporter moiety corresponding to the identity of the nucleotide, and wherein the linker construct is a part of the cleavable cyclic loop nucleotide comprising a cleavable site. In some embodiments, the nucleotides further comprise arresting constructs for slowing or halting the polynucleotide translocation through a nanopore.

11 Claims, 97 Drawing Sheets

Specification includes a Sequence Listing.

Modified dNTPs

Daughter Strand

Opened Loop

X = -O-, -NH-, or $-CH_2-$

Incorporation of allyl dTTP
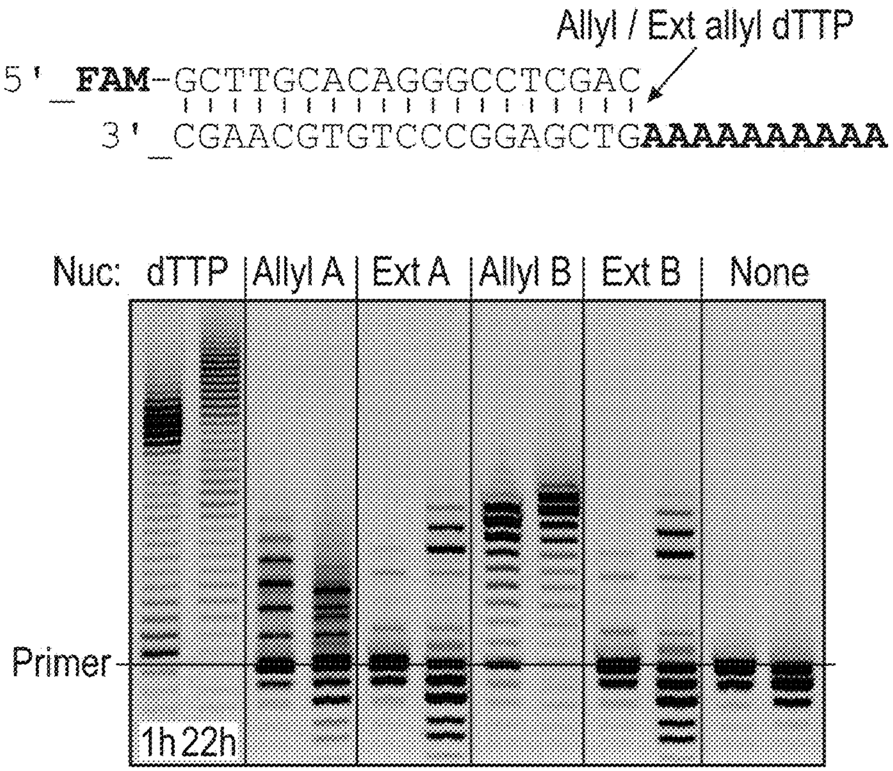
Reaction Conditions:
150nM FAM Primer/Template (+10Ts)
750nM Pol
250 or 50uM Allyl dTTP (or dTTP)
1x Buffer: 50mM Tris 8.0, 50mM KCl, 2mM $MnCl_2$
(Quench with 20mM EDTA, 1:20 Proteinase K)
55°C for 1h, or 22hrs
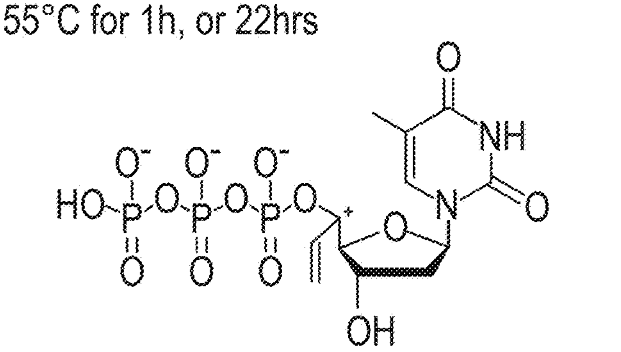
Allyl
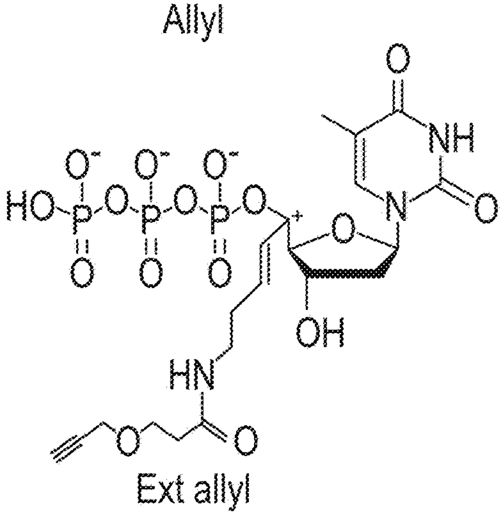
Ext allyl
FIG. 7

CLN-1A 1 2 3 4 5 6 7 8 9 10 11 12

CLN-1B

CLN-1C 1 2 3 4 5 6 7 8 9 10 11 12

CLN-1D

CLN-2

X= O, NH, $CH_2$

Y= O, S, NH

CLN-2A: X= O, Y=O

CLN-2B: X=NH, Y=O

CLN-2C: X=CH2, Y=O

CLN-2A

CLN-2B

CLN-2C

CLN-3

X= O, NH, $CH_2$
Y= O, S, NH

CLN-3A: X= O, Y=O
CLN-3B: X=NH, Y=O
CLN-3C: X=$CH_2$, Y=O

CLN-3A 1 2 3 4 5 6

CLN-3B

CLN-4

CLN-4A

CLN-4C 1 2 3 4 5 6

CLN-5A 1 2 3 4 5

CLN-5C

GLN-6

SNNL-1
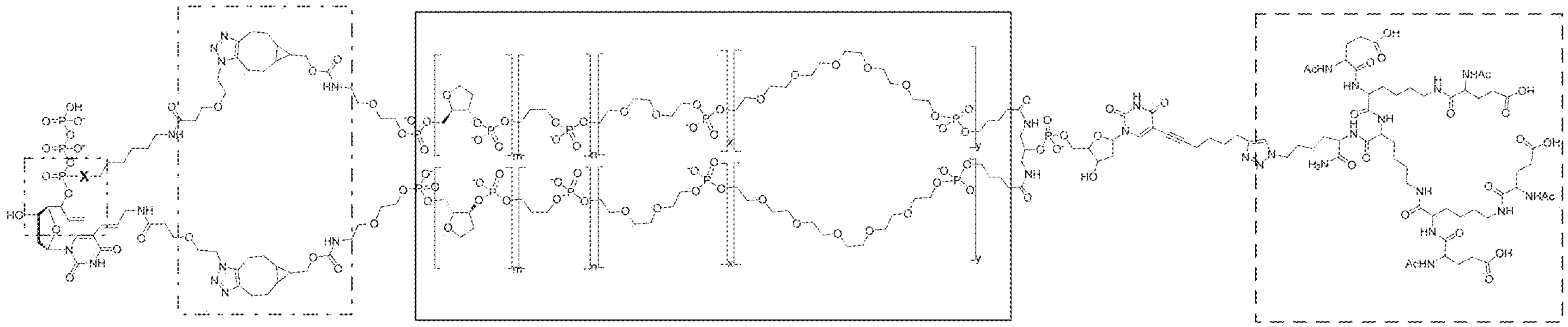
X = O, NH, $CH_2$
Cleavage Conjugation chemistry Cyclic loop Modification
Other modified non-nucleosidic moieties include spC12, spermine, phosphorothioate, methylphosphonate
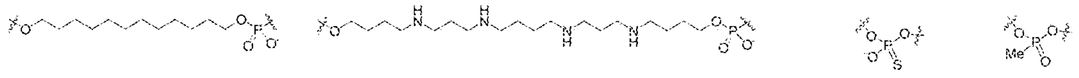
FIG. 33

SPL-1

Cleavage
Conjugation chemistry
Cyclic loop
Modification

X = O, NH, $CH_2$

Other modified moieties include PEG2, 6, 11, 12, Lys(FITC)...

SNL-2

X = O, NH, $CH_2$

Cleavage Conjugation chemistry Cyclic loop Modification

Other modified nucleosidic bases include inosine, nitroindole, LNA, 2'-OMe, 2'-F Other modified non-nucleosidic moieties include spC12, spermine, phosphorothioate, methylphosphonate Other modified amino acid moieties include PEG2, 6, 11, 12, Lys(FITC)...

SNNL-2

X = O, NH, $CH_2$

SPL-2

X = O, NH, $CH_2$

ASL-1

X = O, N, $CH_2$

Other modified nucleosidic bases include inosine, nitroindole, LNA, 2'-OMe, 2'-F Other modified non-nucleosidic moieties include spC12, spermine, phosphorothioate, methylphosphonate Other amino acid residues or moieties include PEG2, 6, 11, 12, Lys(FITC)...

ASL-2

Cleavage

Cyclic loop

Modification

X = O, N, $CH_2$

Other modified nucleosidic bases include inosine, nitroindole, LNA, 2'-OMe, 2'-F Other modified non-nucleosidic moieties include spC12, spermine, phosphorothioate, methylphosphonate Other amino acid residues or moieties include PEG2, 6, 11, 12, Lys(FITC)...

ASL-3

Other modified nucleosidic bases include inosine, nitroindole, LNA, 2'-OMe, 2'-F Other modified non-nucleosidic moieties include spC12, spermine, phosphorothioate, methylphosphonate Other amino acid residues or moieties include PEG2, 6, 11, 12, Lys(FITC)...

4-mer - SNL – 1

Nucleosidic loop

Loop conjugation position: 1-2, 1-3, 1-4, 2-3, 2-4, 3-4

Cleavage chemistry: Allyl, RNA cleavage

Cleavage position: 2nd, 3rd or 4th base

4-mer - SNNL – 1

1
2
3
4

Conjugation chemistry
Cyclic loop
Modification
Cleavage

Non-nucleosidic loop

Loop conjugation position: 1-2, 1-3, 1-4, 2-3, 2-4, 3-4

Cleavage chemistry: Allyl, RNA cleavage

Cleavage position: 2nd, 3rd or 4th base

4-mer - SPL – 1

Peptide loop

Loop conjugation position: 1-2, 1-3, 1-4, 2-3, 2-4, 3-4

Cleavage chemistry: Allyl, RNA cleavage

Cleavage position: 2nd, 3rd or 4th base

4-mer - ASL – 1

1
2
3
4

Cleavage
Conjugation chemistry
Cyclic loop
Modification

Asymmetric loop: nucleosidic, non-nucleosidic, or peptide

Loop conjugation position: 1-2, 1-3, 1-4, 2-3, 2-4, 3-4

Cleavage chemistry: Allyl, RNA cleavage

Cleavage position: 2nd, 3rd or 4th base

1

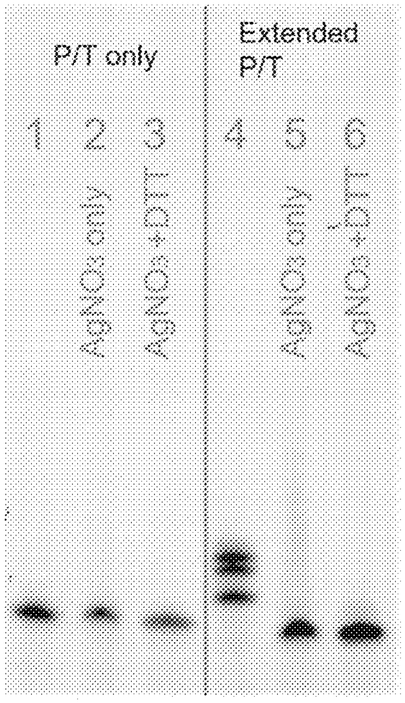
5′ FAM – AACCCGAGGAGGC
3′ TTGGGCTCCTCCGAAAAAAGGTTCGTT
Incorporation Conditions:
1 µM P/T
50 µM Nuc
5% Pol 1901
50mM Tris pH 8.0
5mM NaCl
4mM $MgCl_2$
55°C
Cleavage Conditions:
50 mM $AgNO_3$
15mins
Room temp.
Desalted extended P/T
60 mM DTT
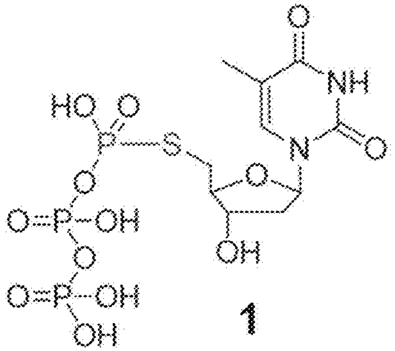
1
FIG. 51

9

10

HPLC
FIG. 54A
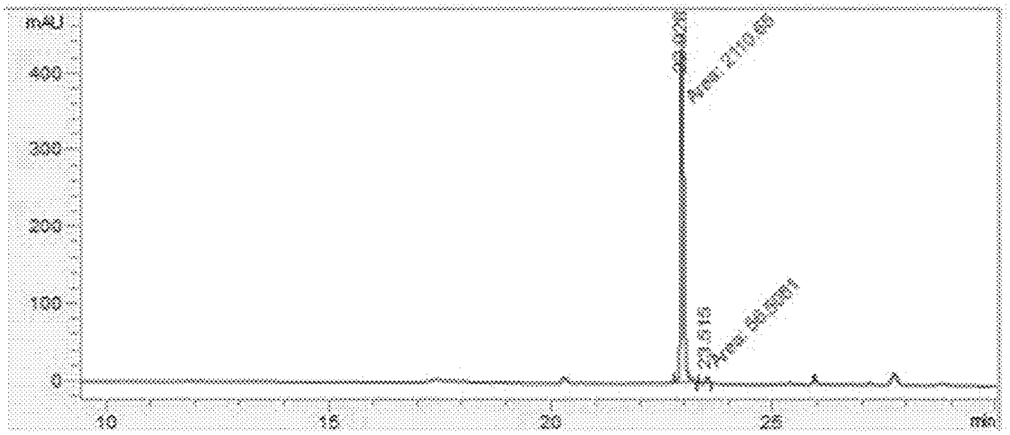
IR
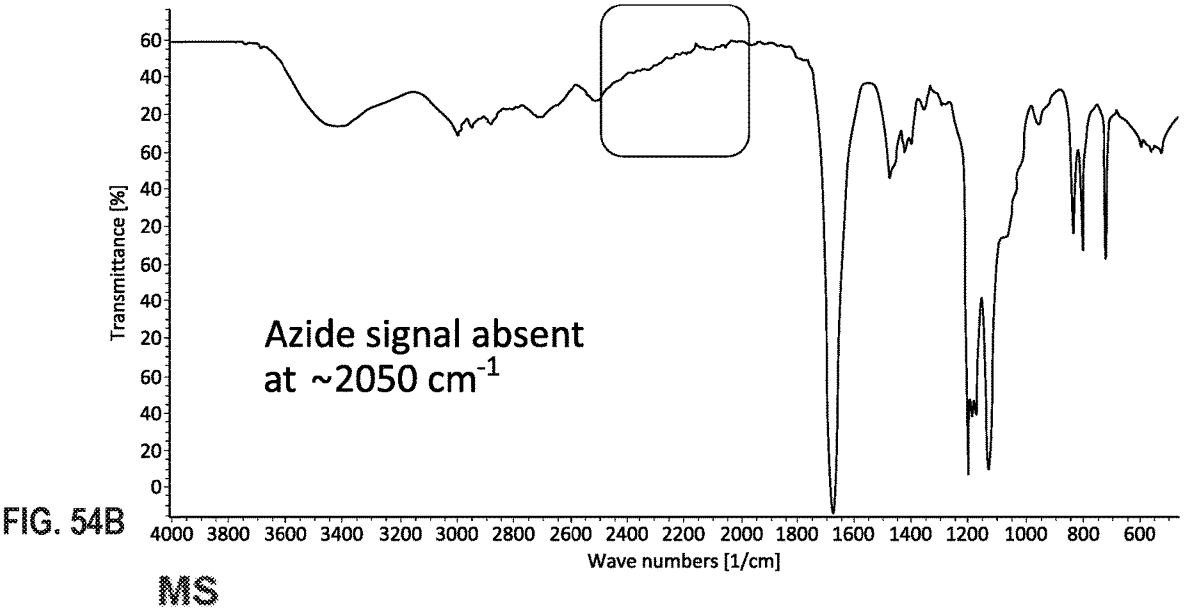
FIG. 54B
MS
FIG. 54C
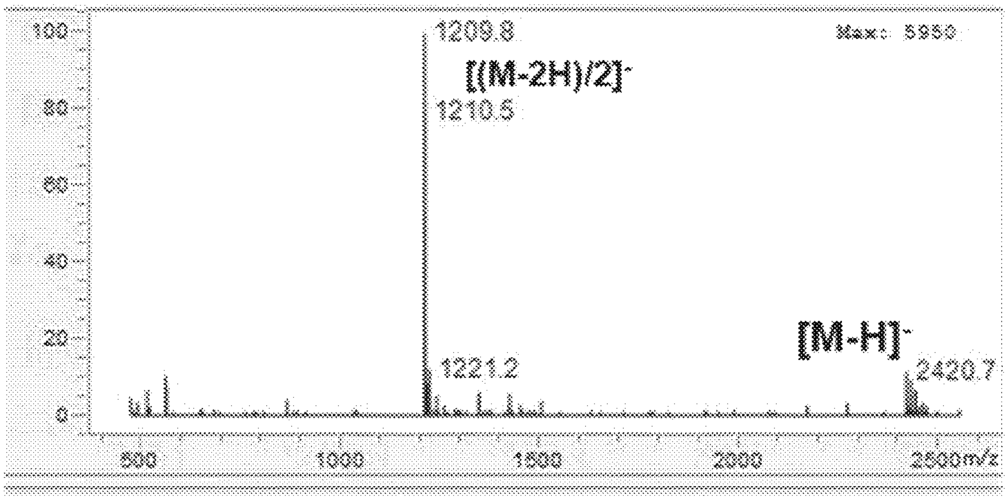

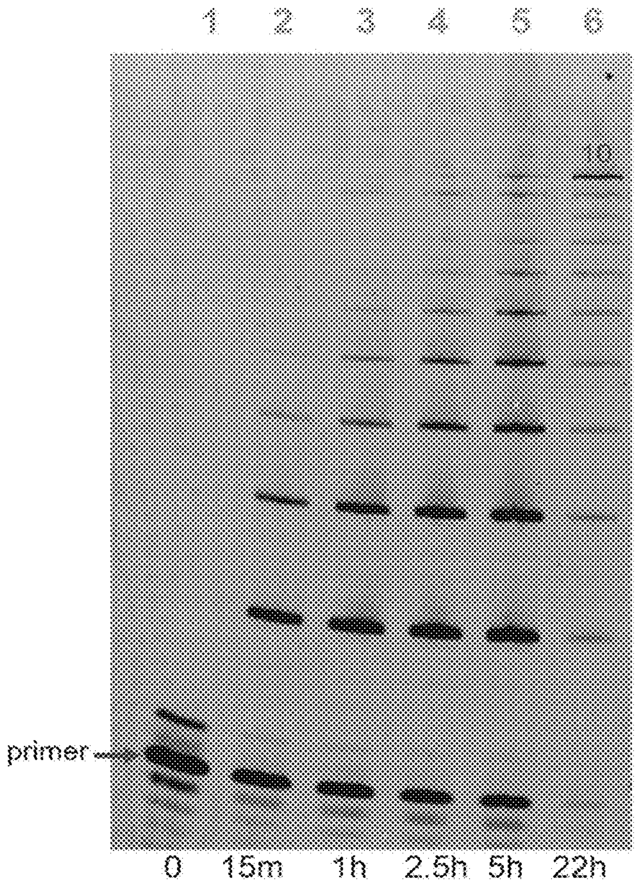
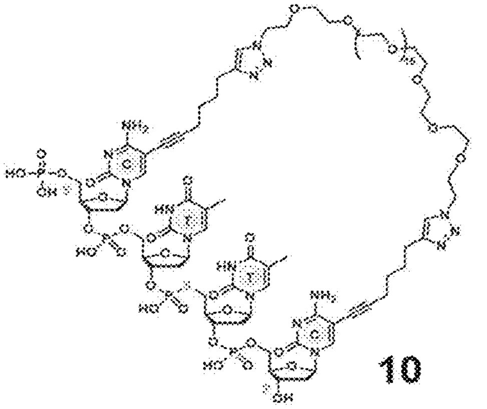
10
Ligation Conditions:
200 nM FAM-Primer
300 nM Template
5 μM oligo
~2 μM Ame ligase
Stick Together buffer
Room temp.
5′ FAM-TTTTTTAATGATAC
3′AAAAAATTACTATGGAAGGAAGGAAGGAAGGAAGGAAGGAAGGAAGGAAGGAAGTATGCGTACGTACTA
FIG. 55

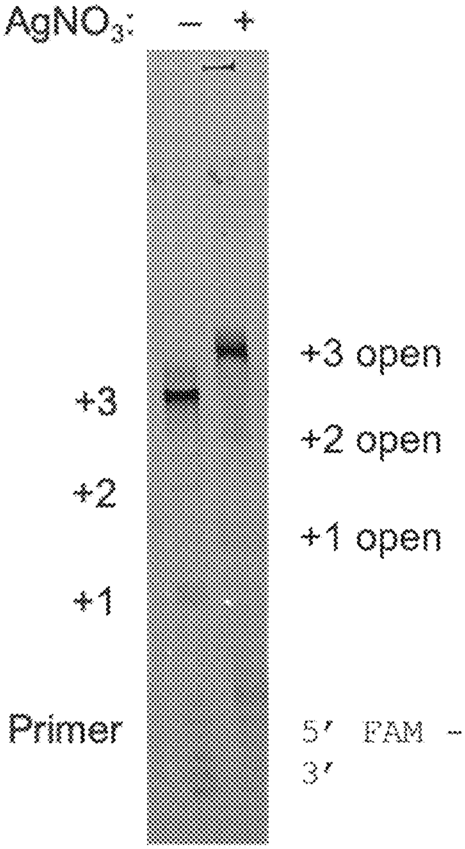
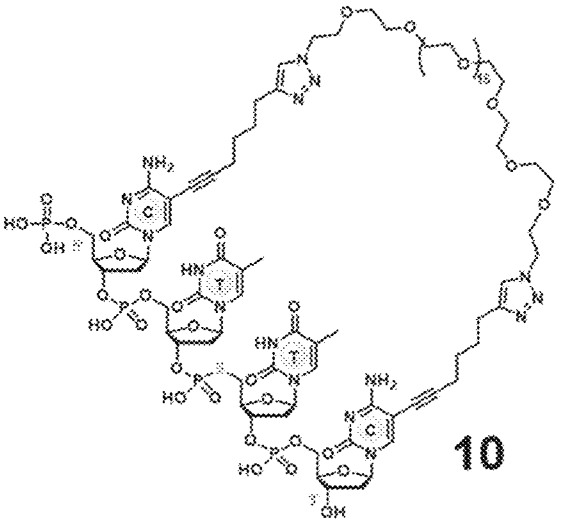
10
5′ FAM - GATCAGATCACTGGC
3′ CTAGTCTAGTGACCGGAAGGAAGGAAGCATT_5′
FIG. 56

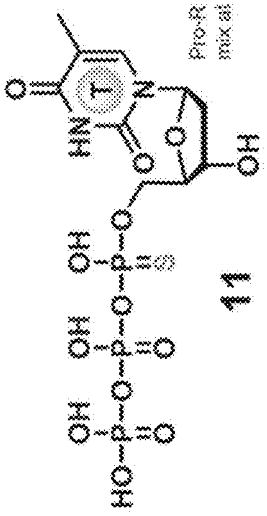
11
Pro-R and Pro-S mix at 50% each
5' FAM – CCTTGCACAGGCCTCGAC
3' GGAACGTGTCCGGAGCTGAAAAAAAAATCGC
Incorporation Conditions:
100 nM P/T
20 µM Nuc
1 µM Pol
20mM Tris pH 8.0
20mM KCl
2mM MnCl₂
Room temp.
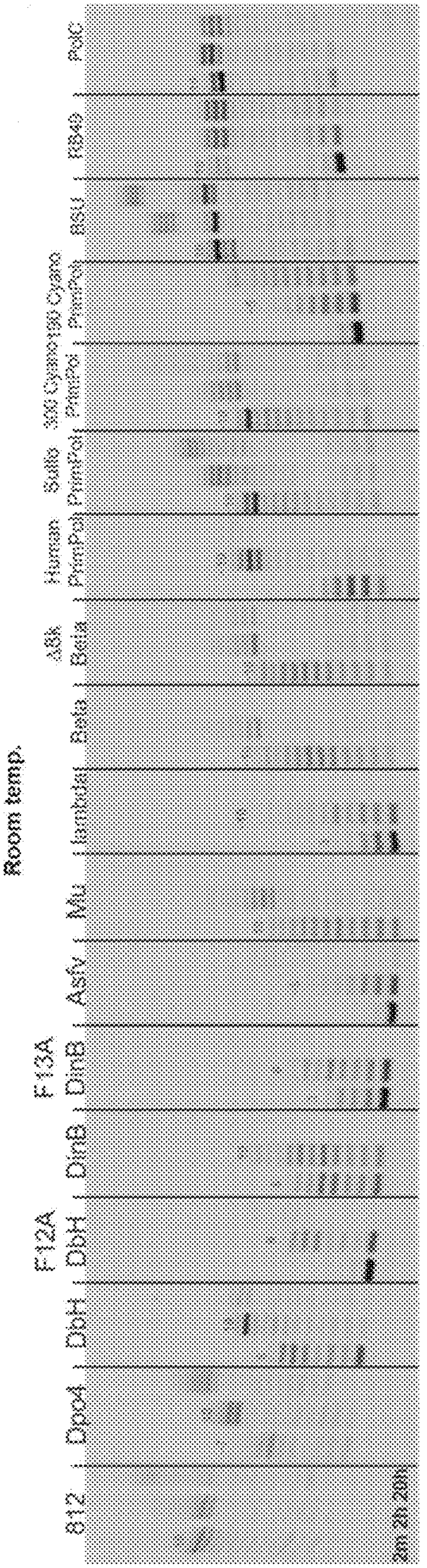
FIG. 58

13

| # | Time | Type | Area | Height | Width | Area% |
|---|---|---|---|---|---|---|
| 1 | 19.765 | MM | 54.3 | 4 | 0.2246 | 2.323 |
| 2 | 24.15 | BV E | 17.3 | 2.4 | 0.0865 | 0.740 |
| 3 | 24.551 | VB R | 2265.2 | 169 | 0.1874 | 96.936 |

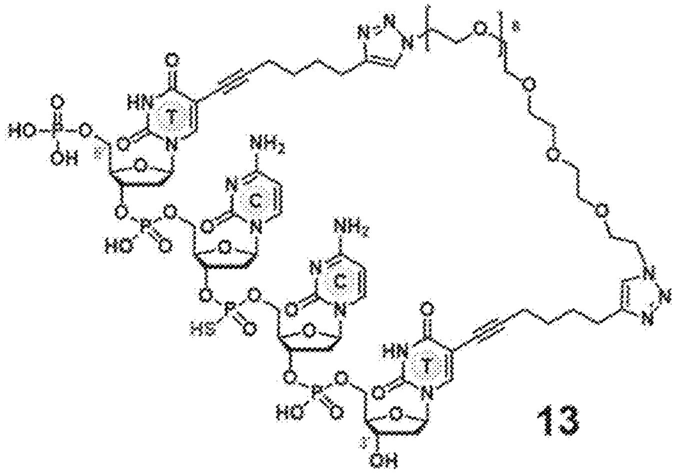
13
Rev
2uM Ligase
10uM Oligo
100nM Template
200nM FAM-Primer
Rm. temp
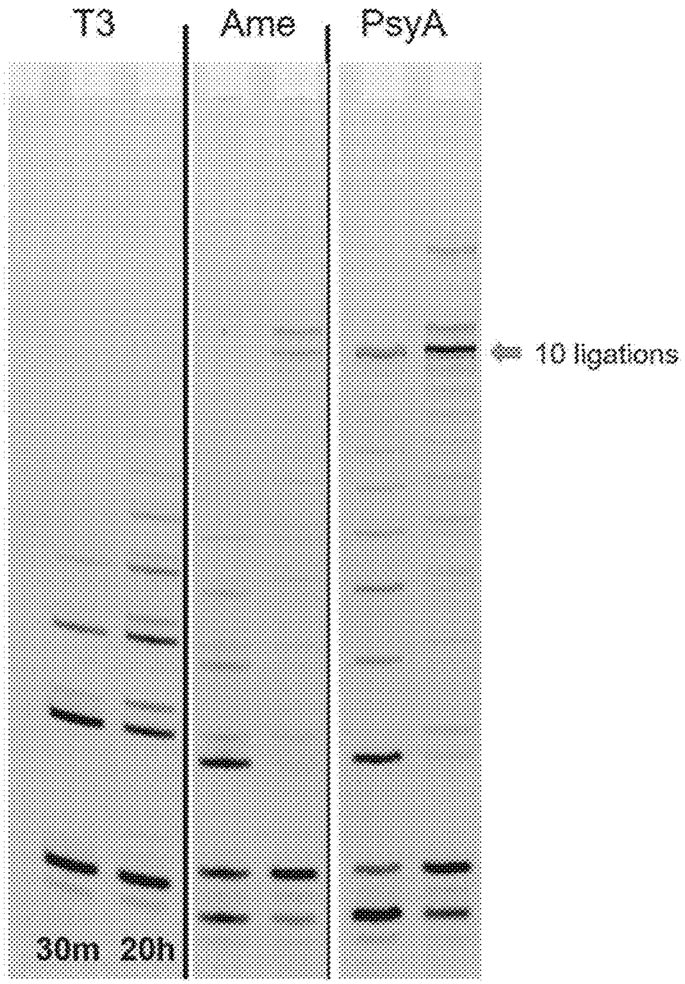
ATACGCATGCATGAT-FAM
3'AAAAAATTACTATGGAAGGAAGGAAGGAAGGAAGGAAGGAAGGAAGGAAGTATGCGTACGTACTA
FIG. 61

Exact Mass: 979.2

1

2

4

5

6

1 2 3 4 6

| Monophosphate starting material | Stage 1 | Intermediate | Stage 2 | Triphosphate intermediate |
|---|---|---|---|---|
| 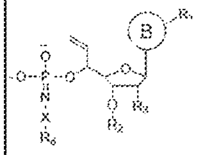 | Conversion of phosphate O-H to O-$R_7$ (better leaving group)<br>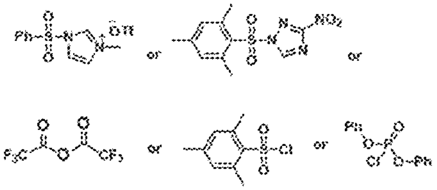<br> | 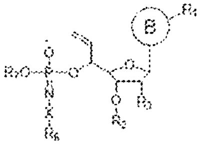<br>$R_7$ = Trifluoro acetyl, Sulfony phenyl or mesitylene | Activate intermediate and couple with pyrophosphate<br>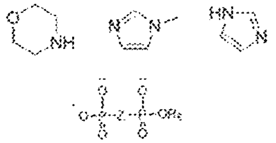<br>$R_5$ = H, 1-2-(Pyrenesulfonyl)ethyl)<br>Z = O, NH, $CH_2$, $CCl_2$, $CBr_2$, $CF_2$, S, Se | 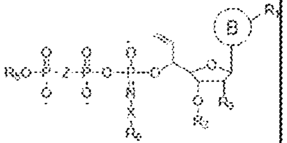<br>$R_5$ = H, 1-2-(Pyrenesulfonyl)ethyl)<br>Z = O, NH, $CH_2$, $CCl_2$, $CBr_2$, $CF_2$, S, Se |
| | Activation of monophosphate<br>DCC or Aldrithiol, $PPh_3$,<br><br>Or $Et_3N$, RT/Heat<br>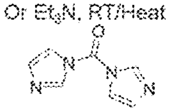 | 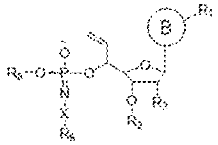<br>$R_8$ = Imidazolinium, morpholino, N-Methylimidazolinium | Couple with pyrophosphate<br>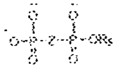<br>$R_5$ = H, 1-2-(Pyrenesulfonyl)ethyl)<br>Z = O, NH, $CH_2$, $CCl_2$, $CBr_2$, $CF_2$, S, Se | |
| | Sequential activation, amidation, oxidation and deprotection<br>1) 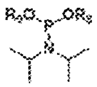<br>$R_9$ = Fm, Bn, Bz, $CH_2CH_2CN$, Boc<br>4,5-Dicyanoimidazole or 5-Ethylthio-1H-Tetrazole or 5-Benzylthio-1H-Tetrazole or 1H-Tetrazole<br>2) DBU<br>3) Piperidine / $NH_4OH$ / $H_2$ / $H^+$ | 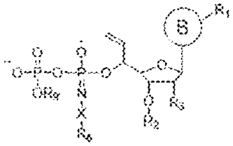<br>$R_{9'}$ = Fm, Bn, Bz, $CH_2CH_2CN$, Boc, H | Sequential activation, amidation, oxidation and deprotection<br>1) 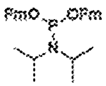<br>4,5-Dicyanoimidazole or 5-Ethylthio-1H-Tetrazole or 5-Benzylthio-1H-Tetrazole or<br>1H-Tetrazole<br>2) DBU<br>3) $NH_4OH$ / $H_2$ / $H^+$ | |

FIG. 70B

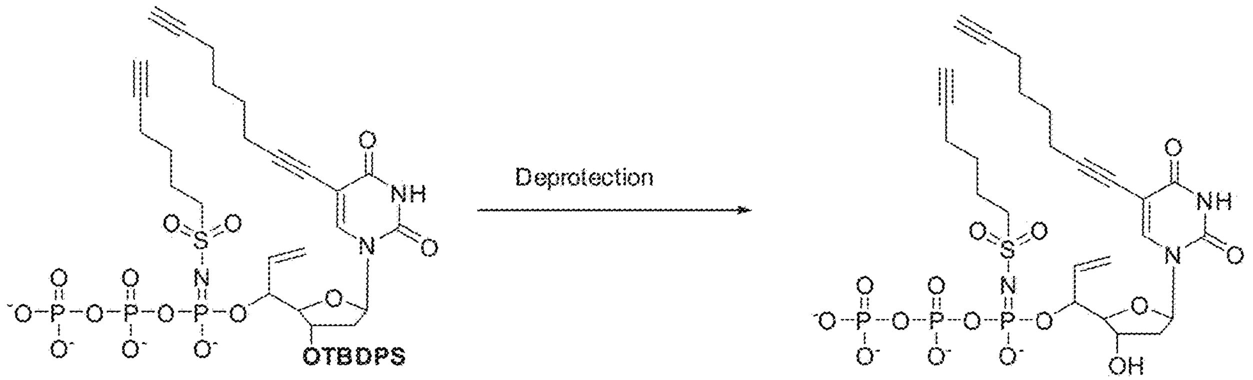

5

6

FIG. 72

| Entry | Reagent and stoichiometry | Final conc. | Procedure and conditions | % of SM 5 left | % conversion to 6 | % degraded (MP) | % impurities |
|---|---|---|---|---|---|---|---|
| 1 | Nucleotide (1 eq., 50 nmol)<br>0.1 M HF-TEA in THF (30 eq.)<br>conc. HF-TEA (3067 eq.)<br>0.2 M imidazole (90 eq.) | 0.2 mM<br>6 mM<br>626 mM<br>18 mM | 1) Sequential addition of 0.1 M HF-TEA and 0.2 M imidazole to nucleotide<br>2) Addition of 0.1 M HF-TEA<br>3) Repeat step 1<br>4) Addition of conc HF-TEA x 2 and 0.2 M imidazole<br>5) Stir overnight at RT. | - | 25 | 41 | 34 |
| 2 | Nucleotide (1 eq., 50 nmol)<br>0.1 M HF-TEA in THF (30 eq.)<br>conc. HF-TEA (3067 eq.)<br>0.2 M Imidazole (80 eq.) | 0.2 mM<br>6 mM<br>626 mM<br>18 mM | 1) Premix 0.1 M HF-TEA and 0.2 M imidazole<br>2) Add conc. HF-TEA<br>3) Add nucleotide<br>4) Stir 4 hr at RT. | 69 | 14 | 5 | 12 |
| 3 | Nucleotide (1 eq. 125 - 800 nmol)<br>0.2 M HF-TEA in THF (30 eq.)<br>0.4 M Imidazole (90 eq.) | 0.72 mM<br>21.5 mM<br>71.4 mM | 1) Premix 0.2 M HF-TEA and 0.4 M imidazole<br>2) Add nucleotide<br>3) Stir 4 hr at RT. | ≤ 10 | 65 ~ 79 | ≤ 6 | 15 ~ 25 |

FIG. 73

Item name: fraction 44 Channel name: 1: Average Time 0.3084 min : TOF MS (50-2000) ~
Item description:

1

2

3

4

5 (R + S)

5 (R)

Or 5 (S)

5 (R + S)

6

5

5 (enantioenriched)

5 (R + S)

6a

6b 5 (S)

5 (R)

Monophosphate

6

*Synthesis of imidazolium/guanidinium azides*
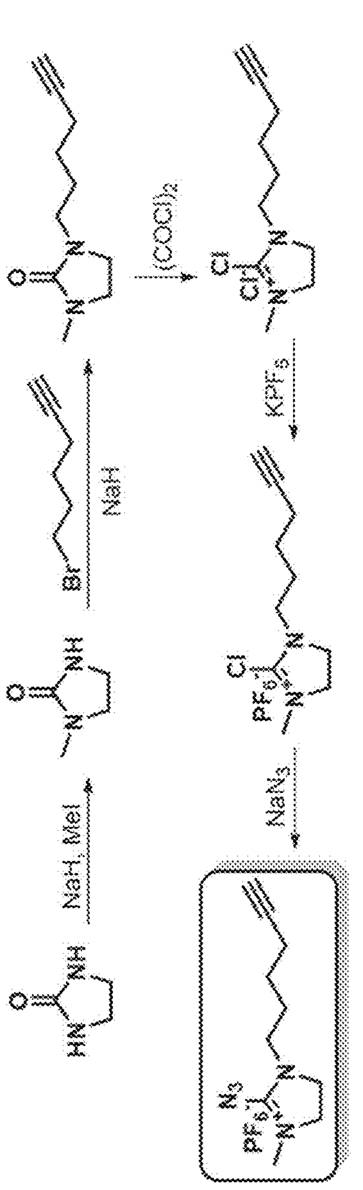
*Synthesis of guanidinium azides*
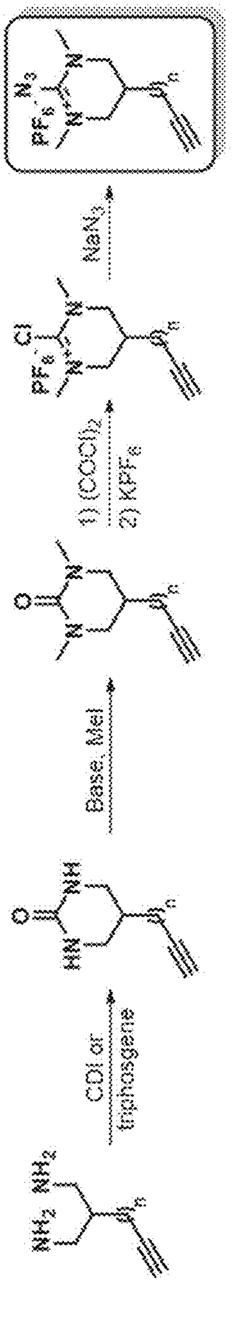
FIG. 82

6
100 nmol 10
49.9 nmol (50% yield)

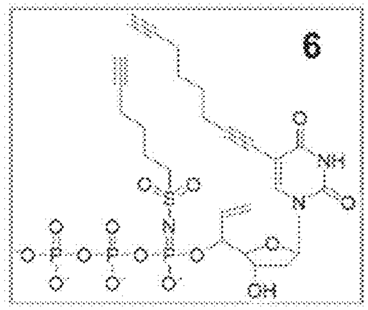
6
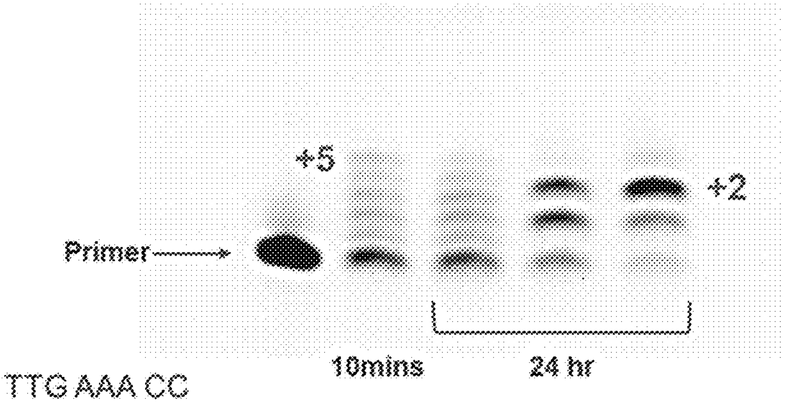
/5Cy5/AAC GCG TTC GAG TTG AAA CC
TTG CGC AAG CTC AAC TTT GGAAAAAAGCAGGA
| | |
|---|---|
| P+T | 100 nM |
| Mod Nuc/Nuc | 20 μM / 80 nM |
| Tris pH 8.0 | 20 mM |
| KCl | 20 mM |
| $MnCl_2$ | 2 mM |
| Dpo4 (NEB) | 5% v/v (1 uM) |
| | r.t. |
FIG. 85

10
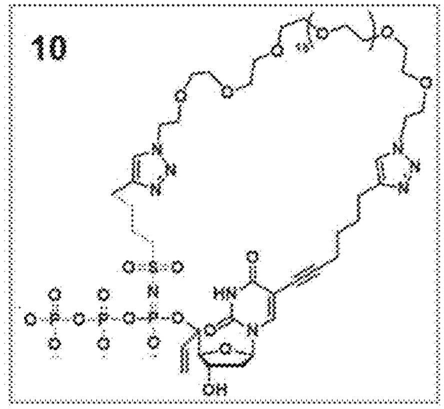
6
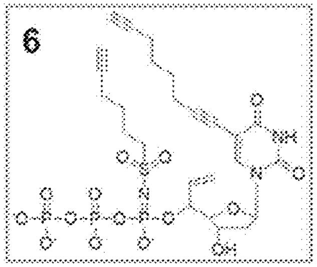
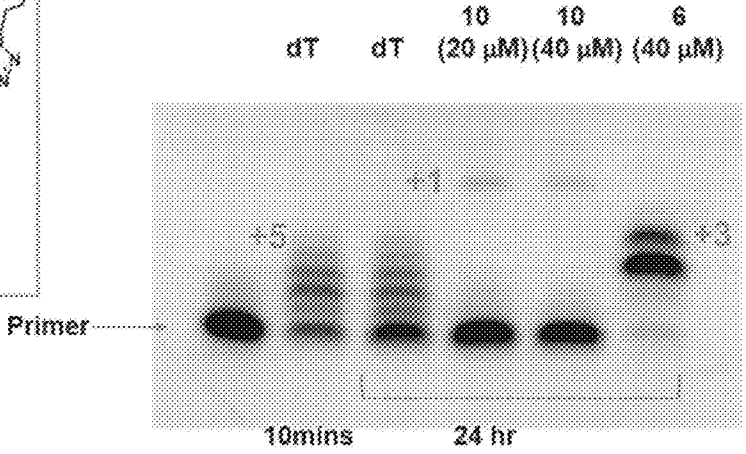
| | |
|---|---|
| **P+T** | 100 nM |
| **Mod Nuc / Nuc** | 20 or 40 µM / 80 nM |
| **Tris pH 8.0** | 20 mM |
| **KCl** | 20 mM |
| **$MnCl_2$** | 2 mM |
| **Dpo4 (NEB)** | 5% v/v (1 uM) |
| | r.t. |
/5Cy5/AAC GCG TTC GAG TTG AAA CC
TTG CGC AAG CTC AAC TTT GGAAAAAAGCAGGA
FIG. 86

10
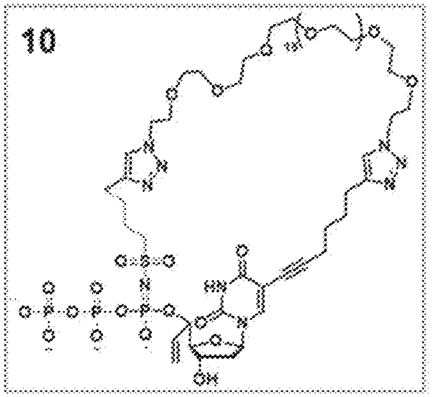
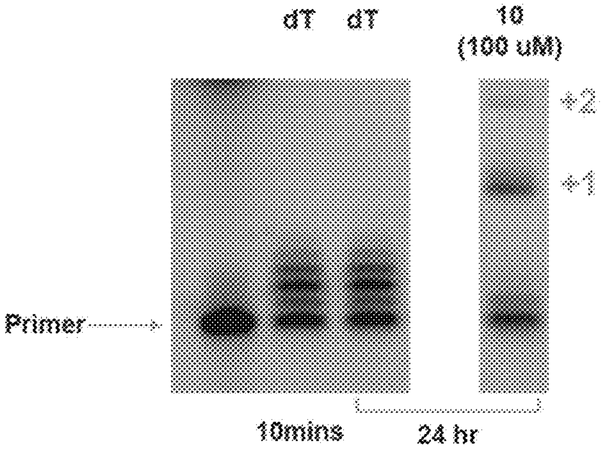
| | |
|---|---|
| **P+T** | 100 nM |
| **Mod Nuc / Nuc** | 100 μM / 80 nM |
| **Tris pH 8.0** | 20 mM |
| **KCl** | 20 mM |
| **$MnCl_2$** | 10 mM |
| **Dpo4 (NEB)** | 10% v/v (2 uM) |
| | 37°C |
/5Cy5/AAC GCG TTC GAG TTG AAA CC
TTG CGC AAG CTC AAC TTT GGAAAAAAGCAGGA
FIG. 87

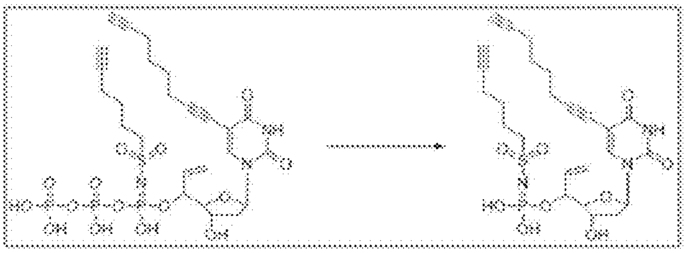
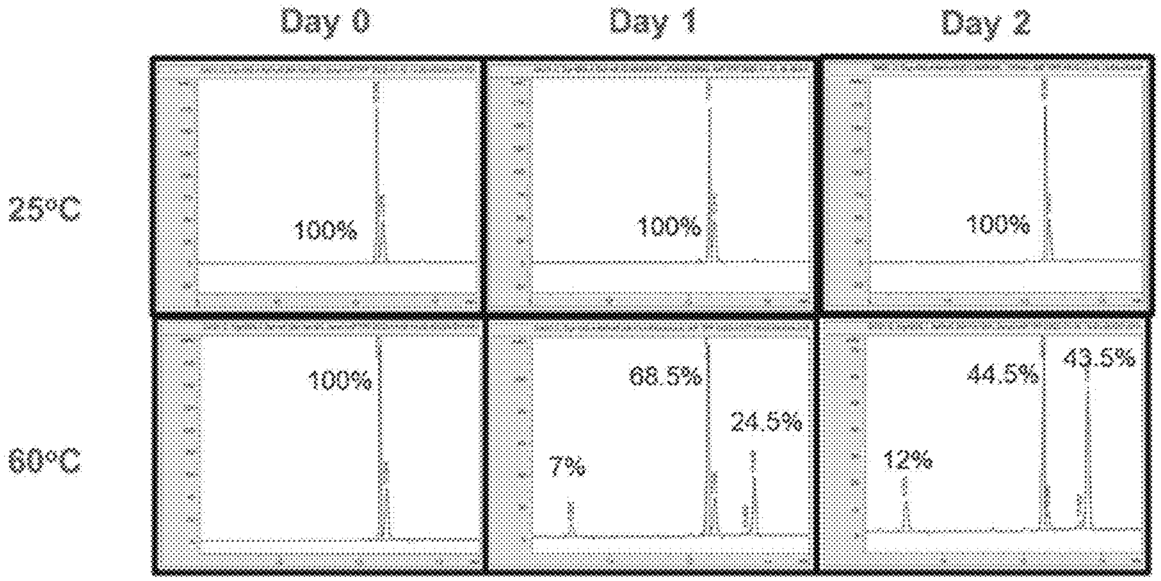
% values are integrated area under the peaks
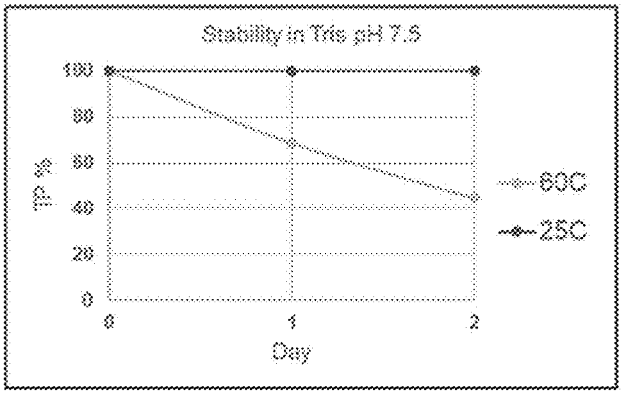
UPLC Method:
Tnart C18 1.9 um 150x3mm
0.5 mL/min
0.25M TEAA (+5 µM Medronic acid) pH 10 / ACN
40°C
Staging conditions:
30 uM Nuc
50 mM Tris pH 7.5
25°C/ 60°C
FIG. 88

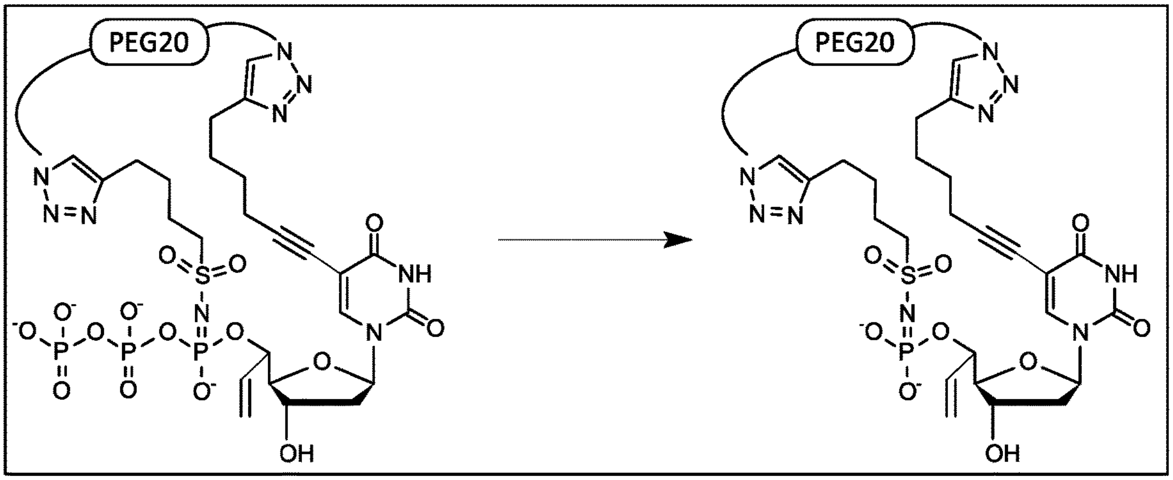
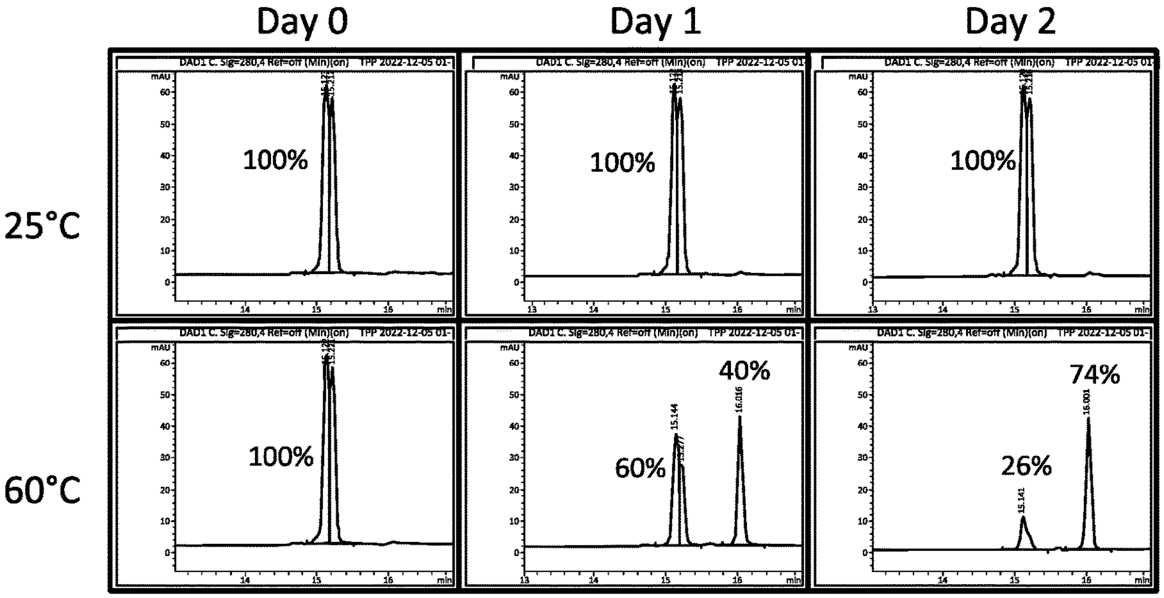
% values are integrated area under the peaks
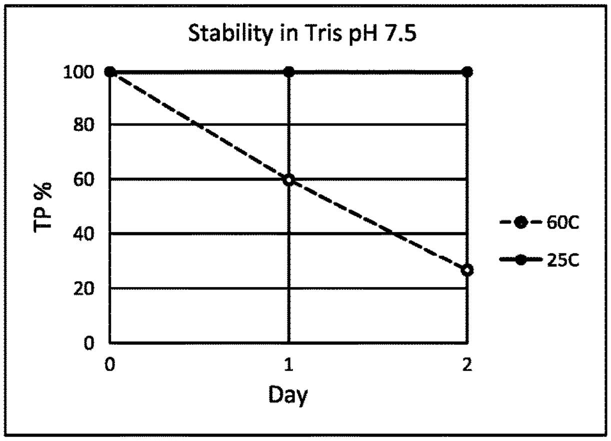
UPLC Method:
Triart C18 1.9 um 150x3mm
0.5 mL/min
0.25M TEAA (+5 μM Medronic acid)
pH 10 / ACN
40°C
Staging conditions:
30 uM Nuc
50 mM Tris pH 7.5
25°C/ 60°C
FIG. 89

Fmoc-Lys(Fmoc)-Lys(Mtt)-resin

B4E-Lys(Mtt)-resin

Compound 1
MW: 5508.01

Compound 2
MW: 5653.10

Compound 3
MW: 5878.18

SEQUENCE LISTING

```
Sequence total quantity: 9
SEQ ID NO: 1            moltype = DNA  length = 38
FEATURE                 Location/Qualifiers
misc_feature            1..38
                        note = Elongated polymer
```

-continued

```
source                  1..38
                        mol_type = other DNA
                        organism = synthetic construct
SEQUENCE: 1
gcttgcacag ggcctcgacg tcgaggccct gtgcaagc                              38

SEQ ID NO: 2            moltype = DNA  length = 38
FEATURE                 Location/Qualifiers
misc_feature            1..38
                        note = Elongated polymer
source                  1..38
                        mol_type = other DNA
                        organism = synthetic construct
SEQUENCE: 2
ccttgcacag ggcctcgacg tcgaggccct gtgcaagg                              38

SEQ ID NO: 3            moltype = DNA  length = 26
FEATURE                 Location/Qualifiers
misc_feature            1..26
                        note = Elongated polymer
source                  1..26
                        mol_type = other DNA
                        organism = synthetic construct
SEQUENCE: 3
aacccgagga ggcgcctcct cgggtt                                           26

SEQ ID NO: 4            moltype = DNA  length = 28
FEATURE                 Location/Qualifiers
misc_feature            1..28
                        note = Elongated polymer
source                  1..28
                        mol_type = other DNA
                        organism = synthetic construct
SEQUENCE: 4
ttttttaatg atacgtatca ttaaaaaa                                         28

SEQ ID NO: 5            moltype = DNA  length = 15
FEATURE                 Location/Qualifiers
misc_feature            1..15
                        note = branch of Elongated polymer
source                  1..15
                        mol_type = other DNA
                        organism = synthetic construct
SEQUENCE: 5
atcatgcatg cgtat                                                       15

SEQ ID NO: 6            moltype = DNA  length = 30
FEATURE                 Location/Qualifiers
misc_feature            1..30
                        note = Elongated polymer
source                  1..30
                        mol_type = other DNA
                        organism = synthetic construct
SEQUENCE: 6
gatcagatca ctggcgccag tgatctgatc                                       30

SEQ ID NO: 7            moltype = DNA  length = 30
FEATURE                 Location/Qualifiers
misc_feature            1..30
                        note = Elongated polymer
source                  1..30
                        mol_type = other DNA
                        organism = synthetic construct
SEQUENCE: 7
tagtacgtac gcatatatgc gtacgtacta                                       30

SEQ ID NO: 8            moltype = DNA  length = 13
FEATURE                 Location/Qualifiers
misc_feature            1..13
                        note = branch of Elongated polymer
source                  1..13
                        mol_type = other DNA
                        organism = synthetic construct
SEQUENCE: 8
tatcattaaa aaa                                                         13

SEQ ID NO: 9            moltype = DNA  length = 40
FEATURE                 Location/Qualifiers
misc_feature            1..40
```

-continued

```
                     note = bifunctional nucleotide 6
source               1..40
                     mol_type = other DNA
                     organism = synthetic construct
SEQUENCE: 9
aacgcgttcg agttgaaacc ggtttcaact cgaacgcgtt                       40
```

CLEAVABLE CYCLIC LOOP NUCLEOTIDES FOR NANOPORE SEQUENCING

CROSS REFERENCE TO RELATED APPLICATIONS

The present application claims priority to U.S. Provisional Application No. 63/338,401 filed on May 4, 2022, the disclosure of which is hereby incorporated by reference herein in its entirety.

REFERENCE TO SEQUENCE LISTING

The present application is being filed along with a Sequence Listing in electronic format. The Sequence Listing is provided as a file entitled "ILLINC.562ASequenceListing.xml" which is 12,300 bytes in size and was created on Oct. 29, 2024. The information in the electronic format of the Sequence Listing is incorporated herein by reference in its entirety.

BACKGROUND

Some polynucleotide sequencing techniques involve performing a large number of controlled reactions on support surfaces or within predefined reaction chambers. The controlled reactions may then be observed or detected, and subsequent analysis may help identify properties of the polynucleotide involved in the reaction. Examples of such sequencing techniques include next-generation sequencing or massive parallel sequencing involving sequencing-by-ligation, sequencing-by-synthesis, reversible terminator chemistry, or pyrosequencing approaches.

Some polynucleotide sequencing techniques utilize a nanopore, which can provide a path for an ionic electrical current. For example, as the polynucleotide traverses through the nanopore, it influences the electrical current through the nanopore. Each passing nucleotide, or series of nucleotides, that passes through the nanopore yields a characteristic blockage current. These characteristic electrical currents of the traversing polynucleotide can be recorded to determine the sequence of the polynucleotide.

SUMMARY

The readhead of nanopores (e.g., the constriction region of nanopores) usually "senses" several bases concurrently along the sample DNA strand, increasing the challenge of accurate nanopore sequencing due to many permutations of signals arising from different sequences. For example, the MspA pore reads about 4 bases as a time, giving rise to at least 4ˆ4=256 different signals that needs to be deconvoluted and resolved.

In one aspect, the disclosed technology provides a method that instead of directly sequencing the sample DNA, a daughter strand is synthesized using cyclic loop nucleotides. In some embodiments, each cyclic loop nucleotide contains a unique barcoding/reporter region that is specific to the original bases (e.g., A, T, C, or G) and a cleavable site. The daughter strand is then "elongated" by cutting the cleavable sites. Consequently, when sequencing the daughter strand, the nanopore can "read" the barcoding/reporter region to identify the base that it is coding for. The linker and barcoding construct that is introduced in the daughter strand via polymerization is designed to occupy the readhead of the nanopore entirely, hence reducing the number of signals to just four, i.e., one per nucleobase. Thus, the disclosed technology allows barcode-based decoding of individual bases. In some embodiments, the cyclic loops contain non-barcoding linker constructs which allow the daughter strand to elongate after cutting the cleavable sites. The non-barcoding linker constructs may produce a distinguishable signal or a distinguishable signal break from signals of the nucleobases when passing through the nanopore, thereby isolating and/or enhance the recorded signals from the nucleobases. Thus, the disclosed technology allows improved resolution of the recorded signal. In some embodiments, the linker construct may contain both barcoding/reporter regions and non-barcoding linker constructs. In some embodiments, the linker construct may be the barcoding/reporter element. In some embodiments, nucleotides and oligonucleotides are modified using heavy atoms (including, for example, sulfur and selenium).

In another aspect, the disclosed technology provides systems, devices, kits, and methods which allow cleavable linkages along the DNA backbone, synthesis of cleavable cyclic loop nucleotides, barcodes for individual base identification, and polymerase mutation for incorporation of modified nucleotides. Systems may be prepared to allow parallel reads in multiple nanopores, such as thousands or millions of nanopores. Accordingly, components of any system may be functionally duplicated to multiply sequencing throughput. Any system may also be adapted with microfluidics or automation.

The systems, devices, kits, and methods disclosed herein each have several aspects, no single one of which is solely responsible for their desirable attributes. Without limiting the scope of the claims, some prominent features will now be discussed briefly. Numerous other examples are also contemplated, including examples that have fewer, additional, and/or different components, steps, features, objects, benefits, and advantages. The components, aspects, and steps may also be arranged and ordered differently. After considering this discussion, and particularly after reading the section entitled "Detailed Description," one will understand how the features of the devices and methods disclosed herein provide advantages over other known devices and methods.

Additional details of exemplary nanopore sequencing devices which can be used with the disclosed technology, and methods of operating the devices, can be found in U.S. Provisional Patent Application Nos. 63/200,868 and 63/169,041, the entirety of each of the disclosures is incorporated herein by reference.

Disclosed herein includes a compound having one of the following structures:

(Ia)

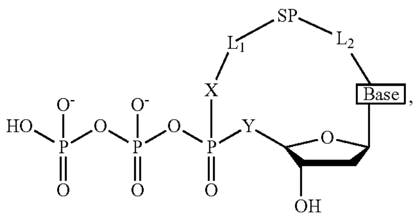,

-continued
(IIa)
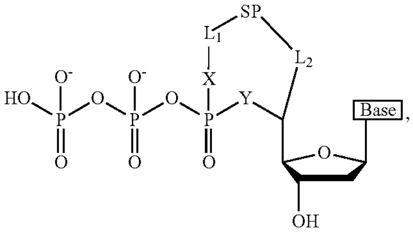
(IIIa)
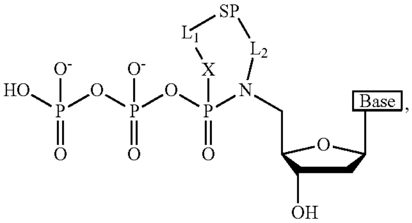
(IVa)
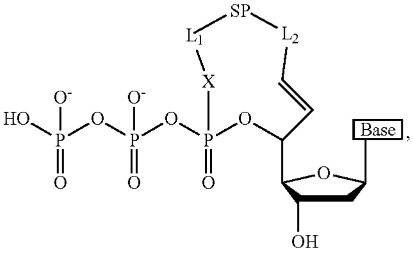
(Va)
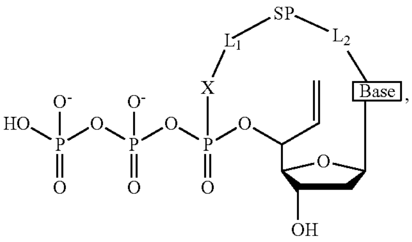
and
(XIIa)
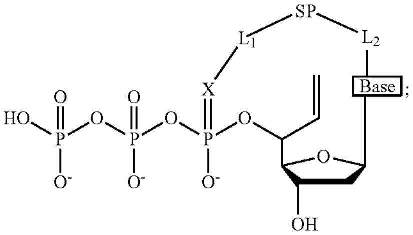
wherein X is —O—, —$CH_2$—, —NH—,
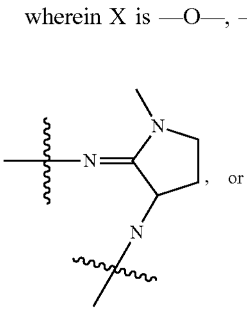
, or
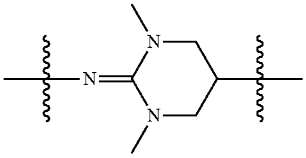
;
X' is =N—$SO_2$—, =NH—CO—, or
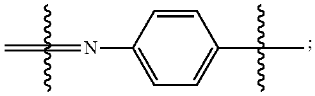 [SMILES: *c1ccc(N=*)cc1]
;
Y is —O—, —S—, —NH—, or —Se—; $L_1$ is a first linking group; $L_2$ is a second linking group; and SP is a spacer.
Disclosed herein also includes an oligonucleotide comprising one of the following structures:
(Ib)
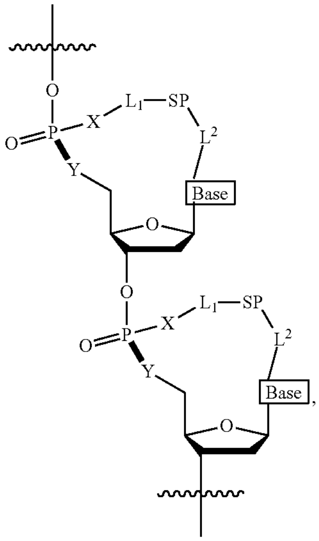
(IIb)
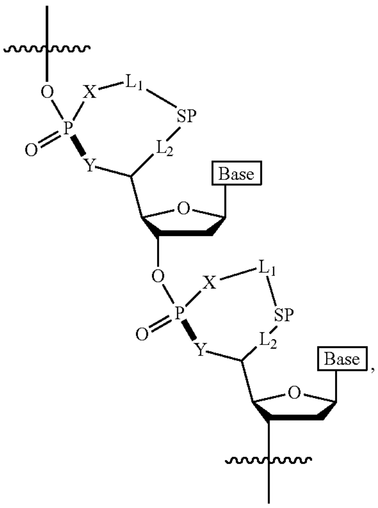

-continued
(IIIb)
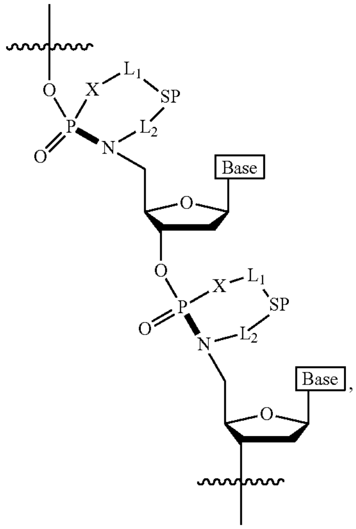
,
(IVb)
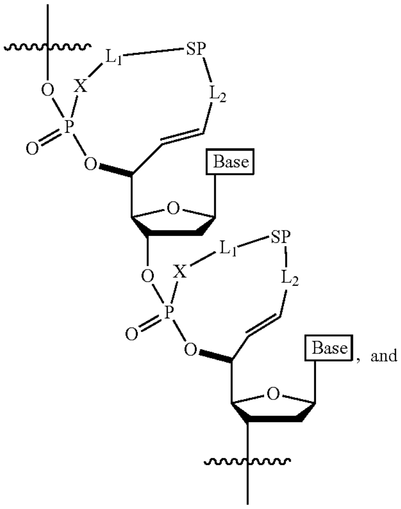
, and
(Vb)
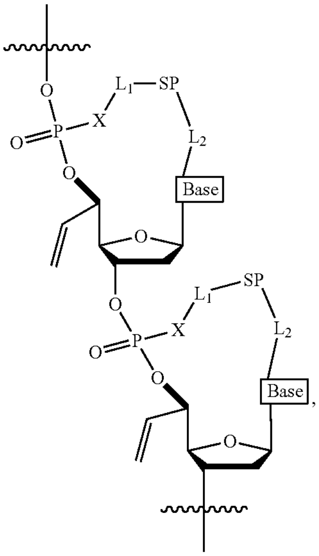
,
-continued
(XIIb)
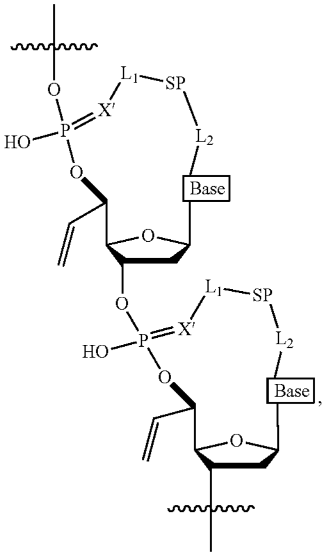
,
(VI)
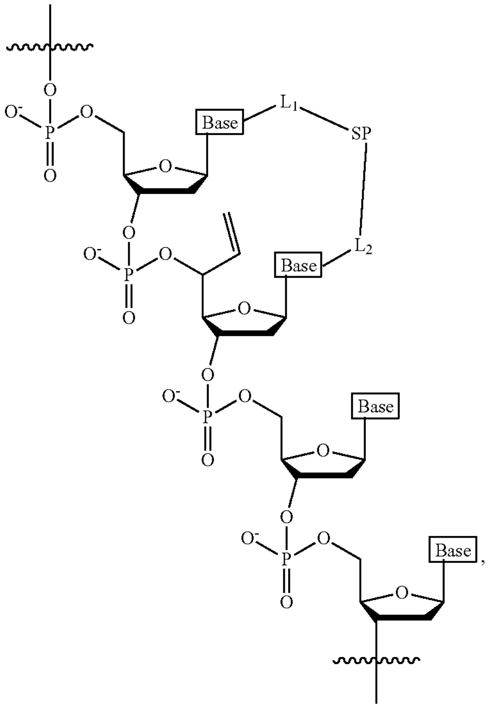
, -continued
(VII)
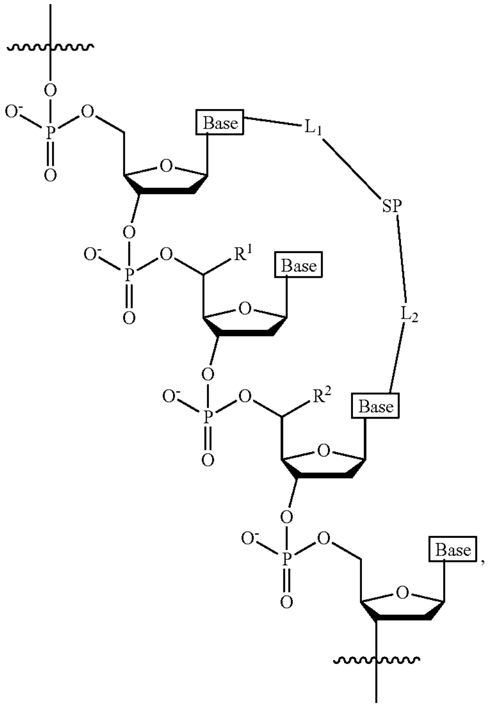
(VIII)
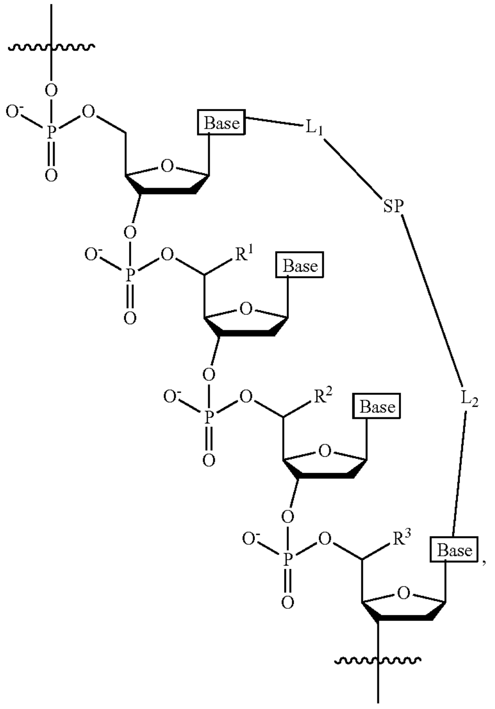
-continued
(IX)
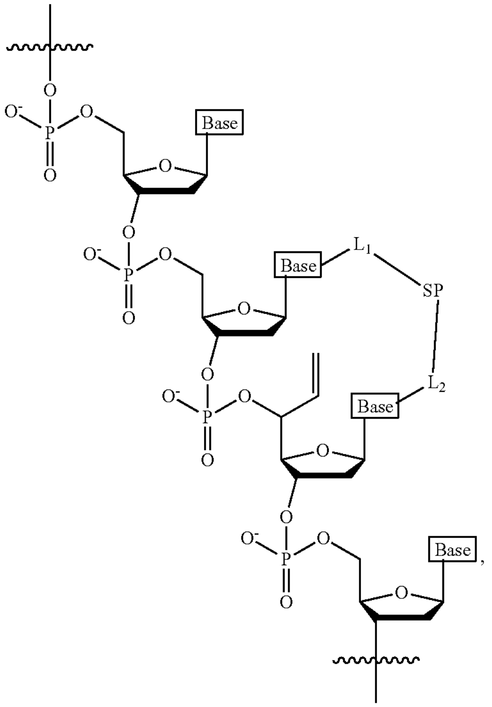
(X)
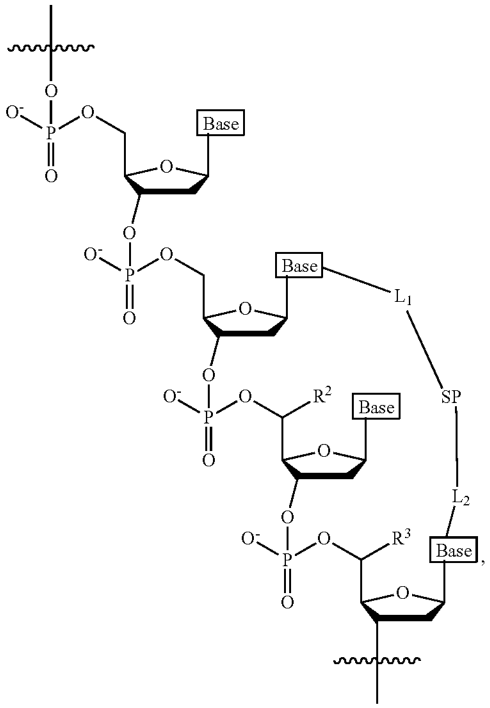

-continued (XI)

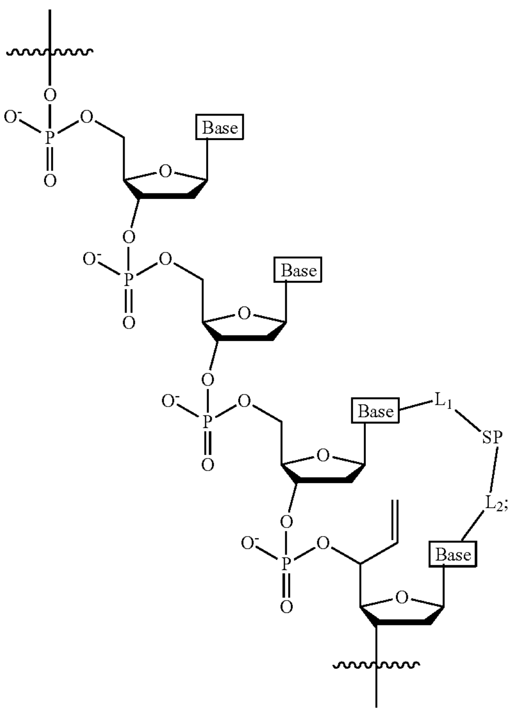

wherein X is —O—, —$CH_2$—, —NH—,

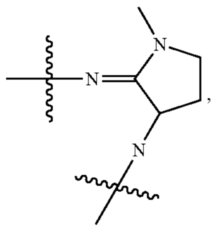

, or

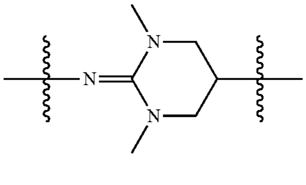

;

X' is =N—$SO_2$—, =NH—CO—, or

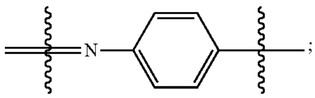 [SMILES: *c1ccc(N=*)cc1]

;

Y is —O—, —S—, —NH—, or —Se—; one of $R^1$, $R^2$, and $R^3$ is allyl, while the others are H, $L_1$ is a first linking group; $L_2$ is a second linking group; and SP is a spacer.

In some embodiments, structure (VII) can further be represented by the following structures:

(VIIa)

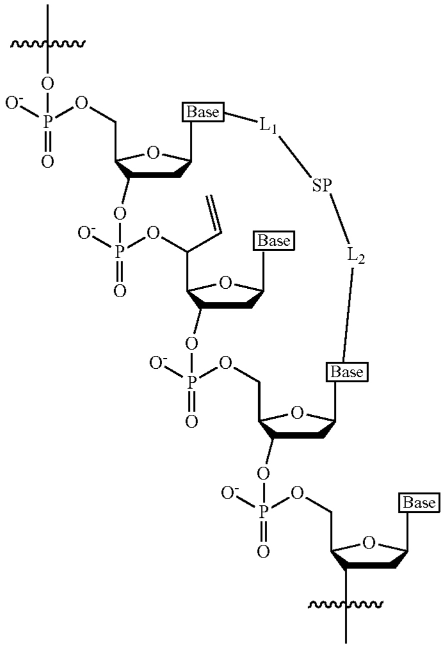

or (VIIb)

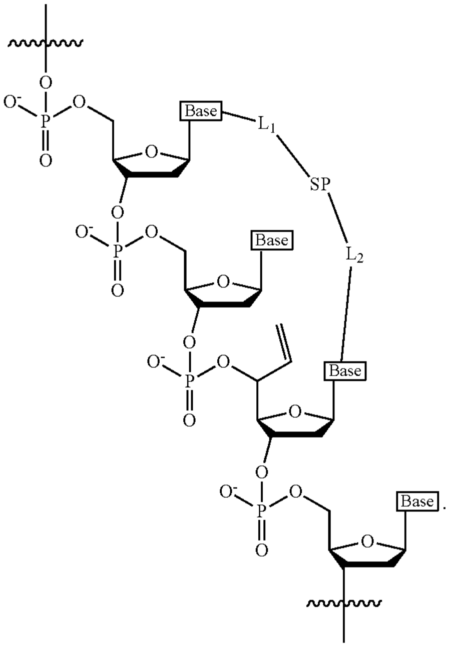

.

In some embodiments, structure (VIII) can further be represented by the following structures:

(VIIIa)
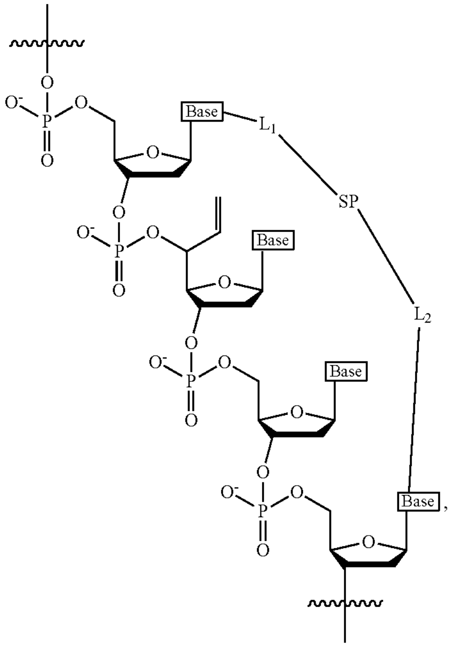
,
-continued
(VIIIc)
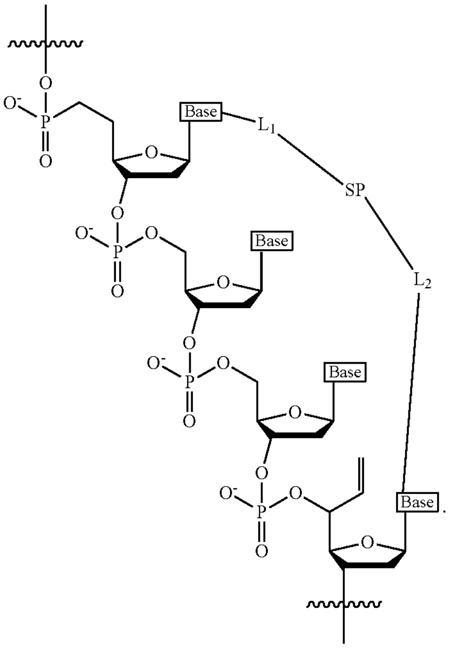
.
In some embodiments, structure (X) can further be represented by the following structures:
(VIIIb)
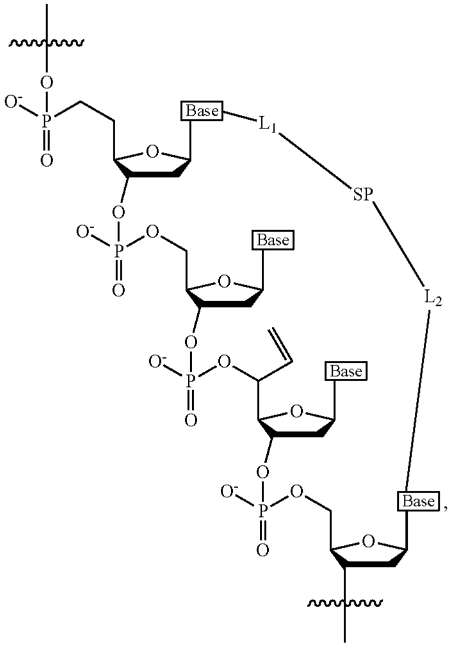
, or
(Xa)
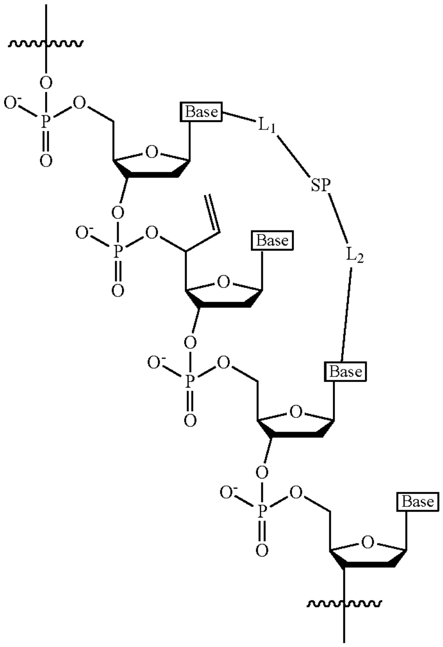
or -continued
(Xb)
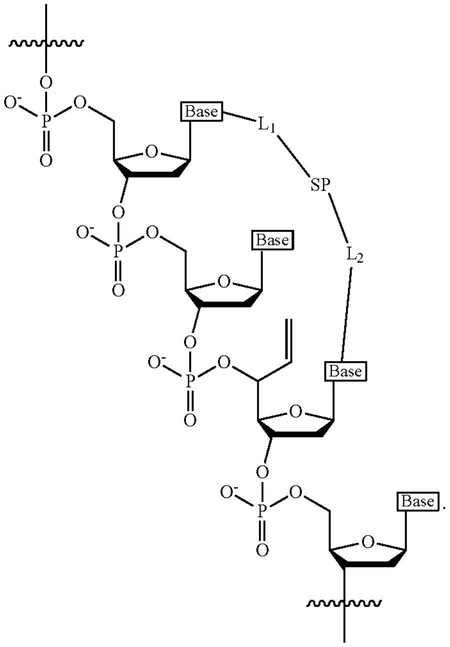
Disclosed herein also includes an oligonucleotide comprising one of the following structures:
(XIIIa)
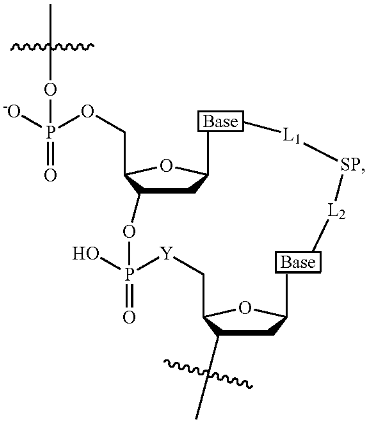
(XIIIb)
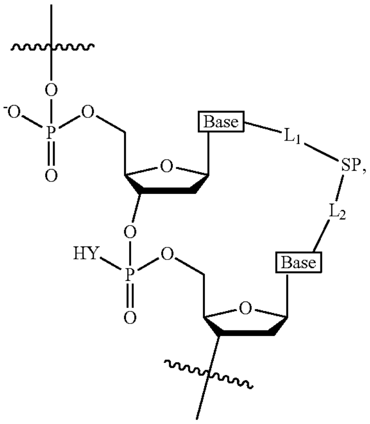
-continued
(XIVa)
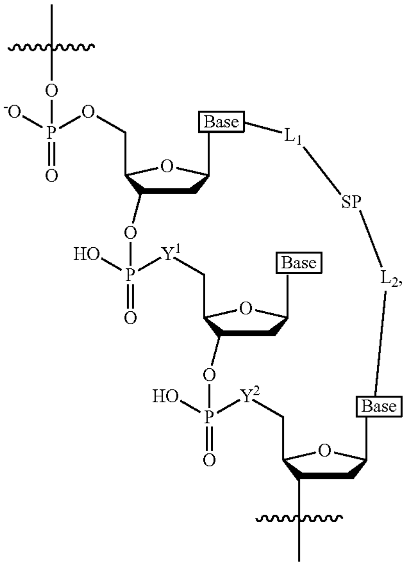
(XIVb)
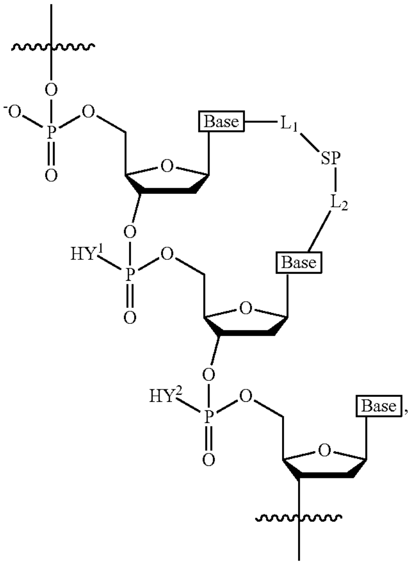

-continued (XVa)

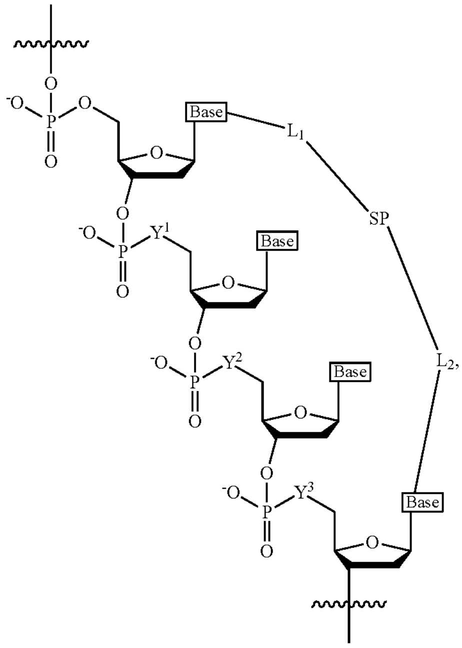

and (XVb)

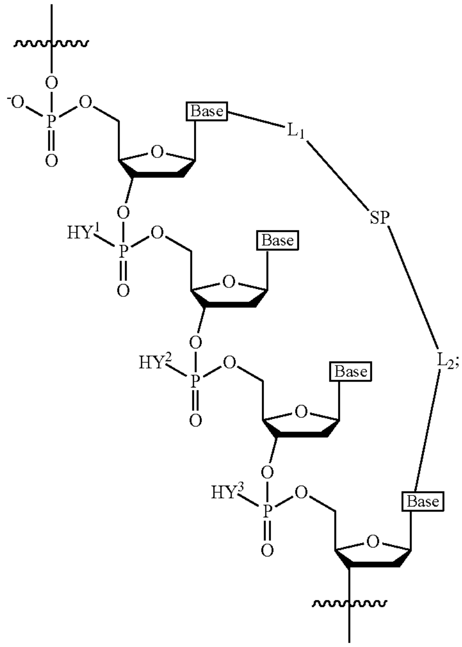

wherein Y is —O—, —S—, —NH—, or —Se—; and one of $Y^1$, $Y^2$, and $Y^3$ is —S— or —Se—, and the others are —O— or —NH—.

In some embodiments, SP comprises one or more of the following moieties: (1) alkyl chains having 5 to 50 carbons, (2) oligonucleotides or modified oligonucleotides having 1 to 100 repeating units, (3) polypeptides having 1 to 100 repeating units, (4) hydrophilic polymers having 1 to 100 repeating units selected from the group consisting of polyethyleneglycol, polyvinyl alcohol, polyacrylamide, polyvinylpyrrolidone, polystyrenesulfonate, and polyethyleneimine, and (5) hydrophobic polymers having 1 to 100 repeating units selected from the group consisting of polylactic acid, polymethylmethacrylate, and polystyrene.

In some embodiments, the hydrophilic polymers are selected from the group consisting of polyethyleneglycol, polyvinyl alcohol, polyacrylamide, polyvinylpyrrolidone, polystyrenesulfonate, and polyethyleneimine. In some embodiments, the hydrophobic polymers are selected from the group consisting of polylactic acid, polymethylmethacrylate, and polystyrene.

In some embodiments, each of $L_1$ and $L_2$ independently comprises a conjugating moiety selected from the group consisting of amine-NHS ester, amine-imidoester, amine-pentafluorophenyl ester, amine-hydroxymethyl phosphine, carboxyl-carbodiimide, thiol-maleimide, thiol-haloacetyl, thiol-pyridyl disulfide, thiol-thiosulfonate, thiol-vinyl sulfone, aldehyde-hydrazide, aldehyde-alkoxyamine, hydroxy-isocyanate, azide-alkyne, azide-phosphine, trans-cyclooctene-tetrazine, norbornene-tetrazine, azide-cyclooctyne, and azide-norbornene.

In some embodiments, $L_1$ and $L_2$ independently further comprises a first linker between the conjugating moiety and X, and a second linker between the conjugating moiety and SP.

In some embodiments, the first linker and the second linker are independently selected from the group consisting of polynucleotide having 1 to 100 repeating units, polypeptide having 1 to 100 repeating units, alkyl chains having 5 to 50 carbons, hydrophilic polymers having 1 to 100 repeating units comprising polyethyleneglycol, polyvinyl alcohol, polyacrylamide, polyvinylpyrrolidone, polystyrenesulfonate, or polyethyleneimine, hydrophobic polymers having 1 to 100 repeating units comprising polylactic acid, polymethylmethacrylate, or polystyrene, and combinations thereof.

In some embodiments, SP further comprises an arresting construct. In some embodiments, the Base further comprises an arresting construct. In some embodiments, the arresting construct is a linear, a branched or a cyclic polymer. In some embodiments, the arresting construct comprises a synthetic hydrophobic polymer, a synthetic hydrophilic polymer, an oligonucleotide/polynucleotide, a peptide/polypeptide, or combinations thereof.

In some embodiments, $L_1$, SP, and $L_2$ are sub-elements of a cyclic loop. In some embodiments, the cyclic loop is symmetric. In some embodiments, the cyclic loop is asymmetric. In some embodiments, the cyclic loop s was synthesized using one or more fo the following: solid phase synthesis, solution phase synthesis, and enzymatic synthesis. In some embodiments, the cyclic loop was synthesized using one or more of the following: linear synthesis, branched synthesis, or segmented synthesis.

Disclosed here in also includes a method for determining a sequence of a polynucleotide in a nanopore-based sequencing system, the method comprising: providing a polynucleotide comprising a plurality of nucleotides, wherein each nucleotide comprises a linker construct, the linker construct having a first end attached to the first position of the nucleotide and a second end attached to the second position of the nucleotide; cleaving a cleavable bond on each of the plurality of nucleotide between the first and the second positions, thereby elongating the polynucleotide to form an elongated polymer; applying a voltage to cause the elongated polymer to insert into and translocate through a nanopore; and (i) detecting and identifying a reporter moiety when the linker construct passes through the nanopore; or (ii) detecting and identifying a base on the nucleotide when the nucleotide passes through the nanopore.

In some embodiments, the linker construct comprises a first linking group, a second linking group, and a spacer between the first and the second linking groups.

In some embodiments, the spacer comprises an oligonucleotide, modified oligonucleotide, or polyphosphate having 1 to 100 repeating units, polypeptide having 1 to 100 repeating units, alkyl chains having 5 to 50 carbons, hydrophilic polymers having 1 to 100 repeating units selected form the group consisting of polyethyleneglycol, polyvinyl alcohol, polyacrylamide, polyvinylpyrrolidone, polystyrenesulfonate, and polyethyleneimine, hydrophobic polymers having 1 to 100 repeating units selected from the group consisting of polylactic acid, polymethylmethacrylate, and polystyrene, and combinations thereof.

In some embodiments, the spacer comprises the reporter moiety, wherein the reporter moiety corresponds to and identifies a nucleotide.

In some embodiments, each of the first and the second linking groups $L_1$ and $L_2$ independently comprises a conjugating moiety selected from the group consisting of amine-NHS ester, amine-imidoester, amine-pentafluorophenyl ester, amine-hydroxymethyl phosphine, carboxyl-carbodiimide, thiol-maleimide, thiol-haloacetyl, thiol-pyridyl disulfide, thiol-thiosulfonate, thiol-vinyl sulfone, aldehyde-hydrazide, aldehyde-alkoxyamine, hydroxy-isocyanate, azide-alkyne, azide-phosphine, transcyclooctene-tetrazine, norbornene-tetrazine, azide-cyclooctyne, and azide-norbornene.

In some embodiments, the elongated polymer further comprises an arresting construct attached to each nucleobase or each linker construct, wherein the arresting construct is configured to slow, pause, or halt the translocation.

In some embodiments, the arresting construct (i.e., modification) is a linear, a branched, or a cyclic polymer. In some embodiments, the arresting construct comprises a synthetic hydrophobic polymer, a synthetic hydrophilic polymer, an oligonucleotide/polynucleotide, a peptide/polypeptide, or combinations thereof. In some embodiments, the nanopore comprises a constriction having an opening with an inner diameter from about 0.6 nm to about 1.2 nm.

In some embodiments, the reporter moiety comprises one or more sub-reporter moieties, wherein the one or more sub-reporter moieties corresponds to and identifies nucleotide or a translocation event. In some embodiments, the reporter moiety comprises two or more sub-reporter moieties, wherein each sub-reporter moiety in the two or more sub-reporter moieties are distinguishable, reproducible, and resolvable. In some embodiments, the two or more sub-reporter moieties comprise crown ethers, cucurbiturils, pillararenes, or cyclodextrins.

Disclosed herein includes a kit for performing a method for determining a sequence of a polynucleotide in a nanopore-based sequencing system, the kit comprising the compound disclosed herein.

Disclosed herein includes a system for determining a sequence of a polynucleotide, the system configured to perform the method disclosed herein.

Disclosed herein includes a system for performing a method for determining a sequence of a polynucleotide comprising a plurality of nucleotides, wherein the nucleotides are selected from any of the compounds disclosed herein.

It should be appreciated that all combinations of the foregoing concepts and additional concepts discussed in greater detail below are contemplated as being part of the inventive subject matter disclosed herein and may be used to achieve the benefits and advantages described herein.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIG. 7 shows experimental data of polymerase incorporation of allyl dTTP.

FIG. 33 schematically illustrates an example of an eighth design of a cyclic loop nucleotide (SNNL-1), where X may be O, NH, or CH2, having an alpha phosphate-base linked symmetrical non-nucleosidic loop, and a arresting construct on the loop.

FIG. 51 illustrates gel results of a cleavage reaction on an extended primer using the bridging P—S nucleotide 1 and DNA polymerase Pol1901.

FIGS. 54A-C illustrates HPLC, IR and MS characterization of the cyclic loop 4-mer oligonucleotide shown in FIG. 53B.

FIG. 55 illustrates non-limiting experimental ligation results to ligate up to 10 of the looped 4-mer oligonucleotide.

FIG. 56 illustrates non-limiting experimental results from the consecutive ligation and cleavage of certain polynucleotides.

FIG. 58 illustrates the incorporation of non-bridging P—S nucleotides using varying polymerases.

FIG. 61 demonstrates ligases to perform up to 10 successive ligation events with the cyclic loop 4-mer oligonucleotide shown in FIG. 59.

FIG. 70B provides exemplary methods to activate the alpha P monophosphate.

FIG. 72 schematically illustrates deprotection of 3'-OTBDPS group to form 3'-OH, resulting in nucleotide 6.

FIG. 73 illustrates HF-TEA and TBAF deprotection methods to assess conversion efficiency and yield of desired triphosphate product.

FIG. 82 illustrates synthesis of exemplary azido variants.

FIG. 85 illustrates results of a bifunctional nucleotide 6 as tested in an incorporation assay using Dpo4 enzyme compared to natural dTTP.

FIG. 86 illustrates results of a bifunctional nucleotide 10 as tested in an incorporation assay using Dpo4 enzyme compared to natural dTTP.

FIG. 87 shows experimental results regarding the incorporation kinetics of a looped nucleotide.

FIG. 88 illustrates stability assays performed on the bifunctional nucleotide 6 and looped nucleotide 10.

FIG. 89 illustrates stability assays performed on the bifunctional nucleotide 6 and looped nucleotide 10.

DETAILED DESCRIPTION

Figure 1:
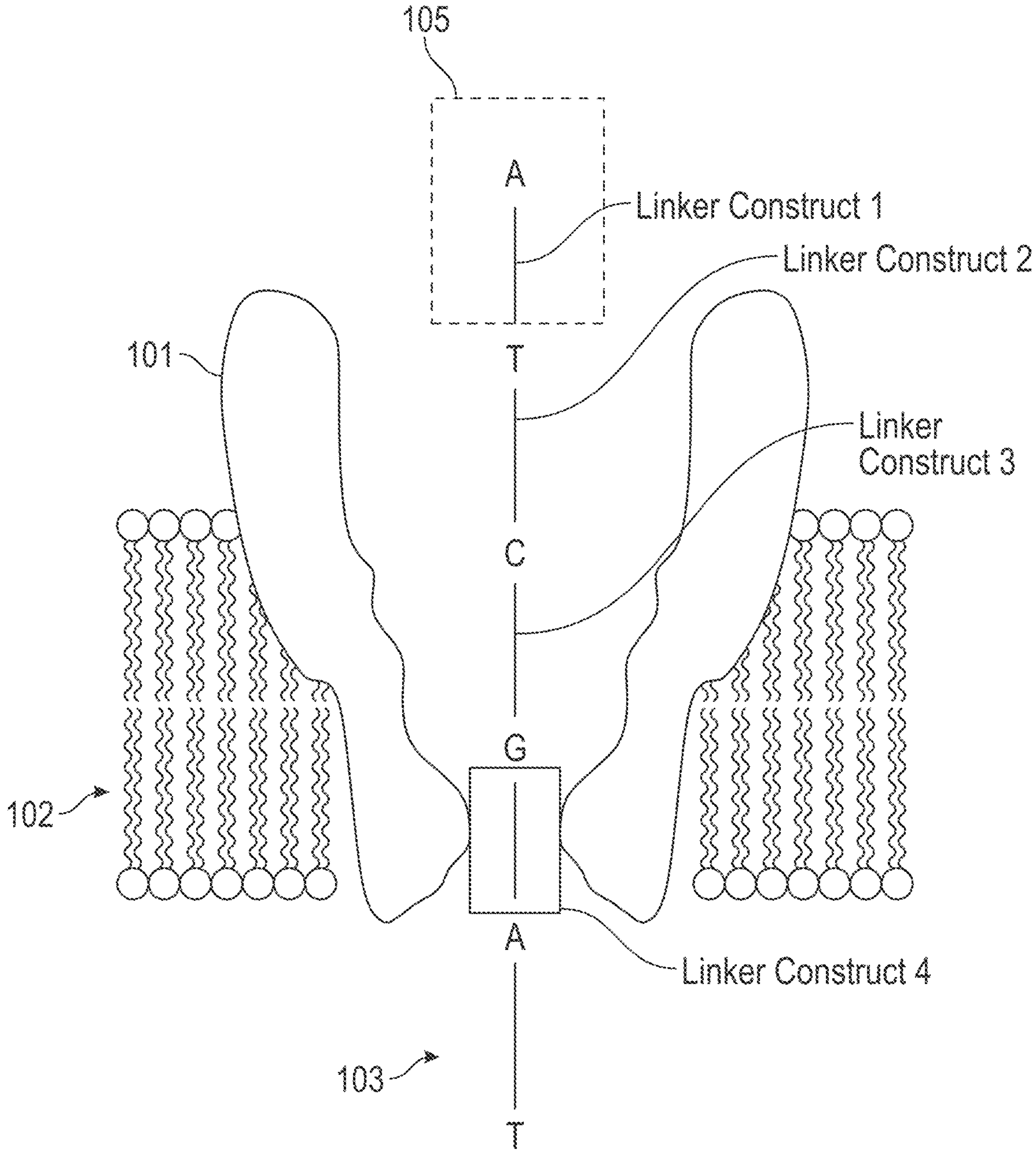
FIG. 1 schematically illustrates an example of sequencing an elongated polynucleotide.

All patents, applications, published applications and other publications referred to herein are incorporated herein by reference to the referenced material and in their entireties. If a term or phrase is used herein in a way that is contrary to or otherwise inconsistent with a definition set forth in the patents, applications, published applications and other publications that are herein incorporated by reference, the use herein prevails over the definition that is incorporated herein by reference.

Definitions

All technical and scientific terms used herein have the same meaning as commonly understood to one of ordinary skill in the art to which this disclosure belongs unless clearly indicated otherwise.

As used herein, the singular forms “a”, “and”, and “the” include plural referents unless the context clearly dictates otherwise. Thus, for example, reference to “a sequence” may include a plurality of such sequences, and so forth.

The terms comprising, including, containing and various forms of these terms are synonymous with each other and are meant to be equally broad. Moreover, unless explicitly stated to the contrary, examples comprising, including, or having an element or a plurality of elements having a particular property may include additional elements, whether or not the additional elements have that property.

As used herein, the term “modified oligonucleotide” refers to a polymeric chain of nucleobases or nucleotides assembled with moieties comprising a modified nucleobase, modified sugar rings (e.g. LNA, constraint ethyl, ethylene bridged, TNA, 2'-Ome, 2'F, 2'-MOE) or nucleobases attached to a scaffold (e.g. unlock, 4'-thio, CeNA, HNA, TNA, GNA, FNA).

As used herein, the term “phosphoramidite analogs” refers to any polymer synthesized using phosphoramidite or related chemistries resulting in the formation of phosphodiester, methylphosphonate, or phosphorothioate bonds between each moiety.

As used herein, the term “modified polyamide” refers to a polymer assembled with individual moieties each having at least 1 amino group and 1 carboxylic acid group, resulting in the formation of amide bonds.

As used herein, the term “nanopore” is intended to mean a hollow structure discrete from, or defined in, and extending across the membrane. The nanopore permits ions, electric current, and/or fluids to cross from one side of the membrane to the other side of the membrane. For example, a membrane that inhibits the passage of ions or water-soluble molecules can include a nanopore structure that extends across the membrane to permit the passage (through a nanoscale opening extending through the nanopore structure) of the ions or water-soluble molecules from one side of the membrane to the other side of the membrane. The diameter of the nanoscale opening extending through the nanopore structure can vary along its length (i.e., from one side of the membrane to the other side of the membrane), but at any point is on the nanoscale (i.e., from about 1 nm to about 100 nm, or to less than 1000 nm). Examples of the nanopore include, for example, biological nanopores, solid-state nanopores, and biological and solid-state hybrid nanopores. In some embodiments, a refers to a pore having an opening with a diameter at its most narrow point of about 0.3 nm to about 2 nm. For example, a nanopore may be a solid-state nanopore, a graphene nanopore, an elastomer nanopore, or may be a naturally-occurring or recombinant protein that forms a tunnel upon insertion into a bilayer, thin film, membrane, or solid-state aperture, also referred to as a protein pore or protein nanopore herein (e.g., a transmembrane pore). If the protein inserts into the membrane, then the protein is a tunnel-forming protein.

As used herein, the term “diameter” is intended to mean a longest straight line inscribable in a cross-section of a nanoscale opening through a centroid of the cross-section of the nanoscale opening. It is to be understood that the nanoscale opening may or may not have a circular or substantially circular cross-section (the cross-section of the nanoscale opening being substantially parallel with the cis/trans electrodes). Further, the cross-section may be regularly or irregularly shaped.

As used herein, “cis” refers to the side of a nanopore opening through which an analyte or modified analyte enters the opening or across the face of which the analyte or modified analyte moves.

As used herein, “trans” refers to the side of a nanopore opening through which an analyte or modified analyte (or fragments thereof) exits the opening or across the face of which the analyte or modified analyte does not move.

As used herein, the term “biological nanopore” is intended to mean a nanopore whose structure portion is made from materials of biological origin. Biological origin refers to a material derived from or isolated from a biological environment such as an organism or cell, or a synthetically manufactured version of a biologically available structure. Biological nanopores include, for example, polypeptide nanopores and polynucleotide nanopores.

As used herein, a “moiety” is one of two or more parts into which something may be divided, such as, for example, the various parts of a tether, a molecule or a probe.

As used herein, a “reporter” is composed of one or more reporter elements or reporter moieties. Reporters include what are known as “tags” and “labels.” The linker construct (when including reporter moiety) or nucleobase residue of the elongated polymer can be considered a reporter. Reporters serve to parse the identity of the target nucleic acid. Reporters may include constituent sub-reporters, and multiple reporters may be present on a single nucleotide. When present in the readhead of a nanopore, reporters provide distinctive and sometimes unique blockage currents at given read voltages.

As used herein, a “linker” is a molecule or moiety that joins two molecules or moieties and provides spacing between the two molecules or moieties such that they are able to function in their intended manner. For example, a linker can comprise a diamine hydrocarbon chain that is covalently bound through a reactive group on one end to an oligonucleotide analog molecule and through a reactive group on another end to a solid support, such as, for example, a bead surface. Coupling of linkers to nucleotides and substrate constructs of interest can be accomplished through the use of coupling reagents that are known in the art (see, e.g., Efimov et al., Nucleic Acids Res. 27: 4416-4426, 1999). Methods of derivatizing and coupling organic molecules are well known in the arts of organic and bioorganic chemistry. A linker may also be cleavable or reversible.

As used herein, the term “heavy atom” refers to any atom used within a molecular structure that is not hydrogen. Heavy atoms used within a modified oligonucleotide may be bridging (e.g. used to connect multiple oligonucleotides), or non-bridging (e.g. not directly linked to multiple oligonucleotides).

As used herein, the term “polypeptide nanopore” is intended to mean a protein/polypeptide that extends across the membrane, and permits ions, electric current, polymers such as DNA or peptides, or other molecules of appropriate dimension and charge, and/or fluids to flow therethrough from one side of the membrane to the other side of the membrane. A polypeptide nanopore can be a monomer, a homopolymer, or a heteropolymer. Structures of polypeptide nanopores include, for example, an α-helix bundle nanopore and a β-barrel nanopore. Example polypeptide nanopores include α-hemolysin, *Mycobacterium smegmatis* porin A (MspA), gramicidin A, maltoporin, OmpF, OmpC, PhoE, Tsx, F-pilus, etc. The protein α-hemolysin is found naturally in cell membranes, where it acts as a pore for ions or molecules to be transported in and out of cells. *Mycobacterium smegmatis* porin A (MspA) is a membrane porin produced by Mycobacteria, which allows hydrophilic molecules to enter the bacterium. MspA forms a tightly interconnected octamer and transmembrane beta-barrel that resembles a goblet and contains a central pore.

As used herein, a “peptide” refers to two or more amino acids joined together by an amide bond (that is, a “peptide bond”). Peptides comprise up to or include 50 amino acids. Peptides may be linear or cyclic. Peptides may be α, β, γ, δ, or higher, or mixed. Peptides may comprise any mixture of amino acids as defined herein, such as comprising any combination of D, L, α, β, γ, δ, or higher amino acids.

As used herein, a “protein” refers to an amino acid sequence having 51 or more amino acids.

A polypeptide nanopore can be synthetic. A synthetic polypeptide nanopore includes a protein-like amino acid sequence that does not occur in nature. The protein-like amino acid sequence may include some of the amino acids that are known to exist but do not form the basis of proteins (i.e., non-proteinogenic amino acids). The protein-like amino acid sequence may be artificially synthesized rather than expressed in an organism and then purified/isolated.

The nanopores disclosed herein may be hybrid nanopores. A "hybrid nanopore" refers to a nanopore including materials of both biological and non-biological origins. An example of a hybrid nanopore includes a polypeptide-solid-state hybrid nanopore and a polynucleotide-solid-state nanopore.

The application of the electric potential difference across a nanopore may force the translocation of a nucleic acid through the nanopore. One or more signals are generated that correspond to the translocation of the nucleotide through the nanopore. Accordingly, as a target polynucleotide, or as a mononucleotide or a probe derived from the target polynucleotide or mononucleotide, transits through the nanopore, the current across the membrane changes due to base-dependent (or probe dependent) blockage of the constriction, for example. The signal from that change in current can be measured using any of a variety of methods. Each signal is unique to the species of nucleotide(s) (or linker constructs with a reporter moiety region) in the nanopore, such that the resultant signal can be used to determine a characteristic of the polynucleotide. For example, the identity of one or more species of nucleotide(s) (or probe) that produces a characteristic signal can be determined.

As used herein, a "nucleotide" includes a nitrogen containing heterocyclic base, a sugar, and one or more phosphate groups. Nucleotides are monomeric units of a nucleic acid sequence. Examples of nucleotides include, for example, ribonucleotides or deoxyribonucleotides. In ribonucleotides (RNA), the sugar is a ribose, and in deoxyribonucleotides (DNA), the sugar is a deoxyribose, i.e., a sugar lacking a hydroxyl group that is present at the 2' position in ribose. The nitrogen containing heterocyclic base can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C−1 atom of deoxyribose is bonded to N−1 of a pyrimidine or N−9 of a purine. The phosphate groups may be in the mono-, di-, or tri-phosphate form. These nucleotides are natural nucleotides, but it is to be further understood that non-natural nucleotides, modified nucleotides or analogs of the aforementioned nucleotides can also be used.

As used herein, "nucleobase" is a heterocyclic base such as adenine, guanine, cytosine, thymine, uracil, inosine, xanthine, hypoxanthine, or a heterocyclic derivative, analog, or tautomer thereof. A nucleobase can be naturally occurring or synthetic. Non-limiting examples of nucleobases are adenine, guanine, thymine, cytosine, uracil, xanthine, hypoxanthine, 8-azapurine, purines substituted at the 8 position with methyl or bromine, 9-oxo-N6-methyladenine, 2-aminoadenine, 7-deazaxanthine, 7-deazaguanine, 7-deaza-adenine, N4-ethanocytosine, 2,6-diaminopurine, N6-ethano-2,6-diaminopurine, 5-methylcytosine, 5-(C3-C6)-alkynylcytosine, 5-fluorouracil, 5-bromouracil, thiouracil, pseudoisocytosine, 2-hydroxy-5-methyl-4-triazolopyridine, isocytosine, isoguanine, inosine, 7,8-dimethylalloxazine, 6-dihydrothymine, 5,6-dihydrouracil, 4-methyl-indole, ethenoadenine and the non-naturally occurring nucleobases described in U.S. Pat. Nos. 5,432,272 and 6,150,510 and PCT applications WO 92/002258, WO 93/10820, WO 94/22892, and WO 94/24144, and Fasman ("Practical Handbook of Biochemistry and Molecular Biology", pp. 385-394, 1989, CRC Press, Boca Raton, LO), all herein incorporated by reference in their entireties.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in manner similar to naturally occurring nucleotides, such as peptide nucleic acids (PNAs) and phosphorothiolate DNA. Unless otherwise indicated, a particular nucleic acid sequence includes the complementary sequence thereof. Nucleotides include, but are not limited to, ATP, dATP, CTP, dCTP, GTP, dGTP, UTP, TTP, dUTP, 5-methyl-CTP, 5-methyl-dCTP, ITP, dITP, 2-amino-adenosine-TP, 2-amino-deoxyadenosine-TP, 2-thiothymidine triphosphate, pyrrolo-pyrimidine triphosphate, and 2-thiocytidine, as well as the alphathiotriphosphates for all of the above, and 2'-O-methyl-ribonucleotide triphosphates for all the above bases. Modified bases include, but are not limited to, 5-Br-UTP, 5-Br-dUTP, 5-F-UTP, 5-F-dUTP, 5-propynyl dCTP, and 5-propynyl-dUTP.

As used herein, the term "signal" is intended to mean an indicator that represents information. Signals include, for example, an electrical signal and an optical signal. The term "electrical signal" refers to an indicator of an electrical quality that represents information. The indicator can be, for example, current, voltage, tunneling, resistance, potential, voltage, conductance, or a transverse electrical effect. An "electronic current" or "electric current" refers to a flow of electric charge. In an example, an electrical signal may be an electric current passing through a nanopore, and the electric current may flow when an electric potential difference is applied across the nanopore.

As used herein, the term "driving force" is intended to mean an electrical current that allows a polynucleotide to translocate through the nanopore. In some embodiments, the electrical current may flow when an electric potential difference is applied across the nanopore.

As used herein, the term "holding force" is intended to mean a resistance that slows and/or stops a polynucleotide to translocate through the nanopore. In some embodiments, the holding force is overcome by the application of a driving force. Thus, the driving force overcomes/overrides the resistance that slows and/or stops a polynucleotide, thereby allowing the polynucleotide to translocate through the nanopore.

As used herein, the term "modification" is intended to mean a moiety attached to a nucleotide. A modification may provide a resistance (in the form of a "holding force") that slows and/or stops a polynucleotide to translocate through the nanopore unless the resistance due to the modification is overcome by a "driving force." The resistance provided by the modification is due to a property of the modification (e.g., size, geometry, and/or non-covalent interaction with the nanopore). Modifications can operate as a ratchet or a brake for the polypeptide translocation through a nanopore. A modification can be attached to any part of the nucleotide and can also be attached to the nucleotide at two locations forming a loop. The modification may also be referred to as an arresting construct.

The aspects and examples set forth herein and recited in the claims can be understood in view of the above definitions.

Overview

A common drawback with nanopore sequencers is that the nanopore is sensitive to multiple bases of a DNA strand in the nanopore, as opposed to reading single base one at a time. For example, the MspA nanopore has a constriction region which serves as a readhead of at least 4 nucleotides (termed a "k-mer"), resulting in minimally 256 (4^4) different permutation of 4-mer sequences that needs to be deconvoluted. For a k-mer of 5 bases, the number of possible signals is 4^5=1,024. A longer readhead will result in an exponential increase in number of signals to be differentiated, which complicates the sequencing readout and increases the complexity of base calling, thus reducing accuracy. Another issue with nanopore sequencers is that the speed of translocation of natural single stranded DNA is in the order of >10 million nucleotides per second, way above the rate that is compatible with electronics and detectors.

In some embodiments, by using cleavable sites along the DNA backbone while conjoining adjacent nucleobases with a barcoding region, the disclosed technology allows the distance between adjacent nucleobases to be increased and negates the need to deconvolute a large number of signals. Once the backbone is cleaved, the reporter portion of the elongated polynucleotide would occupy the entire readhead of the nanopore for highly accurate single molecule sequencing with single base resolution. It has been observed that DNA backbone cleavage may be affected by instabilities arising from the introduction of certain alpha phosphate substitutions. Therefore, stable alpha phosphate substitutions, especially when polynucleotides or oligonucleotides are cleaved to elongate a leading strand, are preferable when synthesizing daughter oligonucleotide strands.

In some embodiments, the disclosed technology allows having 1 nucleobase of the elongated polynucleotide to reside in the readhead at any point in time, successfully reducing the diversity of reads to 4 (A, T, C and G), enabling more accurate sequencing at a lower cost. In some embodiments, the disclosed technology provides high throughput, cheaper and more accurate DNA sequencing.

System and Method

FIG. 1 schematically illustrates an example of sequencing an elongated polynucleotide. A protein nanopore 101 is deposited in a lipid bilayer 102. An elongated polynucleotide 103 translocates through the nanopore 101. The polynucleotide 103 includes linker construct regions between successive nucleotides. By introducing a linker construct between successive nucleotides, the k-mer length can be reduced to 1, resulting in just 4 signals (for A, T, C and G), reducing the complexity of base calling. A characteristic linker/barcode may be assigned to each of the 4 individual bases to achieve base recognition. For example, the signal unit or moiety 105 includes an "A" nucleotide and a corresponding "linker construct 1," which may contain a reporter that serves as the barcode for nucleotide A. Diversity of reads is reduced to 4 with a single barcode characteristic of each nucleobase residing in the nanopore readhead.

By "translocation," it is meant that an analyte (e.g., a polynucleotide, such as DNA) enters one side of an opening of a nanopore and move to and out of the other side of the opening. It is contemplated that any embodiment herein comprising translocation may refer to electrophoretic translocation or non-electrophoretic translocation, unless specifically noted. An electric field may move an analyte or modified analyte. By "interacts," it is meant that the analyte or modified analyte moves into and, optionally, through the opening, where "through the opening" (or "translocates") means to enter one side of the opening and move to and out of the other side of the opening. Optionally, methods that do not employ electrophoretic translocation are contemplated. In some embodiments, physical pressure causes a modified analyte to interact with, enter, or translocate (after alteration) through the opening. In some embodiments, a magnetic bead is attached to an analyte or modified analyte on the trans side, and magnetic force causes the modified analyte to interact with, enter, or translocate (after alteration) through the opening. Other methods for translocation include but not limited to gravity, osmotic forces, temperature, and other physical forces such as centripetal force.

In some embodiments, the nanopore may comprise a solid-state material, such as silicon nitride, modified silicon nitride, silicon, silicon oxide, or graphene, or a combination thereof. In some embodiments, the nanopore is protein that forms a tunnel upon insertion into a bilayer, membrane, thin film, or solid-state aperture. In some embodiments, the nanopore is comprised in a lipid bilayer. In some embodiments, the nanopore is comprised in an artificial membrane comprising a mycolic acid. The nanopore may be a *Mycobacterium smegmatis* porin (Msp) having a vestibule and a constriction zone that define the tunnel. The Msp porin may be a mutant MspA porin. In some embodiments, amino acids at positions 90, 91, and 93 of the mutant MspA porin are each substituted with asparagine. Some embodiments may comprise altering the translocation velocity or sequencing sensitivity by removing, adding, or replacing at least one amino acid of an Msp porin. A "mutant MspA porin" is a multimer complex that has at least or at most 70, 75, 80, 85, 90, 95, 98, or 99 percent or more identity, or any range derivable therein, but less than 100%, to its corresponding wild-type MspA porin and retains tunnel-forming capability. A mutant MspA porin may be recombinant protein. Optionally, a mutant MspA porin is one having a mutation in the constriction zone or the vestibule of a wild-type MspA porin. Optionally, a mutation may occur in the rim or the outside of the periplasmic loops of a wild-type MspA porin. A mutant MspA porin may be employed in any embodiment described herein.

A "vestibule" refers to the cone-shaped portion of the interior of an Msp porin whose diameter generally decreases from one end to the other along a central axis, where the narrowest portion of the vestibule is connected to the constriction zone. A vestibule may also be referred to as a "goblet." The vestibule and the constriction zone together define the tunnel of an Msp porin. A "constriction zone" or the "readhead" refers to the narrowest portion of the tunnel of an Msp porin, in terms of diameter, that is connected to the vestibule. The length of the constriction zone may range from about 0.3 nm to about 2 nm. Optionally, the length is about, at most about, or at least about 0.3, 0.4, 0.5, 0.6, 0.7, 0.8, 0.9, 1.0, 1.1, 1.2, 1.3, 1.4, 1.5, 1.6, 1.7, 1.8, 1.9, 2, or 3 nm, or any range derivable therein. The diameter of the constriction zone may range from about 0.3 nm to about 2 nm. Optionally, the diameter is about, at most about, or at least about 0.3, 0.4, 0.5, 0.6, 0.7, 0.8, 0.9, 1.0, 1.1, 1.2, 1.3, 1.4, 1.5, 1.6, 1.7, 1.8, 1.9, 2, or 3 nm, or any range derivable therein. A "tunnel" refers to the central, empty portion of an Msp porin that is defined by the vestibule and the constriction zone, through which a gas, liquid, ion, or analyte may pass. A tunnel is an example of an opening of a nanopore.

Various conditions such as light and the liquid medium that contacts a nanopore, including its pH, buffer composition, detergent composition, and temperature, may affect the behavior of the nanopore, particularly with respect to its conductance through the tunnel as well as the movement of an analyte with respect to the tunnel, either temporarily or permanently.

In some embodiments, the disclosed system for nanopore sequencing comprises an Msp porin having a vestibule and a constriction zone that define a tunnel, wherein the tunnel is positioned between a first liquid medium and a second liquid medium, wherein at least one liquid medium comprises an analyte polynucleotide, and wherein the system is operative to detect a property of the analyte. The system may be operative to detect a property of any analyte comprising subjecting an Msp porin to an electric field such that the analyte interacts with the Msp porin. The system may be operative to detect a property of the analyte comprising subjecting the Msp porin to an electric field such that the analyte electrophoretically translocates through the tunnel of the Msp porin. In some embodiments, the system comprises an Msp porin having a vestibule and a constriction zone that define a tunnel, wherein the tunnel is positioned in a lipid bilayer between a first liquid medium and a second liquid medium, and wherein the only point of liquid communication between the first and second liquid media occurs in the tunnel. Moreover, any Msp porin described herein may be comprised in any system described herein. In some embodiments, the system may further comprise an amplifier or a data acquisition device. The system may further comprise one or more temperature regulating devices in communication with the first liquid medium, the second liquid medium, or both. The system described herein may be operative to translocate an analyte through an Msp porin tunnel either electrophoretically or otherwise.

Figure 2:
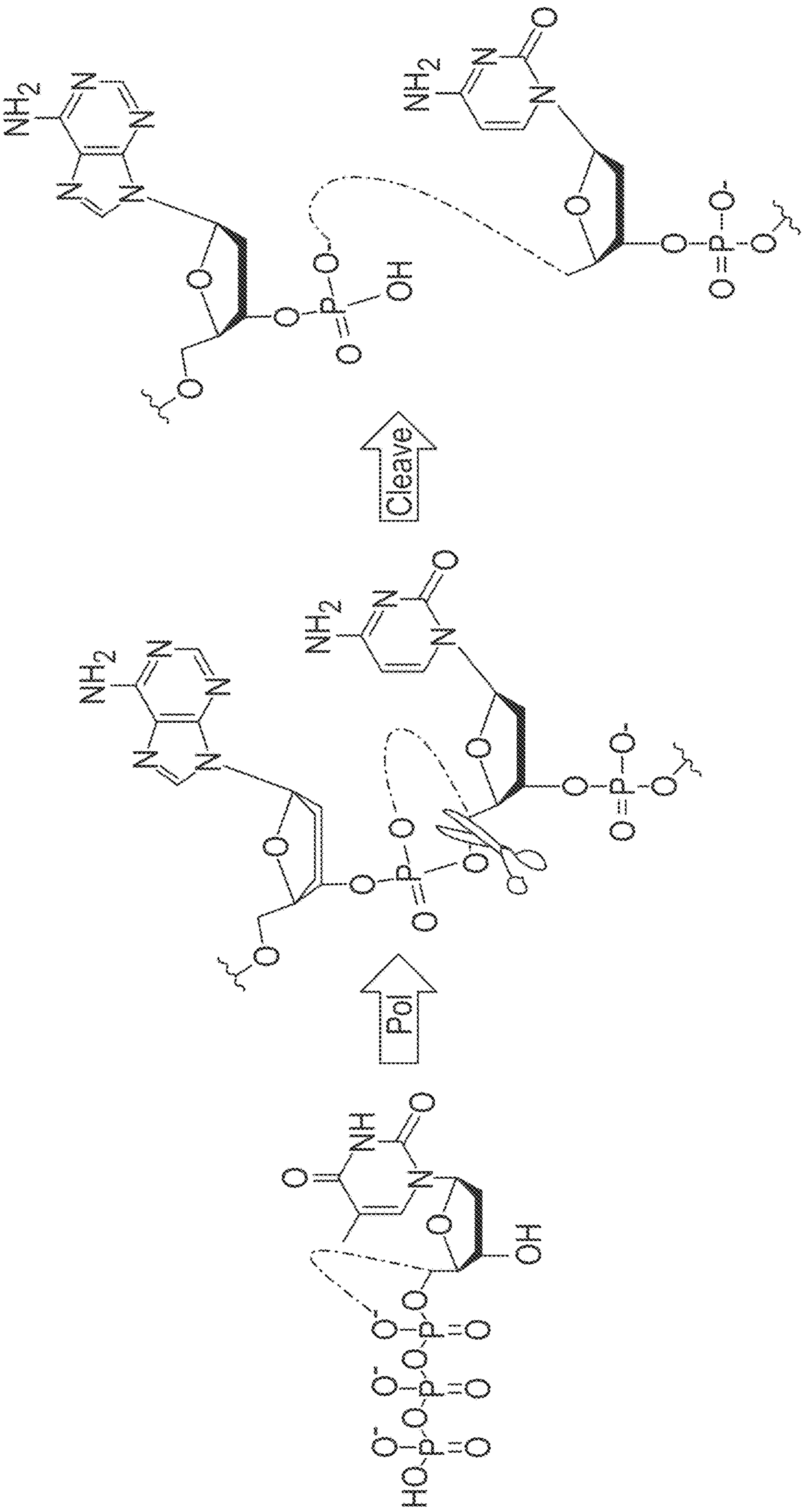
FIG. 2 schematically illustrates an example of elongating a polynucleotide by cleavable cyclic loop nucleotides.

As illustrated in FIG. 2, an elongated polynucleotide 203 may be formed from a polynucleotide having modified nucleotides 210, each modified nucleotide 210 comprises a cyclic loop modification 211. A daughter strand polynucleotide 220 can be synthesized by polymerase from a template DNA using modified nucleotides (e.g., modified dNTPs), 210. In the polymerization process, the modified dNTPs 210 with a cyclic loop 211 is incorporated into a growing daughter strand 220. Once the daughter strand 220 is made, the polynucleotide backbone is cleaved at cleavable sites, allowing the cyclic loop modification 211 to open and result in elongation of the daughter strand polynucleotide 220. The cyclic loop modifications on the modified dNTPs become the linker constructs 206 in the elongated polynucleotide 203 that create distance between adjacent nucleotides.

The polymerase used is an enzyme generally for joining 3'-OH 5'-triphosphate nucleotides, oligomers, and their analogs. Polymerases include, but are not limited to, DNA-dependent DNA polymerases, DNA-dependent RNA polymerases, RNA-dependent DNA polymerases, RNA-dependent RNA polymerases, T7 DNA polymerase, T3 DNA polymerase, T4 DNA polymerase, T7 RNA polymerase, T3 RNA polymerase, SP6 RNA polymerase, DNA polymerase I, Klenow fragment, *Thermophilus aquaticus* DNA polymerase, Tth DNA polymerase, VentR® DNA polymerase (New England Biolabs), Deep VentR® DNA polymerase (New England Biolabs), Bst DNA Polymerase Large Fragment, Stoeffel Fragment, 90N DNA Polymerase, 90N DNA polymerase, Pfu DNA Polymerase, Tfl DNA Polymerase, Tth DNA Polymerase, RepliPHI Phi29 Polymerase, Tii DNA polymerase, eukaryotic DNA polymerase beta, telomerase, Therminator™ polymerase (New England Biolabs), KOD HiFi™ DNA polymerase (Novagen), KOD1 DNA polymerase, Q-beta replicase, terminal transferase, AMV reverse transcriptase, M-MLV reverse transcriptase, Phi6 reverse transcriptase, HIV-1 reverse transcriptase, novel polymerases discovered by bioprospecting, and polymerases cited in US 2007/0048748, U.S. Pat. Nos. 6,329,178, 6,602,695, and 6,395,524 (incorporated by reference). These polymerases include wild-type, mutant isoforms, and genetically engineered variants. "Encode" or "parse" are verbs referring to transferring from one format to another, and refers to transferring the genetic information of target template base sequence into an arrangement of reporters.

After the polymerization process is completed, cleavage at predetermined locations opens the loops and increases the distances between adjacent nucleotides. Cleavage of the daughter strand can be designed to occur at any part of the backbone as long as it occurs within the loop structure between the two positions where the linker construct is attached to the nucleotide structure. Cleavage of the daughter strand along the backbone opens the loops and elongates the daughter strand, leaving the linker construct conjoining the backbone phosphate and the sugar. In embodiments where the linker construct contains a modification configured to interact with the nanopore, the modifications may slow or halt the translocation of the elongated polymer and allow the nucleotides to be read by the nanopore one at a time.

In embodiments where a reporter moiety (such as a reporter barcode) is a part of a linker construct, the cleaved product, i.e., the elongated polymer, exposes a series of reporter moiety, each of which reports the identity of the base to which it corresponds. In embodiments where the linker construct also contains a modification configured to interact with the nanopore, the elongated polymer can be sequenced in the nanopore one barcode at a time.

Cleavable Cyclic Loop Nucleotides

Cleavable cyclic loop nucleotides are nucleotides/nucleotide analogs that are modified to include a linker construct attached to two positions of the nucleotide/nucleotide analog structure. Although "cleavable cyclic loop nucleotide" is used, it includes both modified natural nucleotide and modified nucleotide analogs. The nucleotides and nucleotide analogs useful as described herein include the following compounds:

(NT-1)

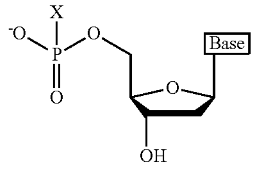

(NT-2)

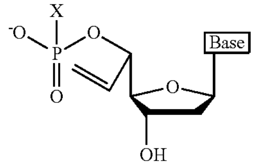

(NT-3)

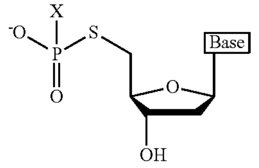

-continued (NT-4)

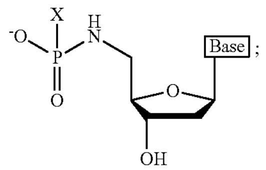

wherein X is NHR, OR, or $CH_2R$; R is H, alkyl, aryl, heteroaryl, cycloalkyl, heterocycloalkyl; and Base is selected from the group consisting of adenine, cytosine, guanine, thymine, and uracil. A linker construct may be conjugated to the nucleotide/nucleotide analog to form a cleavable cyclic loop nucleotide.

The linker construct can be conjugated at one end to the nucleotide/nucleotide analog at by means of either a P—N, P—O, or P—C bond or other P—X heteroatom bond. The other end can be conjugated to (i) any position on the nucleobase in all the structure above, (ii) the 5'-carbon of the ribose sugar in structures NT-1, NT-3, and NT-4, (iii) the N-atom adjacent to the 5'-carbon in structure NT-4, (iv) a 5'-allyl modification in structure NT-2, or (v) any position on the ribose ring. Examples of covalent conjugation chemistries include amine-NHS ester, amine-imidoester, amine-pentafluorophenyl ester, amine-hydroxymethyl phosphine, carboxyl-carbodiimide, thiol-maleimide, thiol-haloacetyl, thiol-pyridyl disulfide, thiol-thiosulfonate, thiol-vinyl sulfone, aldehyde-hydrazide, aldehyde-alkoxyamine, hydroxy-isocyanate, azide-alkyne, azide-phosphine, trans-cyclooctene-tetrazine, norbornene-tetrazine, azide-cyclooctyne, and azide-norbornene. Once the linker construct is conjugated to the nucleotide/nucleotide analog, it forms the cyclic loop portion of the cleavable cyclic loop nucleotide. Thus the cyclic loop comprises -$L_1$-SP-$L_2$-moiety.

Depending on the structure and composition of a cyclic loop, several functions or structures may be present, including one or more of the following: conjugating moieties, linkers, spacers, reporters (reporter elements, barcodes), and arresting constructs.

Conjugating moieties in a cyclic loop modification is formed by the conjugation of the cyclic loop to one or more nucleotides or the conjugation of additional modifications to the cyclic loop. A reactive groups at each end of the spacer moiety reacts with the reactive groups on the bifunctional nucleotide to form the conjugating moieties. In some embodiments, one or more arresting constructs may be attached to the cyclic loop through the conjugating moiety also. Arresting constructs are moieties configured to slow the translocation of the polynucleotide so one or more reporter elements could have a longer dwell time within the nanopore read head in the presence of a driving voltage, permitting identification of the reporter, thus corresponding base. Spacers (SP) distance successive arresting constructs to allow for sufficient decay of an applied pulse voltage before the next arresting construct. Spacers may also serve to elongate any polynucleotide once particular backbone elements are cleaved. Therefore, a cyclic loop is comprised of any number of sub-elements which may serve to affect and attenuate sequencing. In some embodiments, the strength of the background electric field, the type of nanopore, and the properties of a elongated polynucleotide affect translocation speed, efficiency, and accuracy.

Examples of the cleavable cyclic loop nucleotides include:

(I)

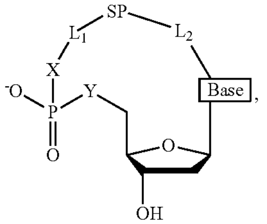

(II)

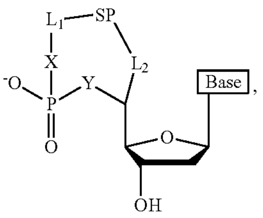

(III)

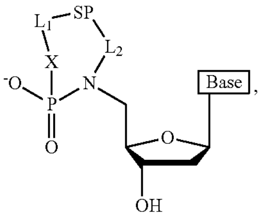

(IV)

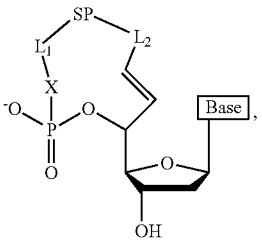

(V)

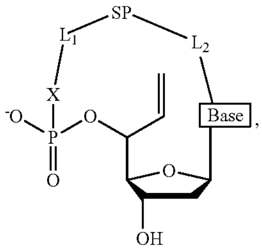

and (XII)

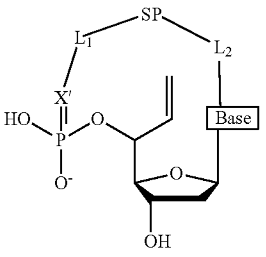

wherein X is —O—, —$CH_2$—, —NH—,

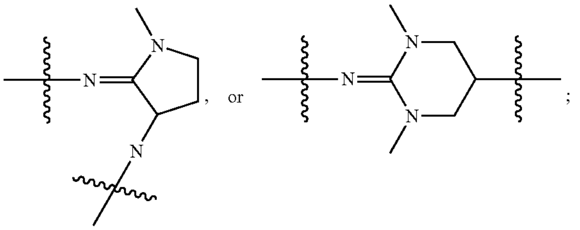

X' is =N—$SO_2$—, =NH—CO—, or

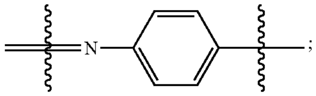

Y is —O—, —S—, —Se—, or —NH—; $L_1$ is a first linking group; $L_2$ is a second linking group; SP is a spacer; and Base is selected from the group consisting of adenine, cytosine, guanine, thymine, and uracil.

Further examples of the cleavable cyclic loop nucleotide compound that may be included in the nanopore sequencing system or the kit for nanopore sequencing are:

(Ia)

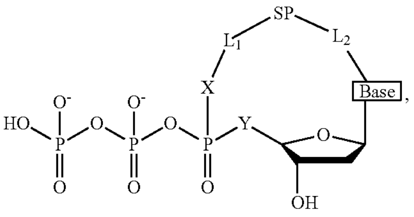

(IIa)

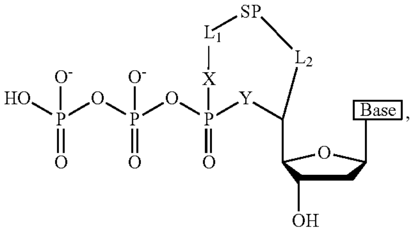

(IIIa)

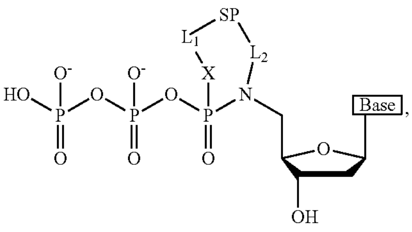

-continued (IVa)

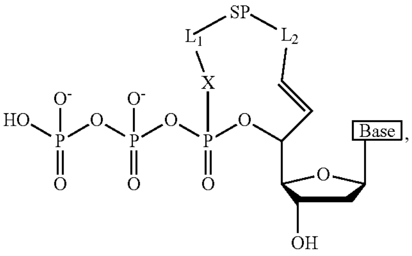

(Va)

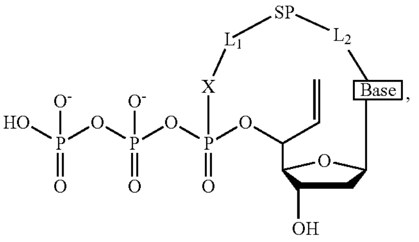

and (XIIa)

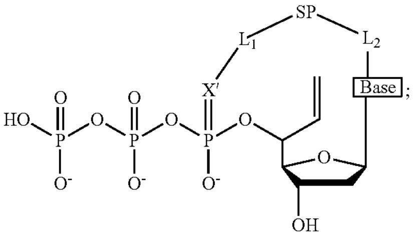

wherein X is —O—, —$CH_2$—, —NH—,

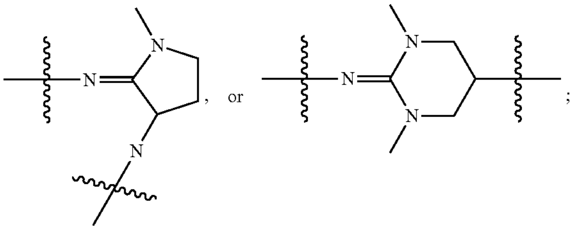

X' is =N—$SO_2$—, =NH—CO—, or

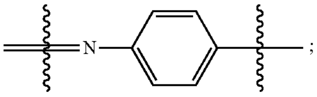 [SMILES: *c1ccc(N=*)cc1]

Y is —O—, —S—, —Se—, or —NH—; $L_1$ is a first linking group; $L_2$ is a second linking group; SP is a spacer; and Base is selected from the group consisting of adenine, cytosine, guanine, thymine, and uracil.

In some embodiments, each of the first linking group $L_1$ and the second linking group $L_2$ independently comprises a conjugating moiety selected from the group consisting of amine-NHS ester, amine-imidoester, amine-pentafluorophenyl ester, amine-hydroxymethyl phosphine, carboxyl-carbodiimide, thiol-maleimide, thiol-haloacetyl, thiol-pyridyl disulfide, thiol-thiosulfonate, thiol-vinyl sulfone, aldehyde-hydrazide, aldehyde-alkoxyamine, hydroxy-isocyanate, azide-alkyne, azide-phosphine, transcyclooctene-tetrazine, norbornene-tetrazine, azide-cyclooctyne, and azide-norbornene. $L_1$ and $L_2$ may or may not be the same.

In some embodiments, each of the first linking group $L_1$ and the second linking group $L_2$ may independently further comprises a linker. A first linker may be present between the conjugating moiety and X (alpha phosphate), and a second linker may be present between the conjugating moiety and SP. In some embodiments, the linker may be selected from the group consisting of hydrophilic polymers (polyethylene glycol, polyvinyl alcohol, polyacrylamide, polyvinylpyrrolidone, polystyrenesulfonate, polyethyleneimine), hydrophobic polymers (polylactic acid, polymethylmethacrylate, polystyrene), oligonucleotides, peptides, polypeptides, aliphatic chains (C5 to C50) and combinations thereof. In some embodiments, the first and the second linkers may independently comprise peptides, polypeptides, alkyl chains, polyethylene glycol, or combinations thereof. In some embodiments, one or more linkers may be absent.

In some embodiments, SP comprises one or more of the following moieties: (1) simple aliphatic chains, such as alkyl chains having 5 to 50 carbons, and substituted aliphatic chains (the substituent may include halo such as chloro, bromo or fluoro, alkyl such as methyl, ethyl or propyl, or aromatic groups such as phenyl or pyridyl), (2) oligonucleotides, modified oligonucleotides or polyphosphates having 1 to 100 repeating units, (3) polypeptides having 1 to 100 repeating units, (4) hydrophilic polymers having 1 to 100 repeating units, examples include polyethyleneglycol, polyvinyl alcohol, polyacrylamide, polyvinylpyrrolidone, polystyrenesulfonate, and polyethyleneimine, and (5) hydrophobic polymers having 1 to 100 repeating units, examples include polylactic acid, polymethylmethacrylate, and polystyrene. In some embodiments, the alkyl chains may be substituted or unsubstituted. In some embodiment, the number of repeating units (monomers) in SP may range from, for example 1-5, 6-10, 11-15, 16-20, 20-25, 26-50, or 50-100, or a combination of any of the foregoing ranges. In some embodiments, the total number of repeating units in SP may be 5-100, 10-100, 10-80, 10-70, 5-60 or 5-50.

The number of the repeating units and the length of the spacer SP may depend on the following factors: (1) the choice of repeating units/monomers—a monomer that is shorter/smaller would likely require more repeats to make up a similar length as compared to a longer monomer; (2) the steric bulk of the spacer—a larger spacer monomer would likely result in steric clash with the nanopore readhead and consequently, a slower translocation speed as compared to a less bulky monomer; (3) the interactions of the spacer with the nanopore—a spacer monomer that is capable of forming stronger interactions (e.g., electrostatic interactions, H-bonding) with nanopore residues is likely to experience slower translocation speed as compared to a monomer that forms weaker interactions (e.g., non-polar interactions); (4) the charge of the selected modifications—a loop with higher net negative charge would experience a higher translocation rate (compared to a lower net negative charged loop) in the presence of an applied voltage.

In some embodiments, phosphoramidite analogs can be assembled into a polymer (polyphosphate) using an oligonucleotide synthesis process, for example, phosphoramidite method. Examples of polyphosphates may include:

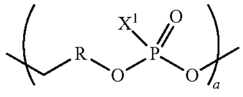
,
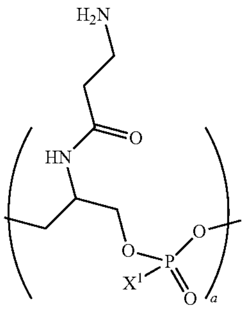
,
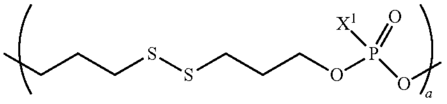
,
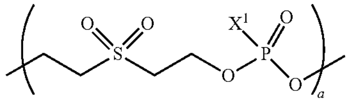
,
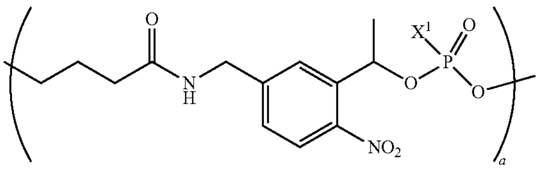
,
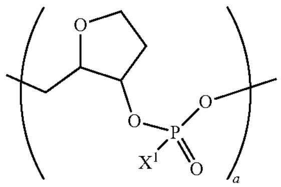
,
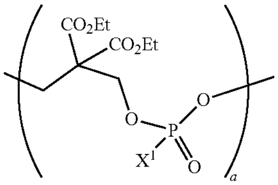
,
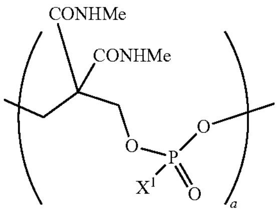
, -continued
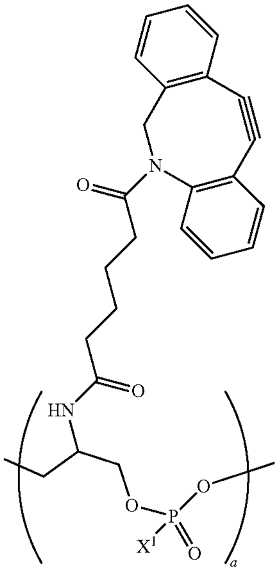
,
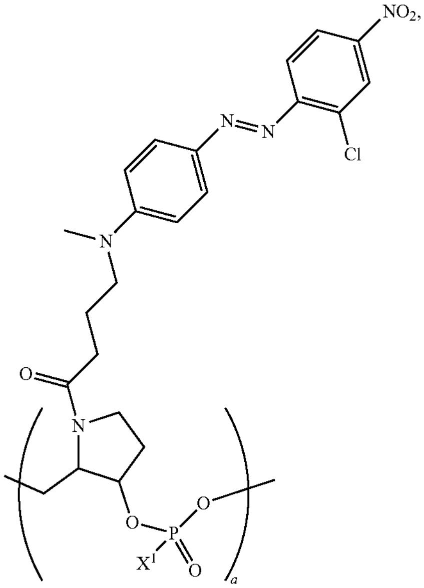
,
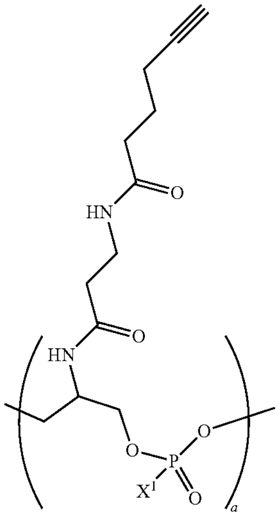
,
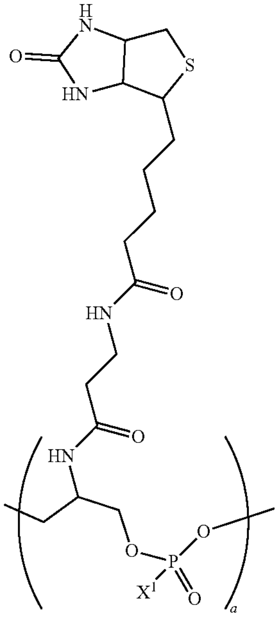
,
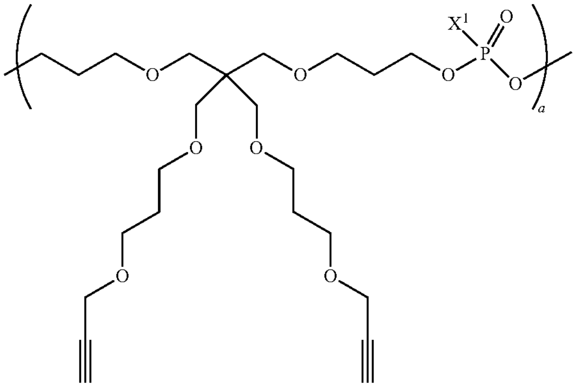
,
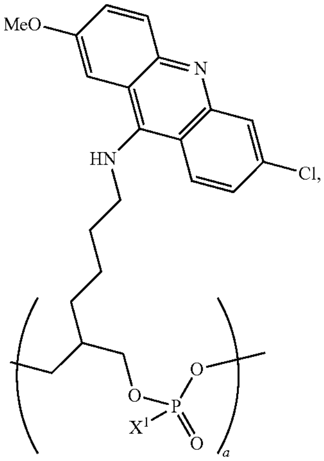
,
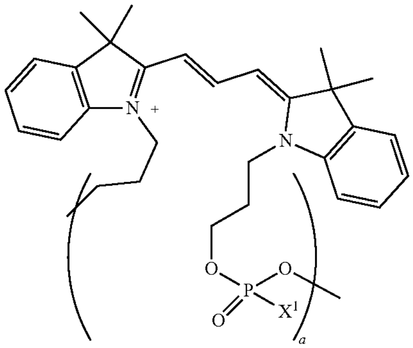
, -continued
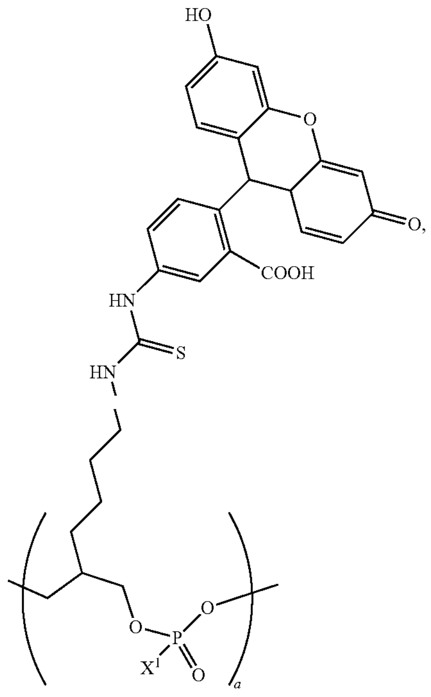
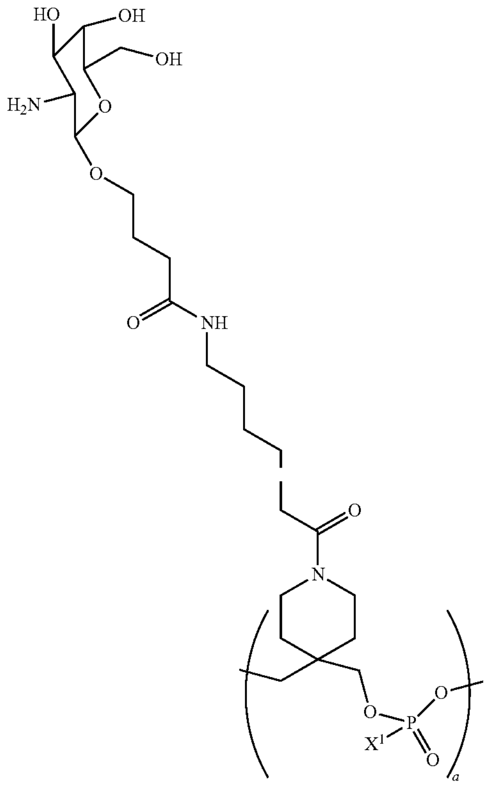
,
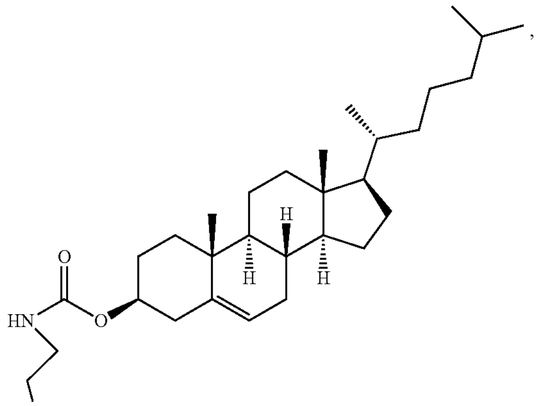
,
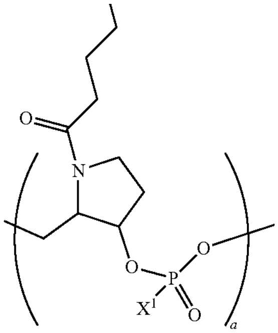

-continued
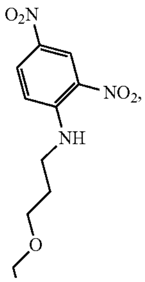
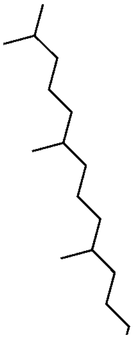
,
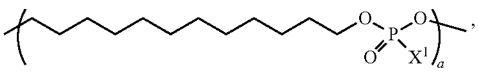
,
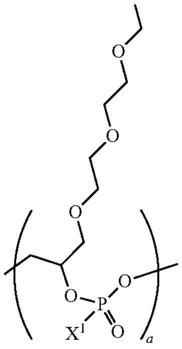
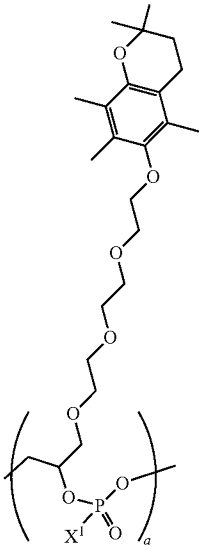
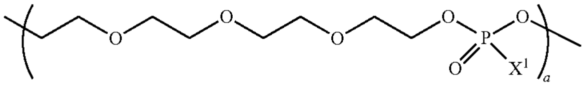
,
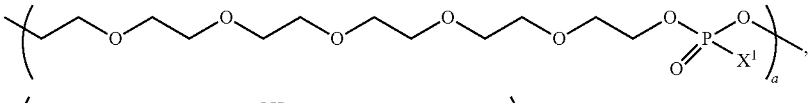
,
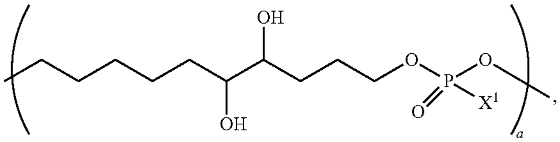
, and
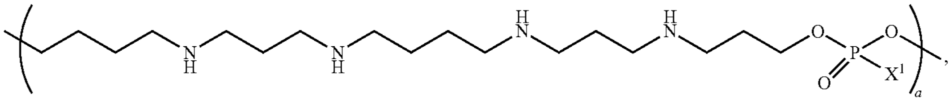
, wherein $X^1$=O$^-$, OMe, or S$^-$, and a is 1-100. In some embodiments, a is 1-5, 6-10, 11-15, 16-20, 20-25, 26-50, or 50-100, or a combination of any of the foregoing ranges.

In some embodiments, polypeptides may be homopolypeptides or heteropolypeptides.

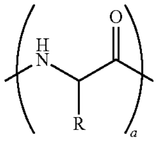

Homopolypeptide

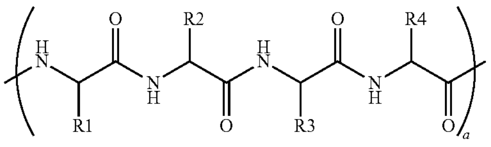

heteropolypeptide wherein and a is 1-100. In some embodiments, a is 1-5, 6-10, 11-15, 16-20, 20-25, 26-50, or 50-100, or a combination of any of the foregoing ranges. Polypeptides can comprise both natural and unnatural amino acid residues, including non-exhaustive examples of residues selected from the following:

L/D-Natural Amino Acids

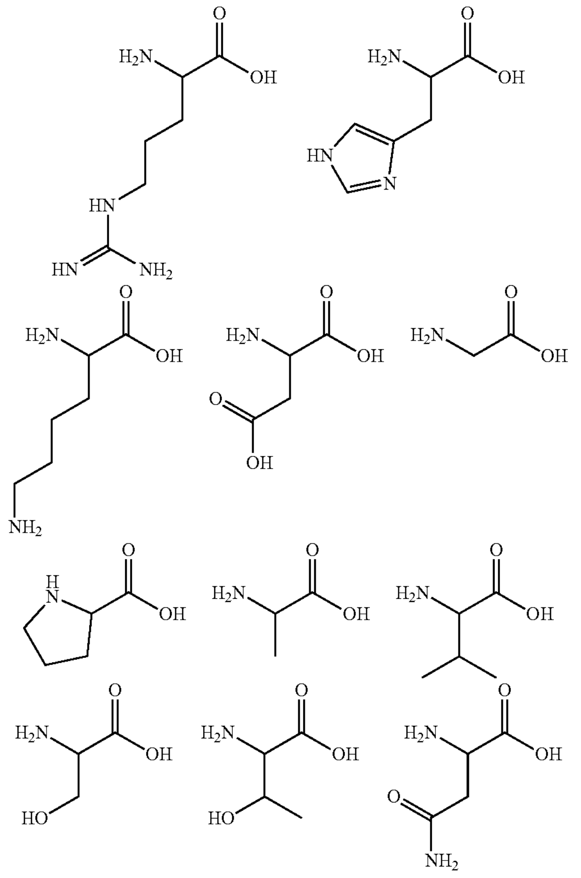

-continued

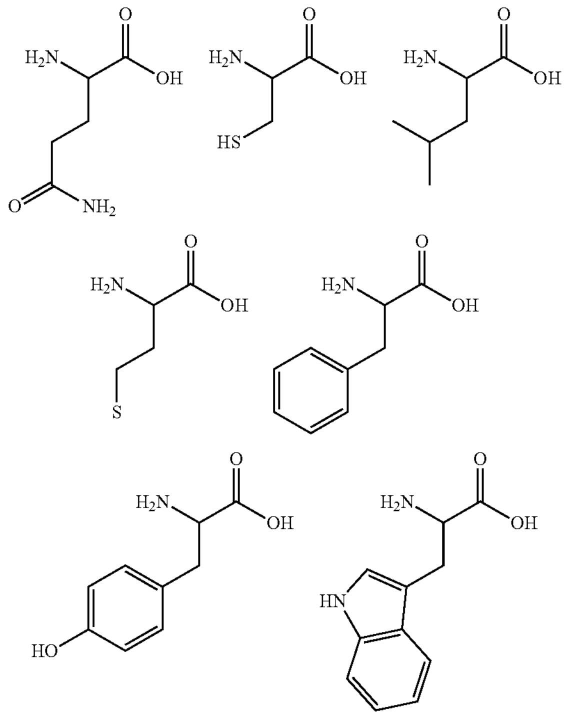

L/D-Unnatural Amino Acids

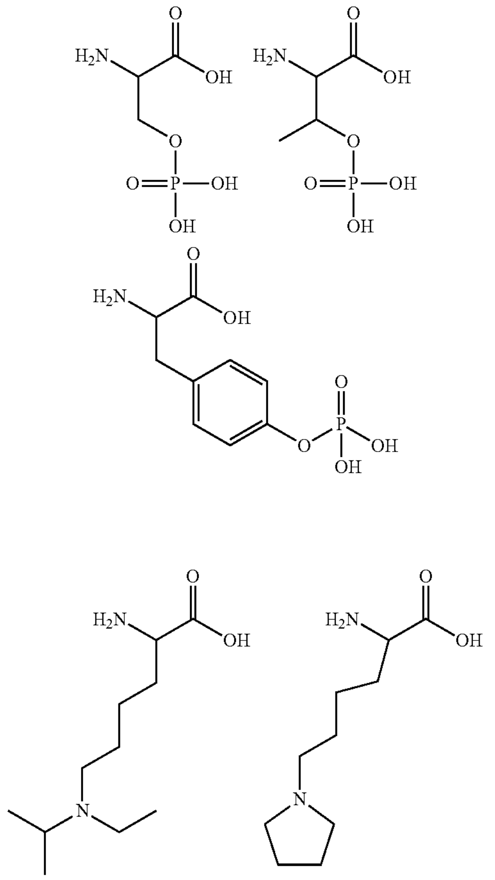

-continued
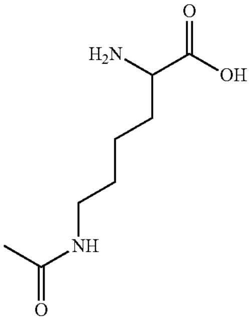
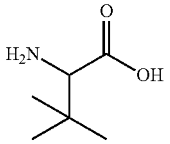
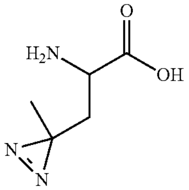
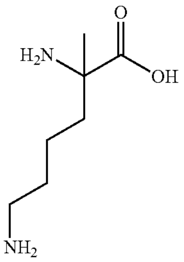
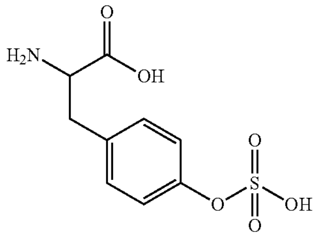
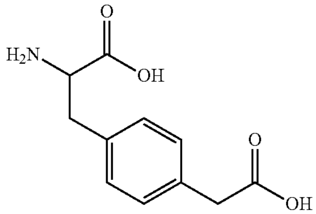
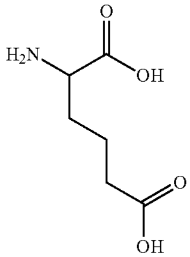
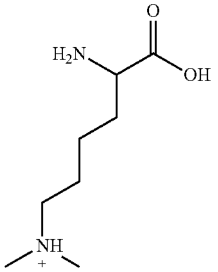
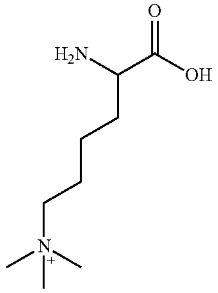
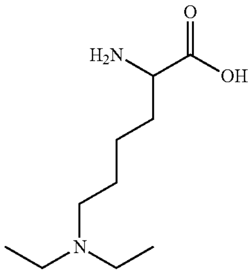
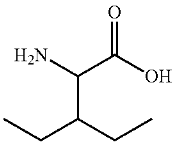
-continued
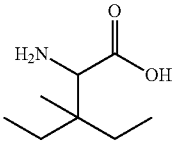
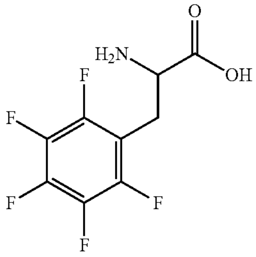
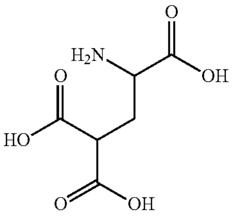
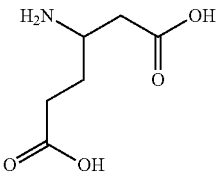
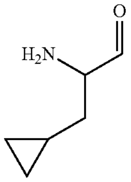
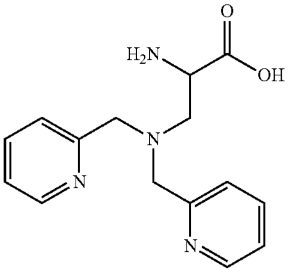
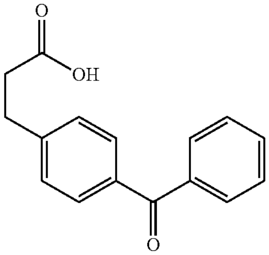
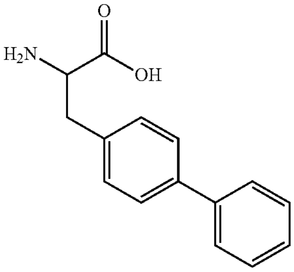
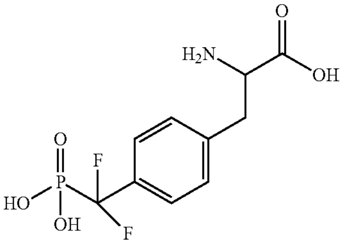
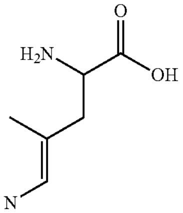
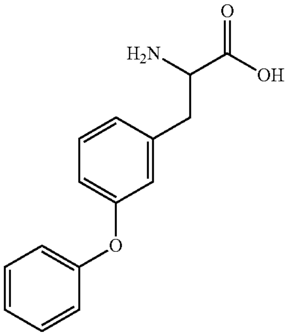
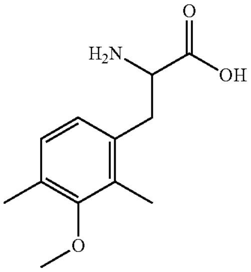

-continued
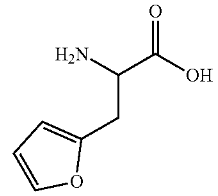
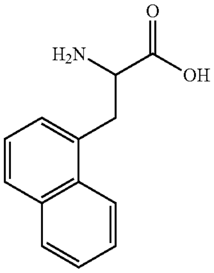
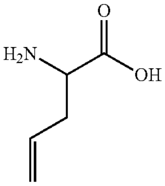
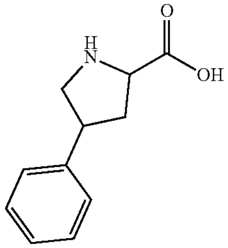
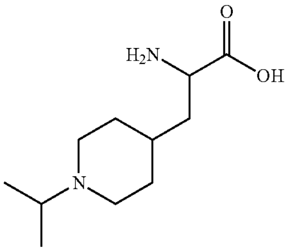
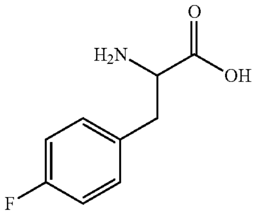
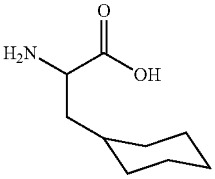
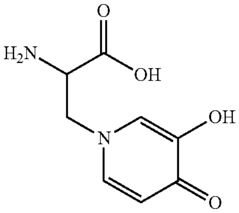
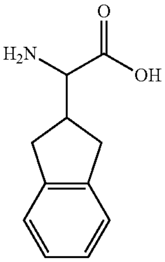
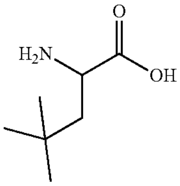
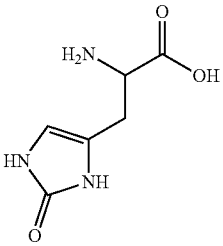
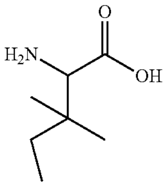
-continued
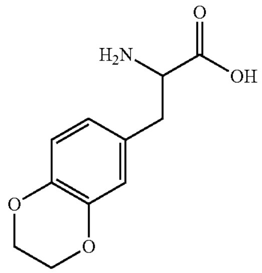
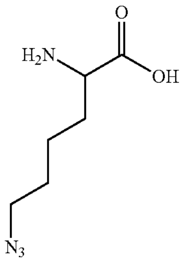
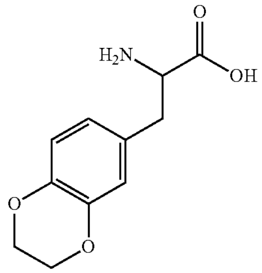
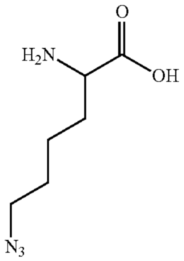
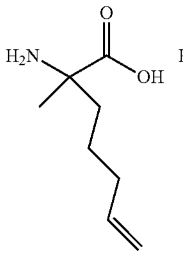
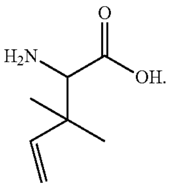
Non-Amino Acids
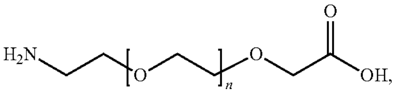
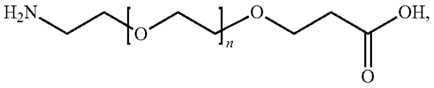
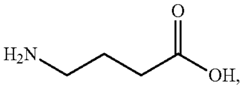
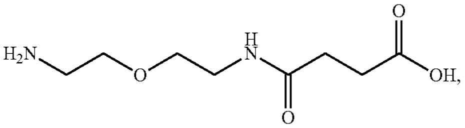
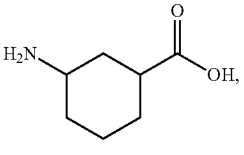
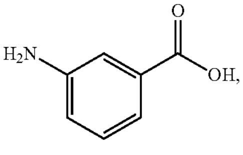
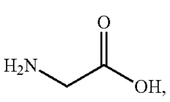
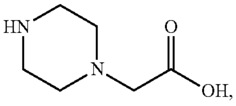

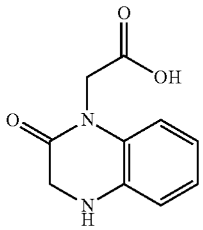
,
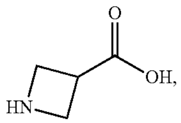
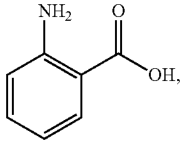
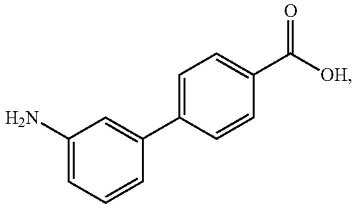
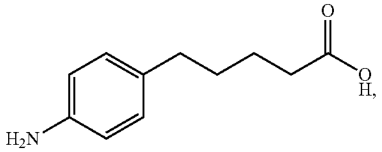
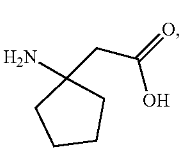
and
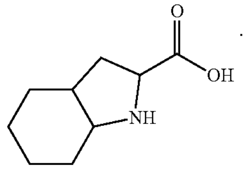
.
In some embodiments, modified oligonucleotides in SP may comprise modified nucleotides and/or modified nucleobases. In some embodiments, examples of modified nucleotides and modified nucleobases include, but are not limited to:
Modified Nucleotides
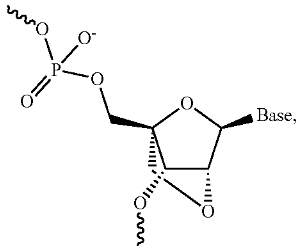
LNA
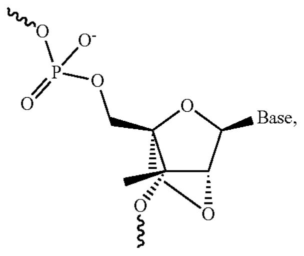
Constraint ethyl
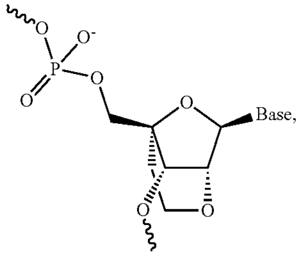
Ethylene bridged nucleic acid
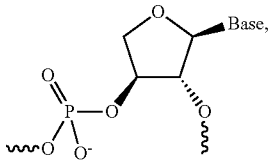
TNA
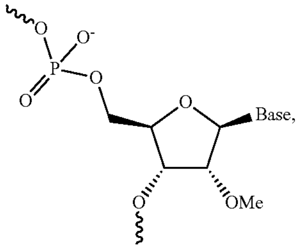
2′-OMe
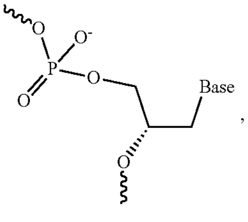
GNA
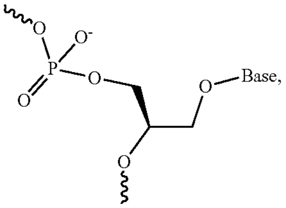
FNA
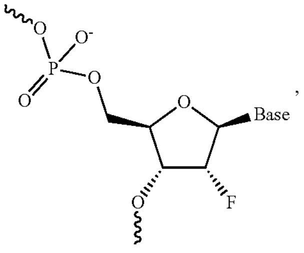
2′-fluoro
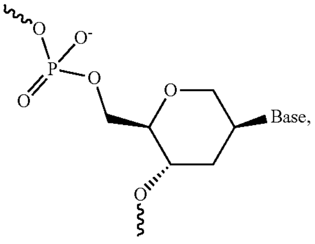
HNA -continued
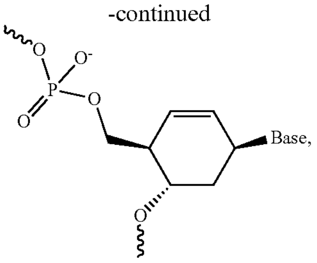
CeNA
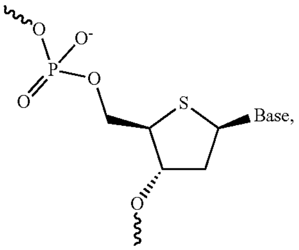
4′-thio
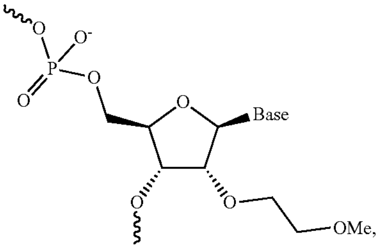
2′-MOE
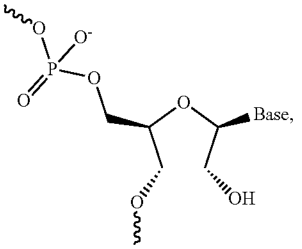
Unlock
and
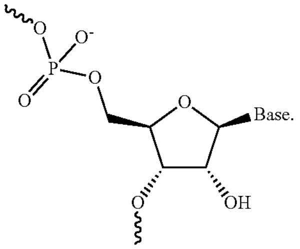
RNA
Modified Nucleobases
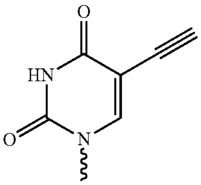
,
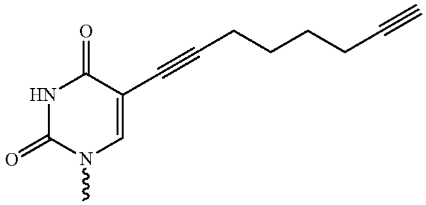
,
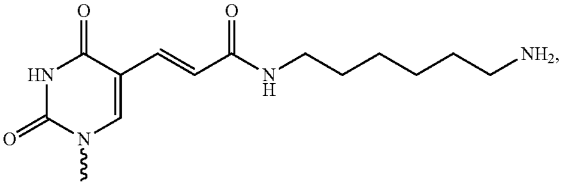
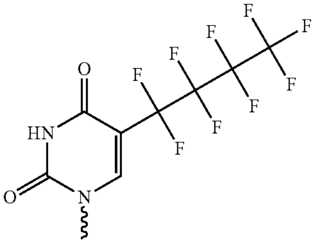
,
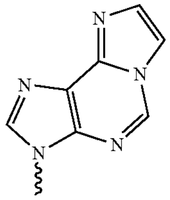
,
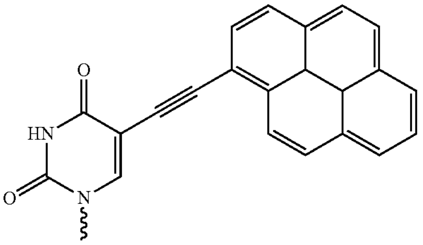
, -continued
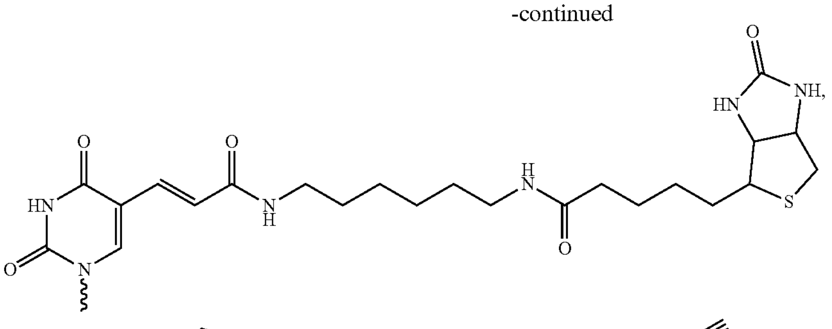
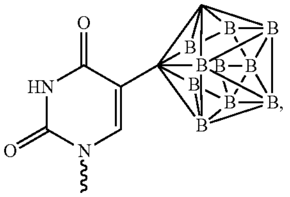
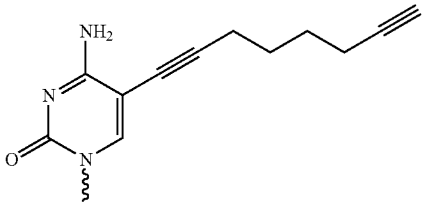
,
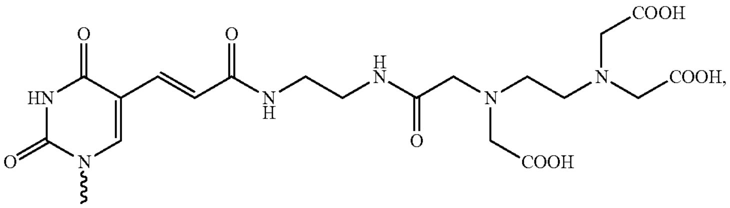
and
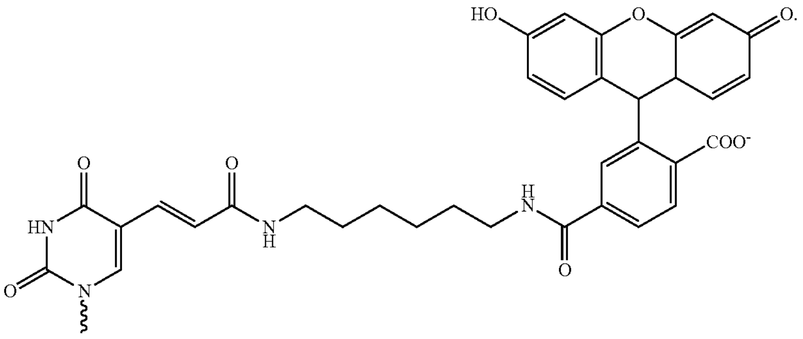
In some embodiments, polyamide compounds may be homopolyamide or heteropolyamides.
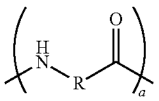
Homopolyamide
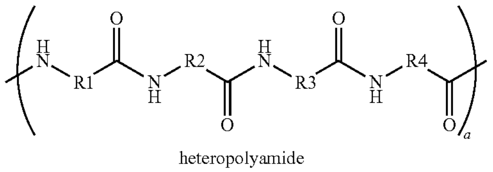
heteropolyamide
Polyamide compounds can include one or more of the following residues:
Polyamides
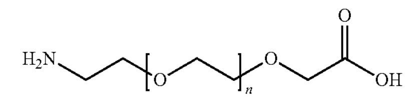
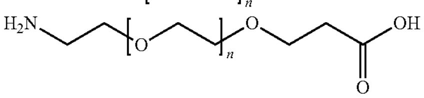
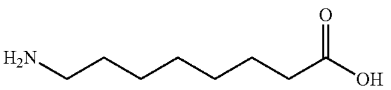
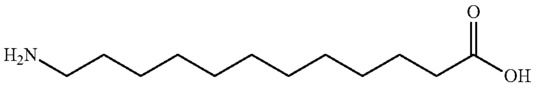

-continued
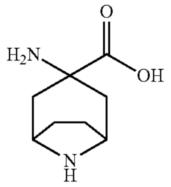
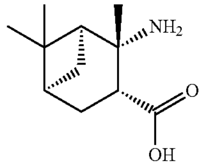
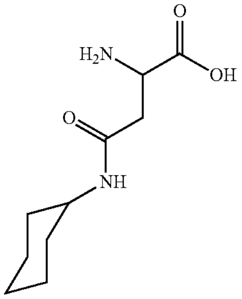
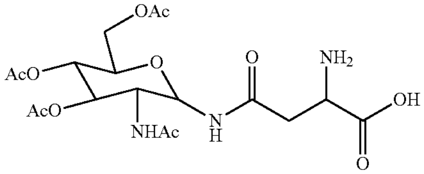
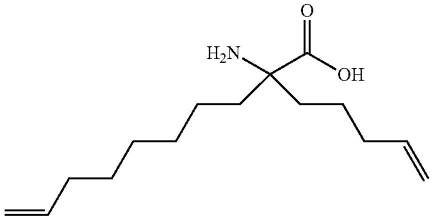
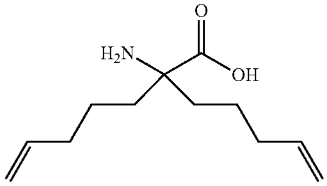
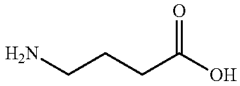
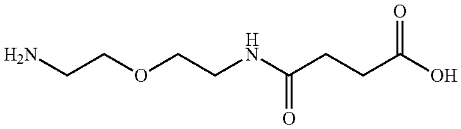
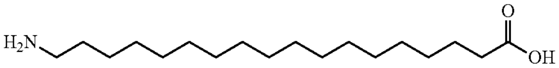
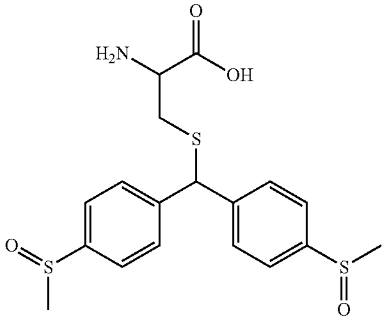
-continued
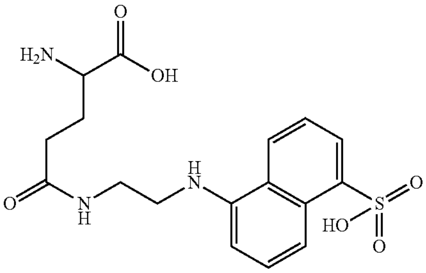
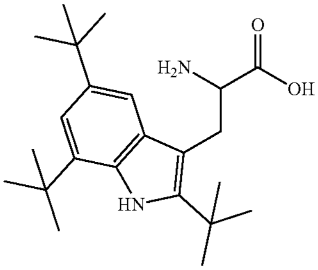
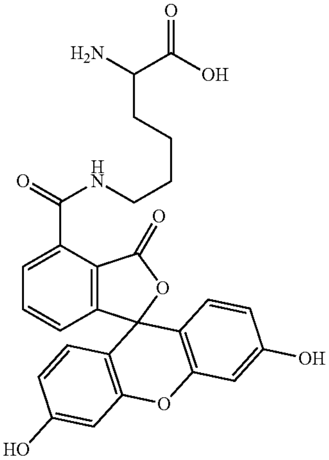
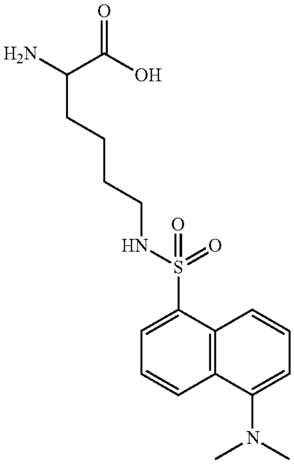
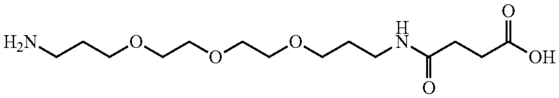
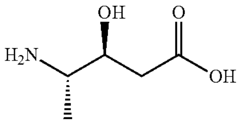

-continued

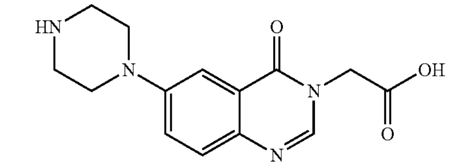

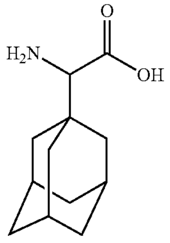

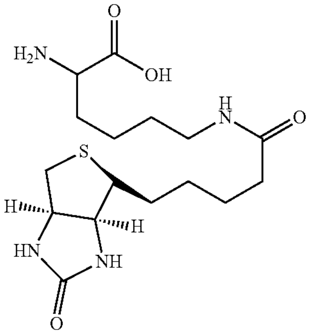

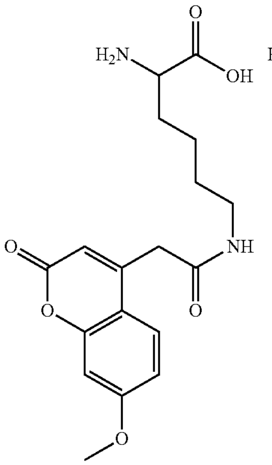

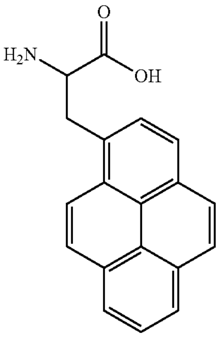

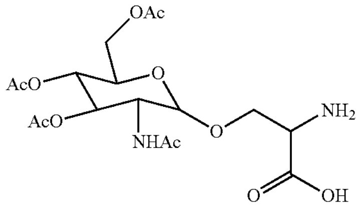

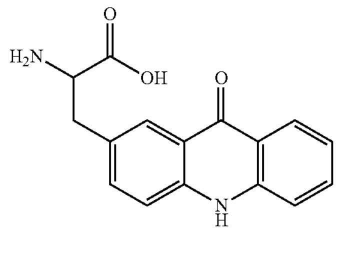

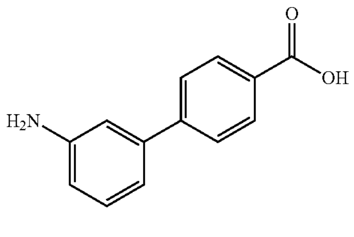

-continued

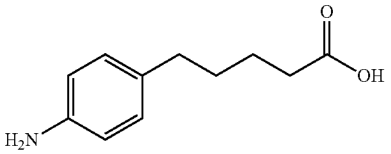 [SMILES: Nc1ccc(CCCCC(=O)O)cc1]

In some embodiments, the spacer may comprise a reporter moiety that correspond to the specific nucleobase. In other embodiments, the spacer may not include a reporter moiety.

In some embodiments, the cleavable cyclic loop nucleotide may further comprise an arresting construct configured to interact with the nanopore. The arresting construct may comprise a linear, a branched or a cyclic polymer, wherein the polymer is selected from a synthetic hydrophobic polymer, a synthetic hydrophilic polymer, an oligonucleotide/polynucleotide, a peptide/polypeptide, and combinations thereof. In some embodiments, the arresting construct may be a side branch attached to the cleavable cyclic loop nucleotide. In some embodiments, the arresting construct may be a side branch attached to the nucleobase of the nucleotide/nucleotide analog. In some embodiments, the arresting construct may be a side branch attached to the cyclic loop—on either the spacer SP or the linking group $L_1$ or $L_2$. In some embodiments, the arresting construct may be integrated into the cyclic loop structure or is a part of the cyclic loop structure. In some embodiments, the arresting construct may be adjacent to the reporter in the cyclic loop structure.

When the arresting construct is attached to the spacer SP portion of the cyclic loop, the arresting construct may be attached to any part of the spacer, for example, in the middle of the spacer chain, on either ends of the spacer chain, or anywhere in between. In embodiments where the arresting construct is attached to the middle of the cyclic loop structure, the cyclic loop may be a symmetrical loop. In embodiments where the arresting construct is attached to other part of the cyclic loop structure, the cyclic loop may be an asymmetrical loop.

The arresting construct may be attached to the cleavable cyclic loop nucleotide through a third linking group $L_3$. In some embodiments, $L_3$ may be a moiety selected from the group consisting of hydrophilic polymers (polyethyleneglycol, polyvinyl alcohol, polyacrylamide, polyvinylpyrrolidone, polystyrenesulfonate, polyethyleneimine), hydrophobic polymers (polylactic acid, polymethylmethacrylate, polystyrene), oligonucleotides, peptides, polypeptides, aliphatic chains (C5 to C50), aromatic groups (phenyl or pyridyl) and combinations thereof.

Figure 93:
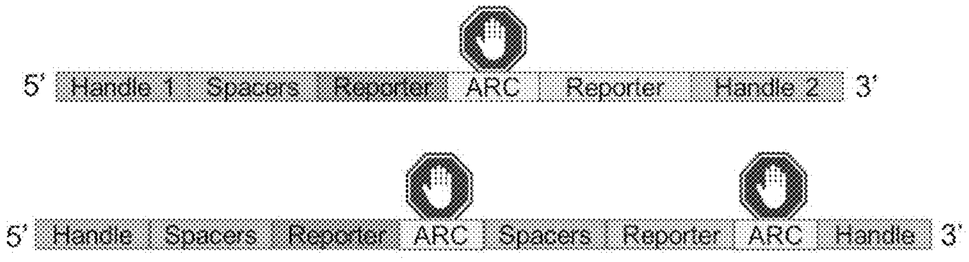
FIG. 93 illustrates non-symmetric cyclic loops.
Figure 94:
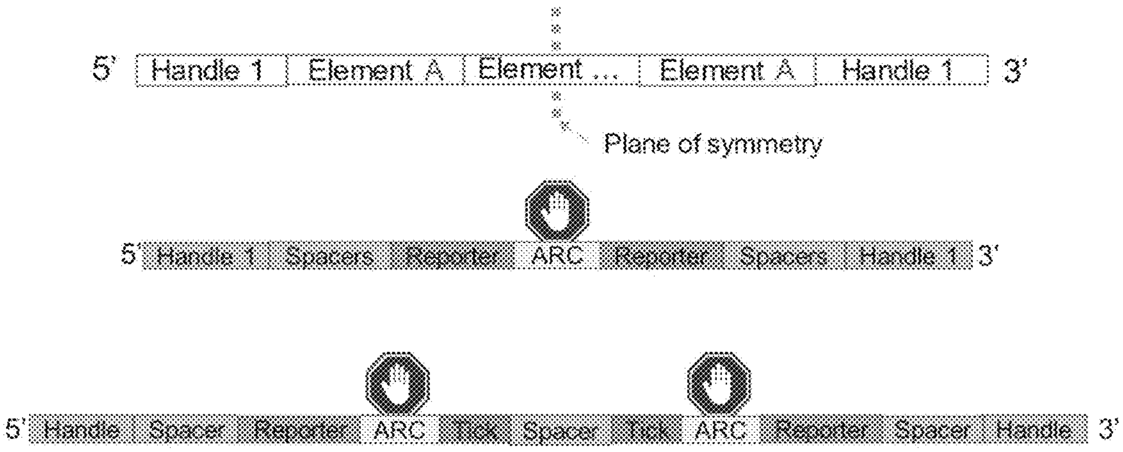
FIG. 94 illustrates symmetric cyclic loops.

The cyclic loop comprises one or more sub-elements, including linkers, conjugating moieties, spacers, arresting constructs, and reporters. The arrangement of sub-elements for a cyclic loop may be asymmetric (i.e. Asymmetric Cyclic Loops—ACLs) or symmetric with respect to the order of sub-elements (i.e. Symmetric Cyclic Loops—SCLs). FIG. 93 illustrates non-limiting examples of ACLs, each cyclic loop comprising any number of conjugating moieties, spacers, reporters, and arresting constructs (ARCs). Asymmetric cyclic loops are polymeric loops in which the sequence of individual sub-elements, or the entire composition are not arranged in a symmetrical fashion. When oriented inside the readhead of a nanopore, an ACL may therefore affect the physiochemical properties, dwell time, holding force, and necessary voltage for translocation. In comparison, symmetric cyclic loops comprise cyclic loops in which subunits are arranged symmetrically. FIG. 94 illustrates non-limiting examples of SCLs, each SCL comprising any number of conjugating moieties (handle), spacers, reporters, and arresting constructs (ARCs). ACL and SCL structures may feature any number of the sub-elements described herein, and may omit specific sub-elements without limitation.

Model Alpha Phosphate Substituted Nucleotides: Imino-P and Other Substitutions

In some embodiments, constituent groups within a nucleotide may possess one or more substitutions compared to naturally occurring nucleotides. In some embodiments, one or more phosphate groups comprising a nucleotide are substituted. In some embodiments, one or more atoms within a nucleotide structure may be substituted with a heteroatom, heteratom isotope, or homoatom isotopes thereof. In some embodiments, provided herein is a stable sulfonyl imino-P substitution ("imino-P") for alpha phosphate substituted nucleotides. Bifunctional nucleotide including imino-P substitution at the alpha phosphate is shown above.

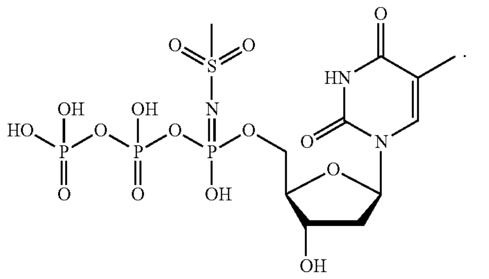 [SMILES: Cc1cn([C@H]2C[C@@H](O)[C@@H](COP(O)(=NS(C)(=O)=O)OP(=O)(O)OP(=O)(O)O)O2)c(=O)[nH]c1=O]

Other useful nucleotides with substitutions at the alpha phosphate include:

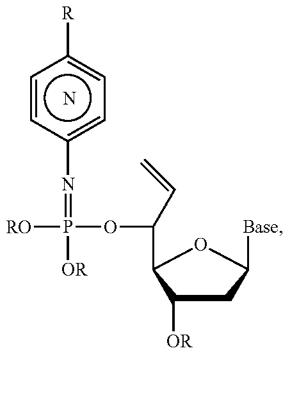

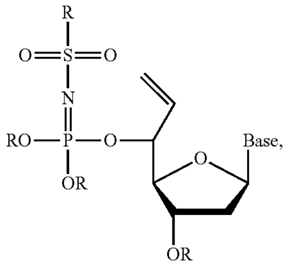

-continued

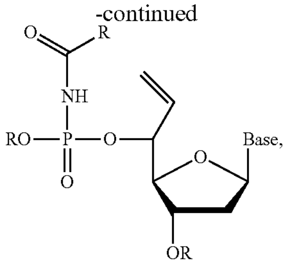

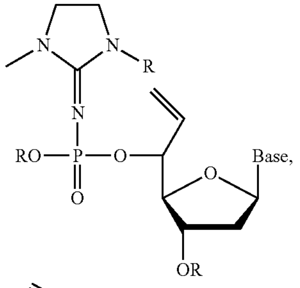

and

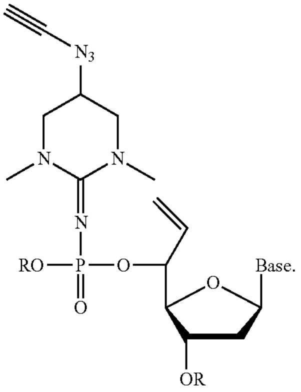

In some embodiments, nucleotides described herein are shelf stable at 25° C. for 2 days. In some embodiments, nucleotides described herein are shelf stable at −25° C. for 2 days. In some embodiments, nucleotides described herein are shelf stable at between −25 to 25° C. for 2 days. In some embodiments, nucleotides described herein are shelf stable at between −25 to 25° C. for 2 days. In some embodiments, nucleotides described herein are shelf stable at between −50 to 50° C. for 2 days. In some embodiments, nucleotides described herein are shelf stable at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50° C. for 2 days. In some embodiments, nucleotides described herein are shelf stable at 25° C. for between 0 and 2 days. In some embodiments, nucleotides described herein are shelf stable at −25° C. for between 0 and 2 days. In some embodiments, nucleotides described herein are shelf stable at between −25 to 25° C. for between 0 and 2 days. In some embodiments, nucleotides described herein are shelf stable at between −25 to 25° C. for between 0 and 2 days. In some embodiments, nucleotides described herein are shelf stable at between −50 to 50° C. for between 0 and 2 days. In some embodiments, nucleotides described herein are shelf stable at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50° C. for between 0 and 2 days. In some embodiments, nucleotides described herein are shelf stable at 25° C. In some embodiments, nucleotides described herein are shelf stable at −25° C. In some embodiments, nucleotides described herein are shelf stable at between −25 to 25° C. In some embodiments, nucleotides described herein are shelf stable at between −25 to 25° C. In some embodiments, nucleotides described herein are shelf stable at between −50 to 50° C. In some embodiments, nucleotides described herein are shelf stable at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50° C.

Cleavable Sites

Cleavable cyclic loop nucleotides comprise certain cleavable sites in bonds which can be broken under controlled conditions such as, for example, conditions for selective cleavage of a phosphorothiolate bond, a photocleavable bond, a phosphoramidite bond, a phosphoramide bond, a 3'-O—B-D-ribofuranosyl-2' bond, a thioether bond, a selenoether bond, a sulfoxide bond, a disulfide bond, deoxyribosyl-5'-3' phosphodiester bond, or a ribosyl-5'-3' phosphodiester bond, as well as other cleavable bonds known in the art. A selectively cleavable bond can be an intra-tether bond or between or within a probe or a nucleobase residue or can be the bond formed by hybridization between a probe and a template strand. Selectively cleavable bonds are not limited to covalent bonds, and can be non-covalent bonds or associations, such as those based on hydrogen bonds, hydrophobic bonds, ionic bonds, pi-bond ring stacking interactions, Van der Waals interactions, and the like.

For example, in some embodiments, the cleavable sites include the P—Y bond/linkage in cleavable cyclic loop nucleotide structures (I) and (II), the P—N bond/linkage in structure (III), and the O—C (5'-C of the ribose sugar) bond/linkage in structures (IV) and (V) and (XII). These bonds are shown as bolded bonds below and can be cleaved under conditions known in the art.

(I)

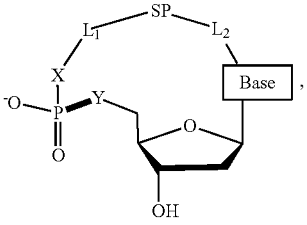

, (II)

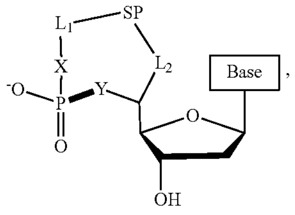

, (III)

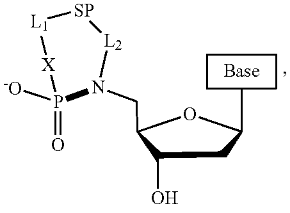

,

-continued (IV)

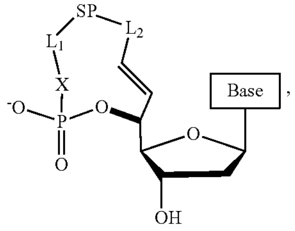

, (V)

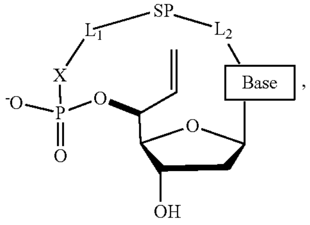

, and (XII)

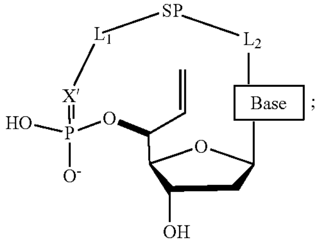

;

wherein X, X', Y, $L_1$, $L_2$, SP and Base are as defined above.

Figure 3:
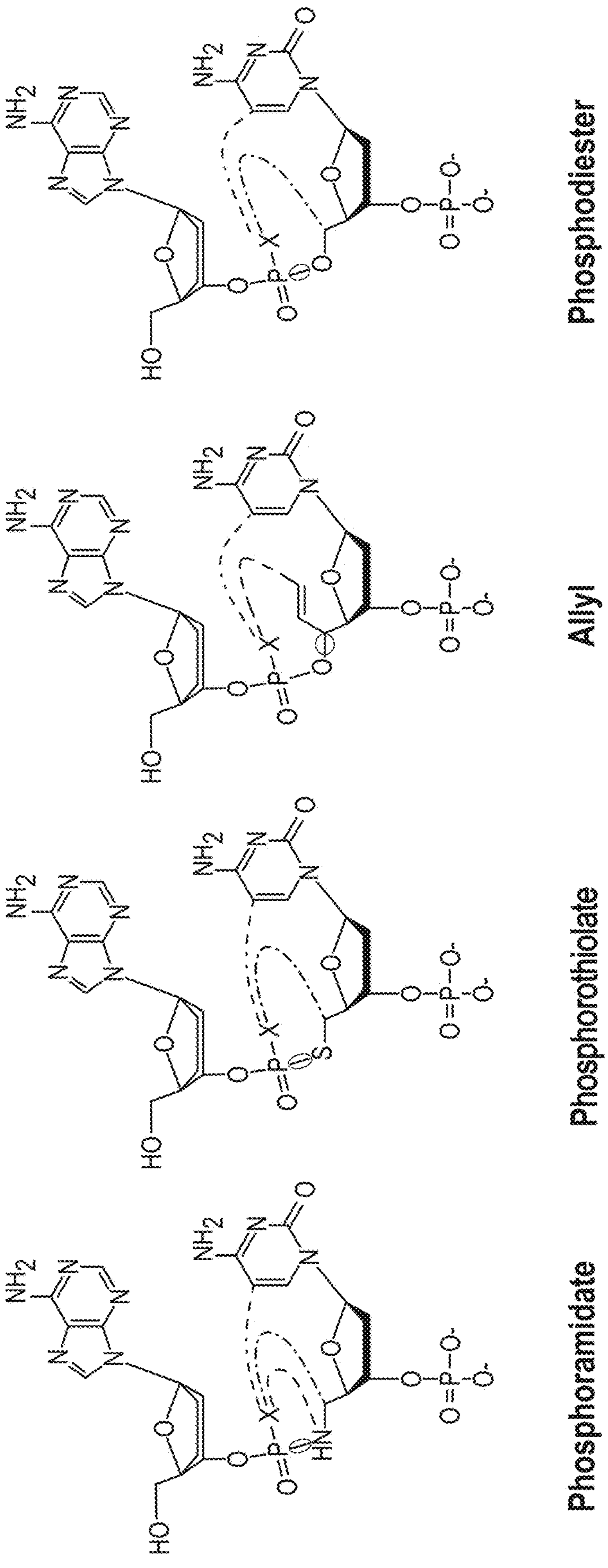
FIG. 3 schematically illustrates examples of cleavable linkages.

FIG. 3 schematically illustrates examples of cleavable linkages. Dashed arcs denote possible linker construct that are conjugated to 2 sections/positions of the same nucleotide. As disclosed herein, there are several attachment points on a nucleotide to which the linker construct (e.g., cyclic loop) may be conjugated to, and the cleavage site has to be situated within the two attachment points.

Figure 4:
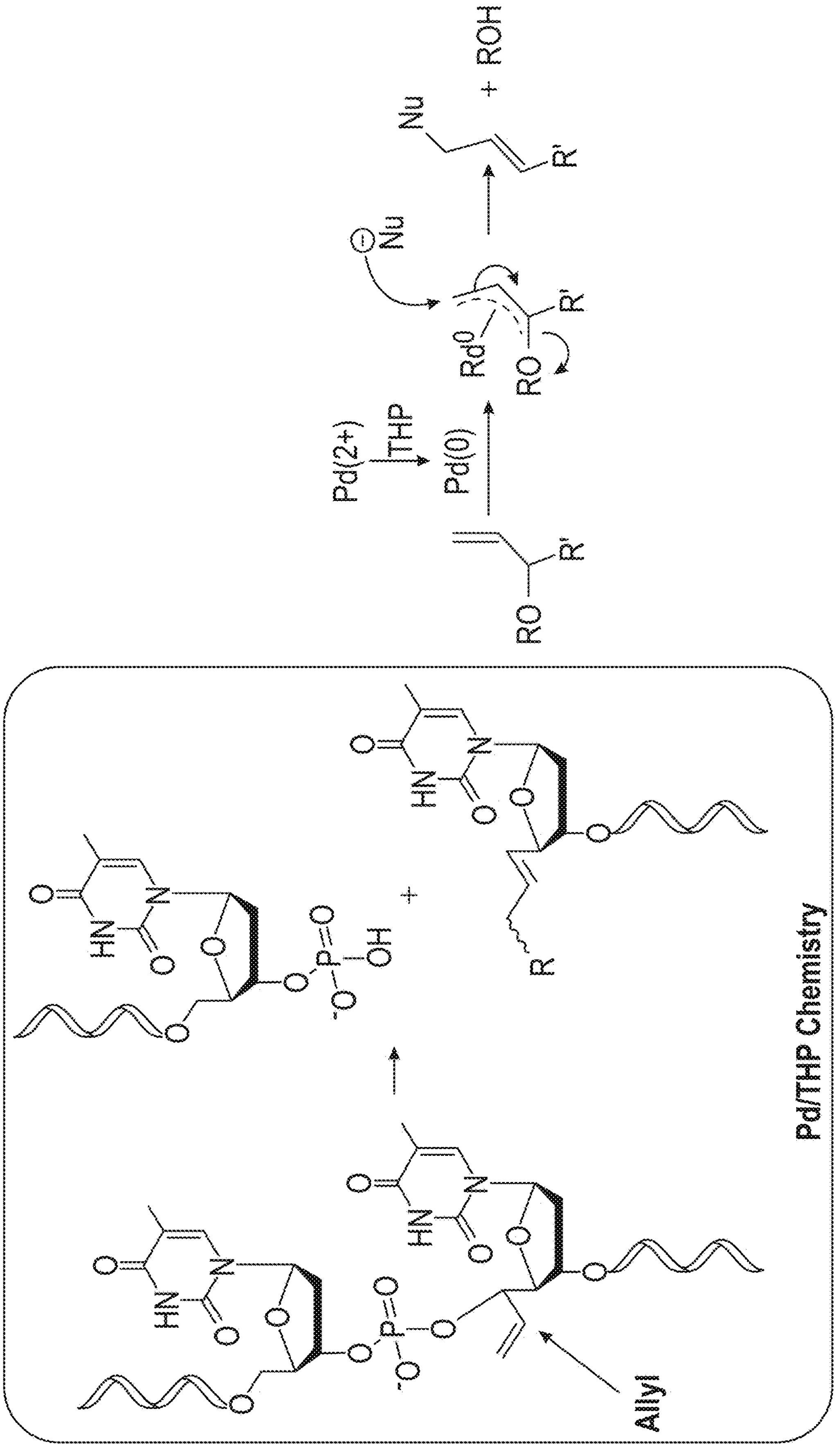
FIG. 4 schematically illustrates an example of using the allyl cleavable chemistry in the disclosed sequencing method.

There are a multitude of cleavable linkages that can be readily incorporated into the existing structure of the oligonucleotide without resulting in significant increase in the length of the DNA backbone. With reference to FIG. 3, the cleavable linkages/bonds in various nucleotides/nucleotide analogs are circled (shown as ). Below are conditions for cleaving these bonds for nucleotide/nucleotide analogs shown in FIG. 3 (from left to right):

1) Phosphoramidate—the circled bond can be cleaved under acidic conditions (e.g., 10 mM sodium citrate-HCl at pH 4.0 or 80% acetic acid).
2) Phosphorothiolate—the circled bond can be cleaved with 50 mM silver nitrate, or iodine in aqueous acetone/pyridine (1:1).
3) Allyl—the circled bond can be cleaved with Pd(0) salts. In one example, FIG. 4 schematically illustrates the allyl cleavable chemistry.
4) Phosphodiester—the circle bond can be cleaved via enzymatic cleavage (e.g., endo-, exo-nucleases or RNAse, basic conditions in the case of RNA ribose).

Method of Making Cyclic Loop Nucleotides

Cyclic loop nucleotides can be made by conjugating a spacer moiety to a bifunctional nucleotide. In some embodiments, the conjugation of the spacer moiety and the bifunctional nucleotide involves click chemistry. The Bifunctional nucleotide designs may be derived from the below:

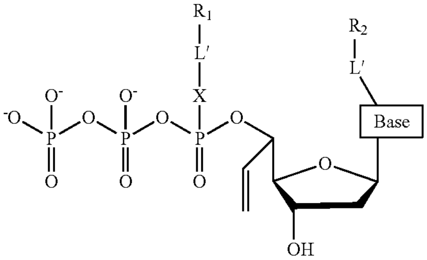
,

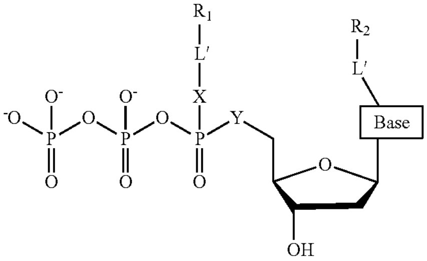
,

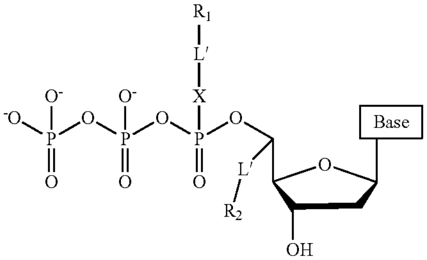
, and

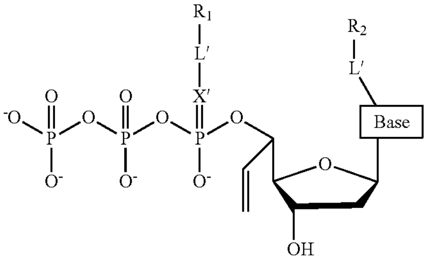
.

$R_1$ and $R_2$ are reactive groups that can utilize click chemistry to conjugate with the spacer SP. In some embodiments, $R_1$ and $R_2$ comprises click chemistry reagents. In some embodiments, $R_1$ and $R_2$ may independently be hydroxyl, thiocyanate, aldehyde, carboxyl, azide (—$N_3$), amine (—$NH_2$), alkyne, bicyclononyne (BCN), dibenzocyclooctyne (DBCO), thiol (—SH), tetrazine, trans-cyclooctyne (TCO), NHS ester, imidoester, pentofluorophenyl ester, hydroxylmethyl phosphine, carbodiimide, maleimide, haloacetyl, pyridyl disulfide, thiosulfonate, vinyl sulfone, hydrazide, alkoxyamine, isocyanate, phosphine, and norbornene. In some embodiments, $R_1$ and $R_2$ are the same. In other embodiments, $R_1$ and $R_2$ may be different.

X may be —O—, —$CH_2$—, —NH—,

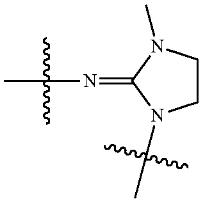
, or

-continued

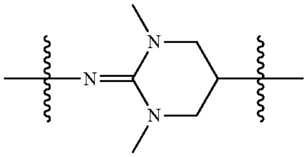
.

X' may be =N—$SO_2$—, =NH—CO—, or

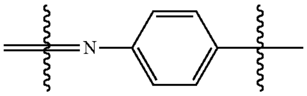
.

Y may be —O—, —S—, —NH—, or —Se—. L' is a linker. In some embodiments, the linker L' may be independently selected from the group consisting of an oligonucleotide or modified oligonucleotide or phosphoramidite analogs having 1 to 100 repeating units, polypeptide having 1 to 100 repeating units, alkyl chains having 5 to 50 carbons, hydrophilic polymers having 1 to 100 repeating units comprising polyethyleneglycol, polyvinyl alcohol, polyacrylamide, polyvinylpyrrolidone, polystyrenesulfonate, or polyethyleneimine, hydrophobic polymers having 1 to 100 repeating units comprising polylactic acid, polymethylmethacrylate, or polystyrene, and combinations thereof. In some embodiments, the linker L' may comprise a reporter encoding the associated nucleobase. In some embodiments, the linker L' may also further comprise an arrest construct configured to interact with the nanopore to slow the translocation of the polynucleotide in which it is incorporated.

Representative examples of the bifunctional nucleotides include:

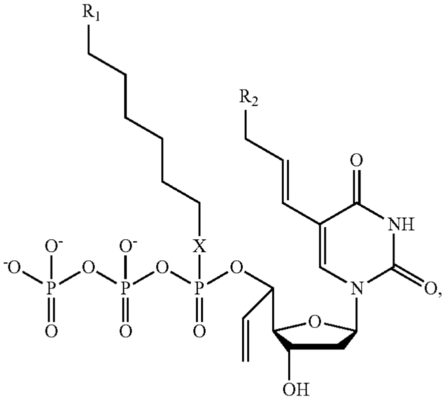
,

-continued

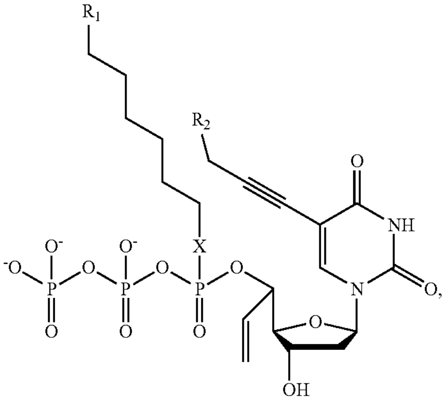

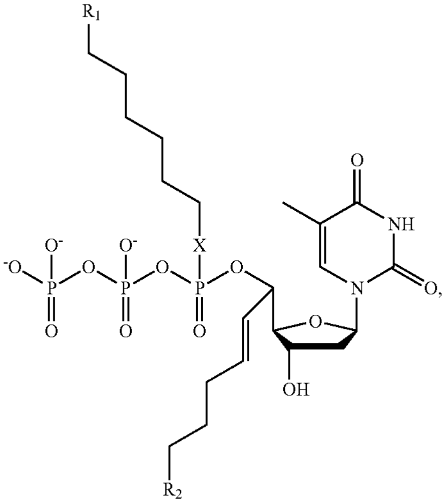

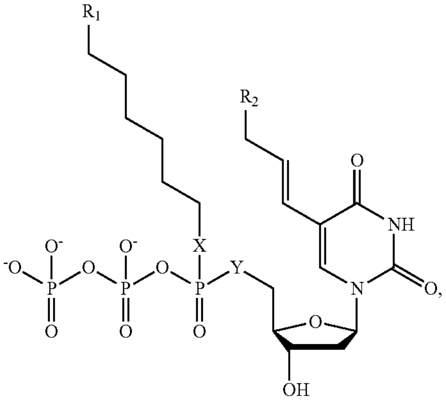

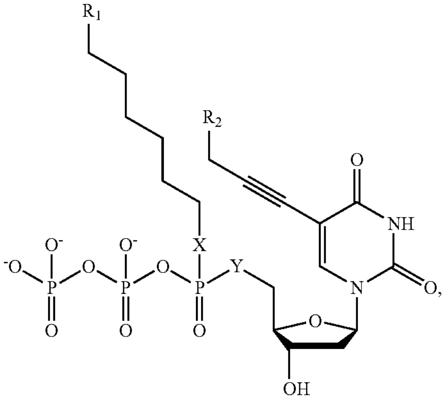

and

-continued

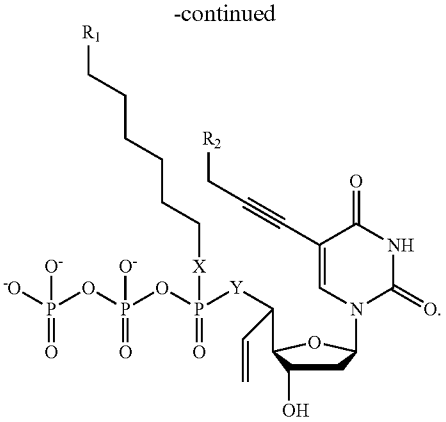

In order to conjugate with a spacer moiety to form the cyclic loop nucleotide, the spacer moiety comprises a spacer SP and reactive groups $R_1$' and $R_2$' on both ends of the spacer moiety where conjugation to the bifunctional nucleotide is desired. In some embodiments, $R_1$' and $R_2$' may be selected from the group consisting of hydroxyl, thiocyanate, aldehyde, carboxyl, azide (—$N_3$), amine (—$NH_2$), alkyne, bicyclononyne (BCN), dibenzocyclooctyne (DBCO), thiol (—SH), tetrazine, trans-cyclooctyne (TCO), N-Hydroxysuccinimide (NHS) ester, imidoester, pentofluorophenyl ester, hydroxylmethyl phosphine, carbodiimide, maleimide, haloacetyl, pyridyl disulfide, thiosulfonate, vinyl sulfone, hydrazide, alkoxyamine, isocyanate, phosphine, and norbornene. In some embodiments, $R_1$' and $R_2$' are the same. In other embodiments, $R_1$' and $R_2$' may be different.

In some embodiments, the spacer moiety may further comprise a linker L" on one or both sides of the SP, such as between SP and $R_1$' and/or between SP and $R_2$'. In some embodiments, each of the linker L" may be independently selected from the group consisting of an oligonucleotide or modified oligonucleotide or phosphoramidite analogs having 10 to 100 repeating units, polypeptide having 1 to 100 repeating units, alkyl chains having 5 to 50 carbons, hydrophilic polymers having 1 to 100 repeating units comprising polyethyleneglycol, polyvinyl alcohol, polyacrylamide, polyvinylpyrrolidone, polystyrenesulfonate, or polyethyleneimine, hydrophobic polymers having 1 to 100 repeating units comprising polylactic acid, polymethylmethacrylate, or polystyrene, and combinations thereof. SP may be any moiety described herein. In some embodiments, the spacer moiety may further comprise an arrest construct, which is designed to slow down the translocation of the polynucleotide through the nanopore.

To form a cyclic loop nucleotide, $R_1$ and $R_2$ of the bifunctional nucleotide react with $R_1$' and $R_2$' of the SP, respectively, to form conjugating moieties. In some embodiments, the conjugating moieties (e.g., $R_1$-$R_1$' and $R_2$-$R_2$') may be independently selected from a non-exhaustive list of chemistries such as: amine-NHS ester, amine-imidoester, amine-pentofluorophenyl ester, amine-hydroxymethyl phosphine, carboxyl-carbodiimide, thiol-maleimide, thiol-haloacetyl, thiol-pyridyl disulfide, thiol-thiosulfonate, thiol-vinyl sulfone, aldehyde-hydrazide, aldehyde-alkoxyamine, hydroxy-isocyanate, azide-alkyne, azide-phosphine, trans-cyclooctene-tetrazine, norbornene-tetrazine, azide-cyclooctyne, and azide-norbornene. Examples of reactive groups $R_1$/$R_2$, $R_1$'/$R_2$', and the resulting conjugating moieties formed by $R_1$-$R_1$' or $R_2$-$R_2$' are shown in the table below. As shown in this table, R and R' indicates the two groups to be joined by reaction between $R_1$ and $R_1'$ or $R_2$ and $R_2'$. One of the two groups may represent the bifunctional nucleotide, and the other group may represent the spacer moiety.

TABLE 1

| $R_1/R_2$ | $R_1'/R_2'$ | conjugating moiety |
|---|---|---|
| 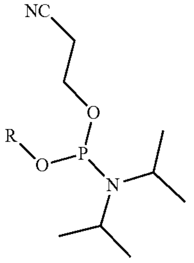 Phosphoramidite | 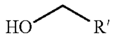 Hydroxyl | 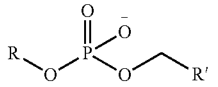 |
| 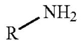 Amine | 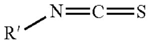 Thiocyanate | 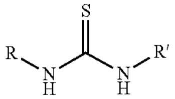 |
| 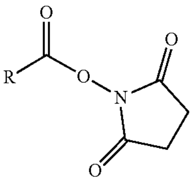 N-Hydroxysuccinimides | 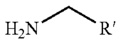 Amine | 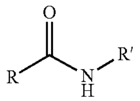 |
| 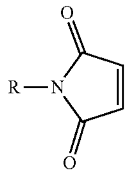 Maleimides | 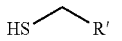 Thiol | 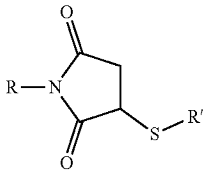 |
| 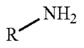 Amine | 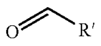 Aldehyde | 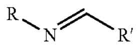 |
| $R—N_3$ Azide | 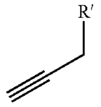 Alkyne | 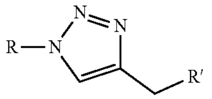 |

Spacer moieties may be generated via one or more synthetic schemes, including solid-phase, solution/liquid phase, and enzymatic based synthesis. Exemplary synthetic methods include polymer synthesized using phosphoramidite chemistry, peptide synthesis, click chemistry, and other bioconjugation methods known in the art, which can result in the formation of phosphodiester, methylphosphonate, or phosphorothioate bonds between each moiety. In some embodiments, synthesis of spacer moieties may be executed linearly. In some embodiments, synthesis of spacer moieties may be executed via branching. In some embodiments, the synthesis of spacer moieties may be executed via joining of specific segments, the segments comprising one or more subelements. Under linear synthesis, constituent subelements (monomers) may be added to a growing chain of subelements which comprise a spacer moiety. In some embodiments, the initiation of synthesis begins at or near one end of a spacer moiety, wherein a first reactive group is configured to attach to a bifunctional nucleotide, and ends at or near the other end of the spacer moiety, wherein a second reactive group is configured to attach to the bifunctional nucleotide. In some embodiments, the first and second reactive groups are chemically distinct. In some embodiments, the first and second reactive groups are chemically identical.

In contrast, branched synthesis (i.e., branching) comprises a synthetic scheme where two or more branches (i.e., arms) of a spacer moiety are generated from an arbitrary starting subunit, thereby generating a resulting spacer moiety atop a solid or liquid-phase support.

In some embodiments, the spacer moieties are synthesized using solid phase synthesis. In solid phase synthesis, a polymeric spacer moiety is synthesized on a solid support in a stepwise fashion, adding a subsequent subelement (monomer) to a growing polymer chain. In some embodiments, spacer moieties are synthesized using solution-phase synthesis. In solution phase synthesis, the spacer moiety is synthesized in solution stepwise, with subelement (monomers) assembling on a growing polymer chain. In some embodiments, the spacer moieties are synthesized using enzymatic synthesis. In enzymatic synthesis, enzymes are used to synthesize a polymeric spacer moiety in a stepwise process. Enzymes may be used to join specific subelements (monomers) with specific chemical bonds. In some embodiments, the spacer moieties are synthesized using a combination of one or more of the following: solid phase synthesis, solution phase synthesis, and enzymatic synthesis.

Figure 90:
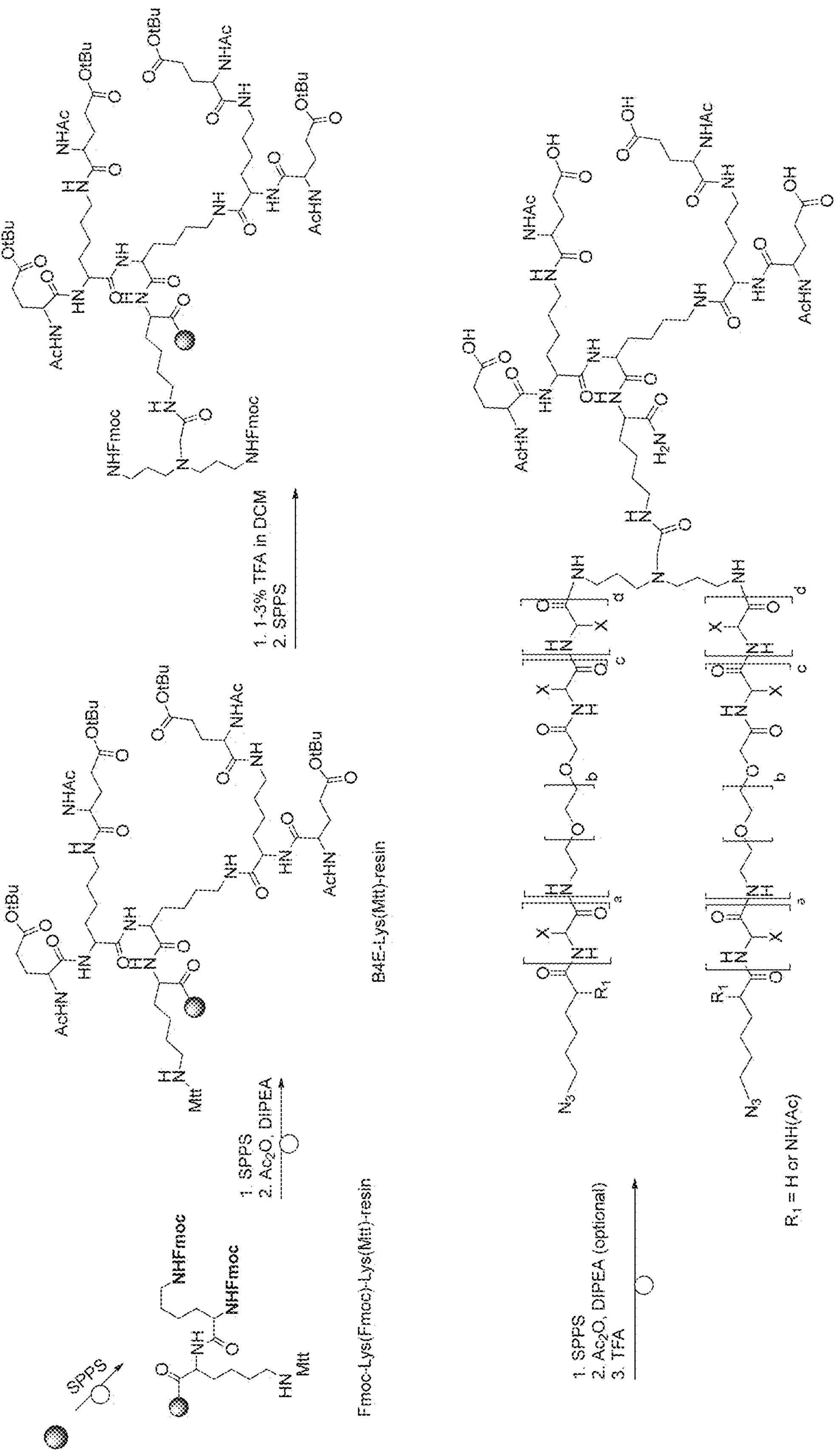
FIG. 90 illustrates an exemplary synthesis of a spacer moiety with an arresting construct.
Figure 91:
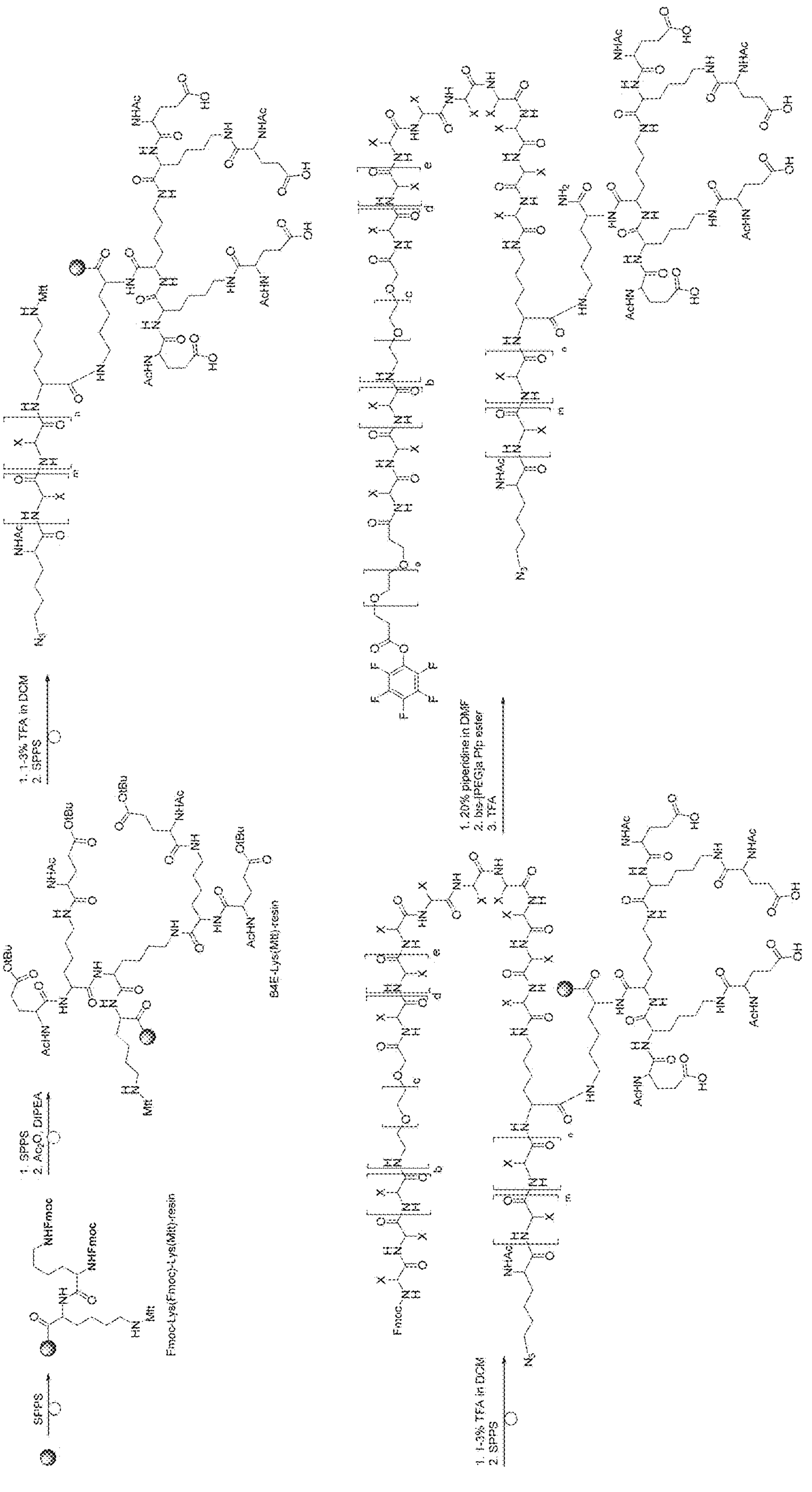
FIG. 91 illustrates another exemplary synthesis of a spacer moiety with an arresting construct.

In some embodiments, an exemplary symmetrical spacer moiety with an arresting construct may be synthesized using a solid-phase synthetic route as shown in FIG. 90. In some embodiments, an exemplary asymmetrical spacer moiety with an arresting construct may be synthesized using a solid-phase synthetic route as shown in FIG. 91.

Figure 92:
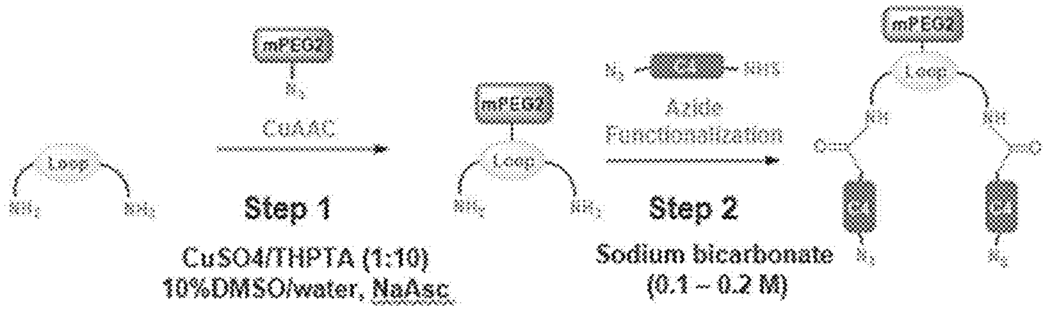
FIG. 92 illustrates another exemplary synthesis of a spacer moiety with an arresting construct.

In some embodiments, an exemplary symmetric spacer moiety with an arresting construct may be synthesized by joining segments in a 2 step process, where a polymeric chain Compound 1 comprising a cyclic loop is attached at step 1 to an arresting construct mPEG2, and at step 2 attaching an azido conjugation moiety to yield compound 3 (see FIG. 92)

Daughter Strand

Compound (Ia), (IIa), (Ma), (IVa), (Va), and (XIIa) may be used as cyclic loop nucleotides for synthesizing a daughter strand. The daughter strand comprises at least one of the compounds (I), (II), (III), (IV), (V), and (XII). In some embodiments, the daughter strand is formed by linking a plurality of compounds (I), a plurality of compound (II), a plurality of compound (III), a plurality of compound (IV), a plurality of compound (V), or a plurality of compound (XII) together into a polynucleotide or an oligonucleotide. The daughter strand comprises one of the following structures:

(Ib)

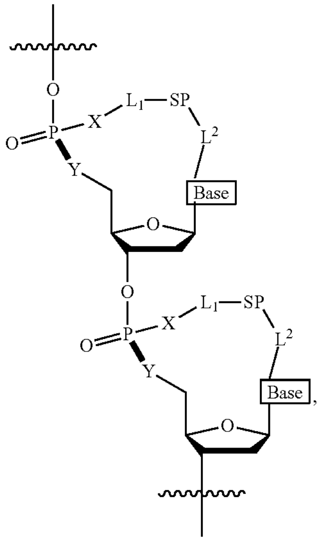

-continued (IIb)

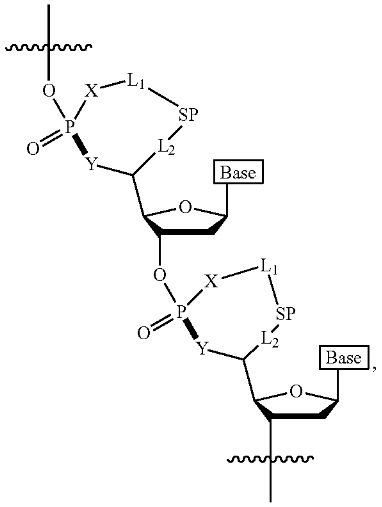

(IIIb)

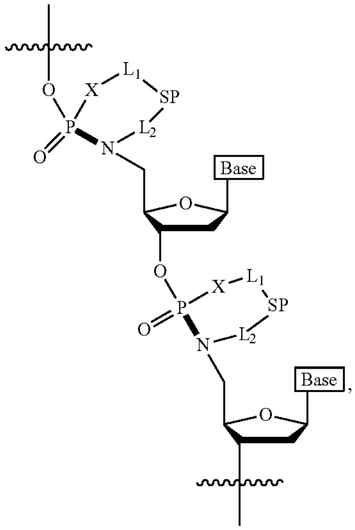

(IVb)

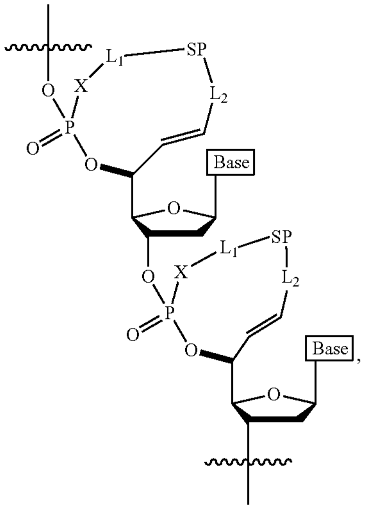

-continued
(Vb)
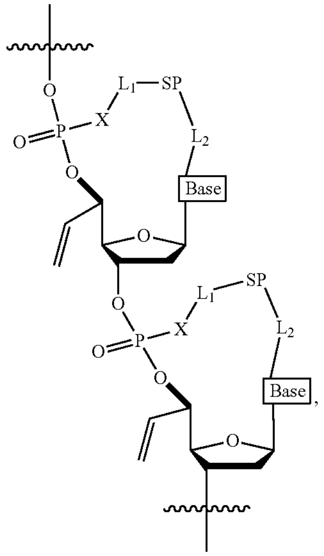
(XIIb)
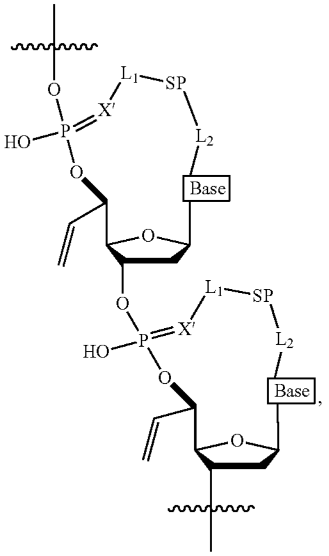
-continued
(VI)
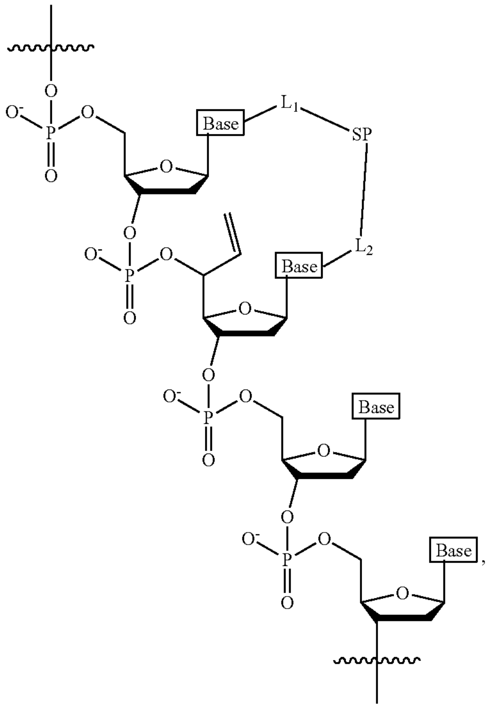
(VII)
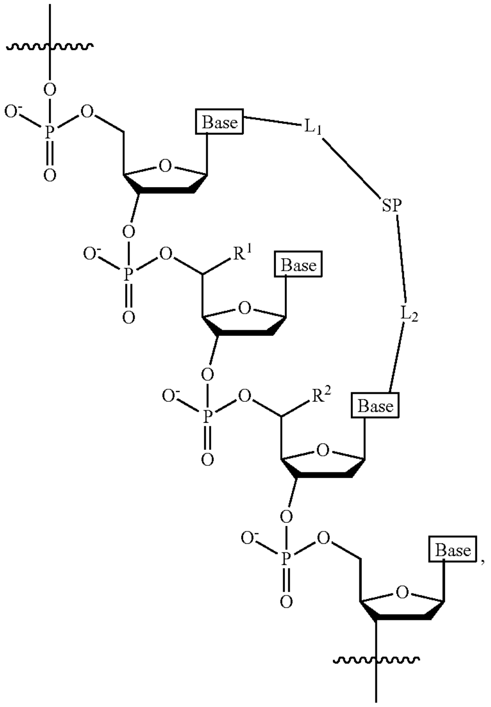

-continued
(VIII)
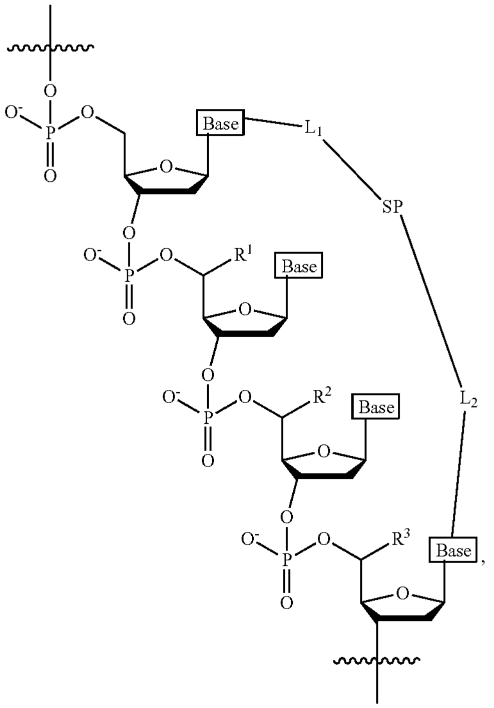
(IX)
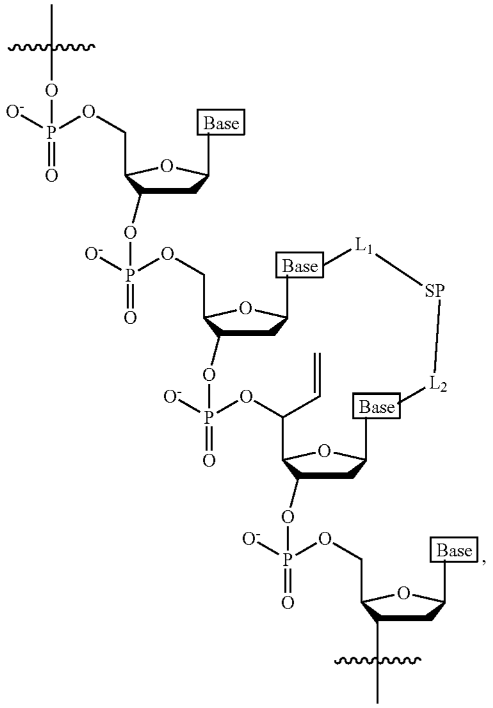
-continued
(X)
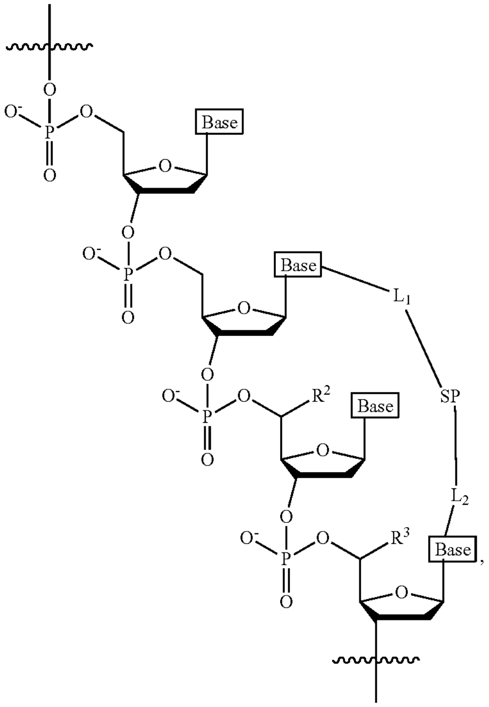
(XI)
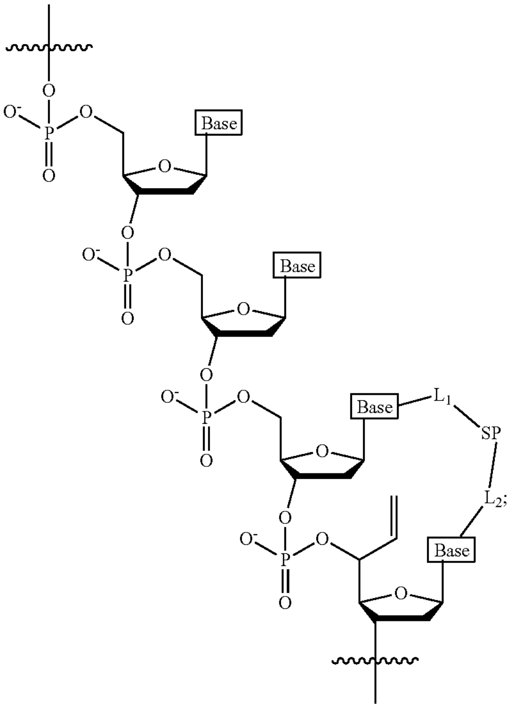
wherein X, X', Y, $L_1$, $L_2$, SP, and Base are as defined above, and the adjacent Bases on the daughter strand may be different or the same.

In some embodiments, structure (VII) can further be represented by the following structures:
(VIIa)
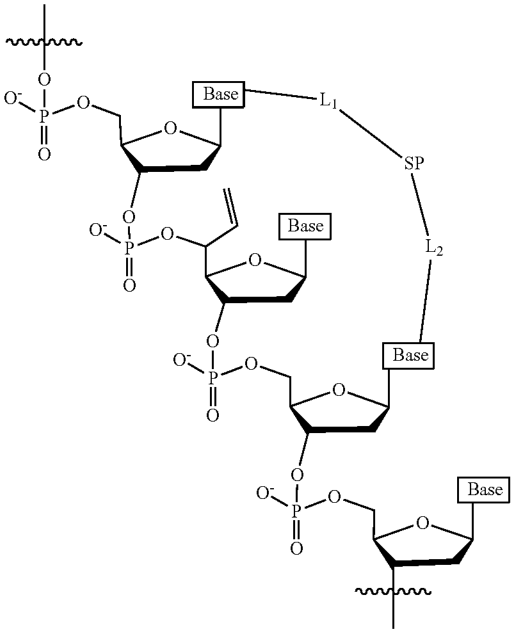
or
(VIIb)
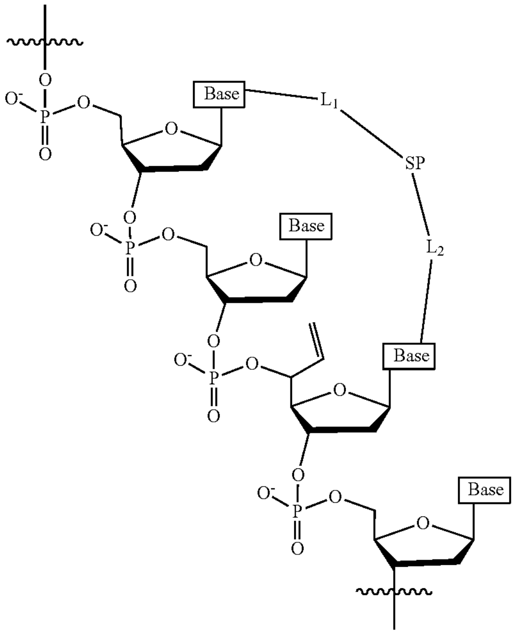
.
In some embodiments, structure (VIII) can further be represented by the following structures:
(VIIIa)
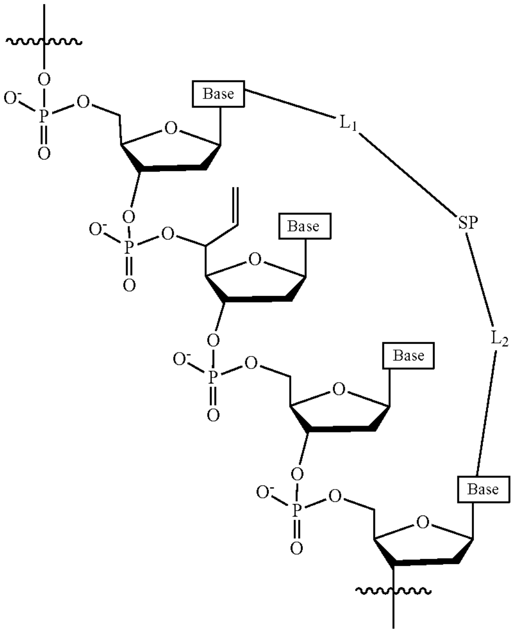
,
(VIIIb)
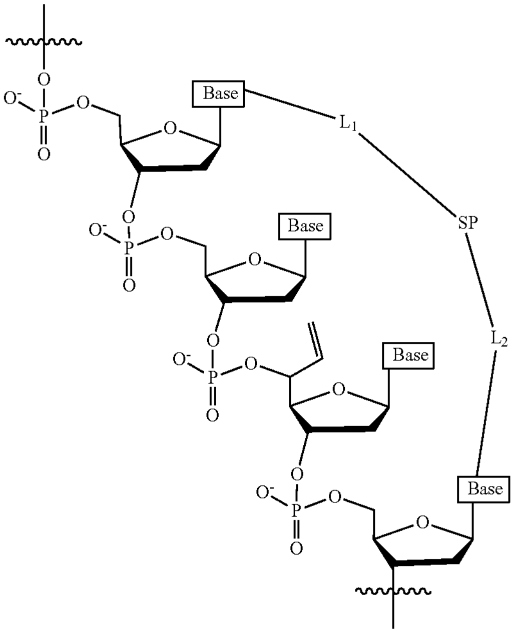
, or -continued
(VIIIc)
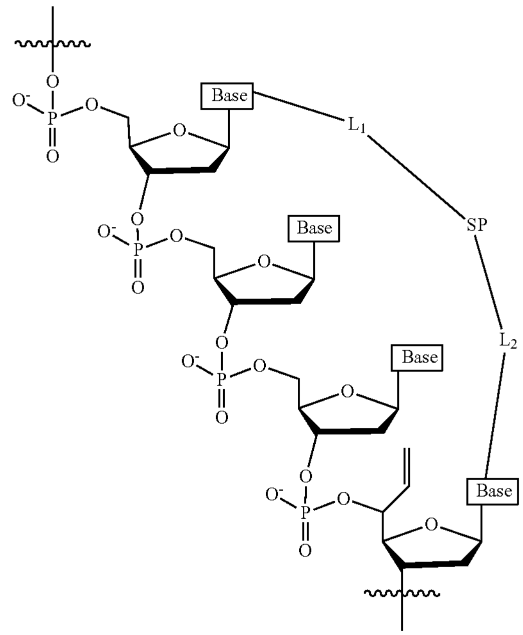
.
-continued
(Xb)
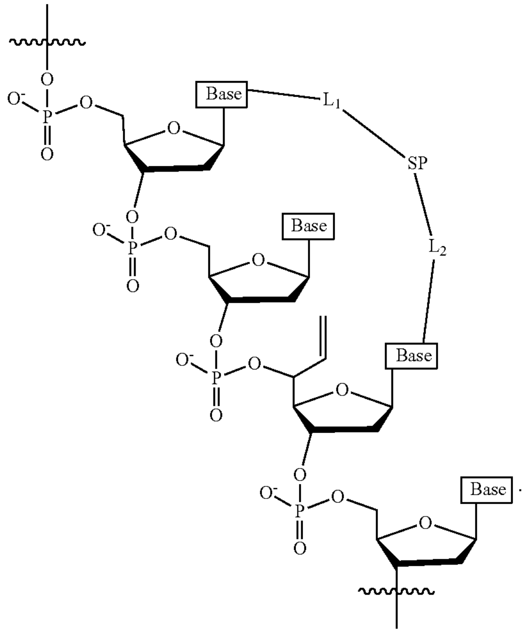
.
In some embodiments, structure (X) can further be represented by the following structures:
(Xa)
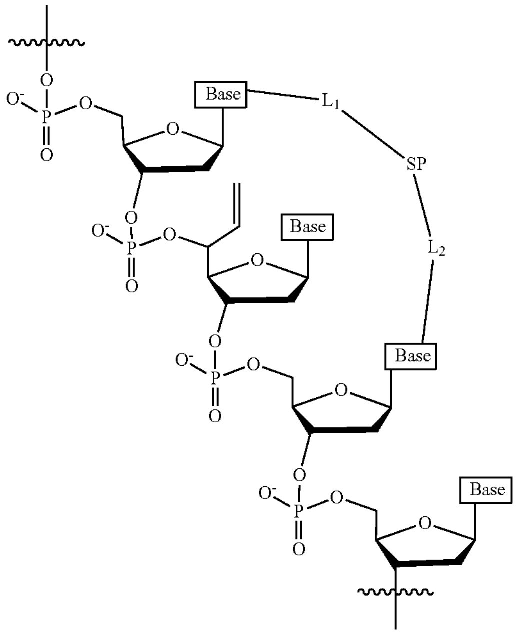
or
Cleavage of Cyclic Loop Nucleotide
The daughter strand can further be subject to a condition disclosed herein suitable for cleaving the cyclic loop nucleotides, elongating the daughter strand to form an elongated polynucleotide:
(Ic)
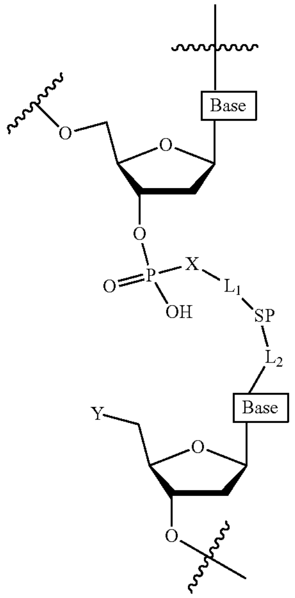
, -continued
(IIc)
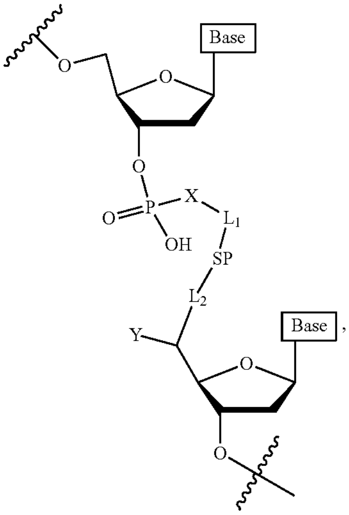
,
(IIIc)
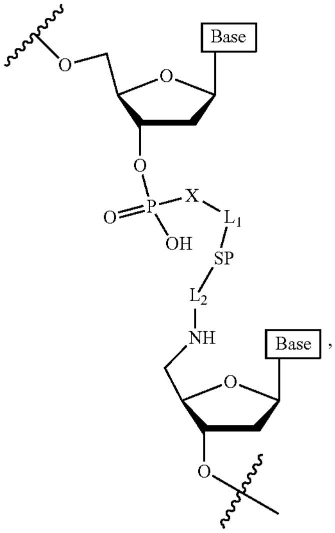
,
-continued
(IVc)
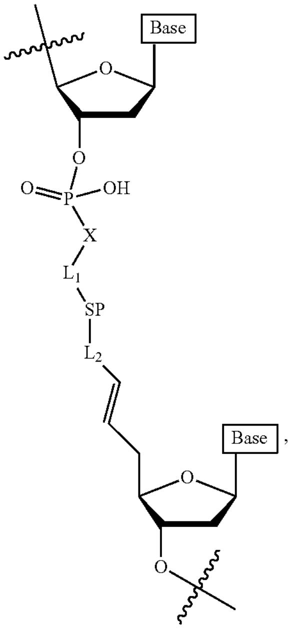
,
(Vc)
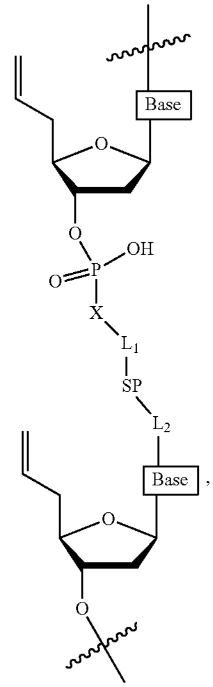
, and -continued (XIIc)

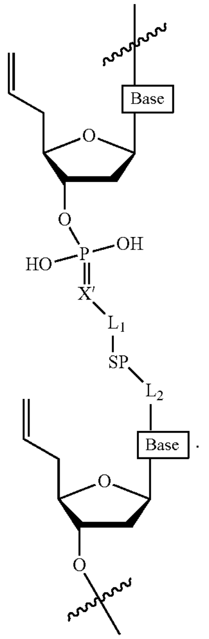

Wherein X, X', Y, $L_1$, $L_2$, SP, and Base are as defined above, and the adjacent Bases on the elongated polymer strand may be different or the same.

Cleavable Cyclic Loop 4-Mer Oligonucleotide

In some embodiment, two ends of a linker construct may be conjugated to 2 nucleobases of a 4-mer oligonucleotide to form a cleavable cyclic loop 4-mer oligonucleotide. An allyl cleavable bond can be situated anywhere along the oligonucleotide backbone in between the two points of conjugations and allow the cyclic loop to be opened upon cleavage. In some embodiments, the conjugation points may be the first and the second bases, the first and the third bases, the first and the fourth bases, the second and the third bases, the second and the fourth bases, or the third and the fourth bases. For example, when the conjugation points are the first and the second bases, the allyl cleavage site may be situated on the backbone between the first and the second bases. When the conjugation points are the first and the third bases, the allyl cleavage site may be situated on the backbone between the first and the third bases. When the conjugation points are the first and the fourth bases, the allyl cleavage site may be situated on the backbone between the first and the fourth bases. When the conjugation points are the second and the third bases, the allyl cleavage site may be situated on the backbone between the second and the third bases. When the conjugation points are the second and the fourth bases, the allyl cleavage site may be situated on the backbone between the second and the fourth bases. When the conjugation points are the third and the fourth bases, the allyl cleavage site may be situated on the backbone between the third and the fourth bases.

In some embodiments, when the conjugation points are the first and the second bases, the allyl group may be located on the $C_5$' of the second nucleotide. When the conjugation points are the first and the third bases, the allyl group may be located on the $C_5$' of the second or the third nucleotide. When the conjugation points are the first and the fourth bases, the allyl group may be located on the $C_5$' of the second, the third, or the fourth nucleotide. When the conjugation points are the second and the third bases, the allyl group may be located on the $C_5$' of the third nucleotide. When the conjugation points are the second and the fourth bases, the allyl group may be located on the $C_5$' of the third or the fourth nucleotide. When the conjugation points are the third and the fourth bases, the allyl group may be located on the $C_5$' of the fourth nucleotide. In some embodiments, heavy atom substituted nucleotides may be used to generate resulting 4-mer oligonucleotides.

Examples of the cleavable cyclic loop 4-mer oligonucleotides include:

(VI)

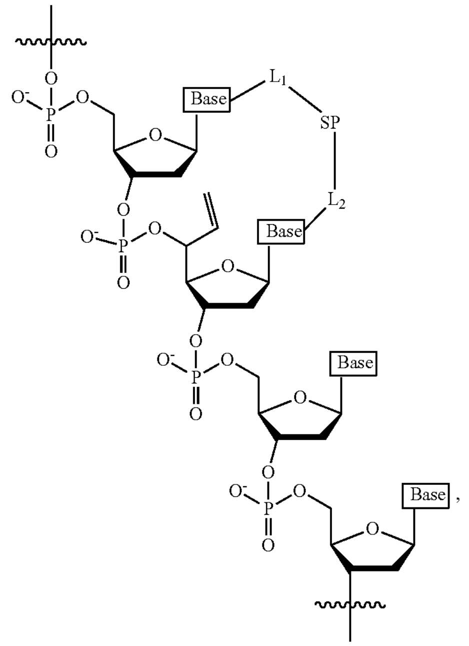

(VII)

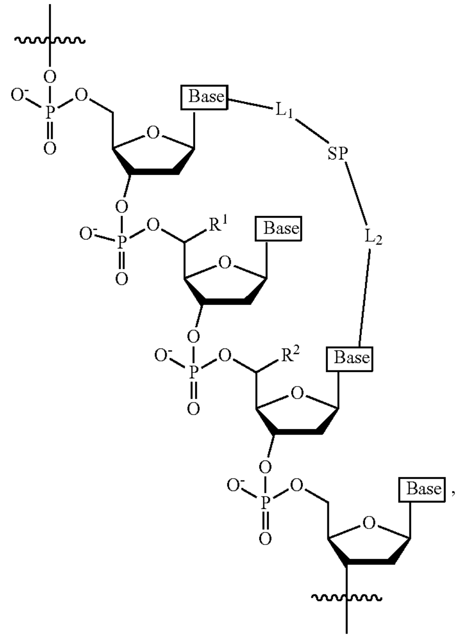

-continued (VIII)

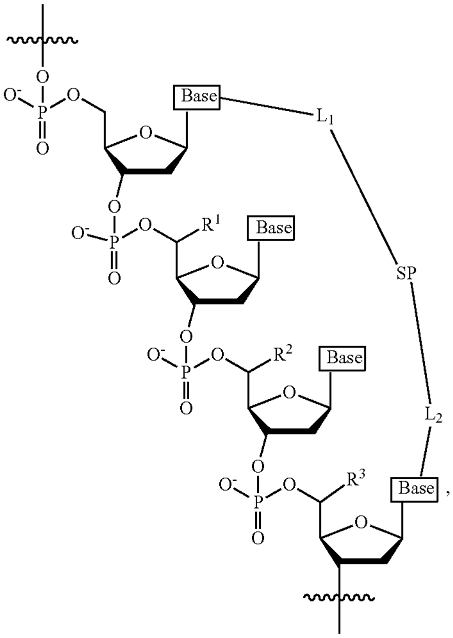

, (IX)

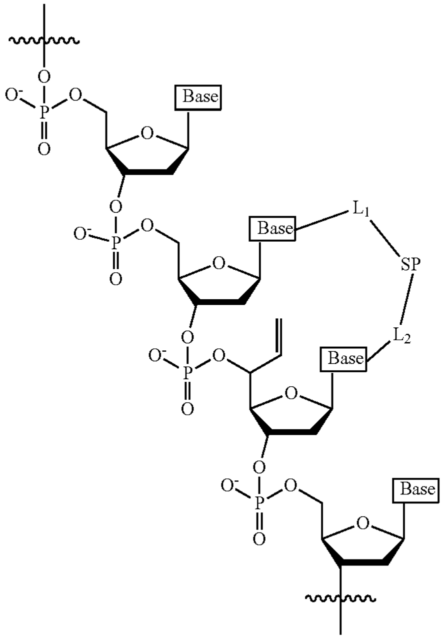

,

-continued (X)

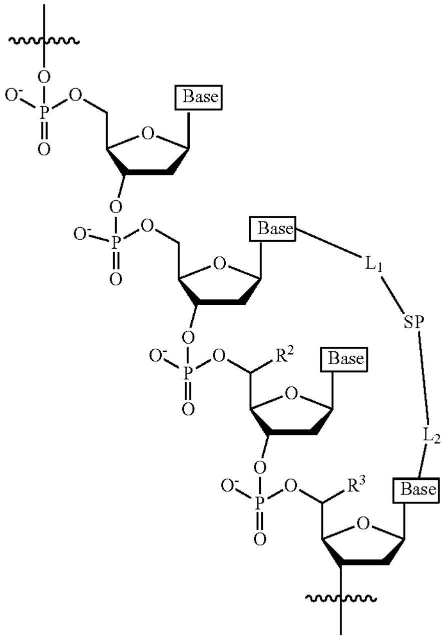

, and (XI)

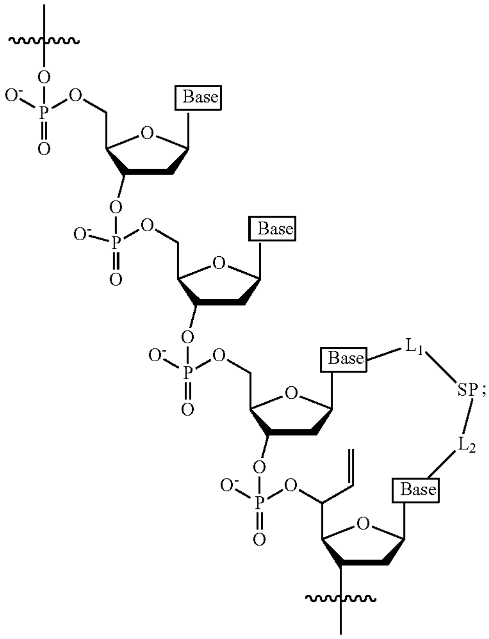

;

wherein $L_1$ is a first linking group; $L_2$ is a second linking group; one of $R^1$, $R^2$, and $R^3$ is allyl while the others are H; SP is a spacer; and Base is selected from the group consisting of adenine, cytosine, guanine, thymine, and uracil.

The cyclic loops can be designed symmetrically or asymmetrically, depending on the conjugation chemistries on the nucleotide. In some embodiments, each of the first linking group $L_1$ and the second linking group $L_2$ independently comprises a conjugating moiety selected from the group consisting of amine-NHS ester, amine-imidoester, amine-pentafluorophenyl ester, amine-hydroxymethyl phosphine, carboxyl-carbodiimide, thiol-maleimide, thiol-haloacetyl, thiol-pyridyl disulfide, thiol-thiosulfonate, thiol-vinyl sulfone, aldehyde-hydrazide, aldehyde-alkoxyamine, hydroxy-isocyanate, azide-alkyne, azide-phosphine, trans-cyclooctene-tetrazine, norbornene-tetrazine, azide-cyclooctyne, and azide-norbornene. $L_1$ and $L_2$ may or may not be the same.

In some embodiments, each of the first linking group $L_1$ and the second linking group $L_2$ may independently further comprises a linker. A first linker may be present between the conjugating moiety and a base in the 4-mer oligonucleotide, and a second linker may be present between the conjugating moiety and another base in the 4-mer oligonucleotide. In some embodiments, the linker may be selected from the group consisting of hydrophilic polymers (polyethylene glycol, polyvinyl alcohol, polyacrylamide, polyvinylpyrrolidone, polystyrenesulfonate, polyethyleneimine), hydrophobic polymers (polylactic acid, polymethylmethacrylate, polystyrene), oligonucleotides, peptides, polypeptides, aliphatic chains (C5 to C50) and combinations thereof. In some embodiments, the first and the second linkers may independently comprise peptides, polypeptides, alkyl chains, polyethylene glycol, or combinations thereof. In some embodiments, one or more linkers may be absent.

In some embodiments, SP (spacer) comprises a polymer. Spacers within a cyclic loop provide buffering distance between successive cyclic loops or successive sub-elements comprising one or more cyclic loops. In some embodiments, the polymer in the SP comprises oligonucleotides, modified oligonucleotides, hydrophilic polymers (polyethylene glycol, polyvinyl alcohol, polyacrylamide, polyvinylpyrrolidone, polystyrenesulfonate, polyethyleneimine), hydrophobic polymers (polylactic acid, polymethylmethacrylate, polystyrene), polypeptides, aliphatic chains (C5 to C50), substituted aliphatic chains (small molecules such as chloro, bromo or fluoro, alkyl such as methyl, ethyl or propyl, or aromatic groups such as phenyl or pyridyl), or combinations thereof. In some embodiments, modified oligonucleotides may include oligonucleotides that do not have a base attached to the sugar, such as

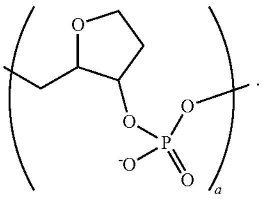
.

In some embodiments, modified oligonucleotides may include phosphoramidite analogs, such as

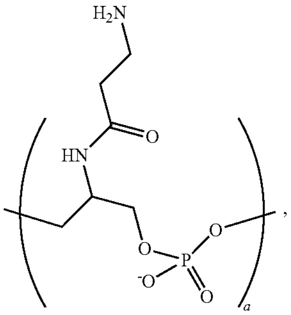
,

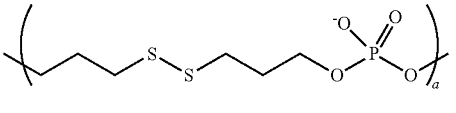
,

-continued

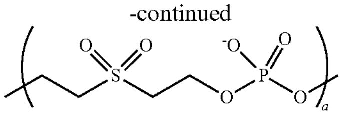
,

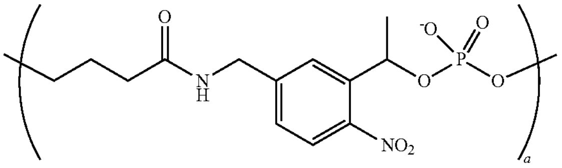

that can be assembled into a polymer using an oligonucleotide synthesis process. In some embodiments, the spacer may comprise a reporter moiety that correspond to the specific nucleobase. In other embodiments, the spacer may not include a reporter moiety (barcode).

In some embodiments, the cyclic loop may comprise one or more barcodes, or reporters, including reporter moieties, sub-reporters, reporter elements, and sub-reporter elements. Examples include, but not limited to, nucleosidic bases, non-nucleosidic bases, peptides or other synthetic polymers such as polyethyleneglycol, polyvinylalcohol, polyacrylamide, polyvinylpyrrolidone, polyethyleneimine, etc. In some embodiments, the reporter element can comprise of macromolecules such as crown ethers, cucurbiturils, pillararenes or cyclodextrins. Conjugation of these macromolecules to the cyclic loop construct is possible through covalent conjugation chemistries such as amine-NHS ester, amine-imidoester, amine-pentofluorophenyl ester, amine-hydroxymethyl phosphine, carboxyl-carbodiimide, thiol-maleimide, thiol-haloacetyl, thiol-pyridyl disulfide, thiol-thiosulfonate, thiol-vinyl sulfone, aldehyde-hydrazide, aldehyde-alkoxyamine, hydroxy-isocyanate, azide-alkyne, azide-phosphine, transcyclooctene-tetrazine, norbornene-tetrazine, azide-cyclooctyne, azide-norbornene. In some embodiments, reporters can be selected from any moiety, including spacers, conjugating moiety, and arresting constructs. In some embodiments, reporters can comprise a plurality of modifications ranging anywhere from 1-10, or 11-15, or 16-20, or 21-25, 26-50, or 50-100 units in length, as long as the reporter provide reproducible signals at a given voltage waveform when resident in the readhead of a nanopore.

In some embodiments, advancement of each nucleotide bearing the one or more barcodes or reporter moieties, corresponds to a translocation event. In some embodiments, the reporter moiety comprises one or more sub-reporter moieties, the sub-reporter moieties configured to identify a translocation event and generate a signal when passed through the readhead of a nanopore. In some embodiments, the reporter moiety comprises two or more sub-reporter moieties, wherein each sub-reporter moiety in the two or more sub-reporter moieties are distinguishable, reproducible, and resolvable. In some embodiments, a cyclic loop may comprise a first set of reporter moieties, and a second set of reporter moieties, wherein the first set of reporter moieties are configured to generate signals to identify particular nucleotides passing through the readhead, and wherein the second set of reporter moieties are configured to generate signals to identify the passage of each nucleotide regardless of nucleotide identity.

Heavy Atom Substituted Oligonucleotides

In some embodiments, heavy atoms (e.g. atoms that are not hydrogen) may be substituted into modified nucleotides. Nucleotides based on naturally occurring triphosphate and phosphodiester bonds may be limiting in regards to various enzymatic processes (e.g. ligation, incorporation). Heavy atoms, including for example, sulfur and selenium, as substitutions in nucleotides can allow for novel biochemistries and applications to cleave, link, incorporate, or otherwise manipulate oligonucleotides. Heavy-atom modified nucleotides may be incorporated, or otherwise ligated into resulting modified polynucleotides.

In some embodiments, phosphorothiolate (bridging P—S) and phosphorothioate (non-bridging P—S) substitutions and methods of generating such substitutions are described. Table 2 illustrates various cleavage reagents which are known to cleave phosphorous-sulfur bonds, including iodine and silver nitrate. In some embodiments, selenium may also be used in replacement of sulphur when generating heavy atom modified nucleotides or oligonucleotides. Selenium modified nucleic acid analogues can also potentially be synthesized and cleaved according to embodiments presented herein. Thus disclosed herein include the following oligonucleotides:

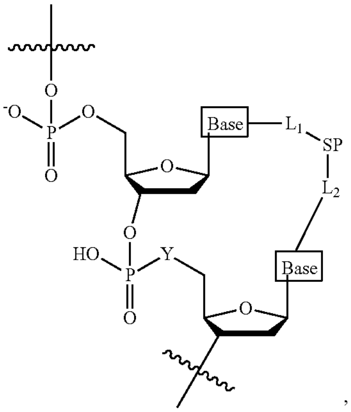

,

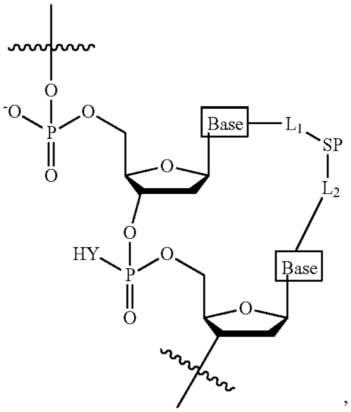

,

-continued

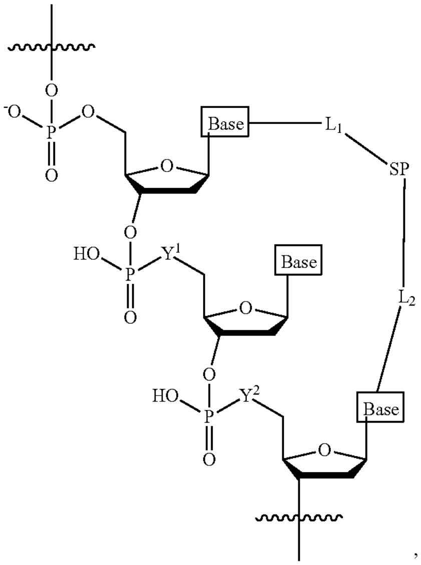

,

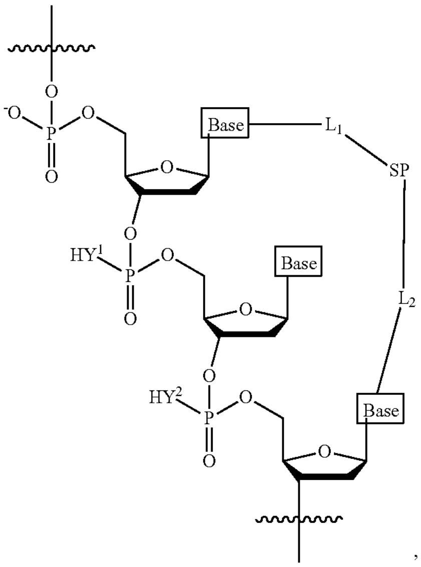

,

-continued

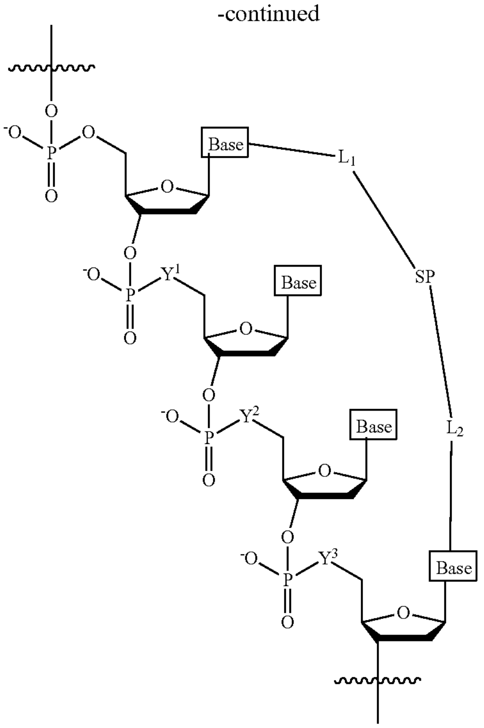

, and

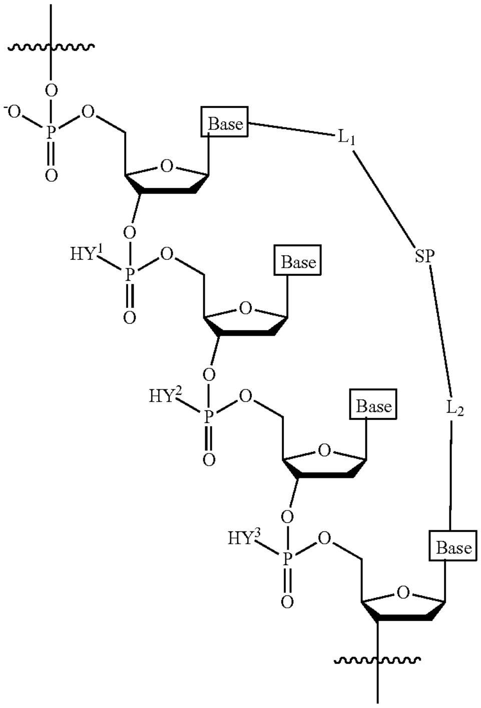

;

wherein Y is —O—, —S—, —NH—, or —Se—; one of $Y^1$, $Y^2$, and $Y^3$ is —S— or —Se—, and the others are —O— or —NH—,

TABLE 2

Cleavage Conditions for Phosphorous-Sulfur Bonds

| Cleavage Reagent | Solvent | Temperature (Centigrade) | Estimated Time (hr) |
|---|---|---|---|
| Iodine | Aqueous Acetone (1:1) | 50 | 8 |
| Iodine | Aqueous pyridine (1:1) | Room Temperature | 2 |
| Silver Nitrate (30 mM) | Water | Room Temperature | 1 |
| Silver Nitrate (50 mM) | Water | Room Temperature | 0.25 |

Some examples of heavy atom substituted nucleotides:

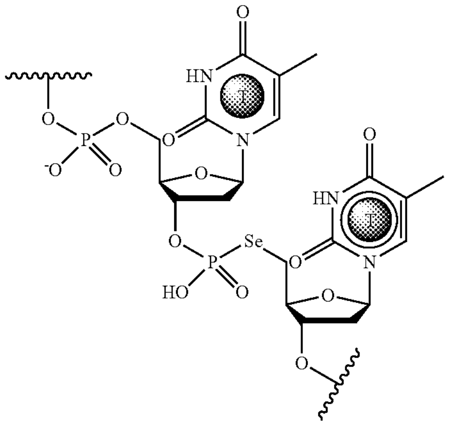

Phosphoroselenolate (bridging P-Se)

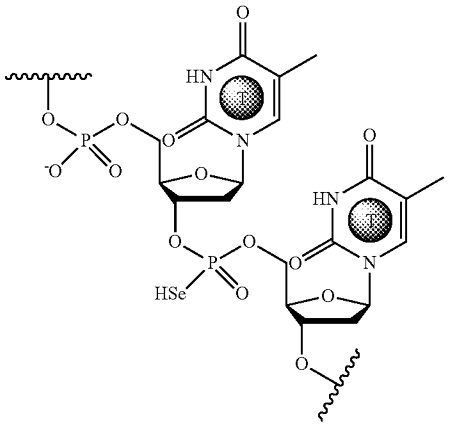

Phosphoroselenoate (non-bridging P-Se)

-continued

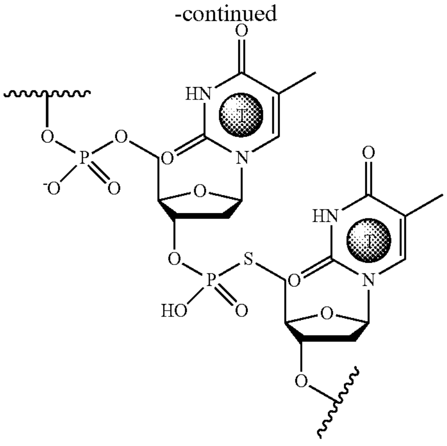

Phosphorothiolate (bridging P-S)

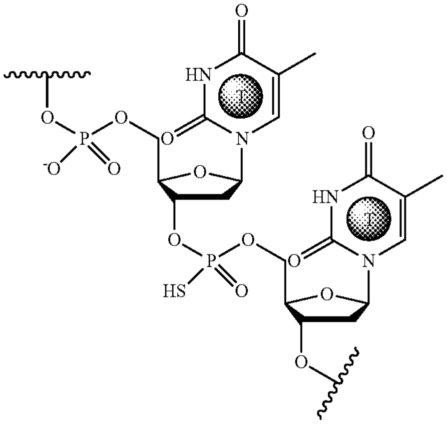

Phosphorothioate (non-bridging P-S)

The number of bridging P—S substitutions for any arbitrary K-mer oligonucleotide can be any number between 1 and K−1. For example, for a 4-mer oligonucleotide, there can be 1 to 3 bridging P—S modifications. In some embodiments, the number of bridging P—S substitutions that can be introduced is between 1 and 10, 1 and 20, 1 and 30, 1 and 40, 1 and 50, 1 and 60, 1 and 70, 1 and 80, 1 and 90, and 1 and 100 substitutions, or any value in between the values of the preceding ranges. In some embodiments, for an oligonucleotide of length K, the number of bridging P—S substitutions may be between 0 and K−1.

For phosphorothioate (non-bridging P—S), iodine is able to cleave the bridging P—O bonds at the site of phosphorothioate selectively in the presence of nucleophiles, including, for example, amines. However, the subsequent bridging P—O bond cleavage is not specific and either the 5' or the 3' end could potentially be cleaved. In addition, efficiency of the cleavage may be affected by the possible conversion of the phosphorothioate to a phosphate.

EXAMPLES

Figure 5:
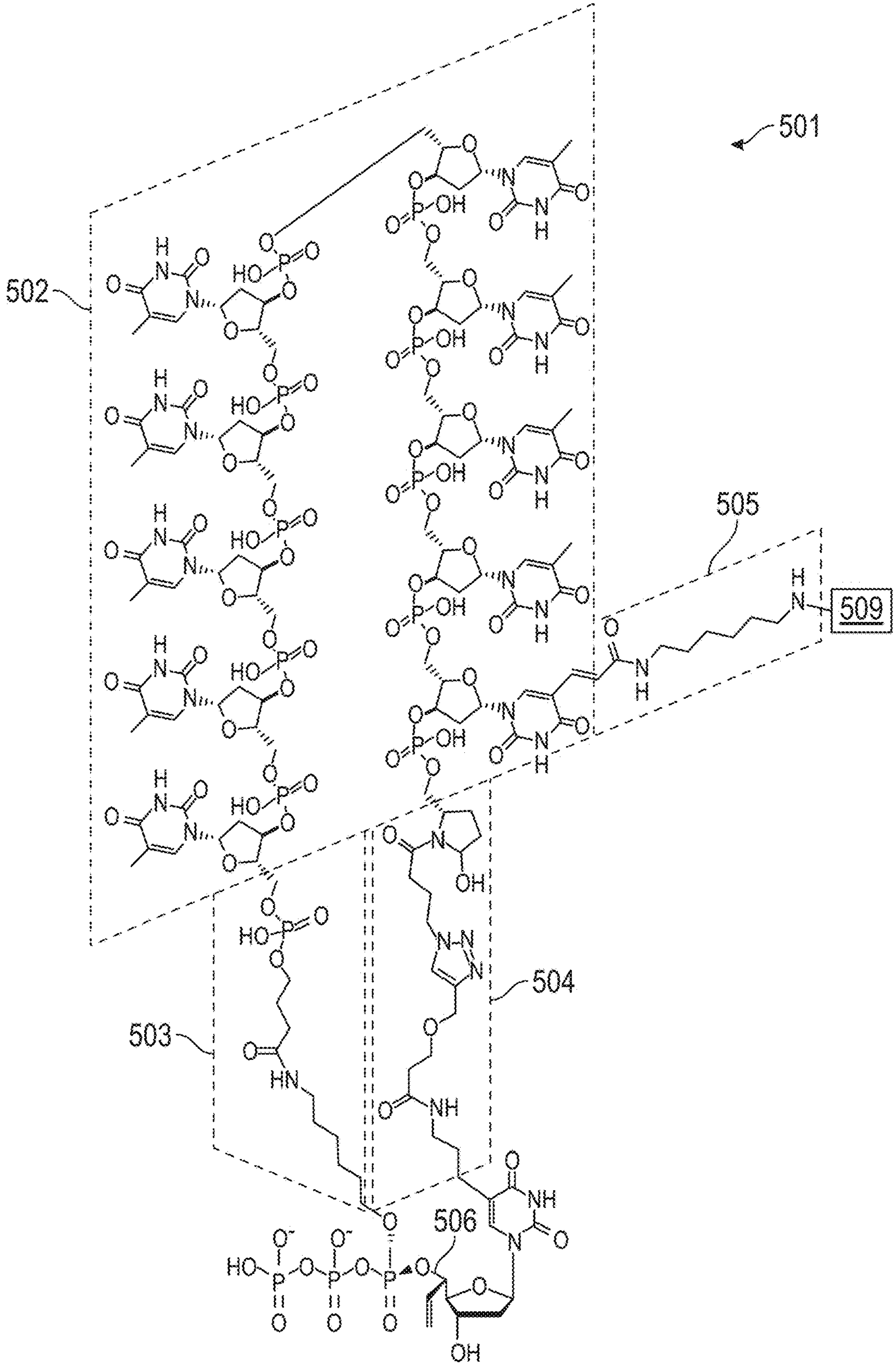
FIG. 5 schematically illustrates an example of an allyl based cleavable cyclic loop nucleotide with 10 Ts as the barcoding region, a phosphate-base linked (PBL) cyclic loop, and a "modification" on the base.

FIG. 5 schematically illustrates an example of an allyl based cleavable cyclic loop nucleotide 501 with 10 Ts as the spacer region 502, a phosphate-base linked (PBL) cyclic loop, and a arresting construct 509 attached to the spacer region 502. One end of the spacer region 502 is attached to the alpha phosphate group of the nucleotide via the first linking group 503, and the other end of the spacer region 502 is attached to the base of the nucleoside via the second linking group 504. The arresting construct 509 is attached to the spacer region 502 via a third linking group 505.

The arresting construct 509 can be constructed of one or more durable, aqueous- or solvent-soluble polymers including, but not limited to, the following segment or segments: polyethylene glycols, polyglycols, polypyridines, polyisocyanides, polyisocyanates, poly(triarylmethyl) methacrylates, polyaldehydes, polypyrrolinones, polyureas, polyglycol phosphodiesters, polyacrylates, polymethacrylates, polyacrylamides, polyvinyl esters, polystyrenes, polyamides, polyurethanes, polycarbonates, polybutyrates, polybutadienes, polybutyrolactones, polypyrrolidinones, polyvinylphosphonates, polyacetamides, polysaccharides, polyhyaluranates, polyamides, polyimides, polyesters, polyethylenes, polypropylenes, polystyrenes, polycarbonates, polyterephthalates, polysilanes, polyurethanes, polyethers, polyamino acids, polyglycines, polyprolines, N-substituted polylysine, polypeptides, side-chain N-substituted peptides, poly-N-substituted glycine, peptoids, side-chain carboxyl-substituted peptides, homopeptides, oligonucleotides, ribonucleic acid oligonucleotides, deoxynucleic acid oligonucleotides, oligonucleotides modified to prevent Watson-Crick base pairing, oligonucleotide analogs, polycytidylic acid, polyadenylic acid, polyuridylic acid, polythymidine, polyphosphate, polynucleotides, polyribonucleotides, polyethylene glycol-phosphodiesters, peptide polynucleotide analogues, threosyl-polynucleotide analogues, glycol-polynucleotide analogues, morpholino-polynucleotide analogues, locked nucleotide oligomer analogues, polypeptide analogues, branched polymers, comb polymers, star polymers, dendritic polymers, random, gradient and block copolymers, anionic polymers, cationic polymers, polymers forming stem-loops, rigid segments and flexible segments.

Figure 6:
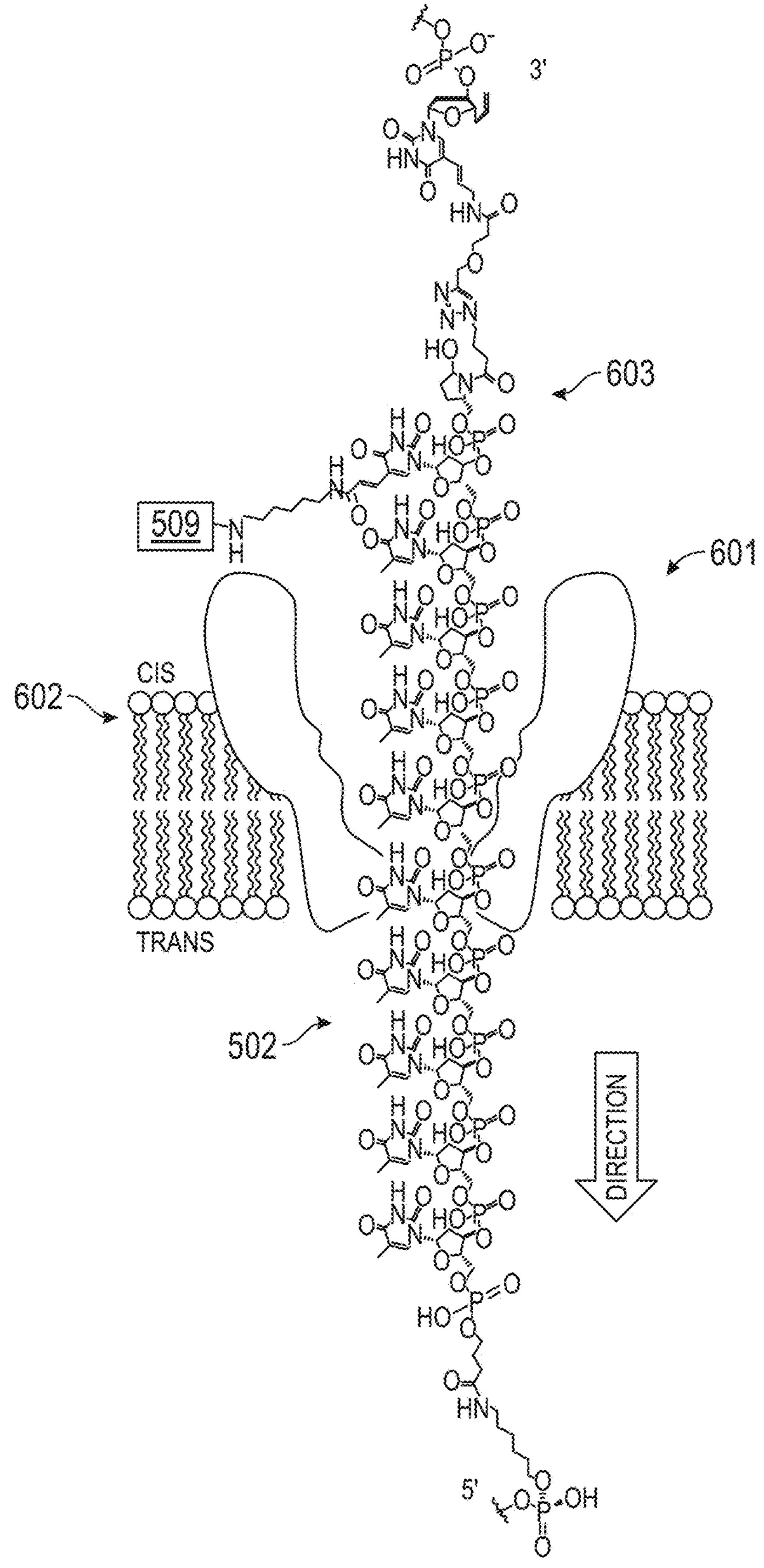
FIG. 6 schematically illustrates an example of sequencing an elongated polynucleotide having modifications.

FIG. 6 schematically illustrates an example of sequencing an elongated polymer 603 having arresting constructs. The elongated polymer 603 is formed after cleaving the O—C bond 506 of the allyl based cleavable cyclic loop nucleotide 501 as shown in FIG. 5. In FIG. 6, A protein nanopore 601 is deposited in a lipid bilayer 602. The elongated polymer 603 translocates through the nanopore 601. The polynucleotide 603 includes a spacer region 502 between successive nucleotides. In this embodiment, the spacer regions 502 comprises a reporter moiety such as a reporter barcode (10 Ts) that corresponds to the nucleotide "T." When the elongated polymer 603 translocates through the nanopore 601, the arresting construct 509 slows or temporary halts the translocation when interaction occurs between the arresting construct 509 and the nanopore 601, allowing the readhead to read the reporter barcode, thereby identifying the nucleotide.

In other embodiments, the arresting construct may be attached to a different location on the linker constructs (such as attaching to the first or the second linking group, or the nucleobase). Adjusting the location of arresting construct attachment, the type/size of arresting construct, the length of the spacer region/linker construct can affect which region of the elongated polymer resides in the nanopore constriction when the translocation is slowed or halted. In some embodiments, the nucleobase may be located in the constriction when the translocation is slowed or halted. Thus the readhead can also read the nucleobase itself, regardless of whether a reporter moiety is included in the spacer.

Figure 9:
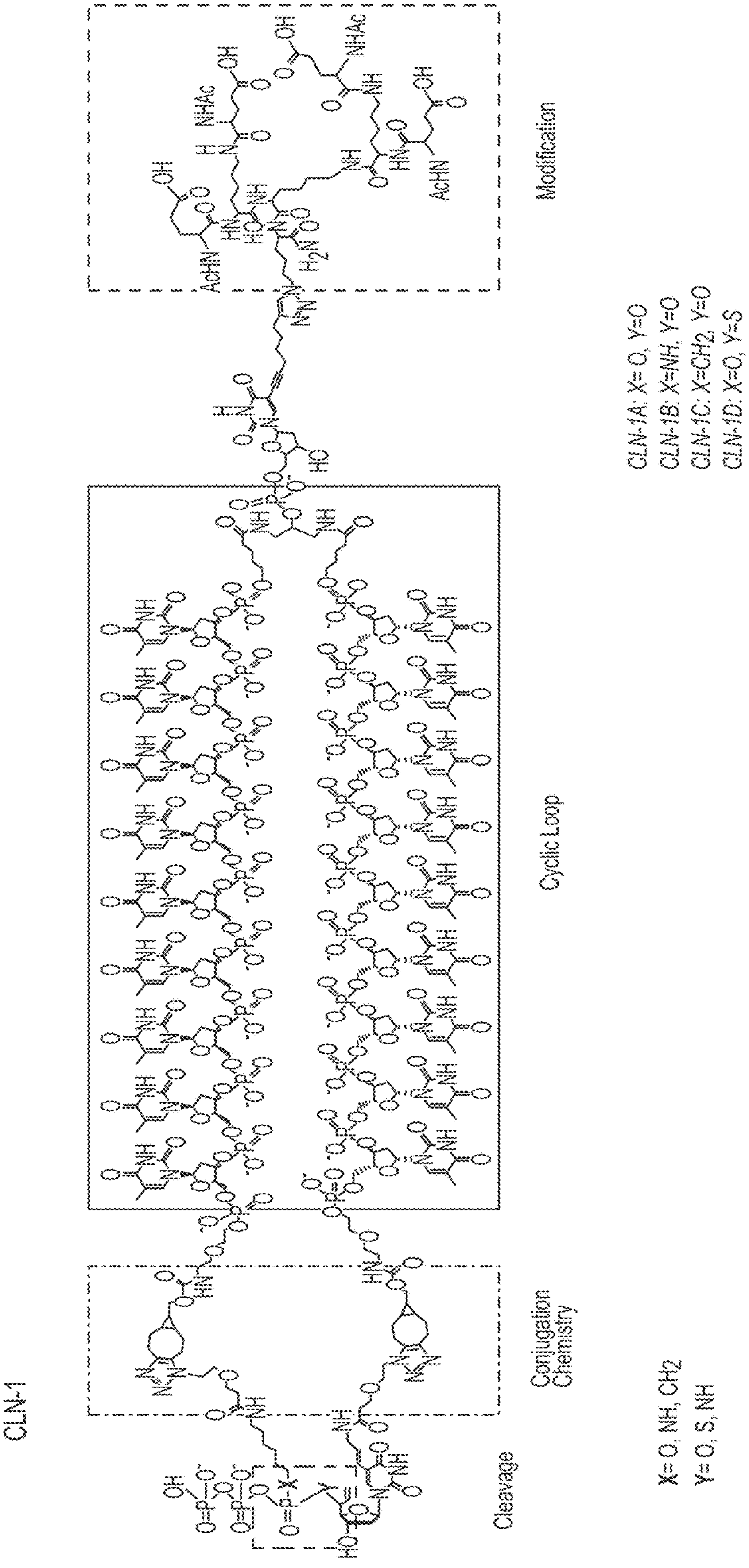
FIG. 9 schematically illustrates an example of a first design of a fully-functional cyclic loop nucleotide (CLN-1).
Figure 10:
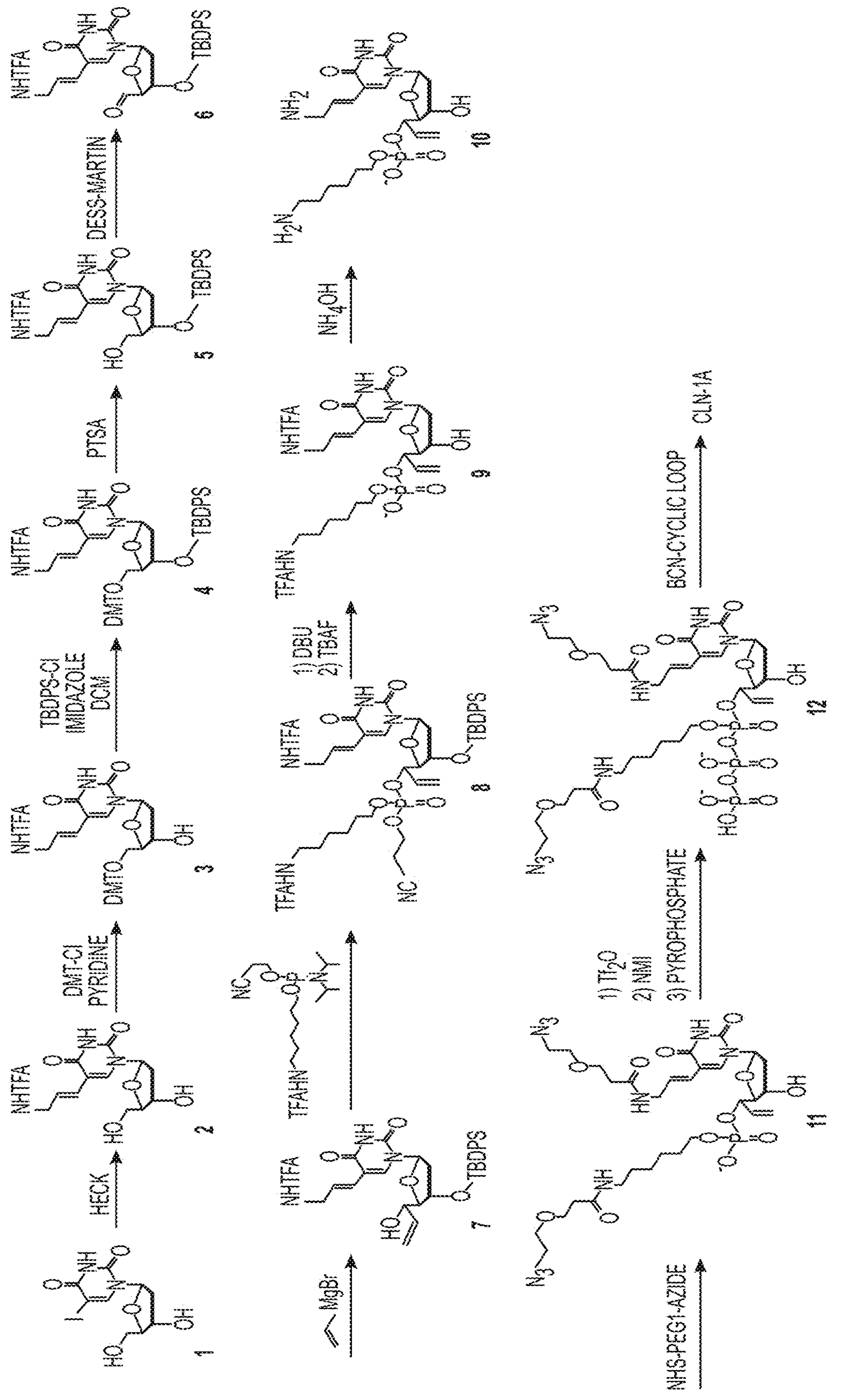
FIG. 10 schematically illustrates an example synthesis process of the fully-functional cyclic loop nucleotide (CLN-1A).
Figure 11:
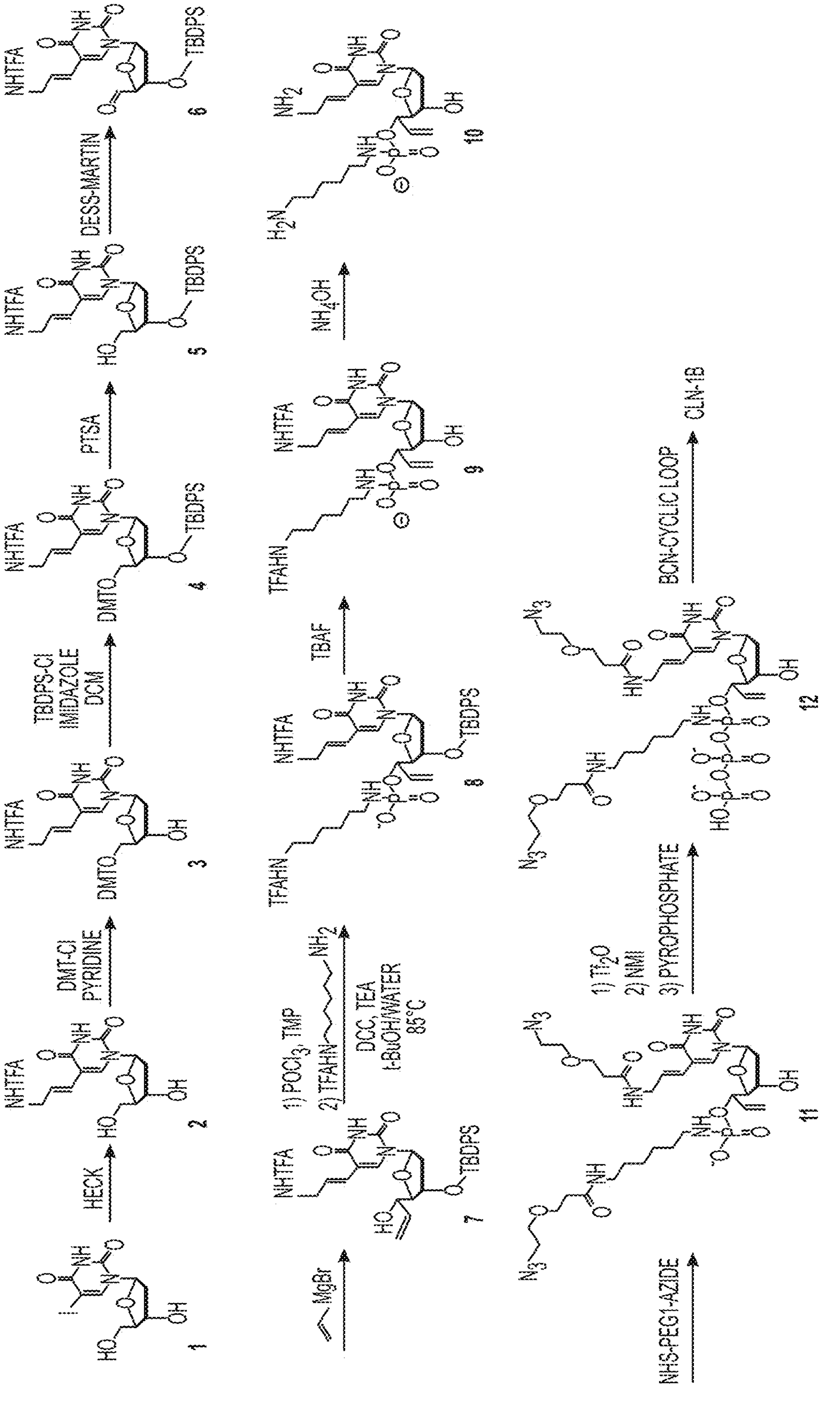
FIG. 11 schematically illustrates an example synthesis process of the fully-functional cyclic loop nucleotide (CLN-1B).
Figure 12:
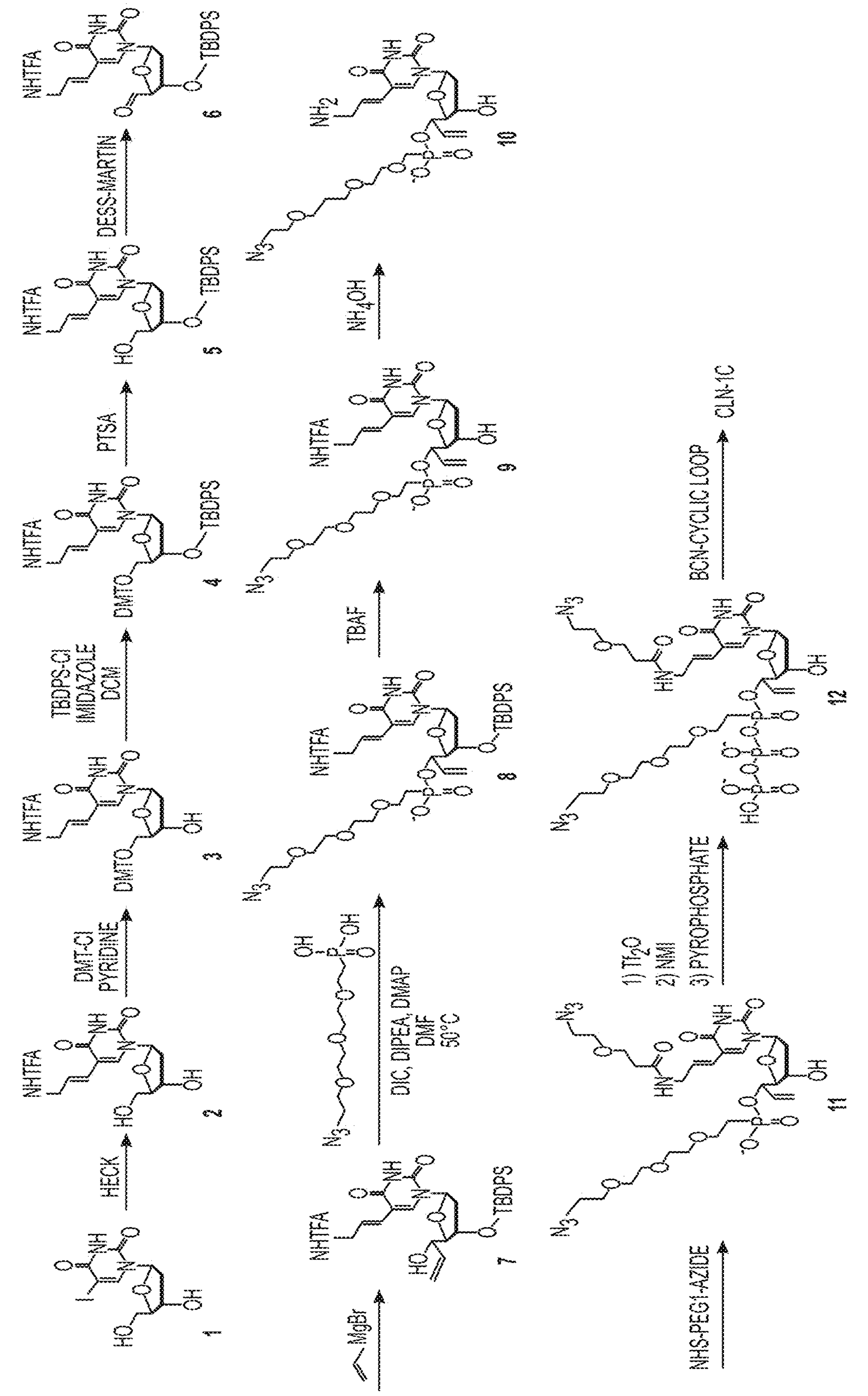
FIG. 12 schematically illustrates an example synthesis process of the fully-functional cyclic loop nucleotide (CLN-1C).
Figure 13:
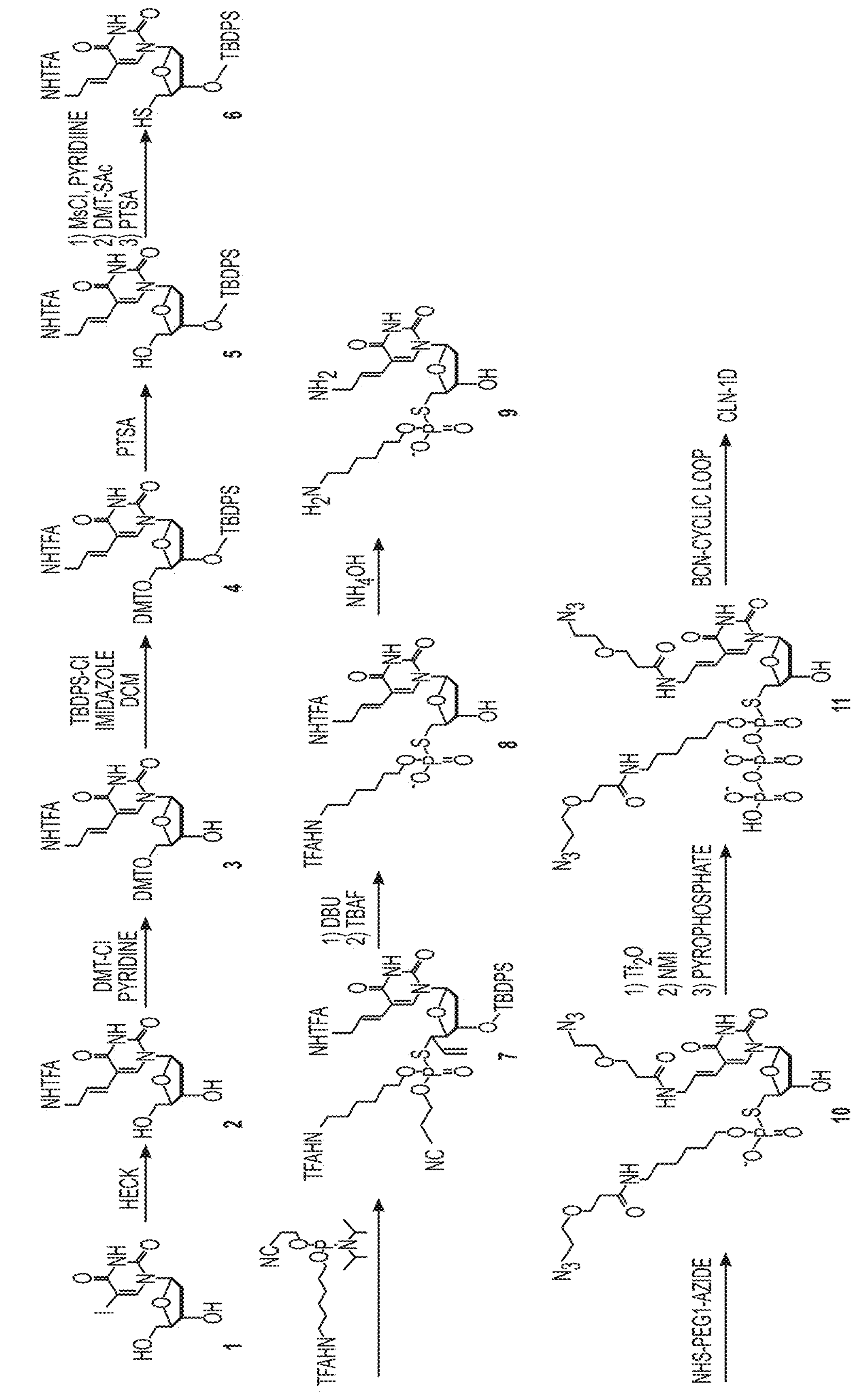
FIG. 13 schematically illustrates an example synthesis process of the fully-functional cyclic loop nucleotide (CLN-1D).

FIG. 9 schematically illustrates an example of a first design of a fully-functional cyclic loop nucleotide (CLN-1), where X may be O, NH, $NSO_2$ or $CH_2$ and Y may be O, S, Se, or NH, having an alpha phosphate-base linked symmetrical loop, and a arresting construct on the loop. FIG. 10 schematically illustrates an example synthesis process of the fully-functional cyclic loop nucleotide (CLN-1A) shown in FIG. 9, with X═O and Y═O. FIG. 11 schematically illustrates an example synthesis process of the fully-functional cyclic loop nucleotide (CLN-1B) shown in FIG. 9, with X═NH and Y═O. FIG. 12 schematically illustrates an example synthesis process of the fully-functional cyclic loop nucleotide (CLN-1C) shown in FIG. 9, with X═$CH_2$ and Y═O. FIG. 13 schematically illustrates an example synthesis process of the fully-functional cyclic loop nucleotide (CLN-1D) shown in FIG. 9, with X═O and Y═S that is compatible with phosphorothiolate cleavage.

Figure 14:
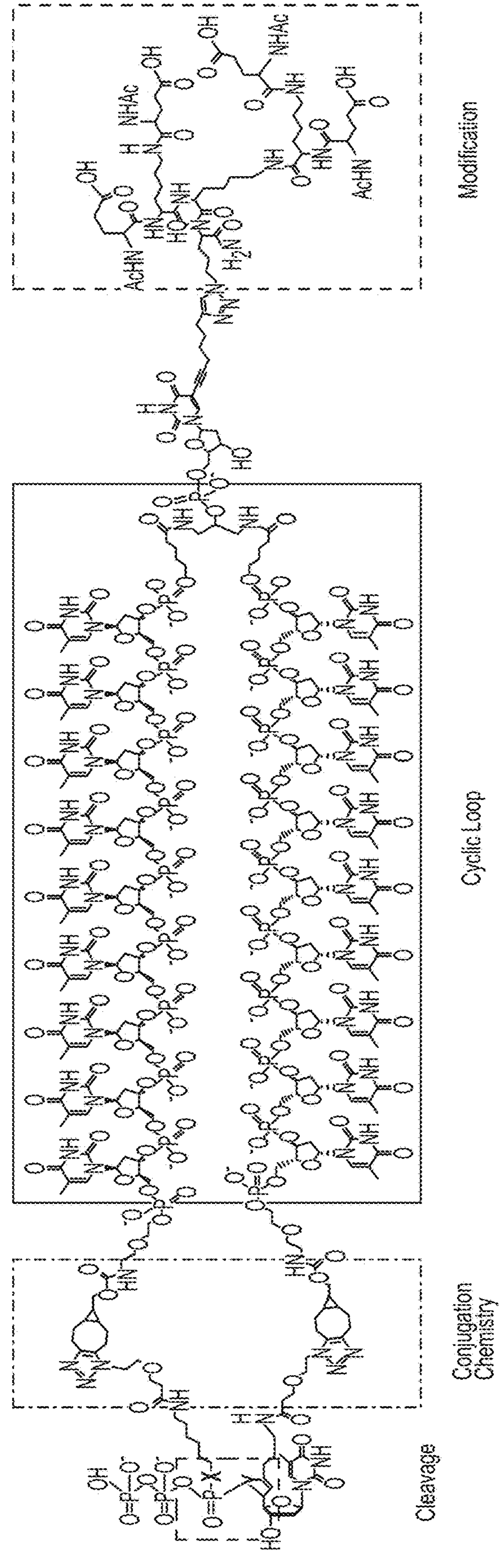
FIG. 14 schematically illustrates an example of a second design of a fully-functional cyclic loop nucleotide (CLN-2).
Figure 15:
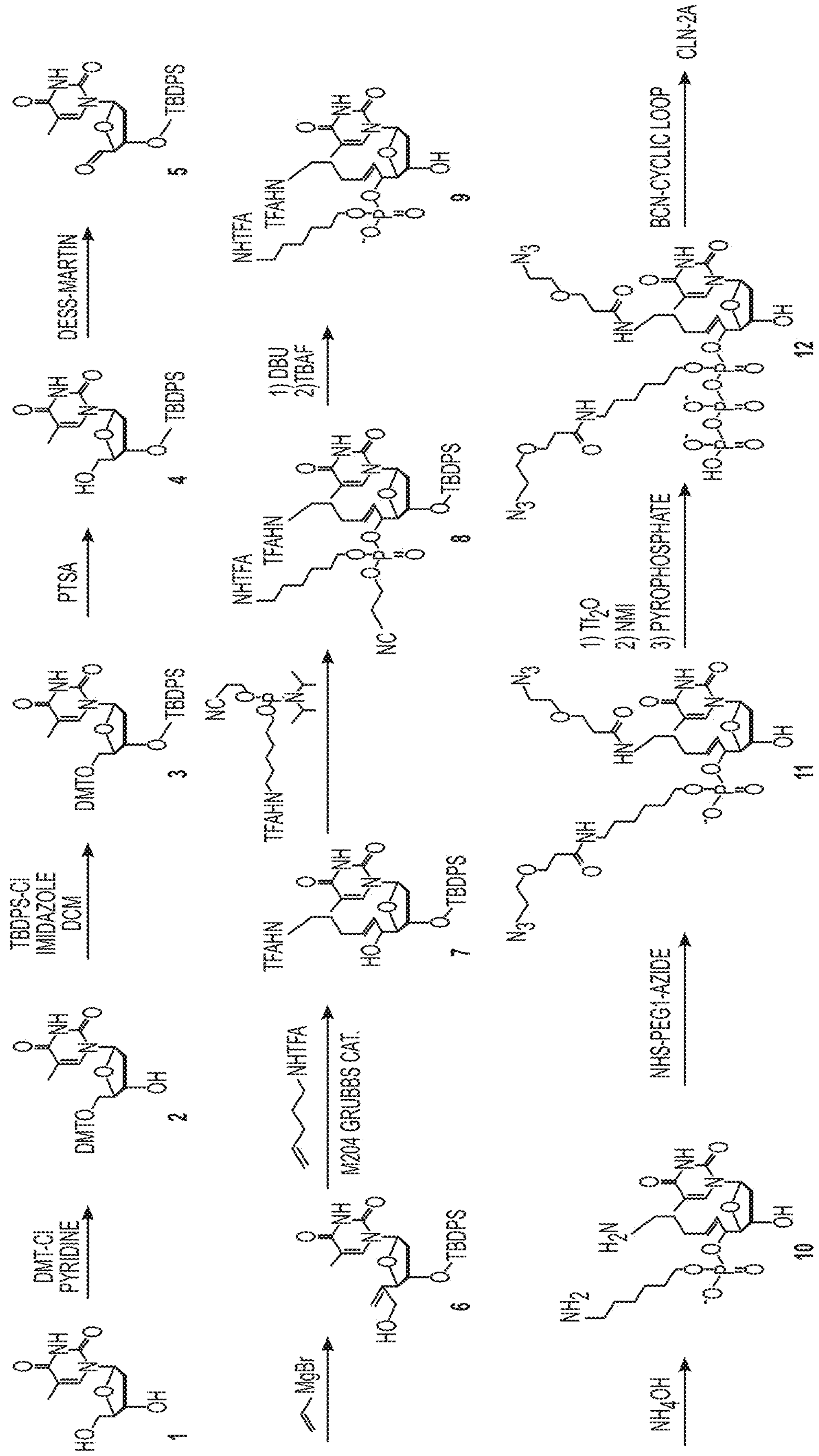
FIG. 15 schematically illustrates an example synthesis process of the fully-functional cyclic loop nucleotide (CLN-2A).
Figure 16:
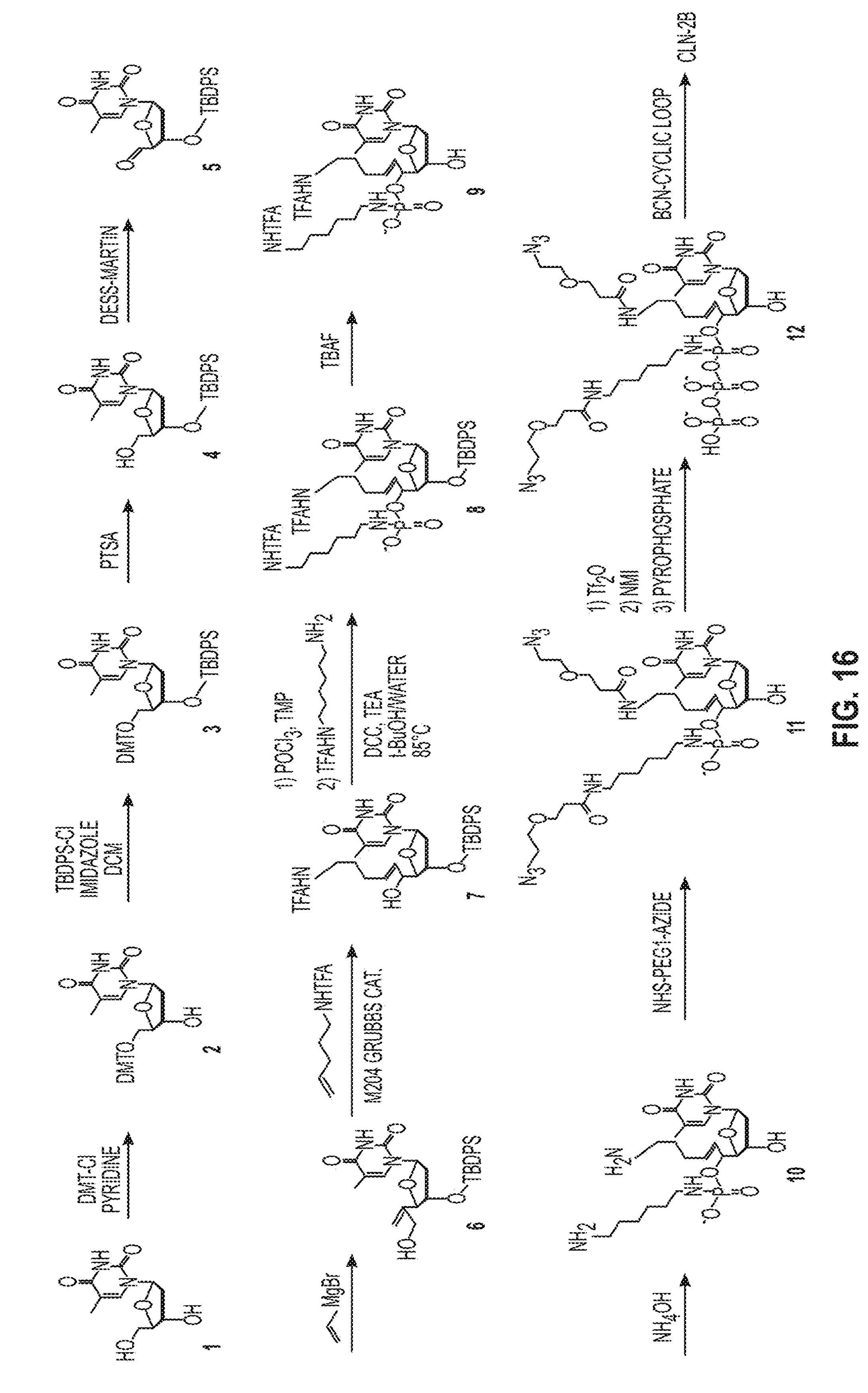
FIG. 16 schematically illustrates an example synthesis process of the fully-functional cyclic loop nucleotide (CLN-2B).
Figure 17:
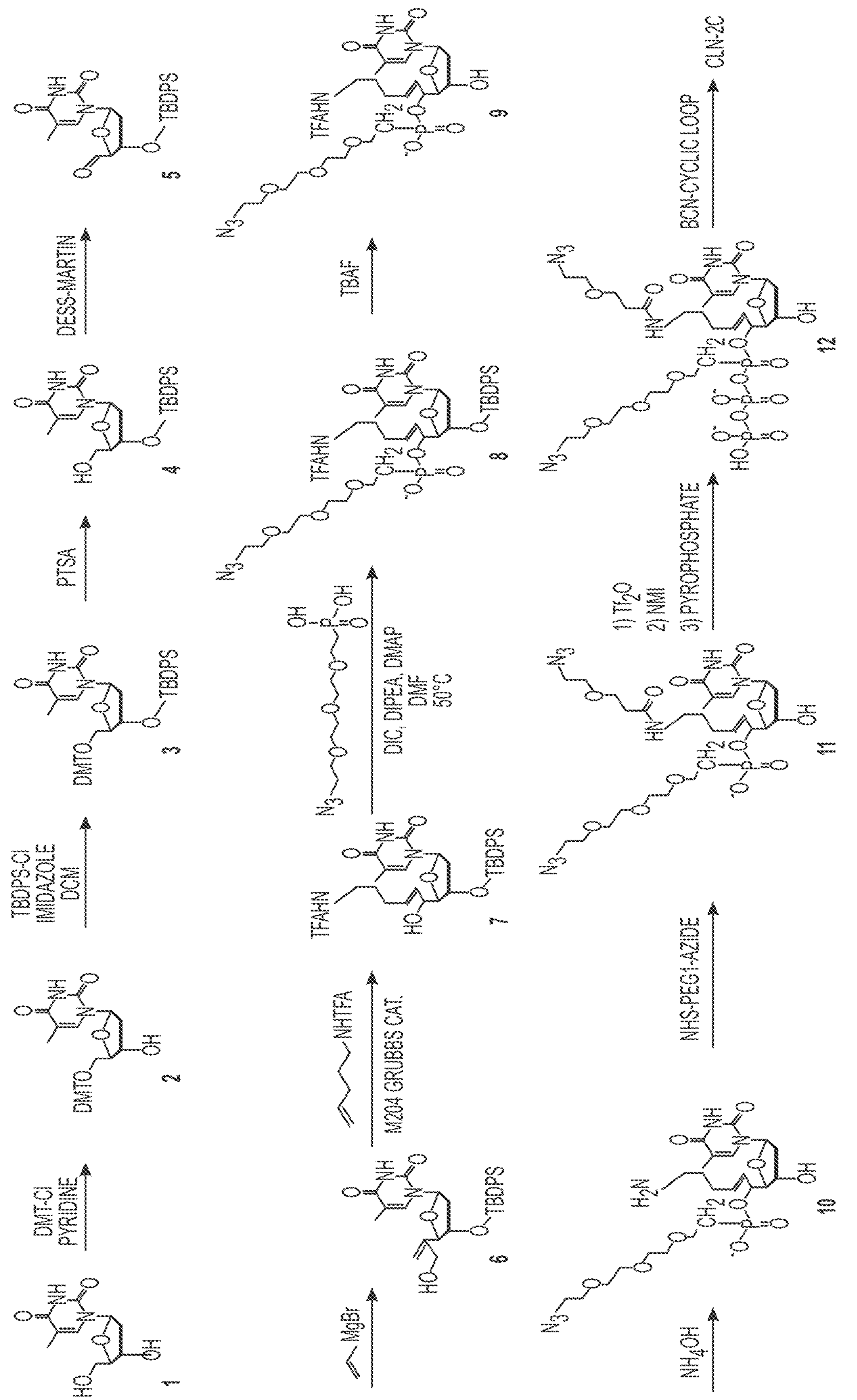
FIG. 17 schematically illustrates an example synthesis process of the fully-functional cyclic loop nucleotide (CLN-2C).

FIG. 14 schematically illustrates an example of a second design of a fully-functional cyclic loop nucleotide (CLN-2), where X may be O, NH, $NSO_2$ or $CH_2$ and Y may be O, S, or NH, having an alpha phosphate-C5' allyl linked symmetrical loop, and a arresting construct on the loop. FIG. 15 schematically illustrates an example synthesis process of the fully-functional cyclic loop nucleotide (CLN-2A) shown in FIG. 14, with X═O and Y═O. FIG. 16 schematically illustrates an example synthesis process of the fully-functional cyclic loop nucleotide (CLN-2B) shown in FIG. 14, with X═NH and Y═O. FIG. 17 schematically illustrates an example synthesis process of the fully-functional cyclic loop nucleotide (CLN-2C) shown in FIG. 14, with X═$CH_2$ and Y═O.

Figure 18:
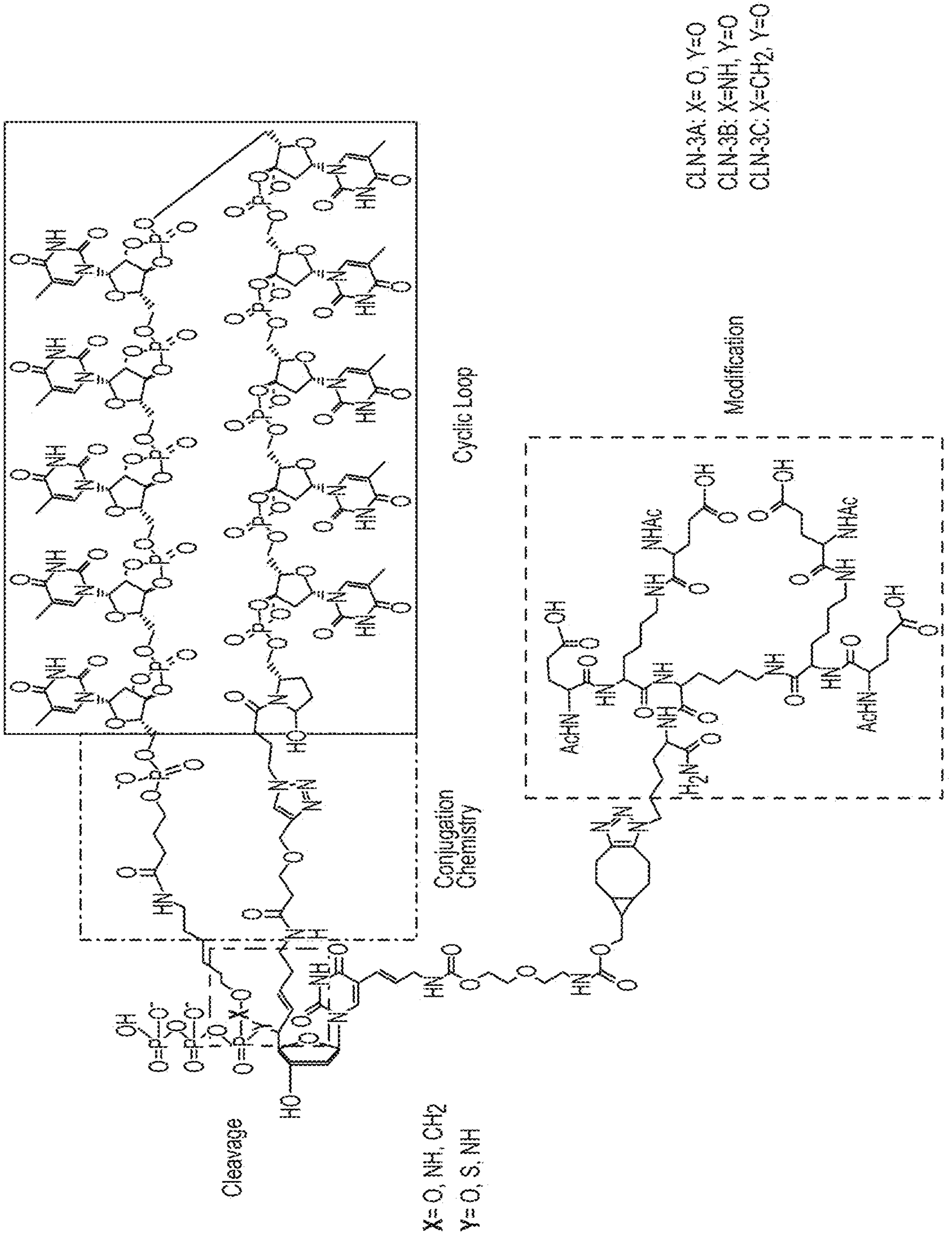
FIG. 18 schematically illustrates an example of a third design of a fully-functional cyclic loop nucleotide (CLN-3), where X may be O, NH, NSO2 or CH2 and Y may be O, S, or NH, having an alpha phosphate-allyl linked non-symmetrical loop, and a arresting construct on the nucleobase.
Figure 19:
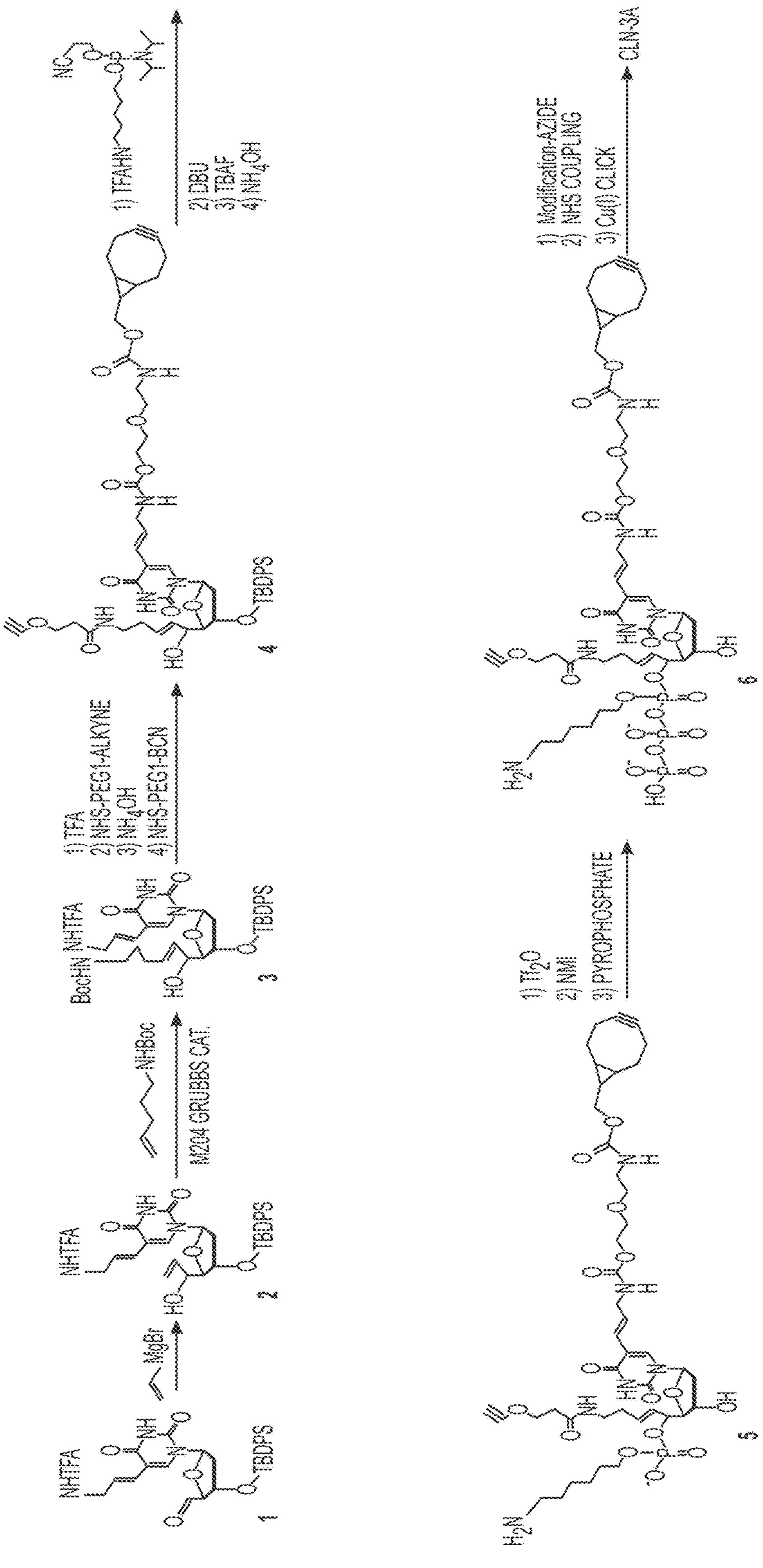
FIG. 19 schematically illustrates an example synthesis process of the fully-functional cyclic loop nucleotide (CLN-3A).
Figure 20:
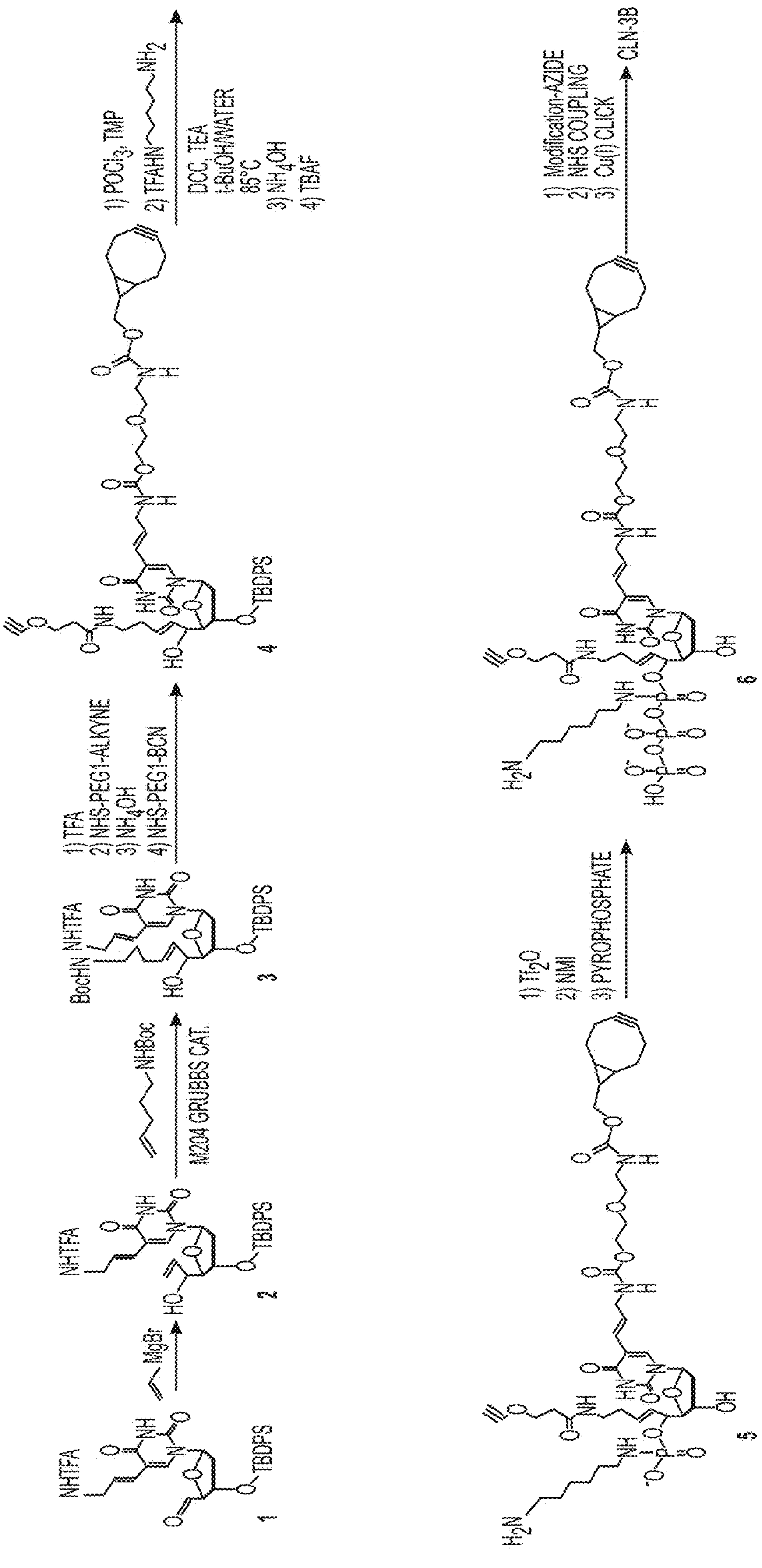
FIG. 20 schematically illustrates an example synthesis process of the fully-functional cyclic loop nucleotide (CLN-3B).
Figure 21:
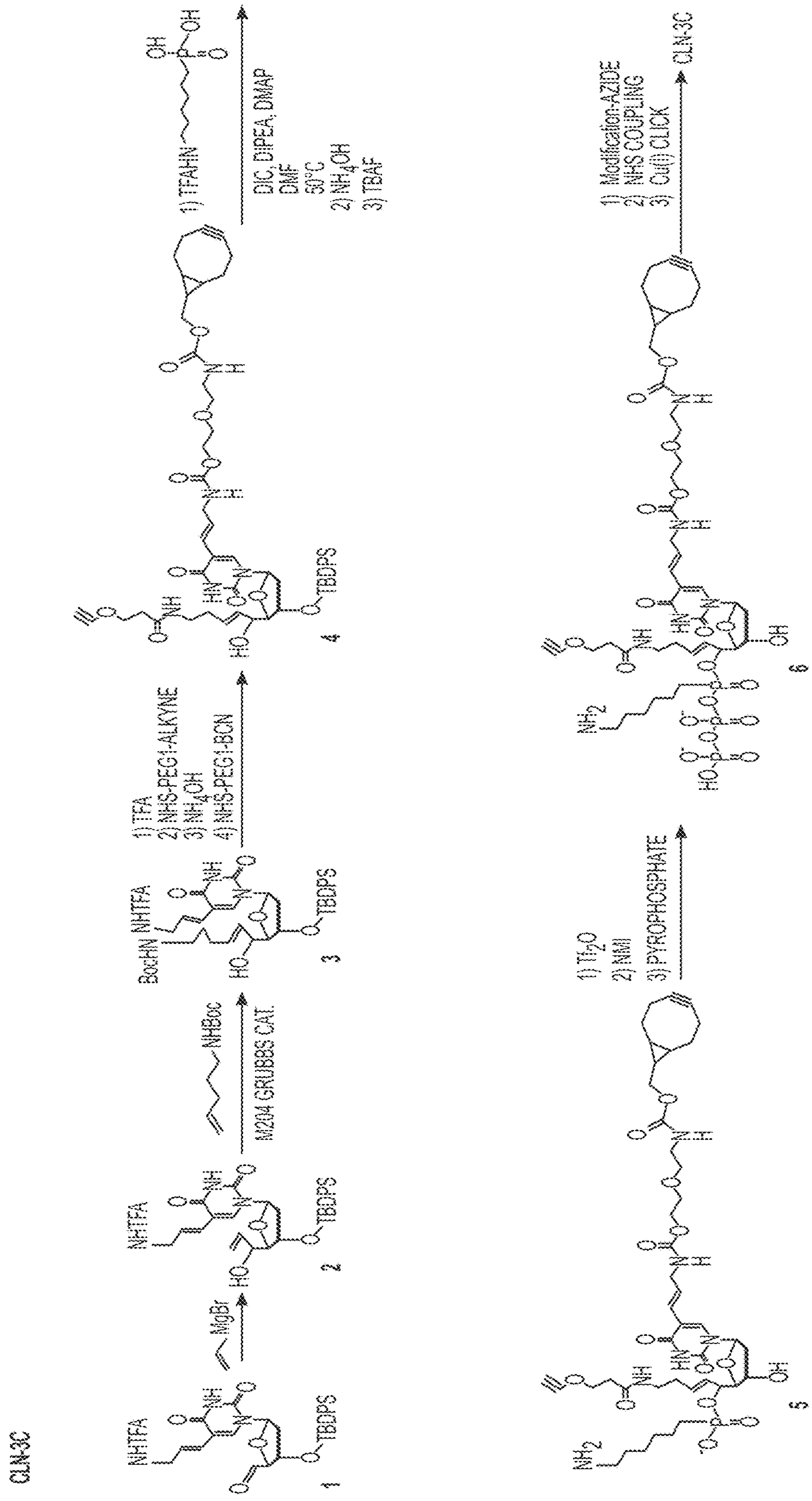
FIG. 21 schematically illustrates an example synthesis process of the fully-functional cyclic loop nucleotide (CLN-3C).

FIG. 18 schematically illustrates an example of a third design of a fully-functional cyclic loop nucleotide (CLN-3), where X may be O, NH, $NSO_2$ or $CH_2$ and Y may be O, S, or NH, having an alpha phosphate-allyl linked non-symmetrical loop, and a arresting construct on the nucleobase. FIG. 19 schematically illustrates an example synthesis process of the fully-functional cyclic loop nucleotide (CLN-3A) shown in FIG. 18, with X═O and Y═O. FIG. 20 schematically illustrates an example synthesis process of the fully-functional cyclic loop nucleotide (CLN-3B) shown in FIG. 18, with X═NH and Y═O. FIG. 21 schematically illustrates an example synthesis process of the fully-functional cyclic loop nucleotide (CLN-3C) shown in FIG. 18, with X═$CH_2$ and Y═O.

Figure 22:
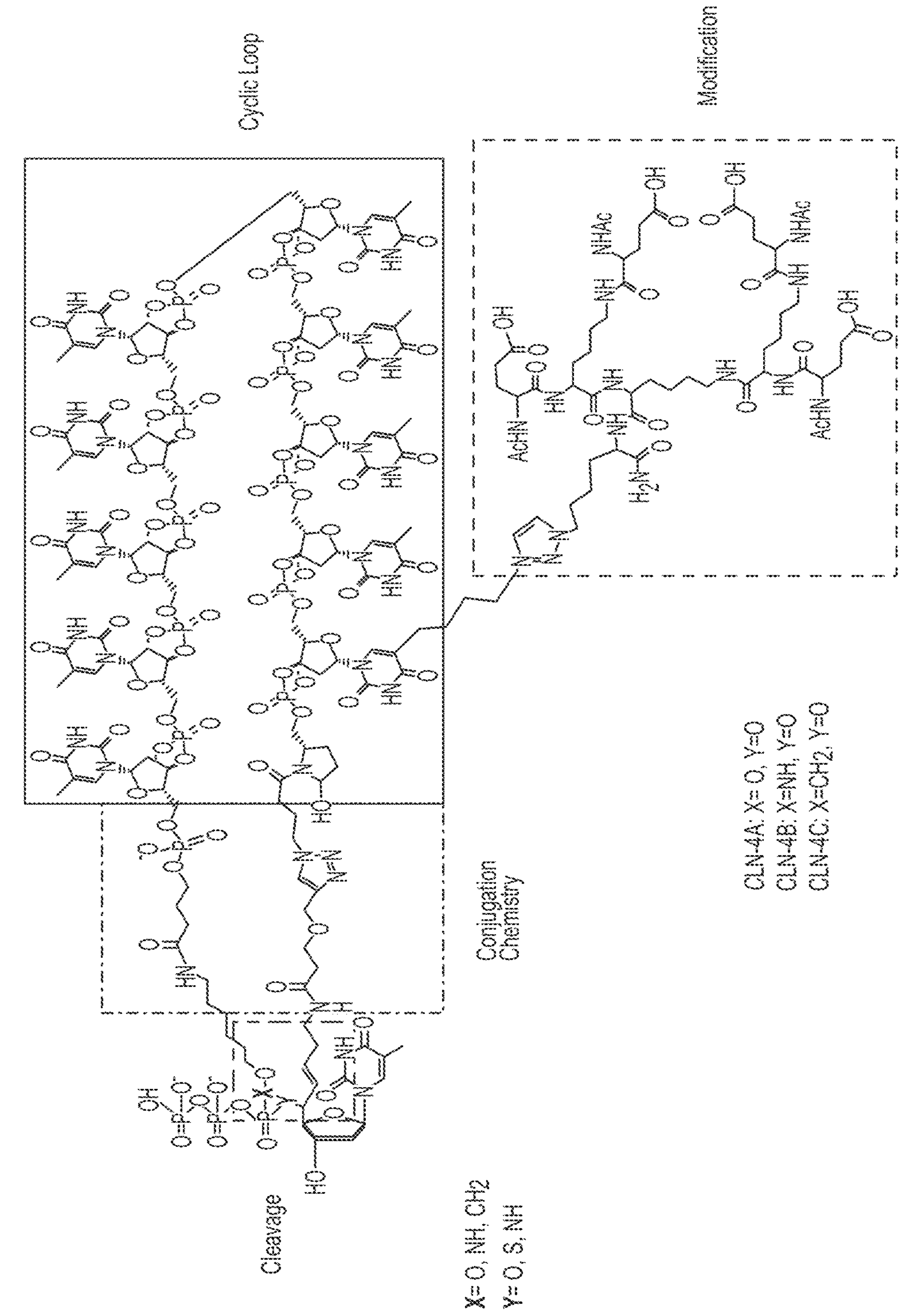
FIG. 22 schematically illustrates an example of a fourth design of a fully-functional cyclic loop nucleotide (CLN-4), where X may be O, NH, NSO2 or CH2 and Y may be O, S, or NH, having an alpha phosphate-allyl linked non-symmetrical loop, and a arresting construct on the loop.
Figure 23:
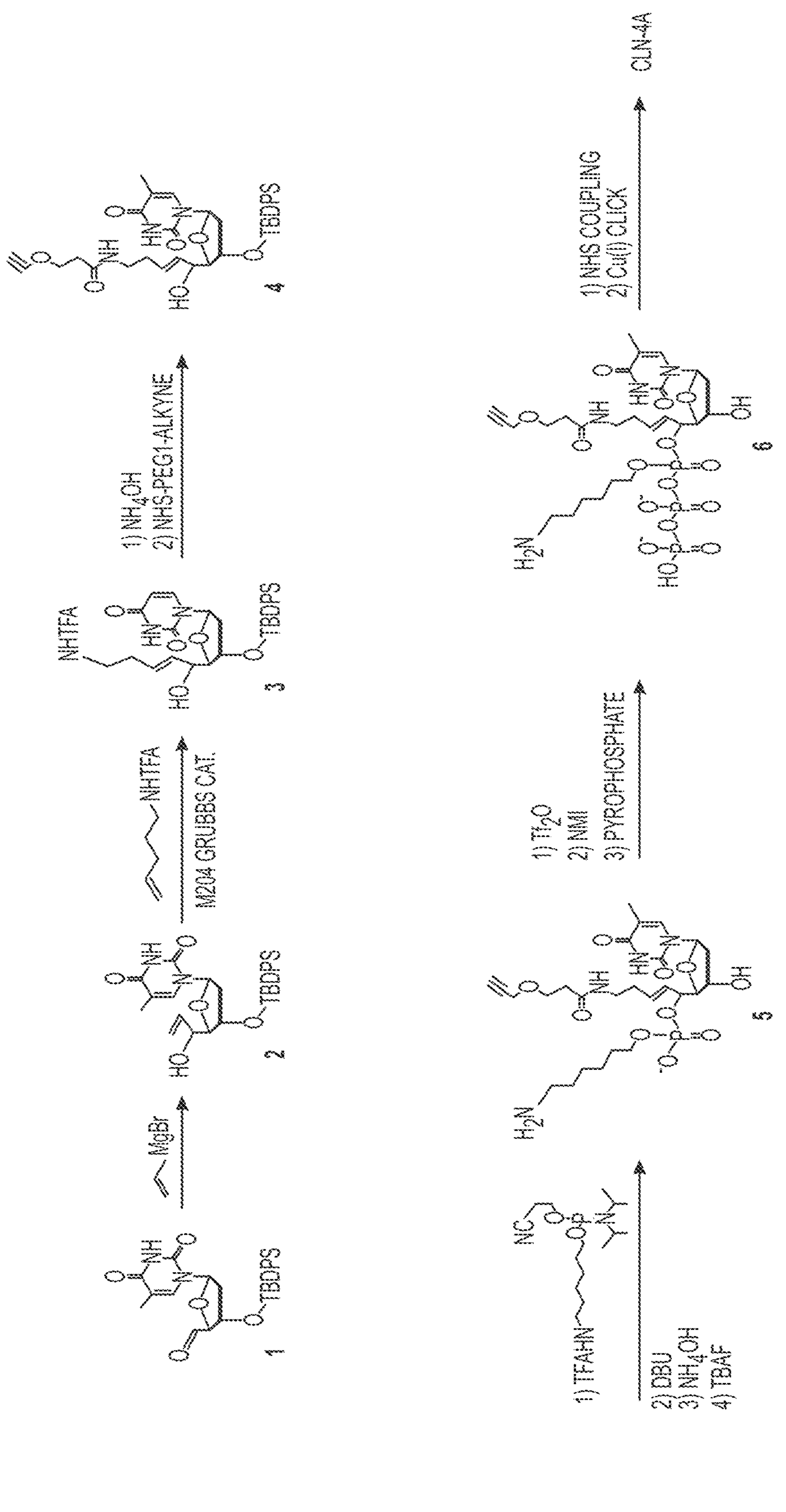
FIG. 23 schematically illustrates an example synthesis process of the fully-functional cyclic loop nucleotide (CLN-4A).
Figure 24:
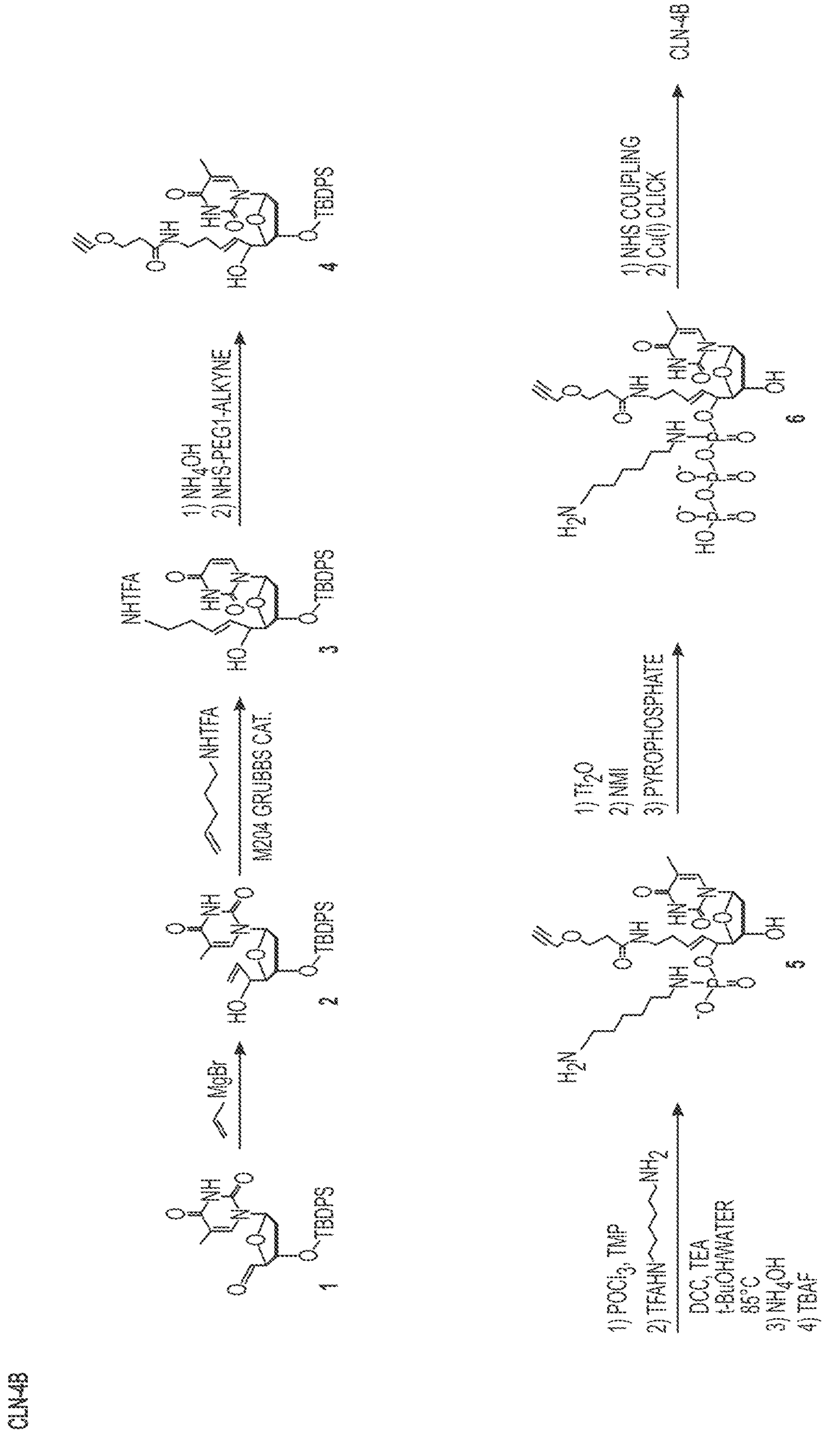
FIG. 24 schematically illustrates an example synthesis process of the fully-functional cyclic loop nucleotide (CLN-4B).
Figure 25:
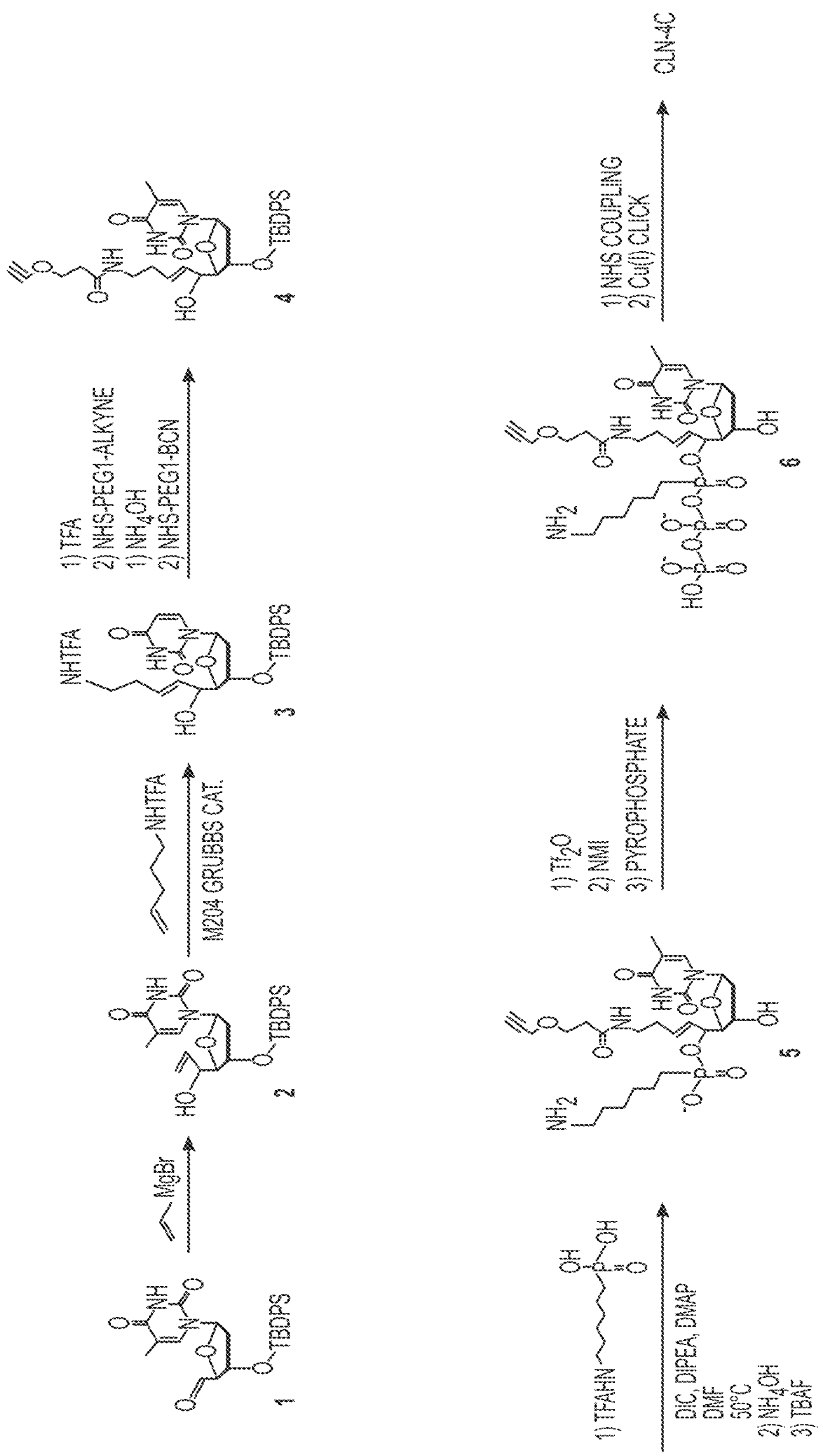
FIG. 25 schematically illustrates an example synthesis process of the fully-functional cyclic loop nucleotide (CLN-4C).

FIG. 22 schematically illustrates an example of a fourth design of a fully-functional cyclic loop nucleotide (CLN-4), where X may be O, NH, $NSO_2$ or $CH_2$ and Y may be O, S, or NH, having an alpha phosphate-allyl linked non-symmetrical loop, and a arresting construct on the loop. FIG. 23 schematically illustrates an example synthesis process of the fully-functional cyclic loop nucleotide (CLN-4A) shown in FIG. 22, with X═O and Y═O. FIG. 24 schematically illustrates an example synthesis process of the fully-functional cyclic loop nucleotide (CLN-4B) shown in FIG. 22, with X═NH and Y═O. FIG. 25 schematically illustrates an example synthesis process of the fully-functional cyclic loop nucleotide (CLN-4C) shown in FIG. 22, with X═$CH_2$ and Y═O.

Figure 26:
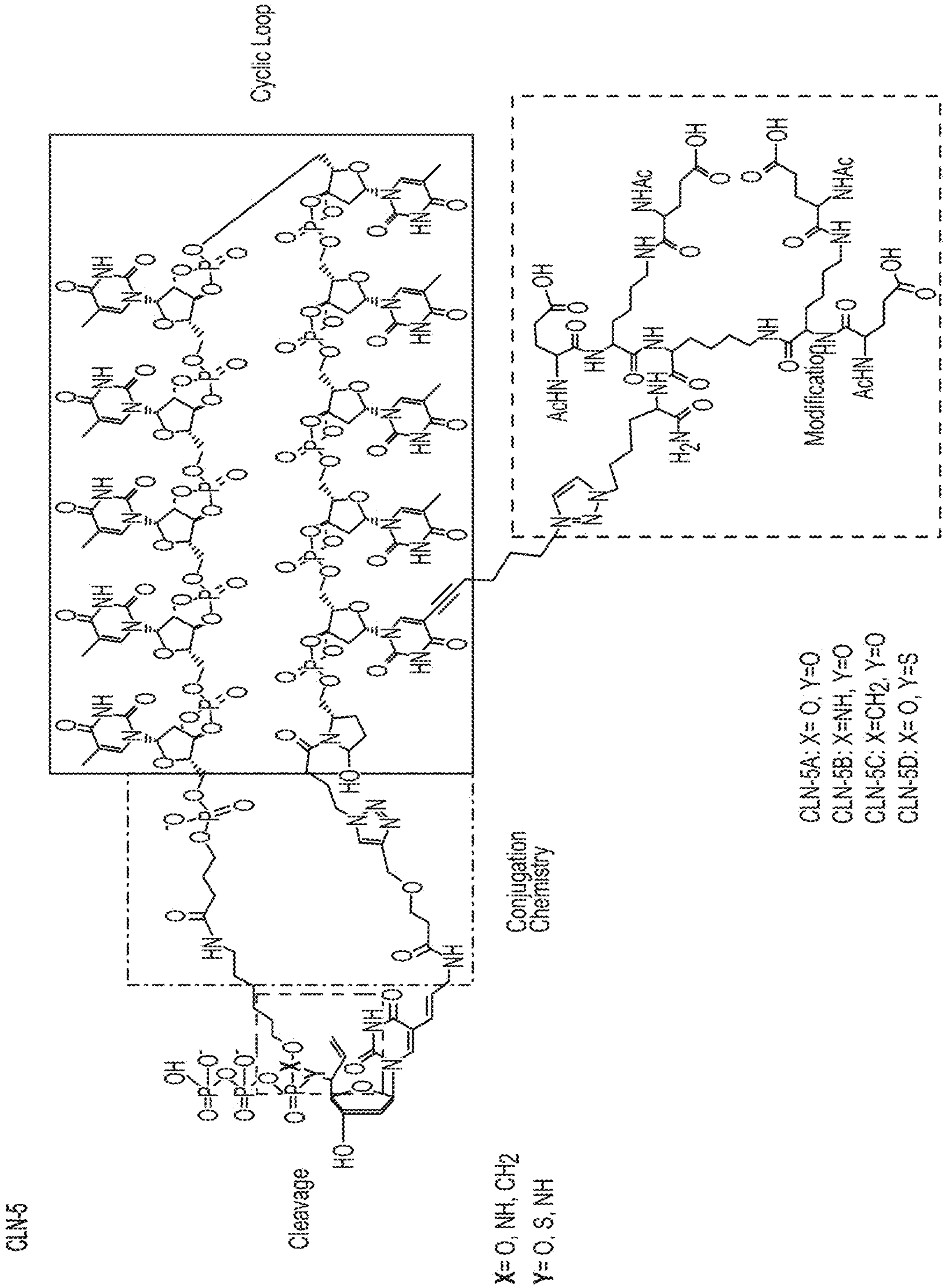
FIG. 26 schematically illustrates an example of a fifth design of a fully-functional cyclic loop nucleotide (CLN-5), where X may be O, NH, NSO2 or CH2 and Y may be O, S, or NH, having an alpha phosphate-base linked non-symmetrical loop, and a arresting construct on the loop.
Figure 27:
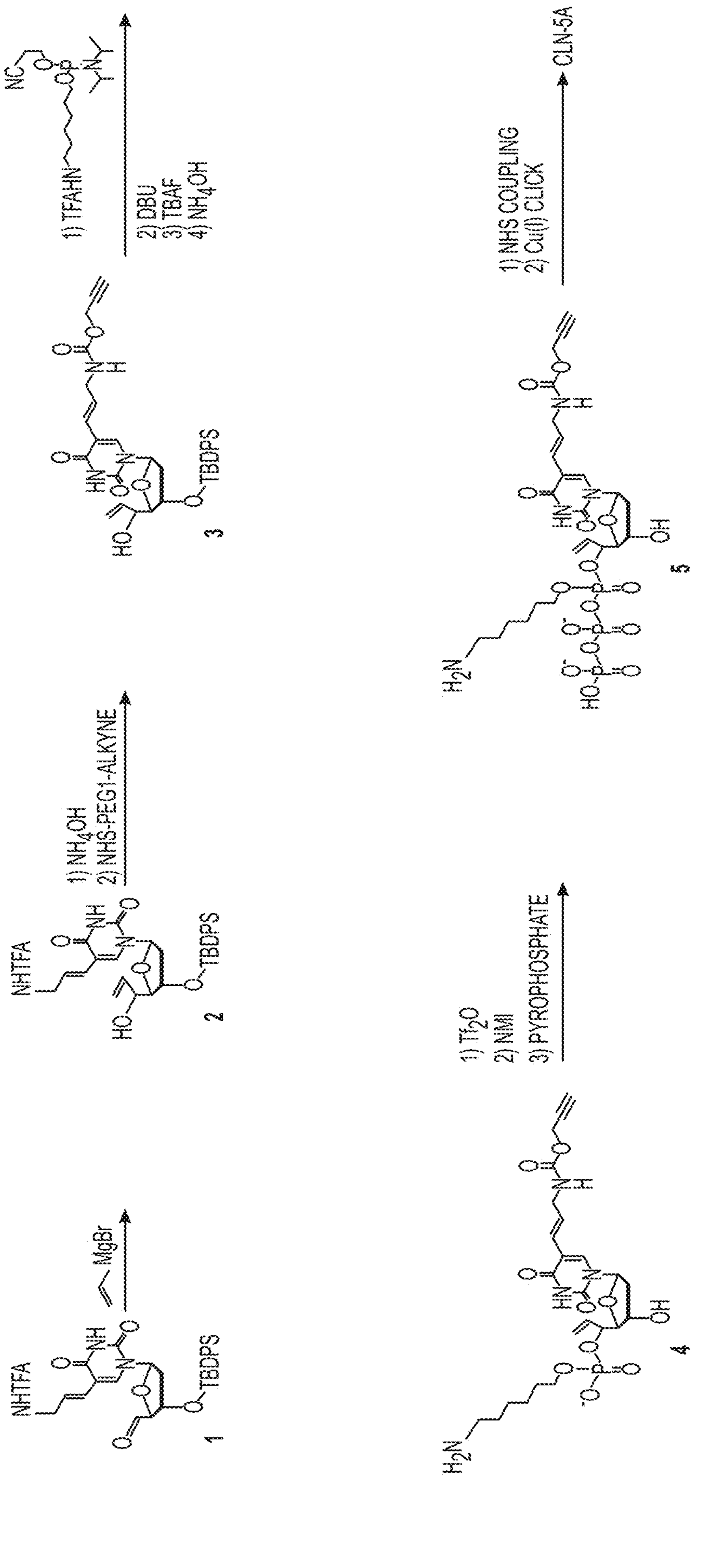
FIG. 27 schematically illustrates an example synthesis process of the fully-functional cyclic loop nucleotide (CLN-5A).
Figure 28:
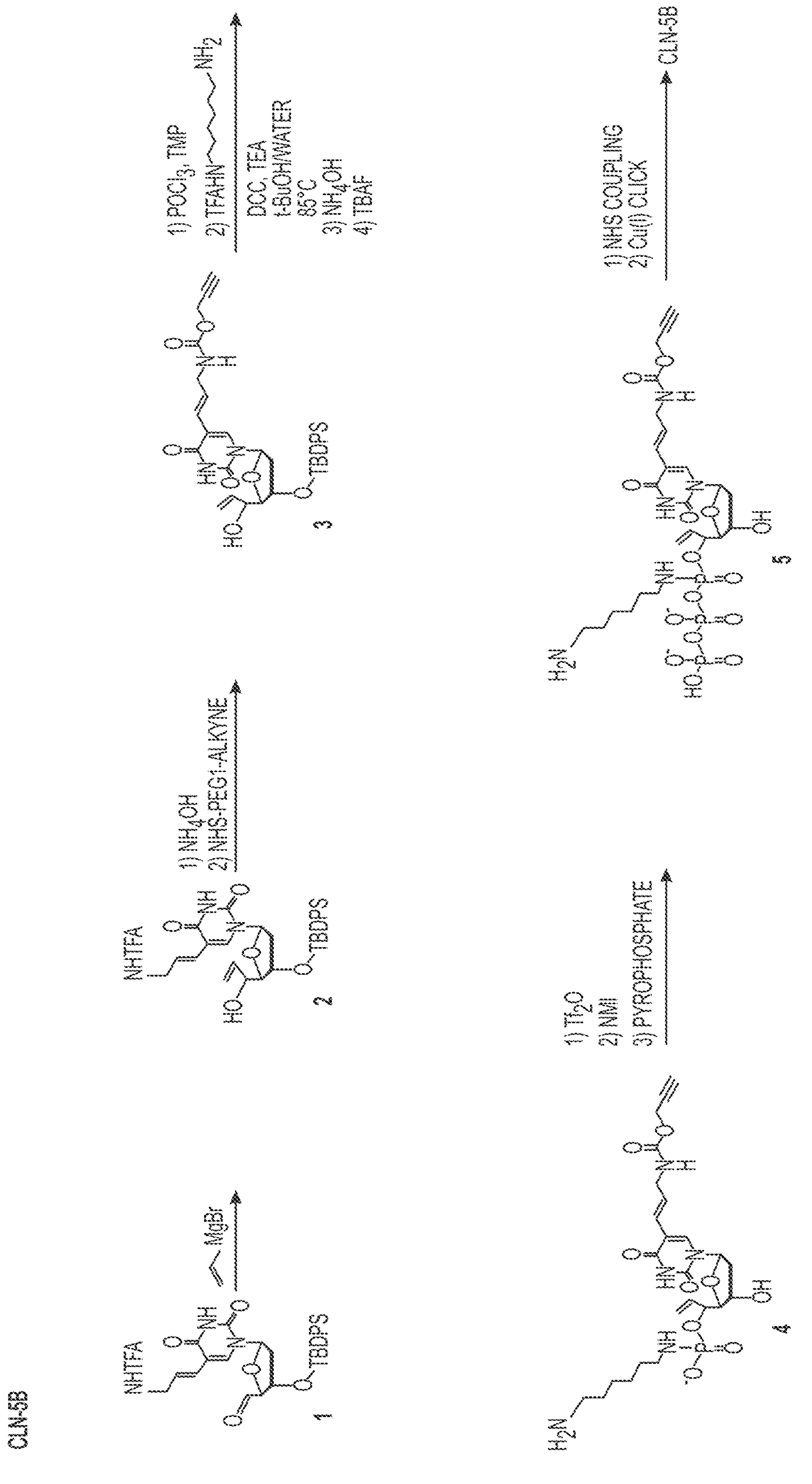
FIG. 28 schematically illustrates an example synthesis process of the fully-functional cyclic loop nucleotide (CLN-5B).
Figure 29:
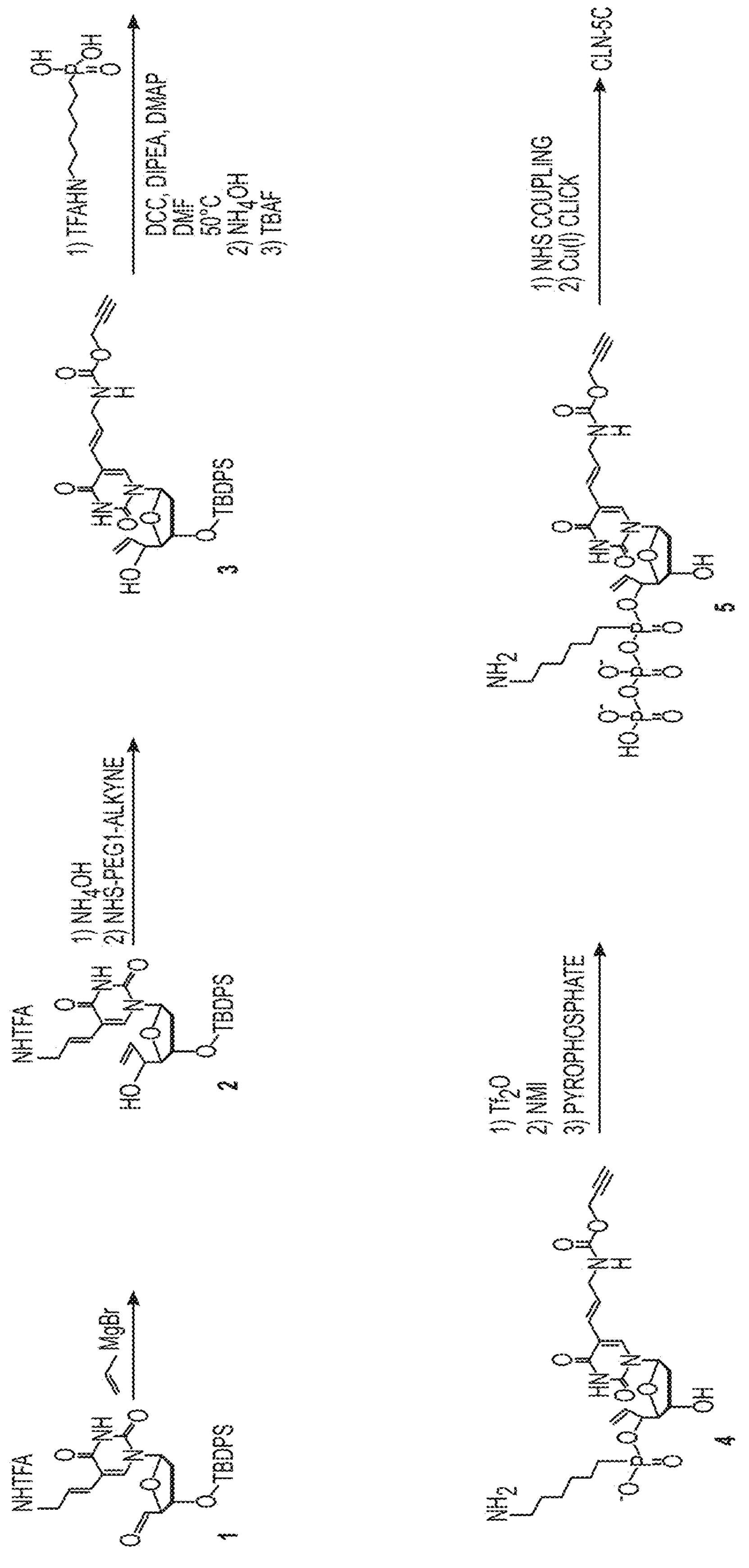
FIG. 29 schematically illustrates an example synthesis process of the fully-functional cyclic loop nucleotide (CLN-5C).
Figure 30:
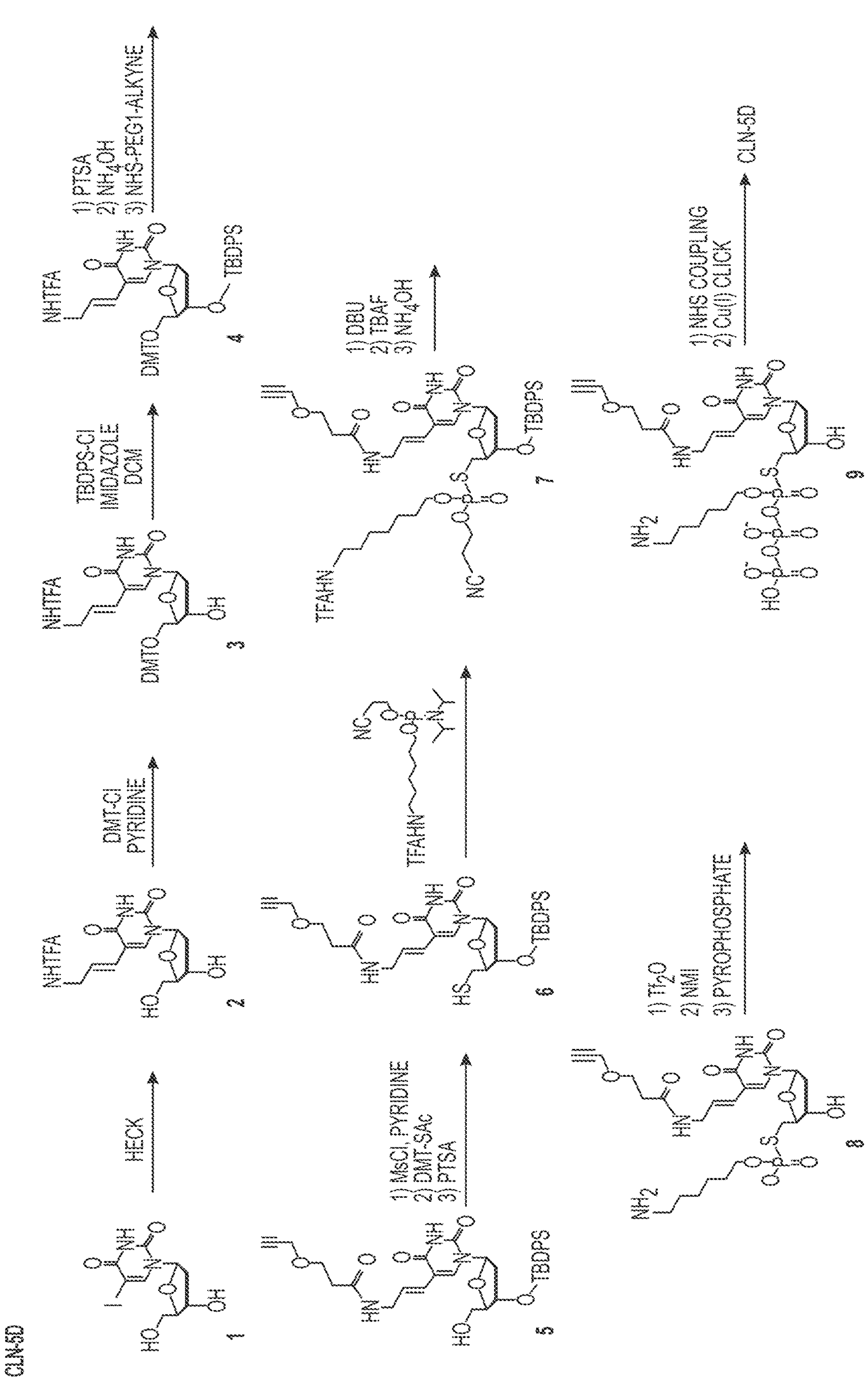
FIG. 30 schematically illustrates an example synthesis process of the fully-functional cyclic loop nucleotide (CLN-5D).

FIG. 26 schematically illustrates an example of a fifth design of a fully-functional cyclic loop nucleotide (CLN-5), where X may be O, NH, $NSO_2$ or $CH_2$ and Y may be O, S, or NH, having an alpha phosphate-base linked non-symmetrical loop, and a arresting construct on the loop. FIG. 27 schematically illustrates an example synthesis process of the fully-functional cyclic loop nucleotide (CLN-5A) shown in FIG. 26, with X═O and Y═O. FIG. 28 schematically illustrates an example synthesis process of the fully-functional cyclic loop nucleotide (CLN-5B) shown in FIG. 26, with X═NH and Y═O. FIG. 29 schematically illustrates an example synthesis process of the fully-functional cyclic loop nucleotide (CLN-5C) shown in FIG. 26, with X═$CH_2$ and Y═O. FIG. 30 schematically illustrates an example synthesis process of the fully-functional cyclic loop nucleotide (CLN-5D) shown in FIG. 26, with X═O and Y═S that is compatible with phosphorothiolate cleavage.

Figure 31:
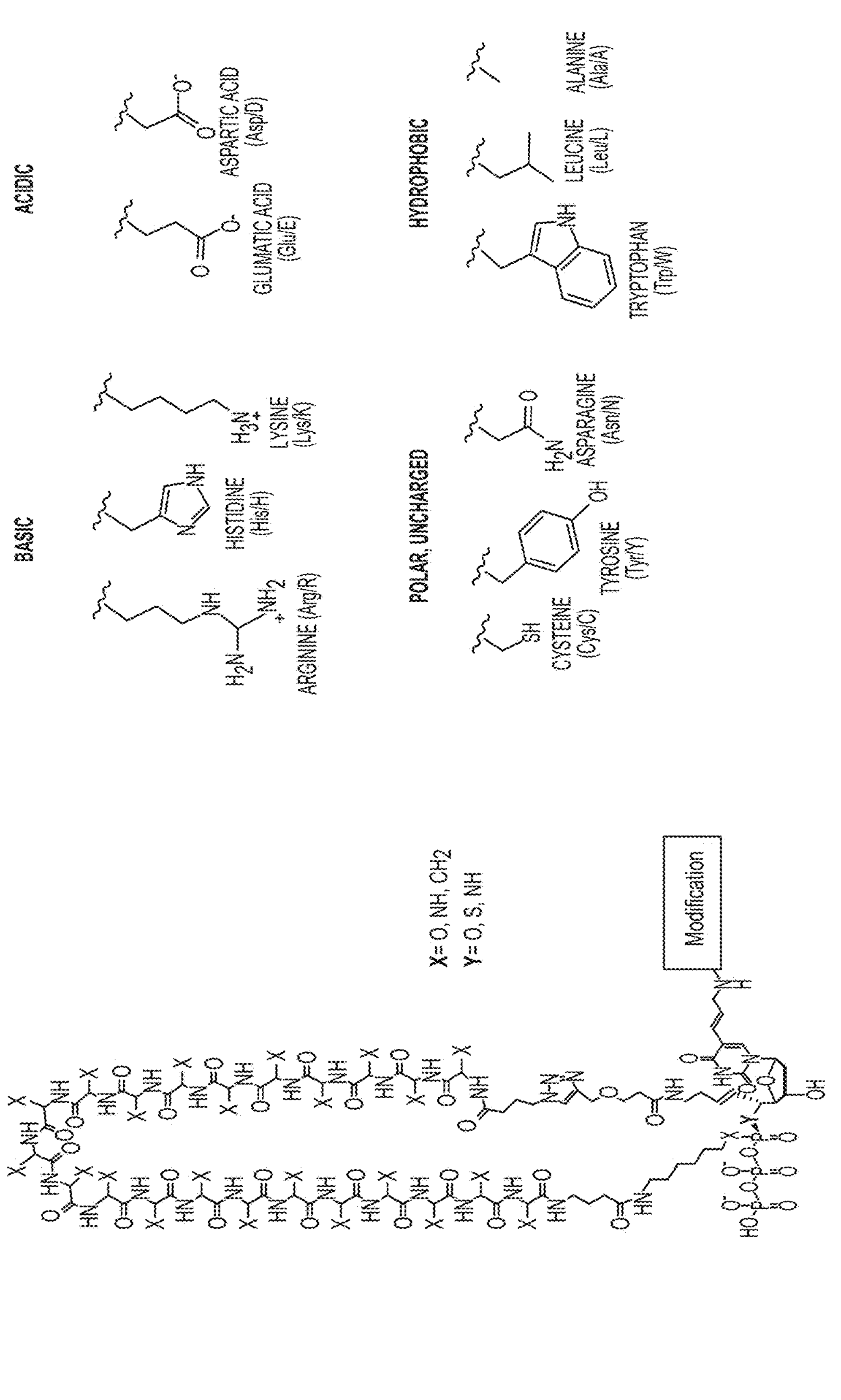
FIG. 31 schematically illustrates an example of a sixth design of a cyclic loop nucleotide (CLN-6), wherein X may be O, NH, NSO2 or CH2 and Y may be O, S, or NH, having a peptide-based cyclic loop, and a arresting construct on the nucleobase.

FIG. 31 schematically illustrates an example of a sixth design of a cyclic loop nucleotide (CLN-6), wherein X may be O, NH, $NSO_2$ or $CH_2$ and Y may be O, S, or NH, having a peptide-based cyclic loop, and a arresting construct on the nucleobase. The peptide-based cyclic loop may comprise various amino acid residues, for example, Arginine, histidine, lysine, glutamic acid, aspartic acid, cysteine, tyrosine, asparagine, tryptophan, leucine, and alanine. The amino acid side chains Z on the cyclic loop are depicted in FIG. 31.

Some of the further examples below relate to symmetrical cyclic loop nucleotides and cyclic loop k-mer oligonucleotides, which may include nucleosidic bases, non-nucleosidic residues, sp9, sp18, abasic nucleotides, C3 moieties, or peptide residues. Some of the further examples below relate to asymmetric cyclic loop nucleotides and cyclic loop k-mer oligonucleotides, which may include nucleosidic bases and non-nucleosidic residues.

Figure 32:
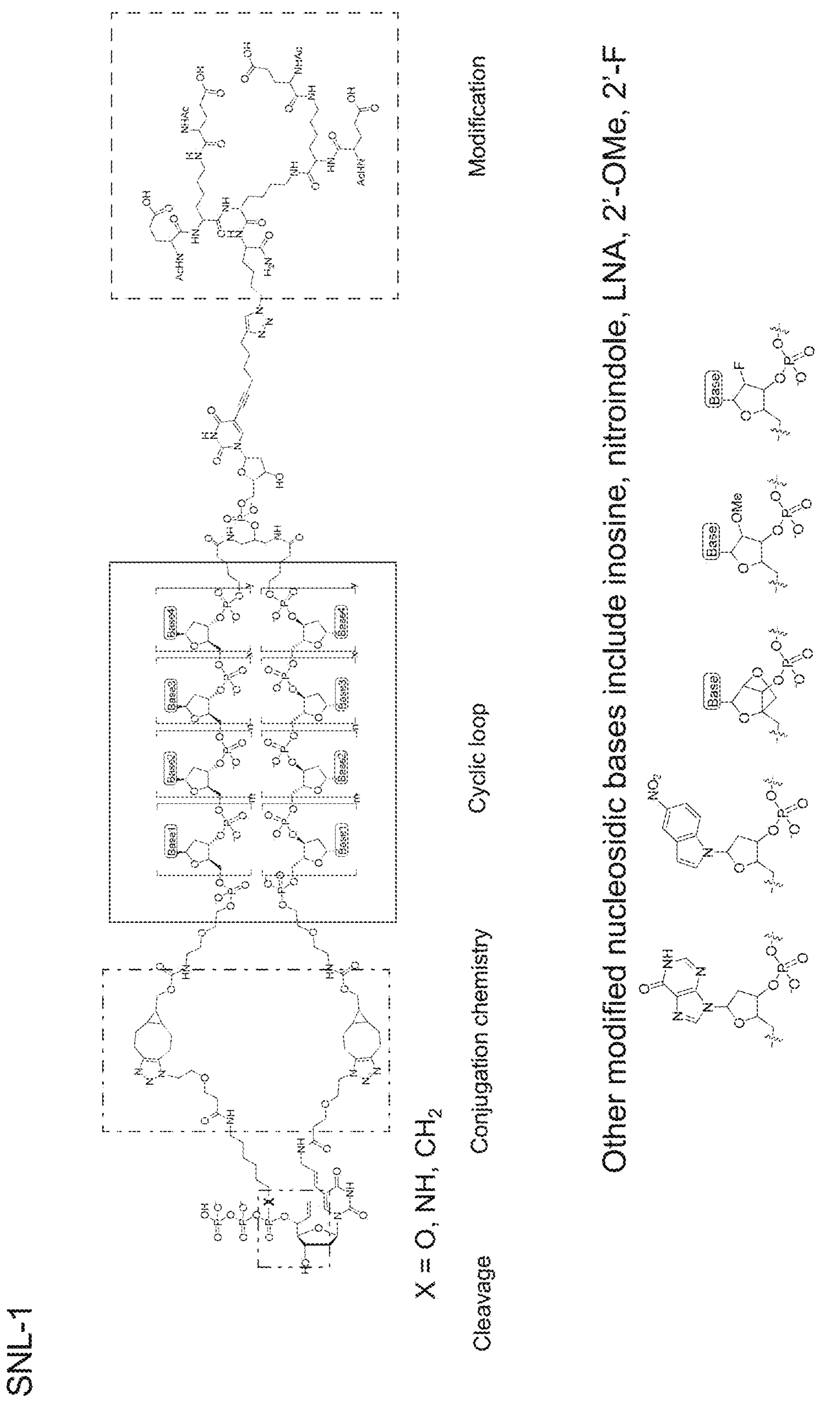
FIG. 32 schematically illustrates an example of a seventh design of a cyclic loop nucleotide (SNL-1), where X may be O, NH, NSO2 or CH2 having an alpha phosphate-base linked symmetrical nucleosidic loop, and a arresting construct on the loop.

FIG. 32 schematically illustrates an example of a seventh design of a cyclic loop nucleotide (SNL-1), where X may be O, NH, $NSO_2$ or $CH_2$ having an alpha phosphate-base linked symmetrical nucleosidic loop, and a arresting construct on the loop. In some embodiments, the cyclic loop may comprise one or more different nucleobases. For example, the nucleoside may include inosine, nitroindole, or the likes. In some embodiments, other nucleosidic bases with modified sugar, for example, locked nucleic acid (LNA), 2'-Ome, or 2'-F, may be used in the cyclic loop. The structures of the non-limiting nucleosidic bases are also depicted in FIG. 32.

FIG. 33 schematically illustrates an example of an eighth design of a cyclic loop nucleotide (SNNL-1), where X may be O, NH, or $CH_2$, having an alpha phosphate-base linked symmetrical non-nucleosidic loop, and a arresting construct on the loop. The cyclic loop may comprise one or more of the following moieties:

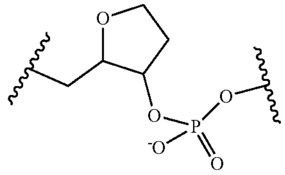
,

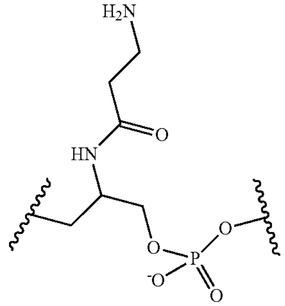
,

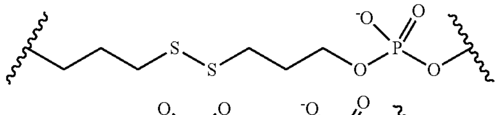
,

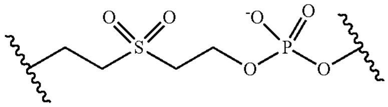
,

-continued

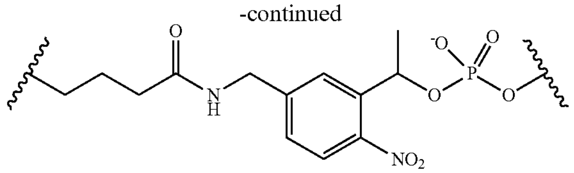

alkyl (C3-C12) phosphate, polyethylene glycol phosphate, other modified non-nucleosidic moieties, for example, spermine, phosphorothioate, or methylphosphonate, may be used in the cyclic loop in some embodiments.

Figure 34:
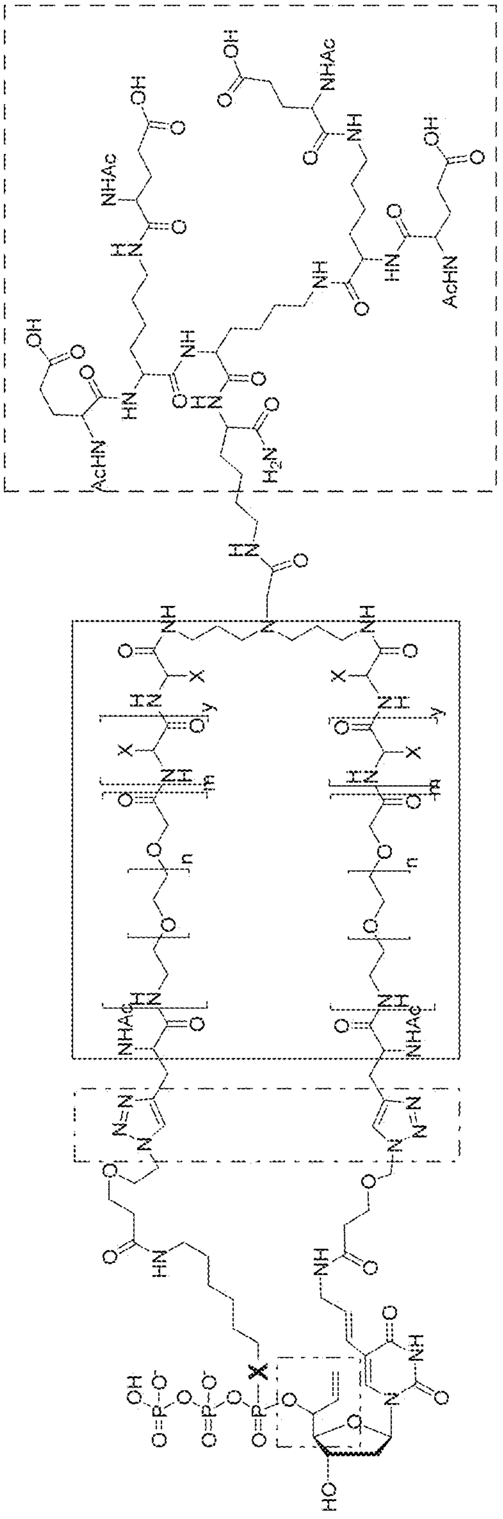
FIG. 34 schematically illustrates an example of a ninth design of a cyclic loop nucleotide (SPL-1), where X may be O, NH, NSO2 or CH2, having an alpha phosphate-base linked symmetrical peptide loop, and a arresting construct on the loop.

FIG. 34 schematically illustrates an example of a ninth design of a cyclic loop nucleotide (SPL-1), where X may be O, NH, $NSO_2$ or $CH_2$, having an alpha phosphate-base linked symmetrical peptide loop, and a arresting construct on the loop. Other modified amino acid residues or moieties that are compatible for use in peptide synthesis, for example PEG2, 6, 11, 12, or Lys(FITC), may be used in some embodiments.

Figure 35:
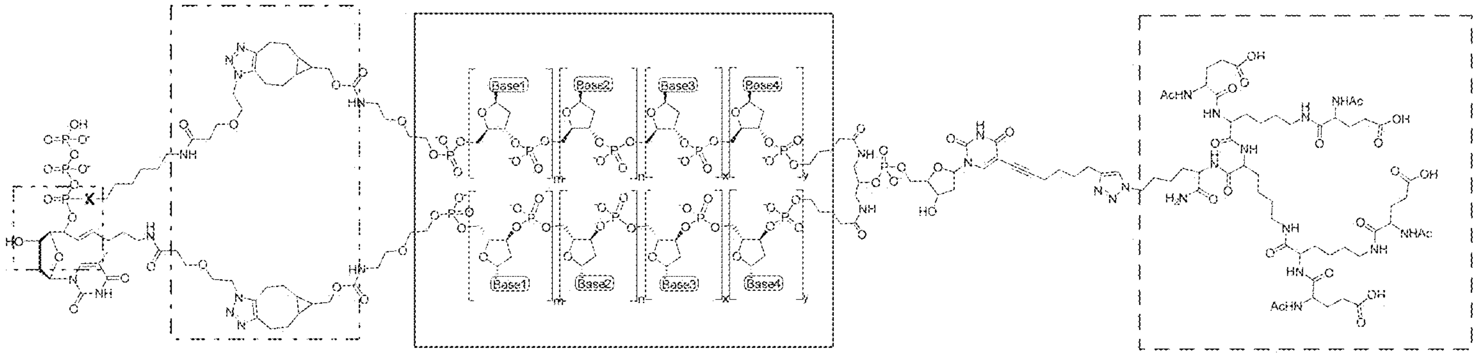
FIG. 35 schematically illustrates an example of a tenth design of a cyclic loop nucleotide (SNL-2), where X may be O, NH, NSO2 or CH2, having an alpha phosphate-allyl linked symmetrical nucleosidic loop, and a arresting construct on the loop.

FIG. 35 schematically illustrates an example of a tenth design of a cyclic loop nucleotide (SNL-2), where X may be O, NH, $NSO_2$ or $CH_2$, having an alpha phosphate-allyl linked symmetrical nucleosidic loop, and a arresting construct on the loop. Other modified nucleosidic bases, for example inosine, nitroindole, LNA, 2'-Ome, or 2'-F, may be used in some embodiments.

Figure 36:
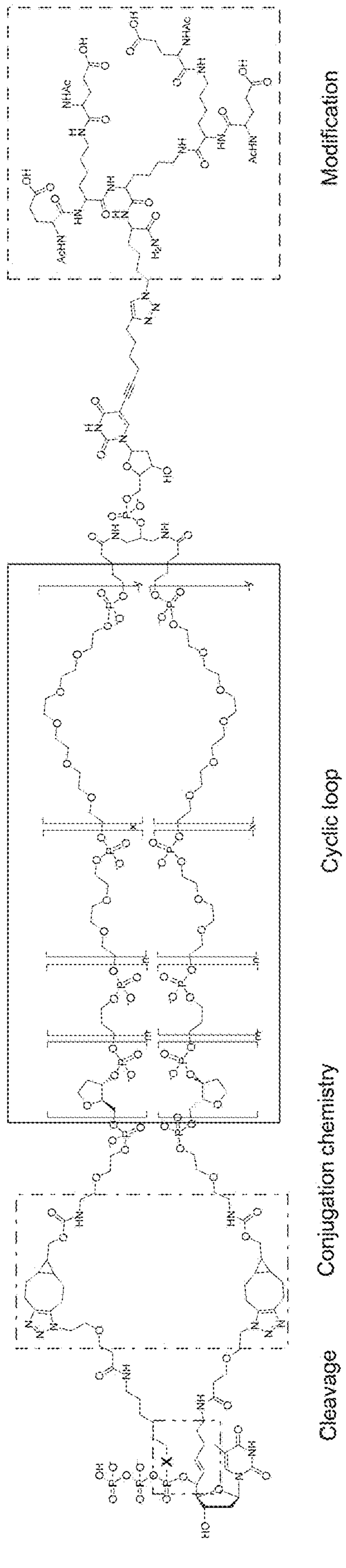
FIG. 36 schematically illustrates an example of an eleventh design of a cyclic loop nucleotide (SNNL-2), where X may be O, NH, NSO2 or CH2 having an alpha phosphate-allyl linked symmetrical non-nucleosidic loop, and a arresting construct on the loop.

FIG. 36 schematically illustrates an example of an eleventh design of a cyclic loop nucleotide (SNNL-2), where X may be O, NH, $NSO_2$ or $CH_2$ having an alpha phosphate-allyl linked symmetrical non-nucleosidic loop, and a arresting construct on the loop. Other modified non-nucleosidic moieties, for example alkyl (C3-C12), spermine, phosphorothioate, or methylphosphonate, may be used in some embodiments.

Figure 37:
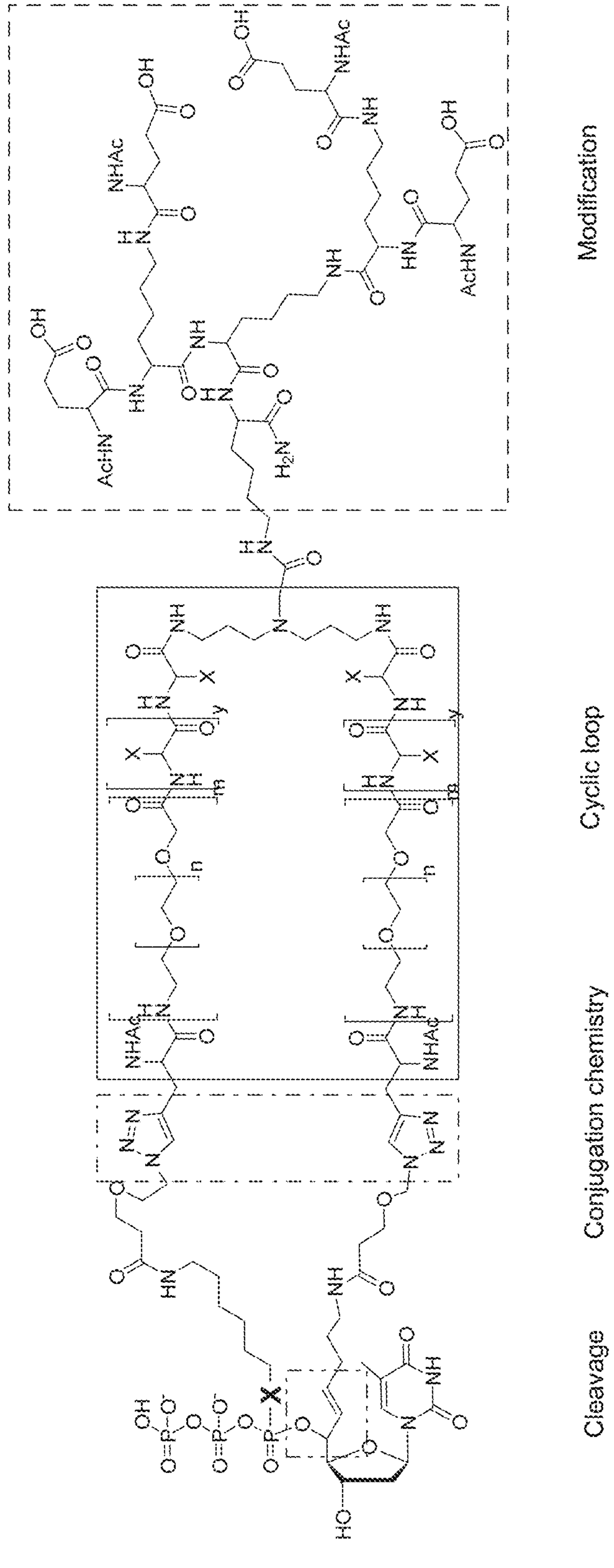
FIG. 37 schematically illustrates an example of a twelfth design of a cyclic loop nucleotide (SPL-2), where X may be O, NH, NSO2 or CH2 having an alpha phosphate-allyl linked symmetrical peptide loop, and a arresting construct on the loop.

FIG. 37 schematically illustrates an example of a twelfth design of a cyclic loop nucleotide (SPL-2), where X may be O, NH, $NSO_2$ or $CH_2$ having an alpha phosphate-allyl linked symmetrical peptide loop, and a arresting construct on the loop. Other modified amino acid residues or moieties that are compatible for use in peptide synthesis, for example PEG2, 6, 11, 12, or Lys(FITC), may be used in some embodiments.

Figure 38:
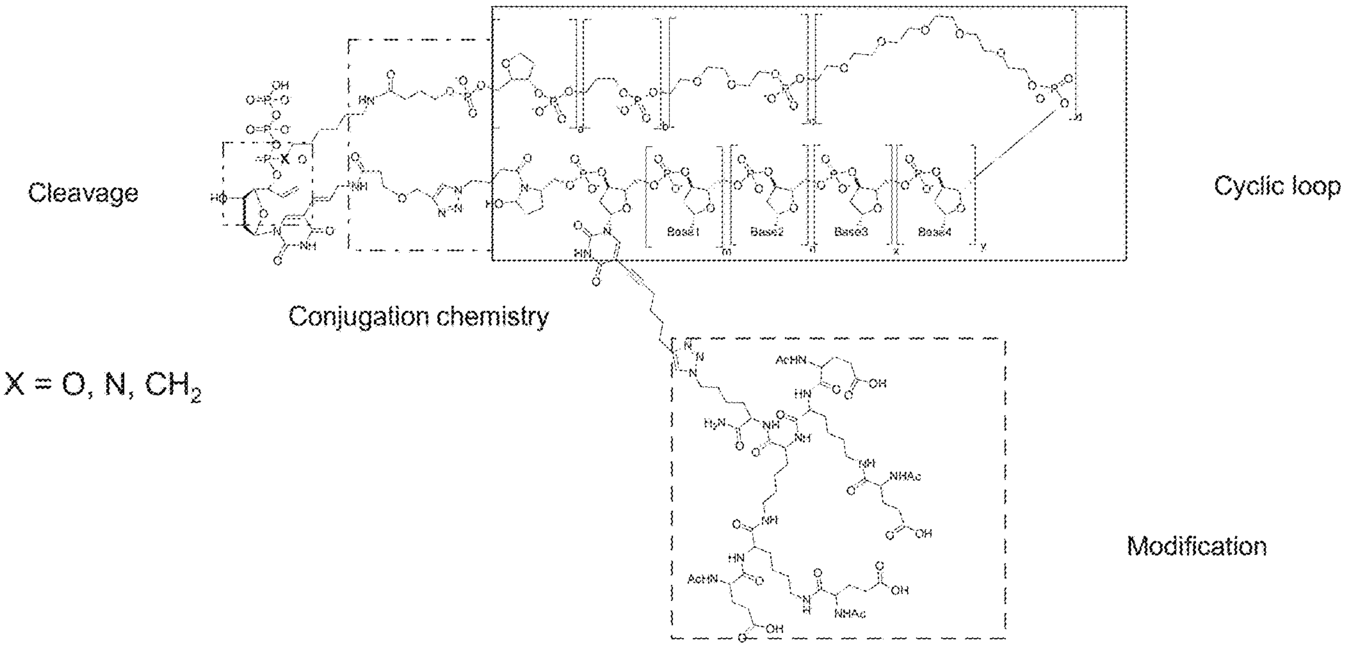
FIG. 38 schematically illustrates an example of a thirteenth design of a cyclic loop nucleotide (ASL-1), where X may be O, NH, NSO2 or CH2, having an alpha phosphate-base linked asymmetrical loop, and a arresting construct on the loop.

FIG. 38 schematically illustrates an example of a thirteenth design of a cyclic loop nucleotide (ASL-1), where X may be O, NH, $NSO_2$ or $CH_2$, having an alpha phosphate-base linked asymmetrical loop, and a arresting construct on the loop. The asymmetrical loop may be formed of a combination of nucleosidic bases, non-nucleosidic moieties, and amino acid residues as shown in the FIG. Other modified nucleosidic bases, for example inosine, nitroindole, LNA, 2'-Ome, or 2'-F, may be used in some embodiments. Other modified non-nucleosidic moieties, for example alkyl (C3-C12), spermine, phosphorothioate, or methylphosphonate, may be used in some embodiments. Other modified amino acid residues or moieties that are compatible for use in peptide synthesis, for example PEG2, 6, 11, 12, or Lys(FITC), may be used in some embodiments.

Figure 39:
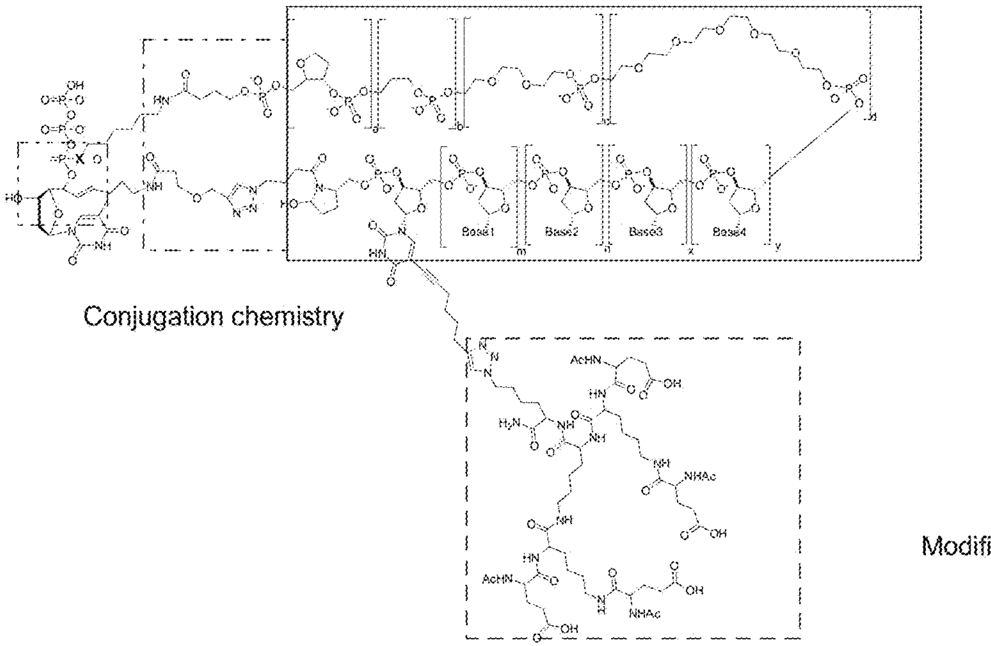
FIG. 39 schematically illustrates an example of a fourteenth design of a cyclic loop nucleotide (ASL-2), where X may be O, NH, NSO2 or CH2 having an alpha phosphate-C5' allyl linked asymmetrical loop, and a arresting construct on the loop.

FIG. 39 schematically illustrates an example of a fourteenth design of a cyclic loop nucleotide (ASL-2), where X may be O, NH, $NSO_2$ or $CH_2$ having an alpha phosphate-C5' allyl linked asymmetrical loop, and a arresting construct on the loop. The asymmetrical loop may be formed of a combination of nucleosidic bases, non-nucleosidic moieties, and amino acid residues as shown in the FIG. 39. Other modified nucleosidic bases, for example inosine, nitroindole, LNA, 2'-Ome, or 2'-F, may be used in some embodiments. Other modified non-nucleosidic moieties, for example spC12, spermine, phosphorothioate, or methylphosphonate, may be used in some embodiments. Other modified amino acid residues or moieties that are compatible for use in peptide synthesis, for example PEG2, 6, 11, 12, or Lys(FITC), may be used in some embodiments.

Figure 40:
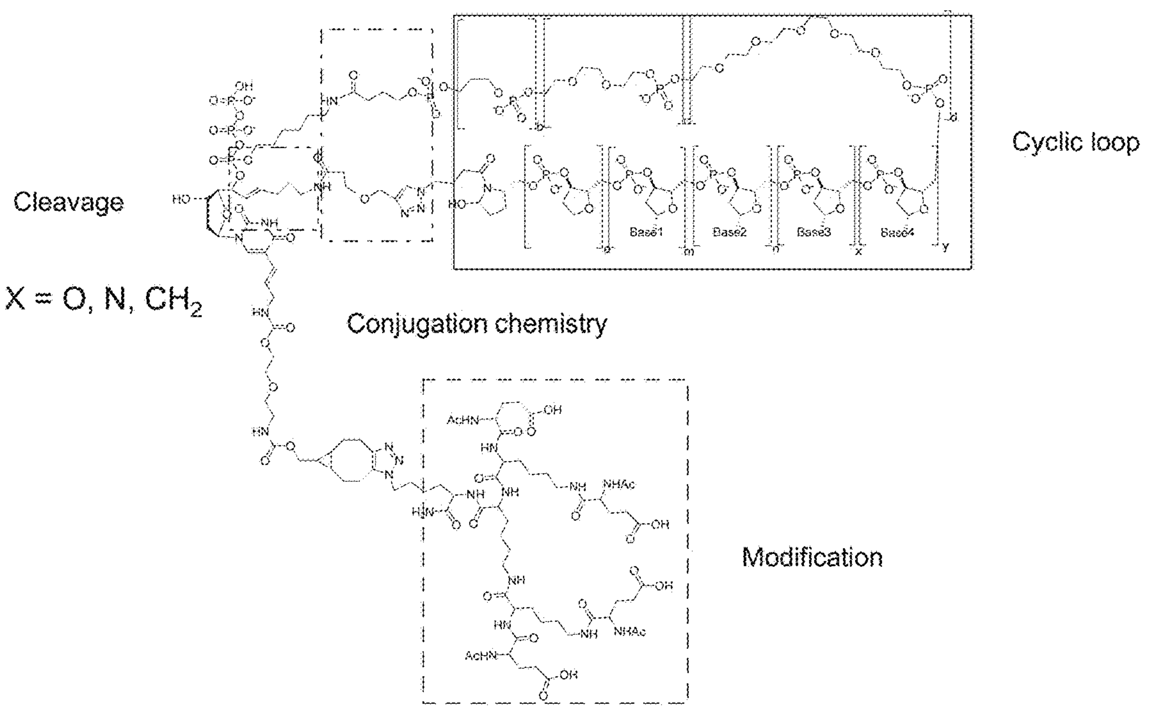
FIG. 40 schematically illustrates an example of a fifteenth design of a cyclic loop nucleotide (ASL-3), where X may be O, NH, NSO2 or CH2, having an alpha phosphate-C5' allyl linked asymmetrical loop, and a arresting construct on the nucleobase.

FIG. 40 schematically illustrates an example of a fifteenth design of a cyclic loop nucleotide (ASL-3), where X may be O, NH, $NSO_2$ or $CH_2$, having an alpha phosphate-C5' allyl linked asymmetrical loop, and a arresting construct on the nucleobase. The asymmetrical loop may be formed of a combination of nucleosidic bases, non-nucleosidic moieties, and amino acid residues as shown in the FIG. 40. Other modified nucleosidic bases, for example inosine, nitroindole, LNA, 2'-Ome, or 2'-F, may be used in some embodiments. Other modified non-nucleosidic moieties, for example alkyl (C3-C12), spermine, phosphorothioate, or methylphosphonate, may be used in some embodiments. Other modified amino acid residues or moieties that are compatible for use in peptide synthesis, for example PEG2, 6, 11, 12, or Lys(FITC), may be used in some embodiments.

Figure 41:
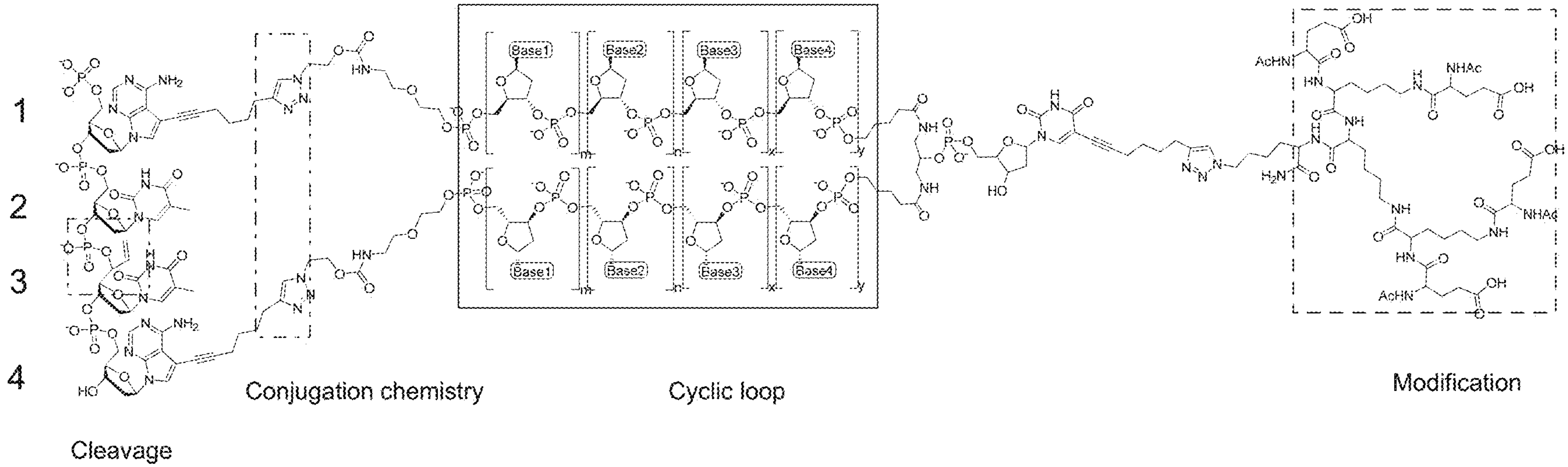
FIG. 41 schematically illustrates an example of a sixteenth design of a cyclic loop 4-mer oligonucleotide (4-mer—SNL-1), having 4-mer oligo with a symmetrical nucleosidic loop, and a arresting construct on the loop.

FIG. 41 schematically illustrates an example of a sixteenth design of a cyclic loop 4-mer oligonucleotide (4-mer—SNL-1), having 4-mer oligo with a symmetrical nucleosidic loop, and a arresting construct on the loop. The loop conjugation positions may be the 1-2, 1-3, 1-4, 2-3, 2-4, or 3-4 bases; the cleavage chemistry may be RNA cleavage, or allyl cleavage; and the cleavage position may be the $2^{nd}$, $3^{rd}$ or $4^{th}$ base.

Figure 42:
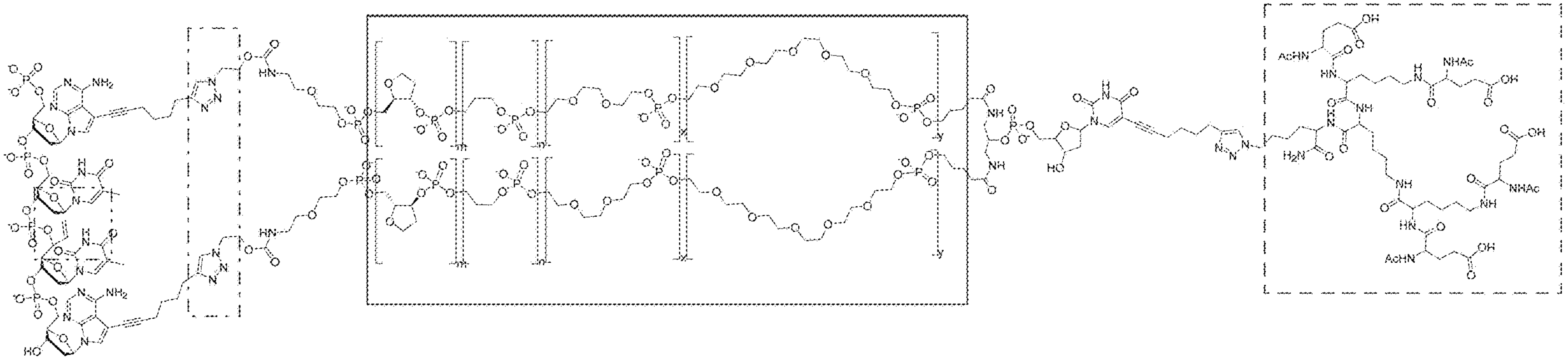
FIG. 42 schematically illustrates an example of a seventeenth design of a cyclic loop 4-mer oligonucleotide (4-mer—SNNL-1), having 4-mer oligo with a symmetrical non-nucleosidic loop, and a arresting construct on the loop.

FIG. 42 schematically illustrates an example of a seventeenth design of a cyclic loop 4-mer oligonucleotide (4-mer—SNNL-1), having 4-mer oligo with a symmetrical non-nucleosidic loop, and a arresting construct on the loop. The loop conjugation positions may be the 1-2, 1-3, 1-4, 2-3, 2-4, or 3-4 bases; the cleavage chemistry may be RNA cleavage, or allyl cleavage; and the cleavage position may be the $2^{nd}$, $3^{rd}$ or $4^{th}$ base.

Figure 43:
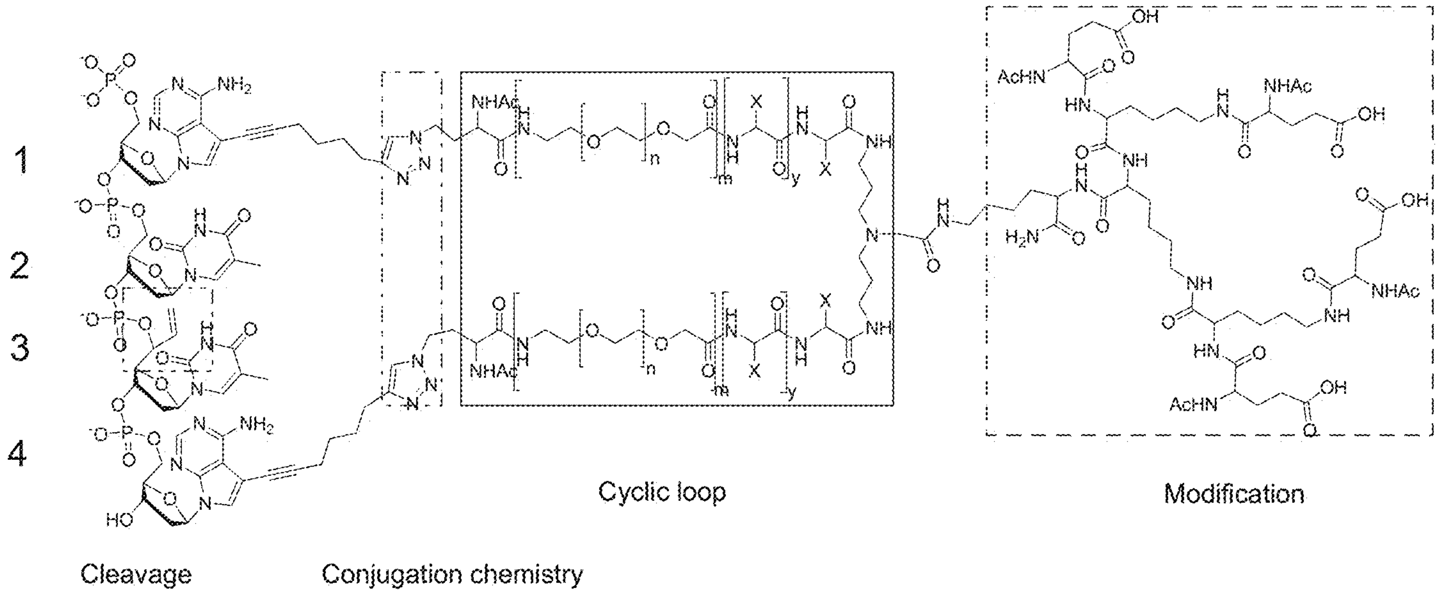
FIG. 43 schematically illustrates an example of an eighteenth design of a cyclic loop 4-mer oligonucleotide (4-mer—SPL-1), having 4-mer oligo with a symmetrical peptide loop, and a arresting construct on the loop.

FIG. 43 schematically illustrates an example of an eighteenth design of a cyclic loop 4-mer oligonucleotide (4-mer—SPL-1), having 4-mer oligo with a symmetrical peptide loop, and a arresting construct on the loop. The loop conjugation positions may be the 1-2, 1-3, 1-4, 2-3, 2-4, or 3-4 bases; the cleavage chemistry may be RNA cleavage, or allyl cleavage; and the cleavage position may be the $2^{nd}$ $3^{rd}$ or $4^{th}$ base.

Figure 44:
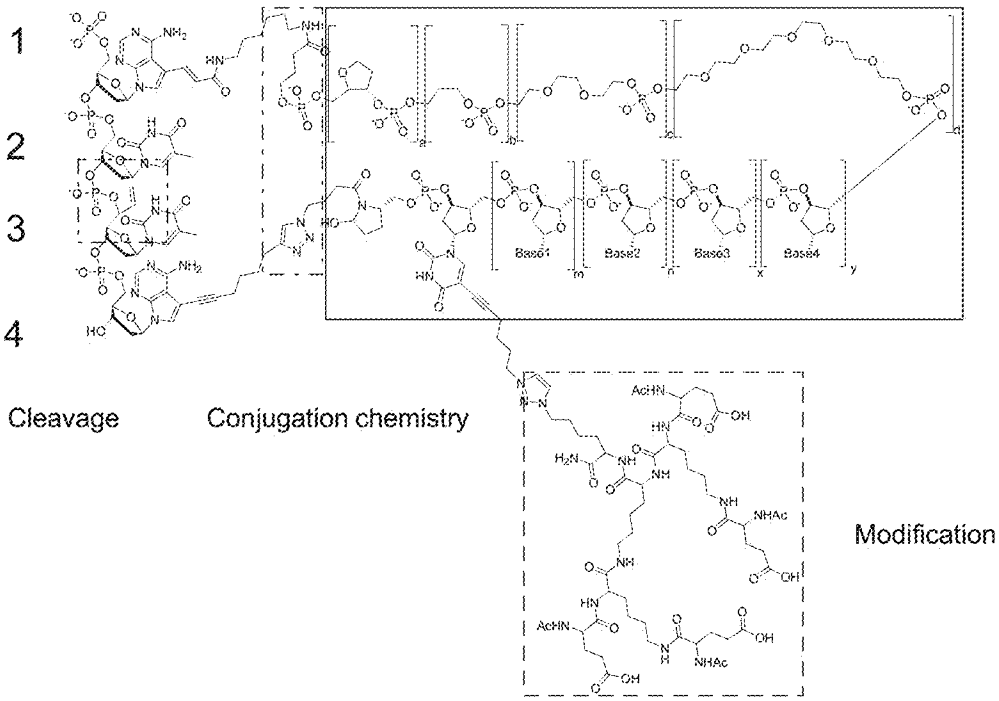
FIG. 44 schematically illustrates an example of a nineteenth design of a cyclic loop 4-mer oligonucleotide (4-mer—ASL-1), having 4-mer oligo with an asymmetrical loop, and a arresting construct on the loop.

FIG. 44 schematically illustrates an example of a nineteenth design of a cyclic loop 4-mer oligonucleotide (4-mer—ASL-1), having 4-mer oligo with an asymmetrical loop, and a arresting construct on the loop. The asymmetrical loop may be formed of a combination of nucleosidic bases, non-nucleosidic moieties, and amino acid residues. The loop conjugation positions may be the 1-2, 1-3, 1-4, 2-3, 2-4, or 3-4 bases; the cleavage chemistry may be RNA cleavage, or allyl cleavage; and the cleavage position may be the $2^{nd}$, $3^{rd}$ or $4^{th}$ base.

Figure 45:
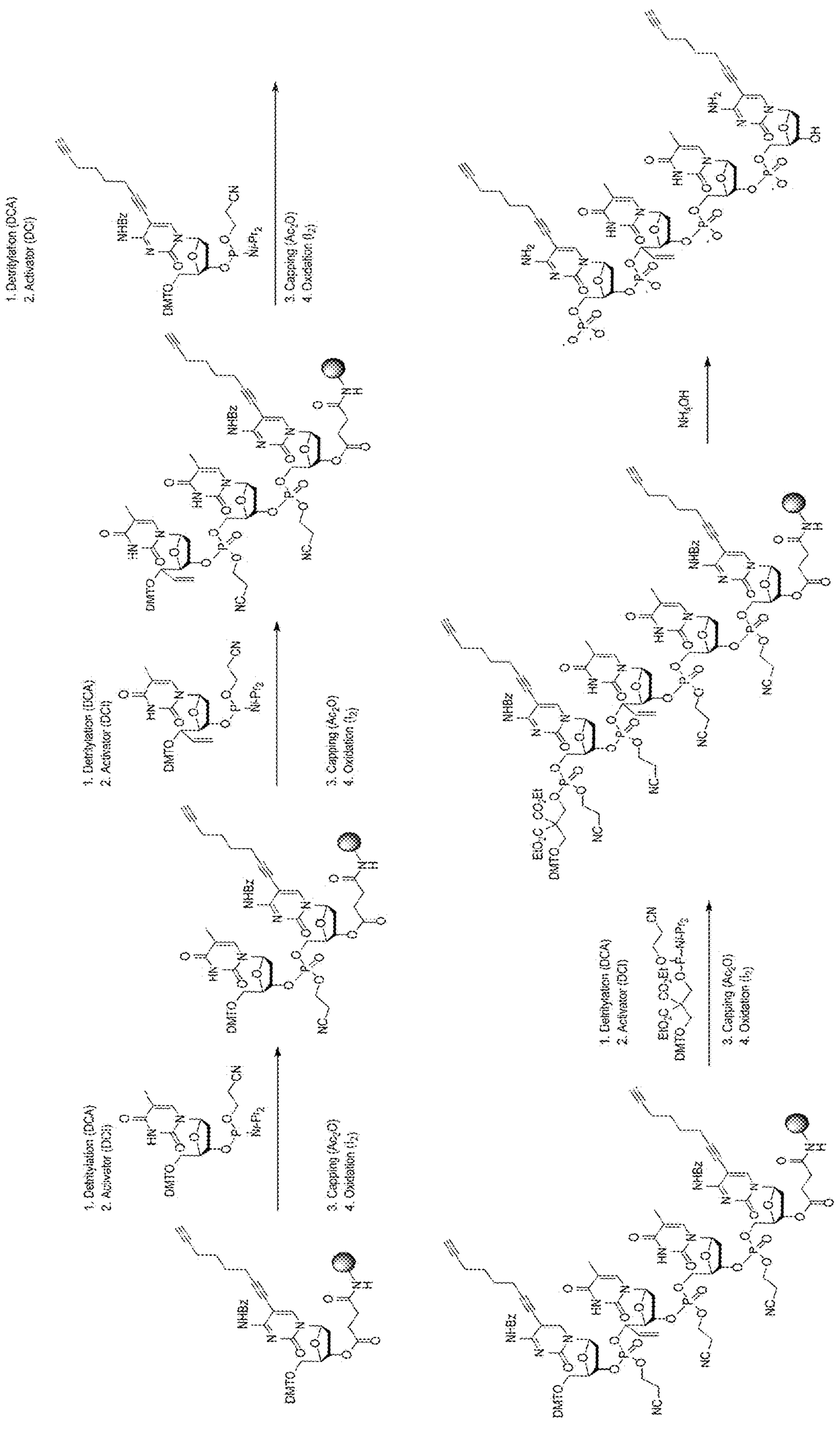
FIG. 45 schematically illustrates an example synthesis process for generating a 4-mer oligonucleotide that may be used to make a cleavable cyclic loop 4-mer oligonucleotide.

FIG. 45 schematically illustrates an example synthesis process of one embodiment of 4-mer oligonucleotide that may be used to make a cleavable cyclic loop 4-mer oligonucleotide.

Example 1: Synthesis and Incorporation of Nucleotide with 5'-Allyl Arresting Construct into Modified Polynucleotide The synthesis of nucleotide with a 5'-allyl arresting construct, and subsequent demonstration that the modified nucleotides can be incorporated by polymerase, followed by cleavage of the allyl group are described.

FIG. 7 shows unexpected and successful experimental results of polymerase incorporation of allyl dTTP. A polymerase incorporated "allyl dTTP" and "ext allyl dTTP" to a template and primer combination, as indicated by the arrow in FIG. 7, for up to 10 successive incorporations. The reaction conditions as well as the definitions of "allyl dTTP" and "ext allyl dTTP" are given in the right panel of FIG. 7. Moreover, "A" and "B" are referring to the optically pure diastereomers arising from the C5' allyl carbon center.

FIG. 7 shows twelve lanes in the gel image. Lanes 1 (starting from the left), 3, 5, 7, 9 and 11 were loaded with reactions run for an hour; and Lanes 2, 4, 6, 8, 10 and 12 were loaded with reactions run for 22 hours. Lanes 1 and 2 show: controls with natural dTTP without any arresting constructs (Note, bands above +10 are seen due to the use of a homopolymeric A template, a common observation). Lanes 3 and 4 show: one isomer of Allyl dTTP ("Allyl A dTTP") is used, the isomer arise from the C-stereogenic center (marked with "+" in the structure shown on the right panel of FIG. 7). Up to +7 incorporation observed after 1 h. Extended duration of 22 h shows exo activity. Lanes 5 and 6 show: one isomer of ext allyl dTTP ("Ext Allyl A dTTP") is used. Up to +7 incorporation observed after 22 h. Slower incorporation possibly due to increased sterics. Lanes 7 and 8 show: the other isomer of Allyl dTTP ("Allyl B dTTP") is used. Up to +10 incorporation observed after 22 h. Lanes 9 and 10 show: the other isomer of ext allyl dTTP ("Ext Allyl B dTTP") is used. Up to +7 incorporation observed after 22 h. Lanes 11 and 12 show: negative controls without any nucleotides added.

Figure 8:
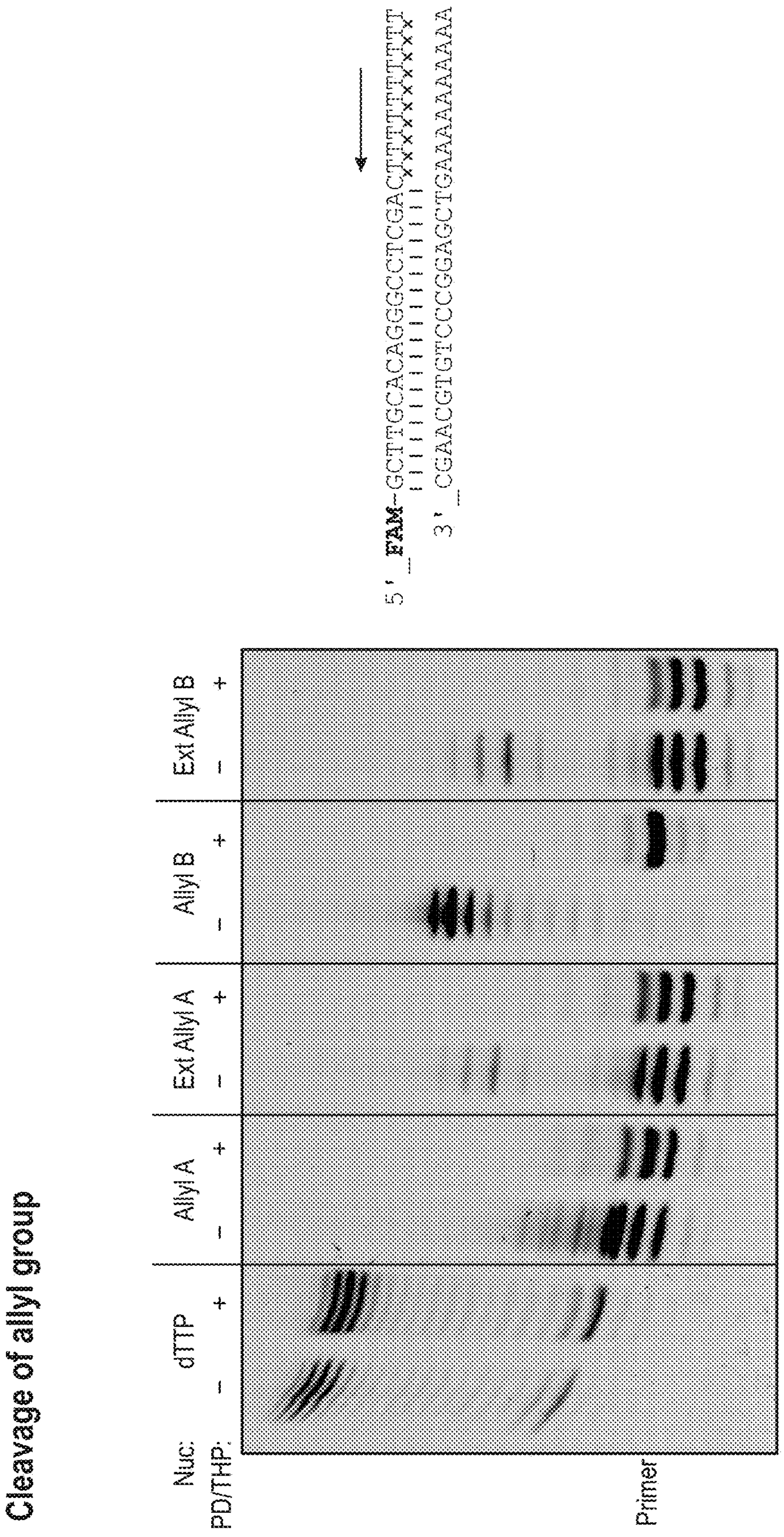
FIG. 8 shows experimental data of cleavage of allyl group.

FIG. 8 shows unexpected and successful experimental results of cleavage of allyl group. After incorporating the nucleotides, samples were treated with 100 mM Pd/THP solution at 37° C. for 1 h to cleave the allyl bonds. Lanes 1, 3, 5, 7 and 9 were loaded with samples after incorporation but not treated with Pd/THP. Lanes 2, 4, 6, 8 and 10 were loaded with the samples after treating with Pd/THP. Lane 1 and 2 show: no allyl groups were present, so no change with and without treating with Pd/THP. Lanes 3 versus 4, 5 versus 6, 7 versus 8, and 9 versus 10 show: treating with Pd/THP reduces the higher bands back to the baseline, demonstrating successful cleavage of the allyl groups.

Example 2: Use of Bridging P—S Nucleotides to Generate Modified Polynucleotides and Subsequent Cleavage The synthesis of modified nucleotide with a bridging P—S substitution, and subsequent demonstration that the modified nucleotides can be incorporated by polymerase, followed by cleavage of the phosphorus-sulfur bond are described.

a. Synthesis of Bridging P—S Nucleotides

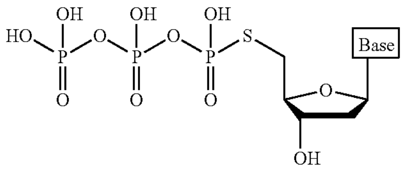

Figure 46:
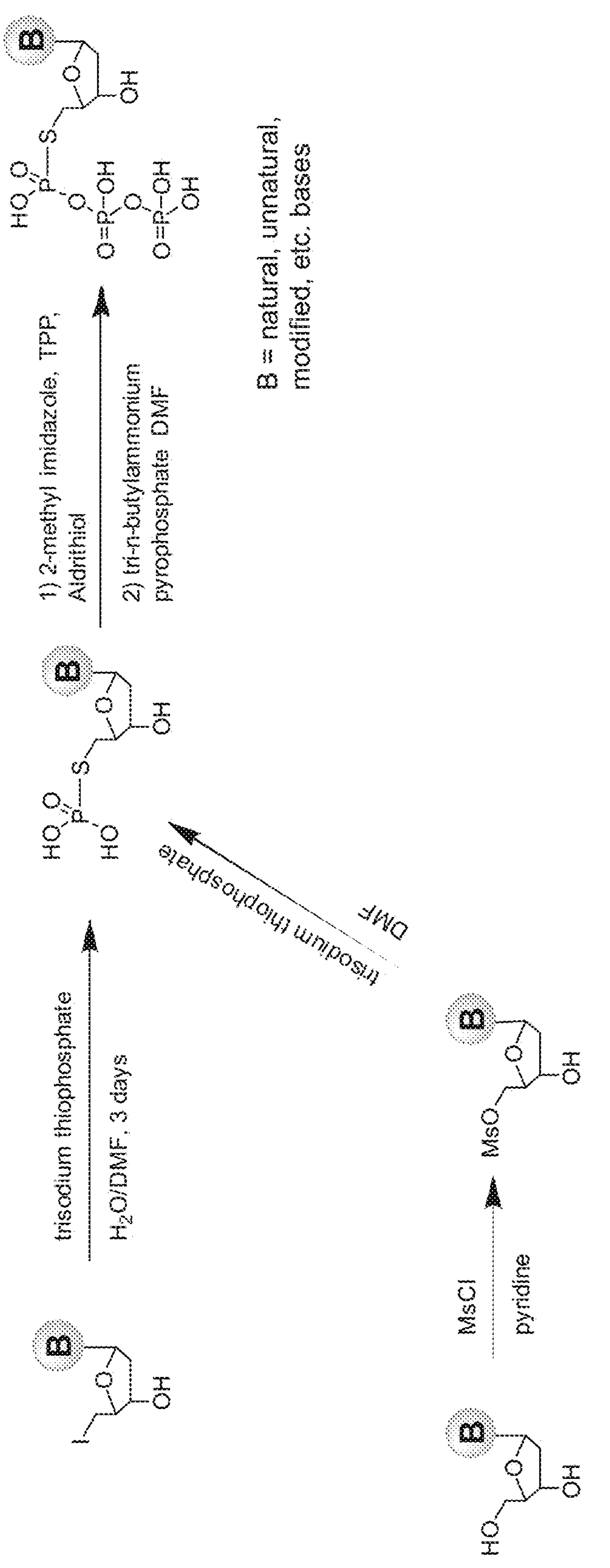
FIG. 46 schematically illustrates an example of a chemical schema (Scheme I) for the synthesis of a bridging P—S nucleotide, the product being Nucleotide 1.
Figure 47A:
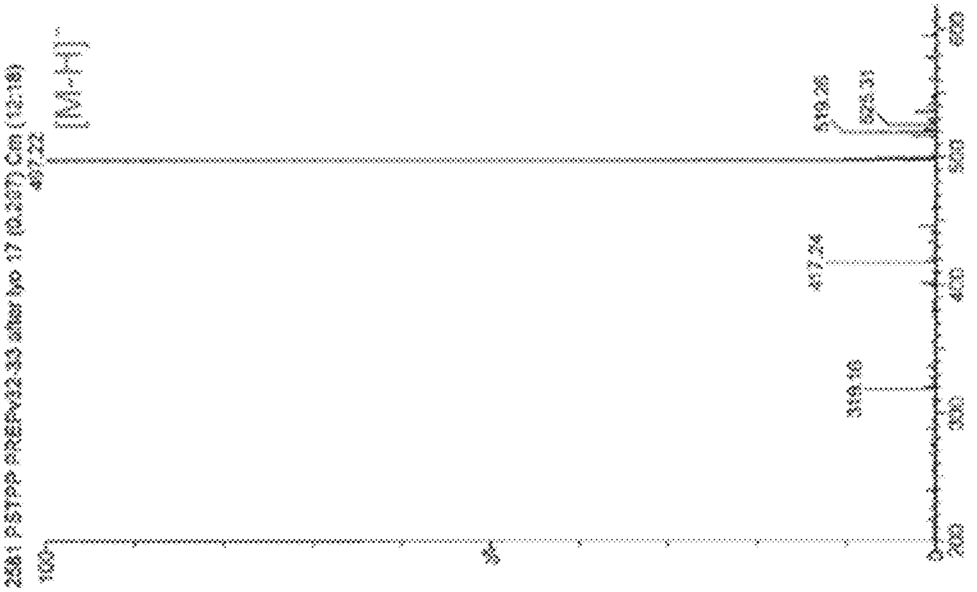
FIG. 47A illustrates non-limiting characterization of a phosphorothiolate (bridging P—S) nucleotide made according to Scheme I.
Figure 47B:
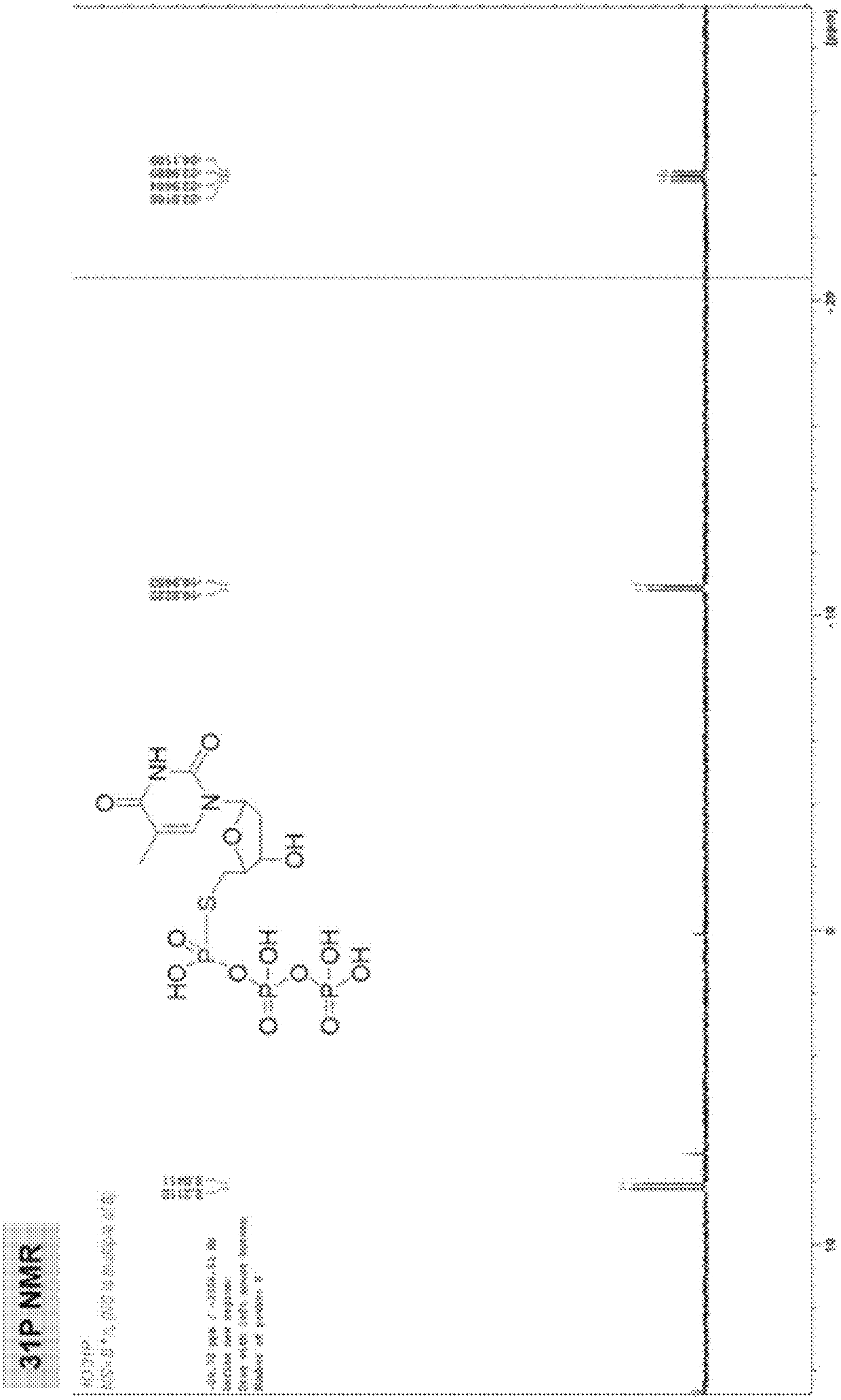
FIG. 47B illustrates non-limiting characterization of a phosphorothiolate (bridging P—S) nucleotide made according to Scheme I.

A heavy atom substituted nucleotide with bridging P—S substitution is made according to the synthesis scheme shown in FIG. 46. FIGS. 47A and 47B show the mass spectrum and the NMR spectrum of an example of such nucleotide.

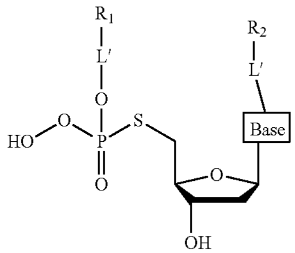

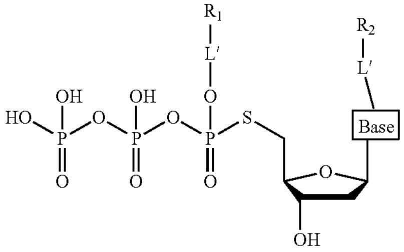

Figure 48:
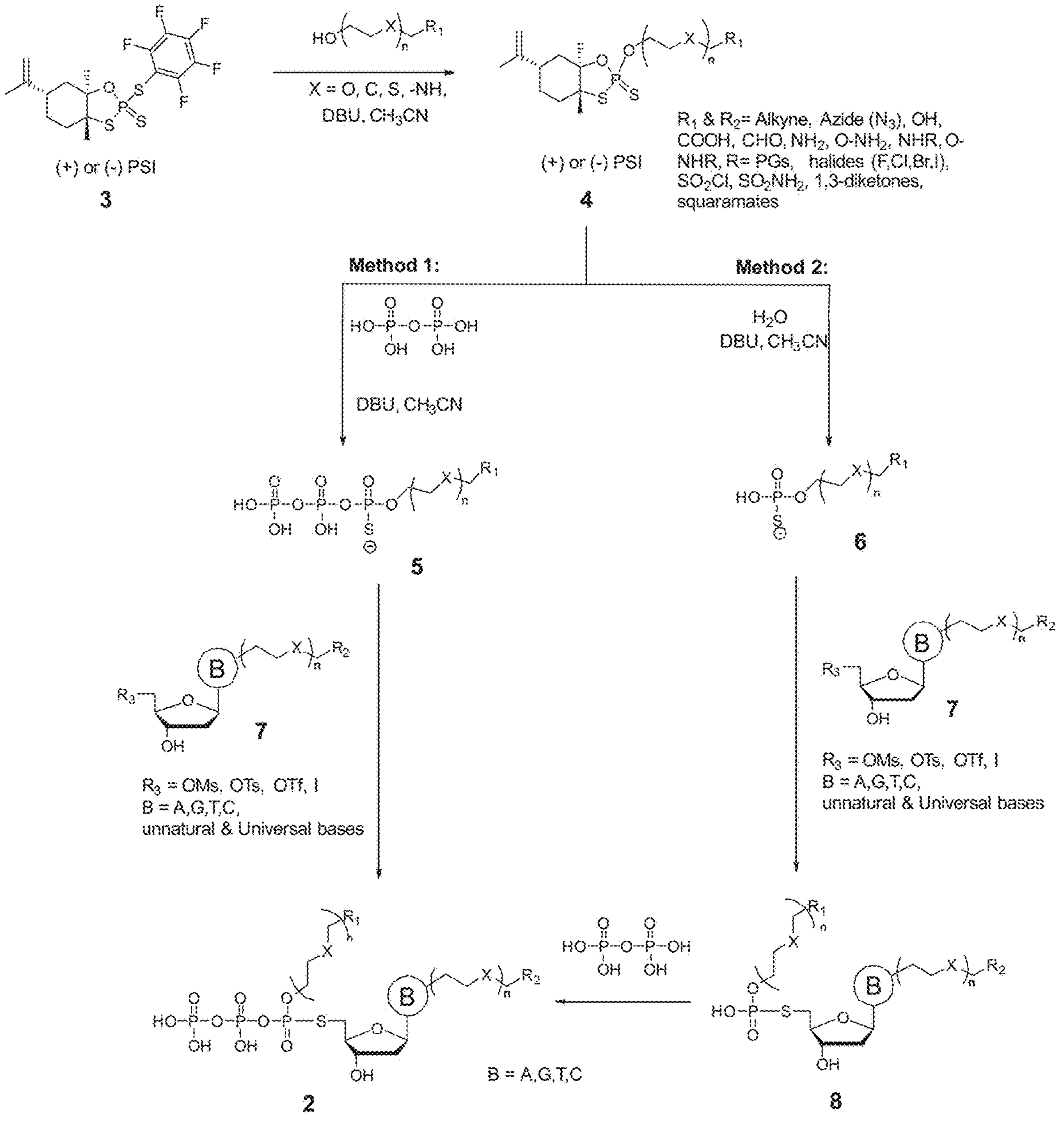
FIG. 48 schematically illustrates Scheme II, an alternative method of generating a bridging P—S nucleotide.
Figure 49:
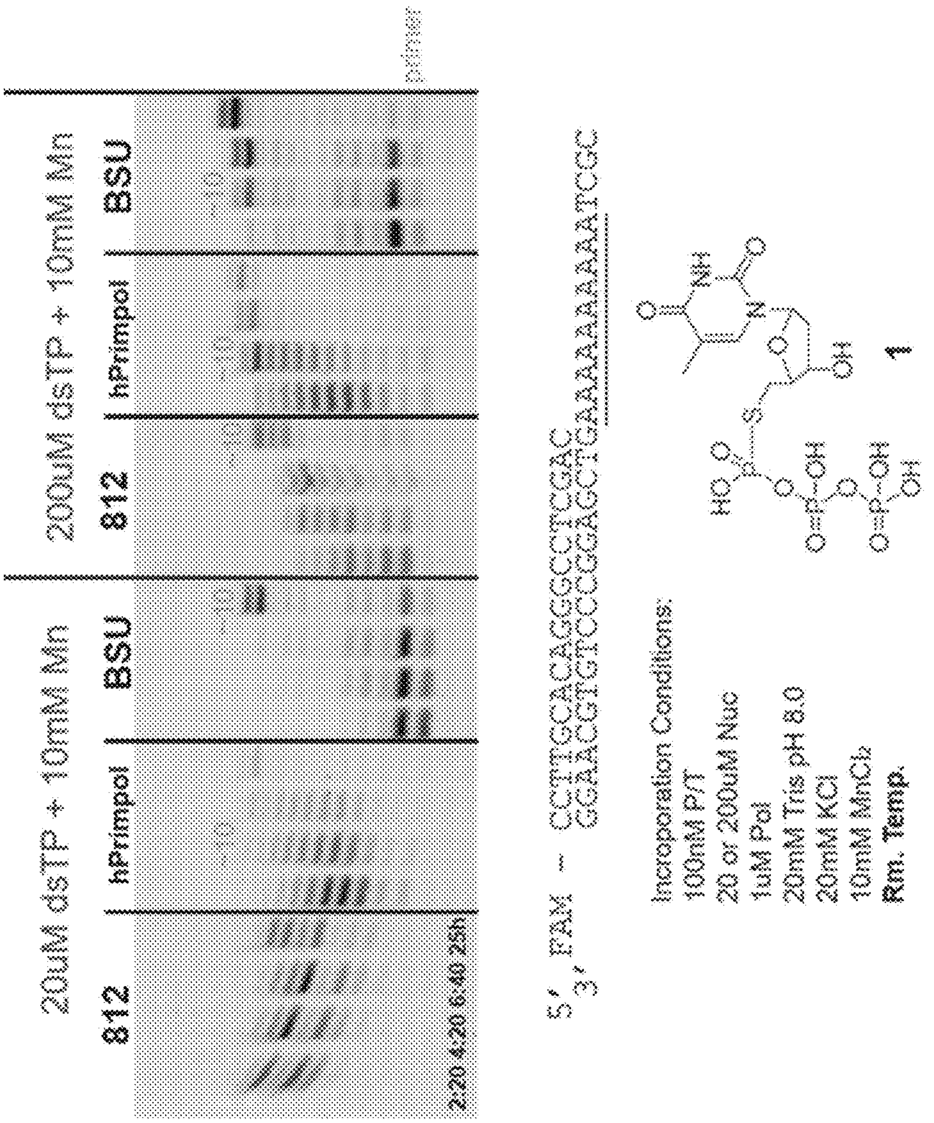
FIG. 49 illustrates experimental data from the incorporation of a poly-A tail formed by bridging P—S(phosphorothiolate) deoxyribonucleotides.

A bifunctional nucleotide with a bridging P—S substitution can also be made according to the reaction scheme in FIG. 48.

b. Incorporation of Heavy-Atom Substituted Nucleotides to Generate a Modified Polynucleotide FIG. 49 shows the results of incorporation of a poly-A tail formed by bridging P—S(phosphorothiolate) deoxyribonucleotides (nucleotide 1) to generate DNA oligonucleotides with continuous phosphorothiolate backbones. Specifically, incorporation was tested using multiple polymerases, including Pol812, 1901, hPrimpol, and BSU. Positive signal for each heavy atom substituted nucleotide incorporated into an oligonucleotide strand was observed for each tested polymerase.

c. Cleavage of Phosphorothiolate Heavy-Atom Modified Nucleotides

Figure 50A:
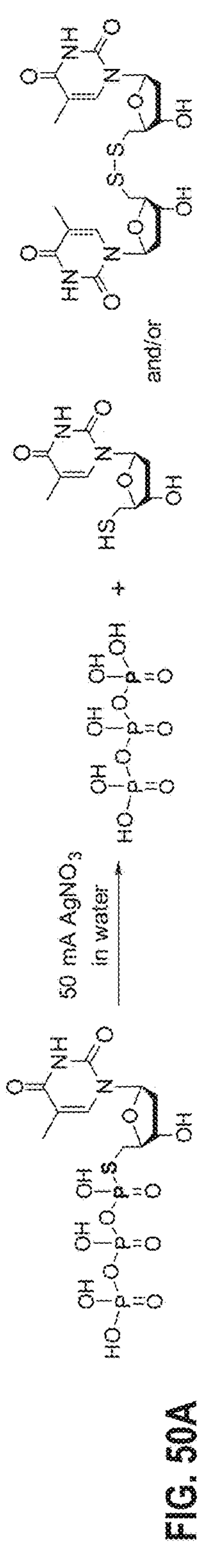
FIG. 50A is a reaction scheme of the cleavage of the phosphorous-sulfur bond by silver nitrate through a bridging P—S nucleotide.
Figure 50B:
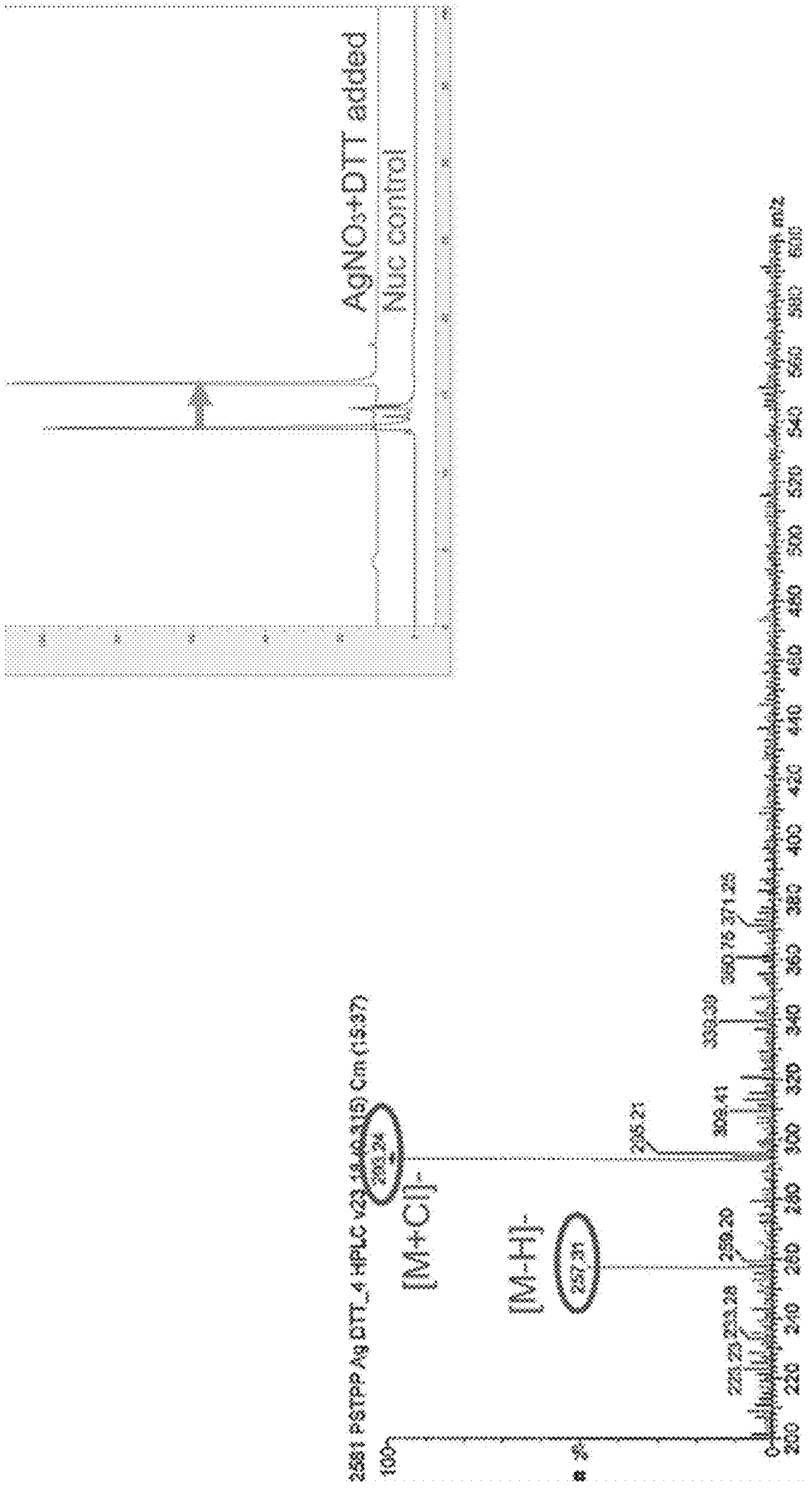
FIG. 50B demonstrates experimental results obtained from cleaved product analysis after cleavage of the phosphorous-sulfur bond by silver nitrate through a bridging P—S nucleotide.

FIG. 50A is a reaction scheme of the cleavage of the phosphorous-sulfur bond by silver nitrate through a bridging P—S nucleotide 1. Silver nitrate was added to the nucleotide 1, and DTT was added 15 mins later and incubated for 1 hour. The cleavage by use of silver nitrate is specific to the P—S bond, thereby generating a 5'-S nucleoside (shown in FIG. 50A). FIG. 50B illustrates an HPLC chromatograph of the nucleotide (control) and the cleavage product after DTT addition and ESI-MS data of the cleavage product.

The cleavage reaction as described above was applied to a primer that was extended using the bridging P—S nucleotide 1 and DNA polymerase Pol1901 (see FIG. 51. Lane 4). The gel analysis showed that silver nitrate and silver nitrate+DTT are able to cleave the oligonucleotides cleanly as shown in Lanes 5 and 6 of FIG. 51, respectively.

Example 3: Generation of 4-Mer Oligonucleotide with Bridging P—S Substitutions The synthesis and characterization of a oligonucleotide with P—S bridging substitutions is described.

a. Synthesis of Bridging P—S Oligonucleotides

Figure 52:
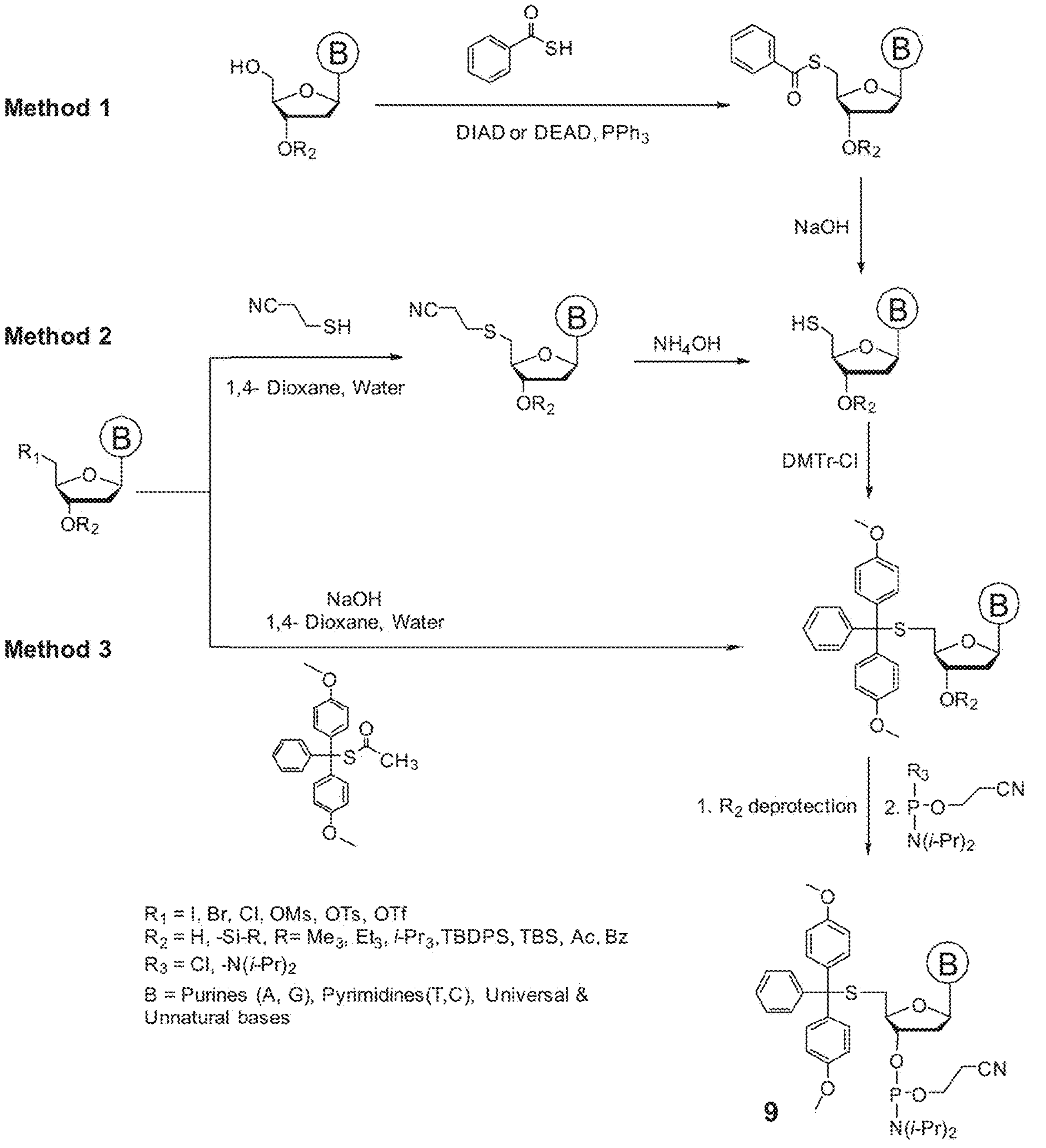
FIG. 52 schematically illustrates the synthesis of a 5' SDMT phosphoramidite "9" through multiple methods.
Figure 53A:
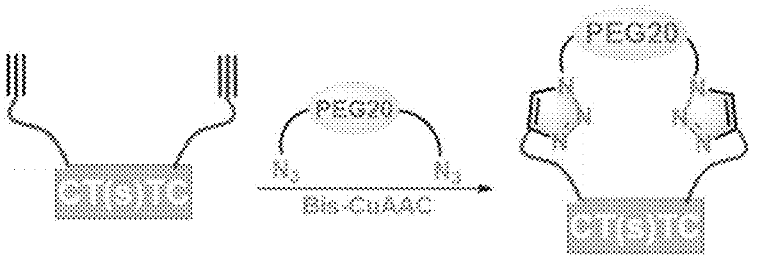
FIG. 53A illustrates one embodiment of the conjugating a spacer moiety to a 4-mer oligonucleotide.
Figure 53B:
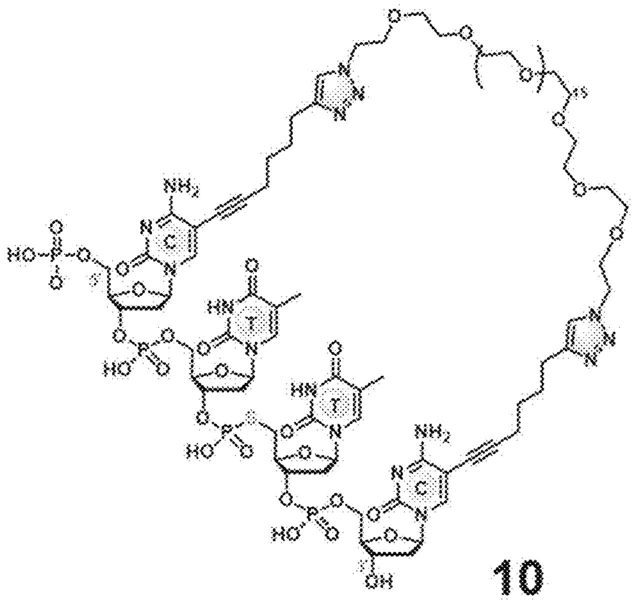
FIG. 53B illustrates one embodiment of the cyclic loop 4-mer oligonucleotide.

The briding P—S substitution found in a 4-mer oligonucleotide is structurally located similarly to the bridging P—S nucleotide. The number of bridging P—S substitutions that a k-mer oligonucleotide can introduce to the growing strand each time can be any number between 1 and k−1. For example, for a 4-mer oligonucleotide there can be 1 to 3 bridging P—S substitutions. The P—S substitution was introduced to a 4-mer oligonucleotide via the 5'SDMT phosphoramidite 9. FIG. 52 schematically illustrates the synthesis of a 5'SDMT phosphoramidite 9 through 3 methods. The 5'SDMT phosphoramidite 9 is then introduced to a 4-mer oligonucleotide and ligated, generating a substitution to the 4-mer oligonucleotide via 5'SDMT phosphoramidite 9. Post synthetic modifications such as conjugating a cyclic loop on the modified oligonucleotide product, can be added as demonstrated in FIG. 53A. A 4-mer oligonucleotide with a bridging P—S substitution and a cyclic loop attached to the first and the last nucleobase of the 4-mer oligo nucleotide (Oligonucleotide 10) is shown in FIG. 53B. FIGS. 54A-C illustrates HPLC, IR, and MS characterization of the resulting cyclic loop 4-mer oligonucleotide.

b. Ligation/Cleavage of Bridging P—S Oligonucleotides

Wildtype ligase Ame was used to ligate up to 10 cyclic loop modified 4-mer oligonucleotide 10. FIG. 55 illustrates that wildtype ligase Ame was able to ligate up to 10 of the cyclic loop 4-mer oligonucleotide 10 after 2.5 hours, with improved ligation efficiency at 22 hours. Signal from a ligated oligonucleotide can be observed most strongly at lane 6, corresponding to 22 hours.

FIG. 56 illustrates that upon consecutive ligation, cleavage of the newly synthesized strand generates a longer strand that runs slower (higher up in position) in gel due to the influence of an incorporated PEG loop (and expansion after selective cleavage of the polynucleotide backbone).

Example 3 therefore illustrates the successful synthesis of a cyclic loop 4-mer oligonucleotide 10, and that the cyclic loop remained closed in the ligation process. Moreover, the ligation was successful in generating the new synthetic strand, and lastly, the new synthetic strand can be selectively and efficiently cleaved using silver nitrate to generate an elongated strand.

Example 4: Use of Non-Bridging P—S Nucleotides to Generate Modified Polynucleotides and Subsequent Cleavage a. Synthesis of Non-Bridging P—S Nucleotides

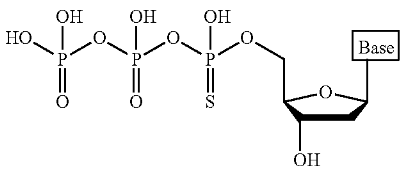

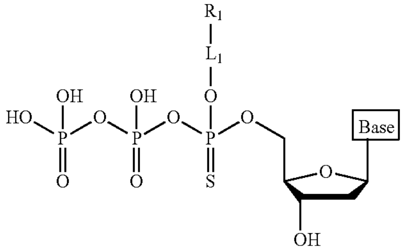

Figure 57A:
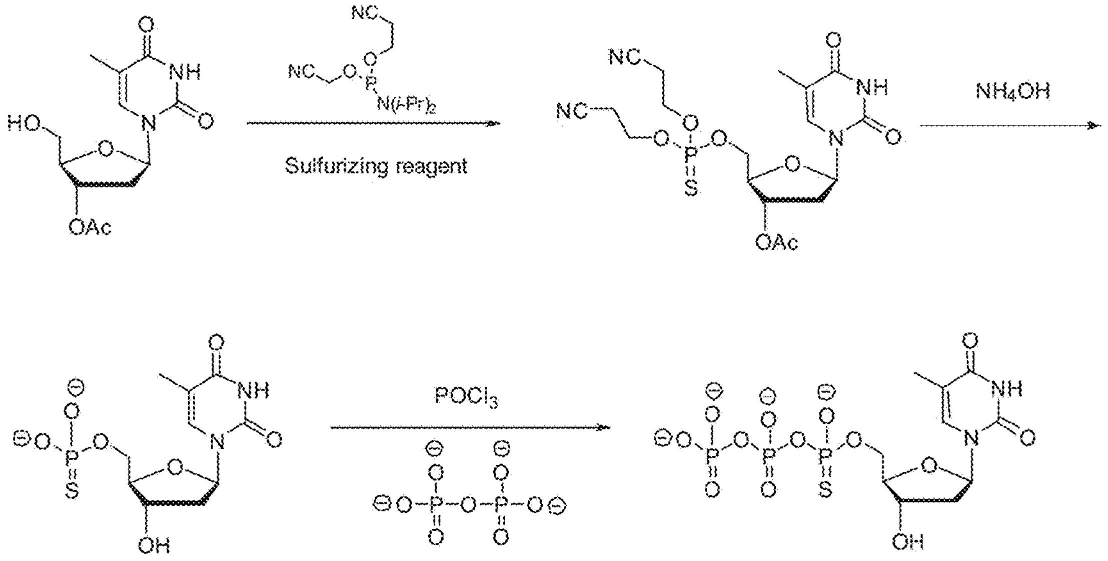
FIG. 57A is a reaction schemes for the synthesis of one embodiment of non-bridging P—S nucleotides.
Figure 57B:
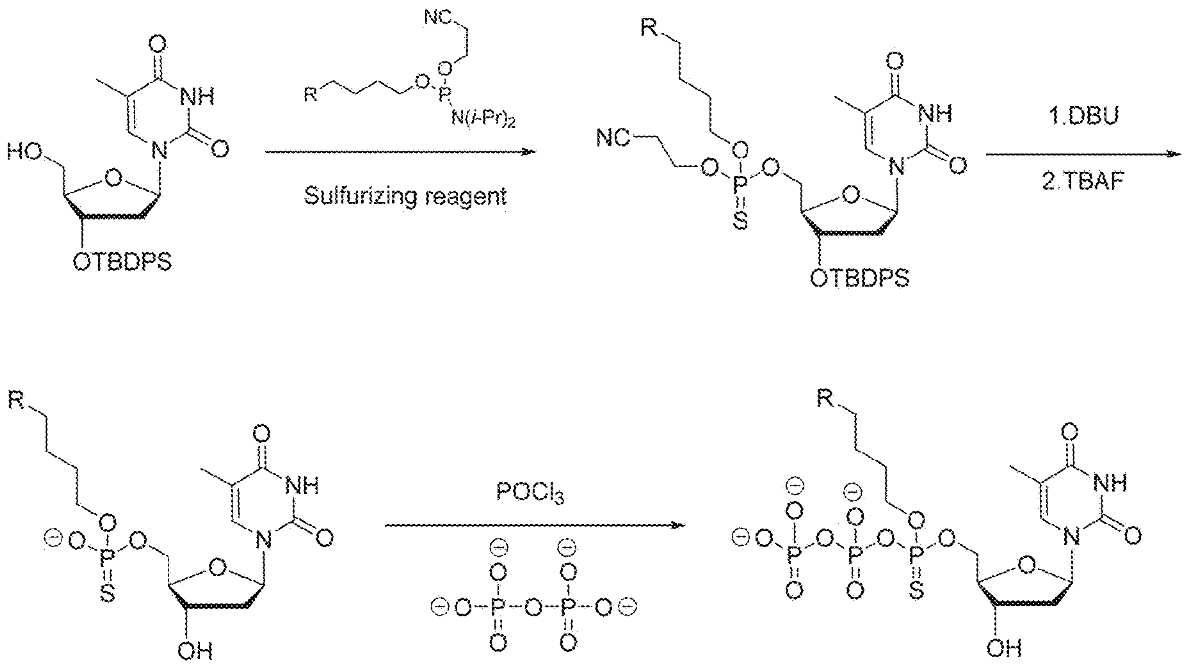
FIG. 57B is a reaction schemes for the synthesis of another embodiment of non-bridging P—S nucleotides.
Figure 59:
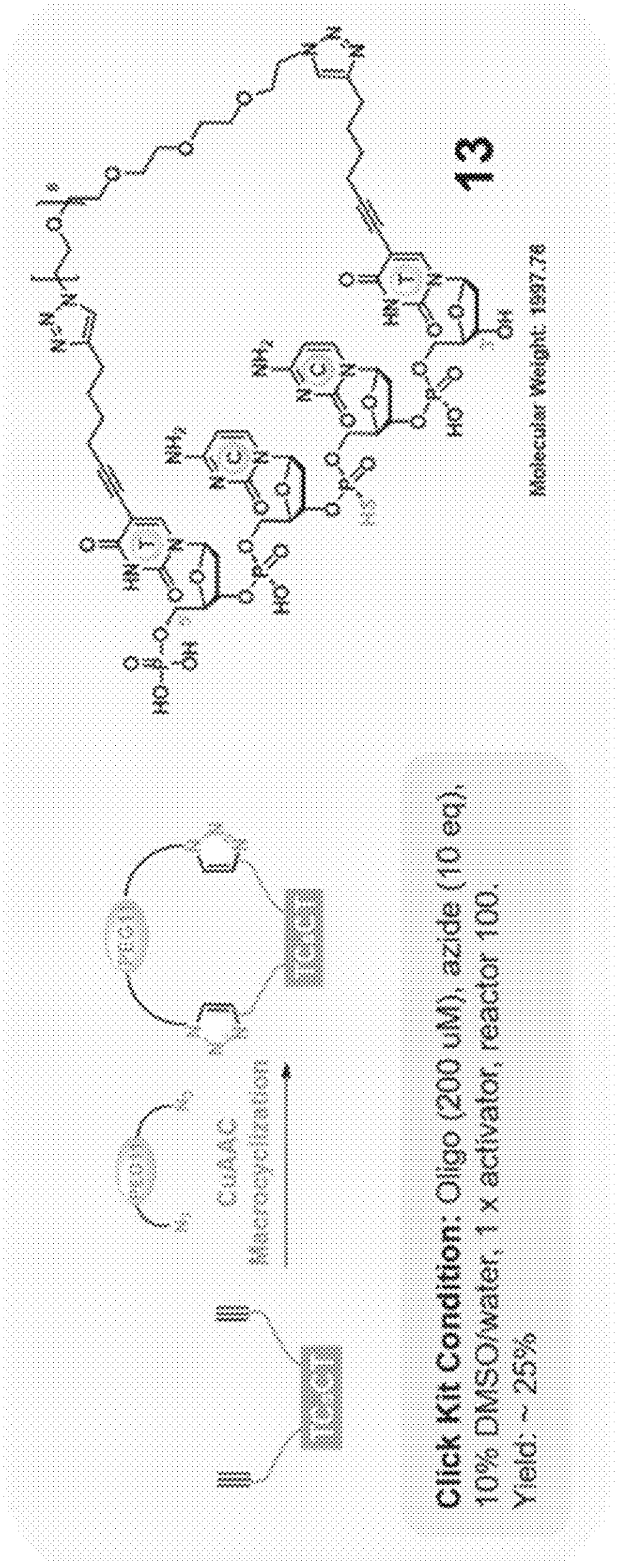
FIG. 59 schematically illustrates conjugation of a spacer moiety with a functionalized 4-mer oligonucleotide to form a cyclic loop 4-mer oligonucleotide.
Figure 60A:
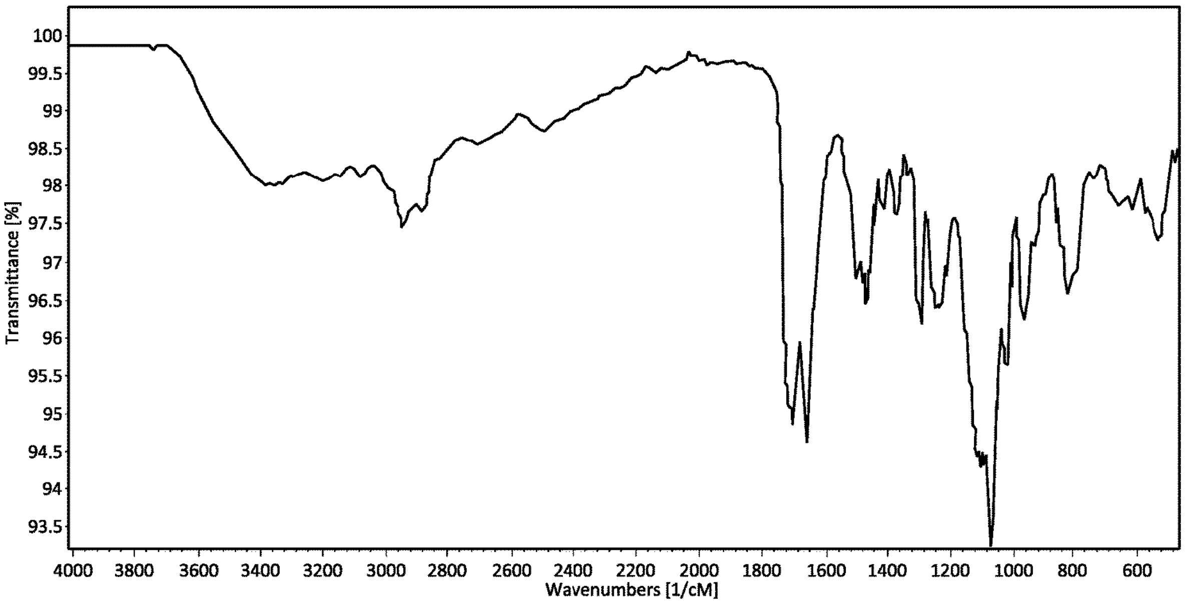
FIGS. 60A-D schematically illustrates characterization of a 4-mer oligonucleotide shown in FIG. 59
Figure 60B:
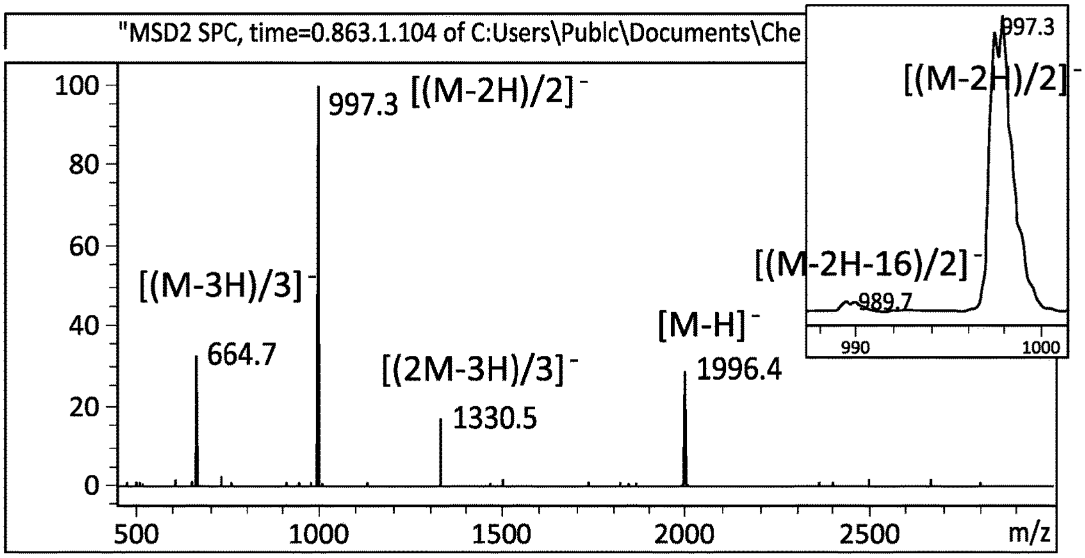
Figure 60C:
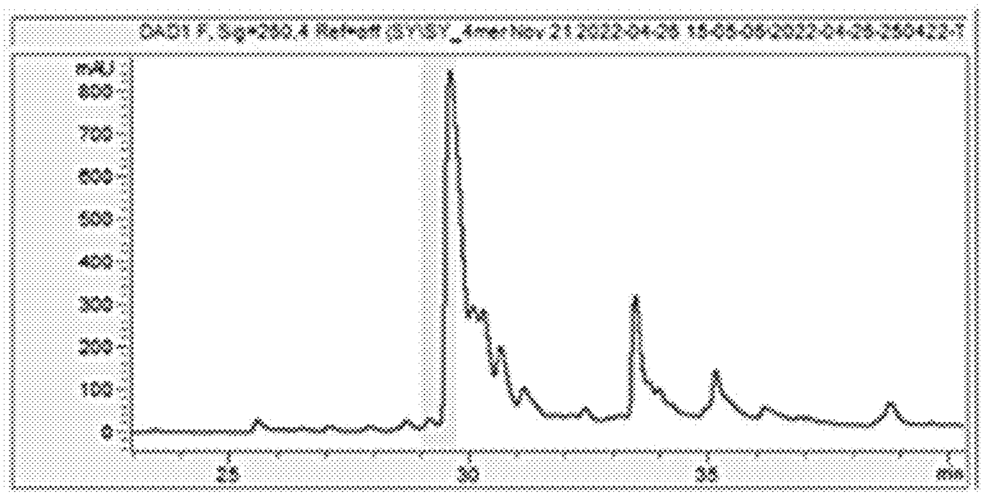
Figure 60D:
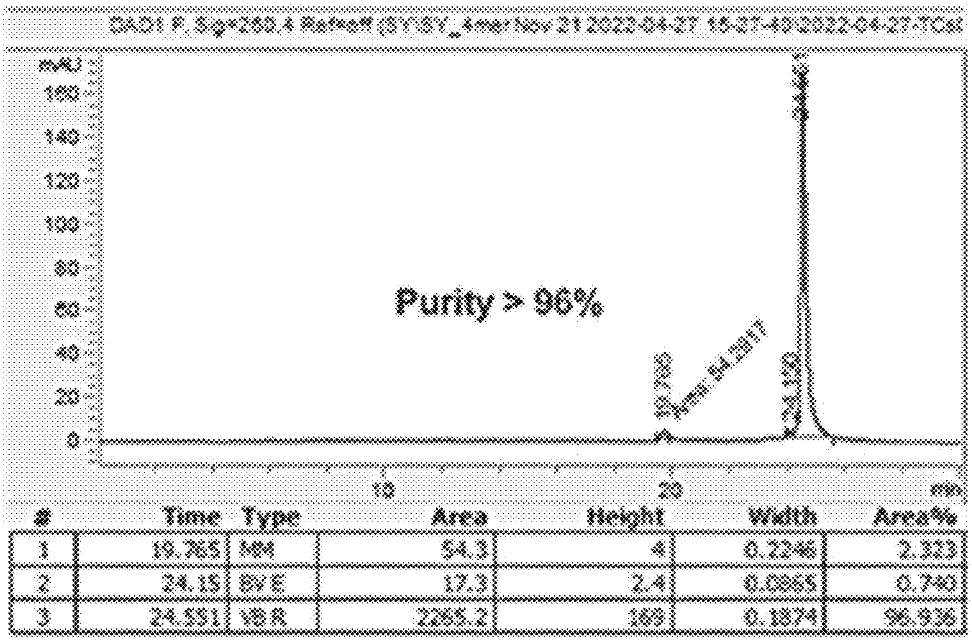

Prior to enzymatic incorporation, modified nucleotides must be synthesized. A phosphorothioate (non-bridging P—S) triphosphate nucleotide as show above was made according to the synthetic scheme in FIG. 57A. A phosphorothioate (non-bridging P—S) triphosphate nucleotide with functionalization at the alpha phosphate was made according to the synthetic scheme in FIG. 57B.

b. Incorporation of Non-Bridging P—S Nucleotides

Non-bridging P—S nucleotide was incorporated by several wildtype polymerases as shown in FIG. 58—including 812, Dpo4, DbH, DinB, Asfy, Mu, lambdai, 8k beta, Human PrimPoli, SulfoPrimPol, 300 Cyano PrimPol, 190 Cyano PrimPol, BSU, RB49, and PolC.

Example 5: Generation of 4-Mer Polynucleotide with Non-Bridging P—S Substitutions The synthesis and characterization of a polynucleotide with P—S non-bridging substitutions is described herein.

a. Synthesis of Non-Bridging P—S Oligonucleotides

FIGS. 59 and 60A-D schematically illustrates a 4-mer oligonucleotide 13 that was synthesized using a sulfurizing agent such as DDT to generate the phosphorothioate modification at the site of interest, with resulting diasteromers separated via HPLC.

b. Ligation of Non-Bridging P—S Oligonucleotides

FIG. 61 demonstrates wildtype Ame and PsyA ligases that were able to perform up to 10 successive ligation events with the cyclic loop 4-mer oligonucleotide 13 within 20 hours.

c. Cleavage of Non-Bridging P—S Oligonucleotides

Figure 62A:
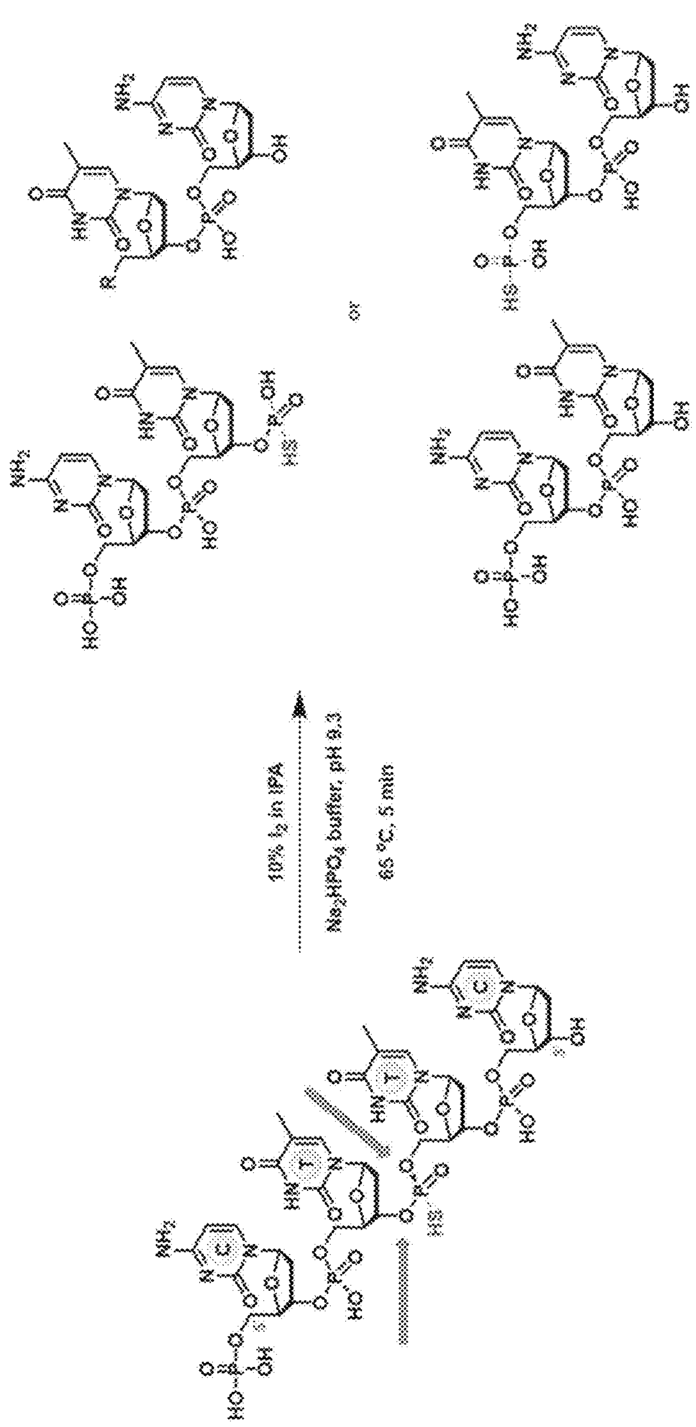
FIG. 62A illustrates the use of iodine to cleave the bridging P—O bonds at the site of a phosphonothioate.
Figure 62B:
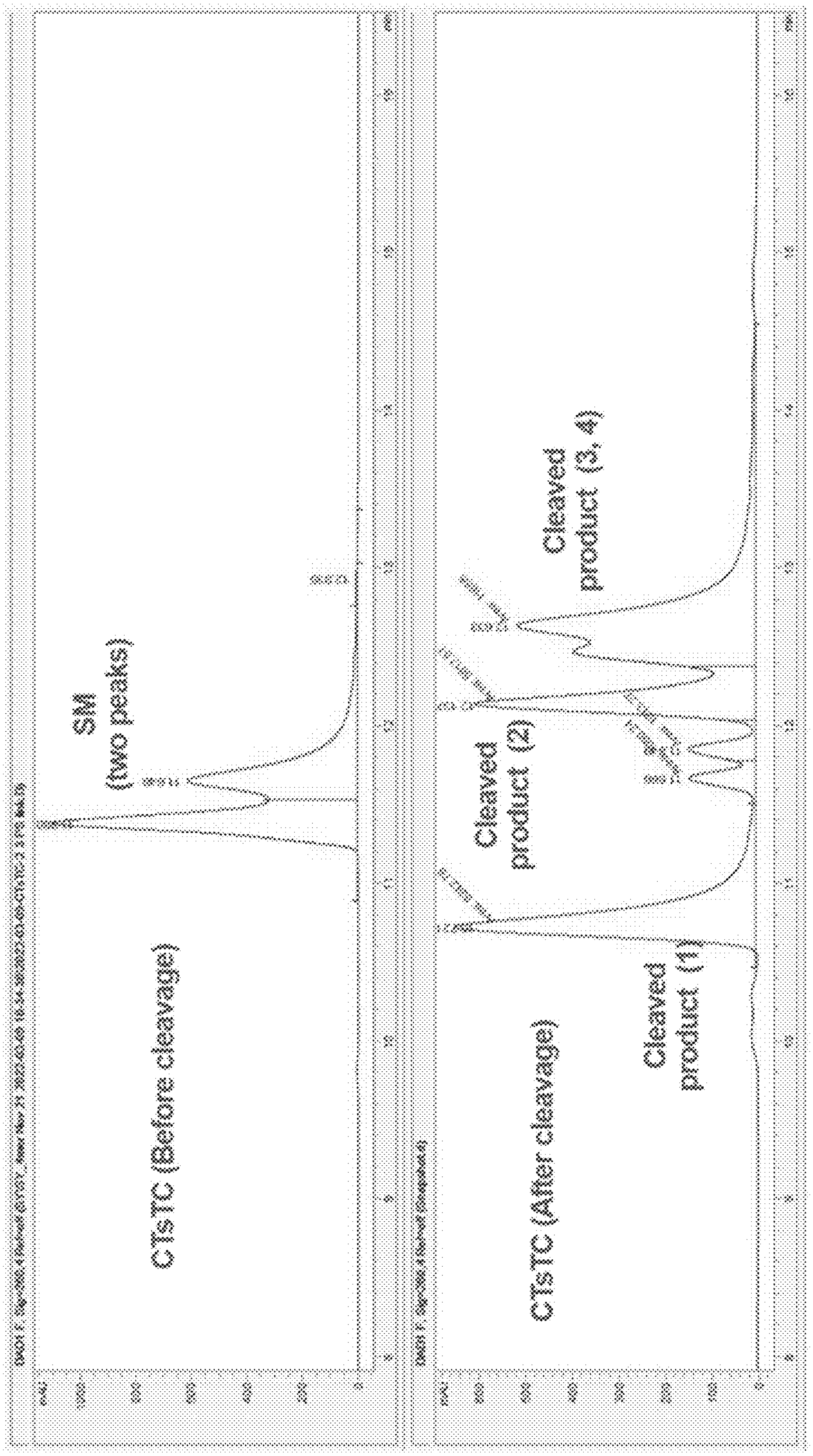
FIG. 62B illustrates characterization before and after P—O bond cleavage.

FIG. 62A illustrates using iodine to cleave the bridging P—O bonds at the site of phosphorothioate selectively in the presence of nucleophiles like amines. However, the subsequent bridging P—O bond cleavage is not specific and either the 5' or the 3' end could potentially be cleaved, giving four potential products (FIG. 62B)

Example 6: Nucleotide with Imino-P Substitution at Alpha Phosphate

Figure 63:
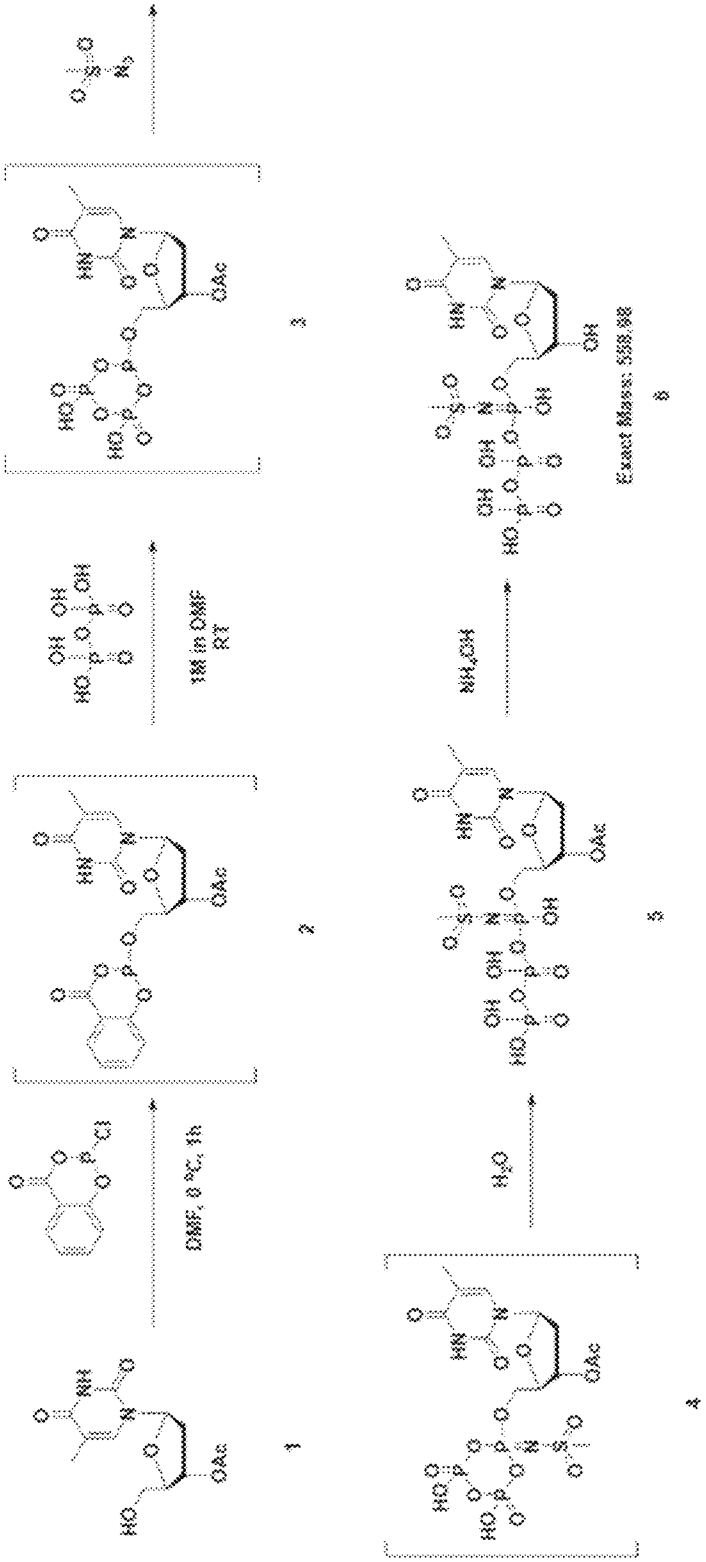
FIG. 63 is a reaction scheme for the synthesis of an imino-P substituted nucleotide.

FIG. 63 schematically illustrates the model synthesis of an imino-P substitution of on the alpha phosphate of a nucleotide. The imino-P nucleotide was stable in 50 mM $KH_2PO_4$ buffer at pH 5.5 and 7.5 across 2 day time period at 25° C. No degradation of imino-P was observed after 2 days at both pH 5.5 and 7.5.

Figure 64:
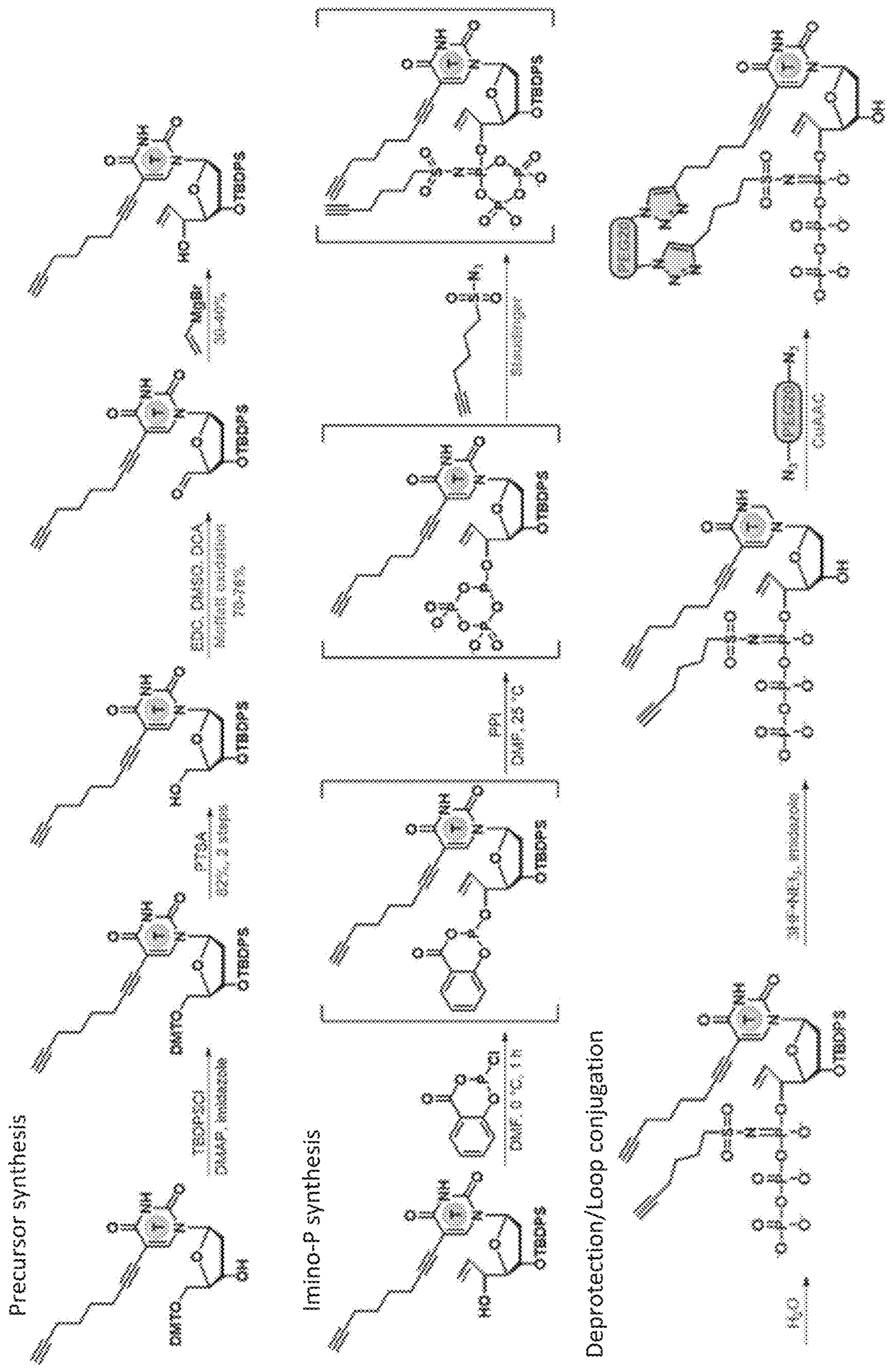
FIG. 64 is a reaction scheme for the synthesis of a cyclic loop nucleotide with imino-p substitution according to an embodiment.
Figure 65:
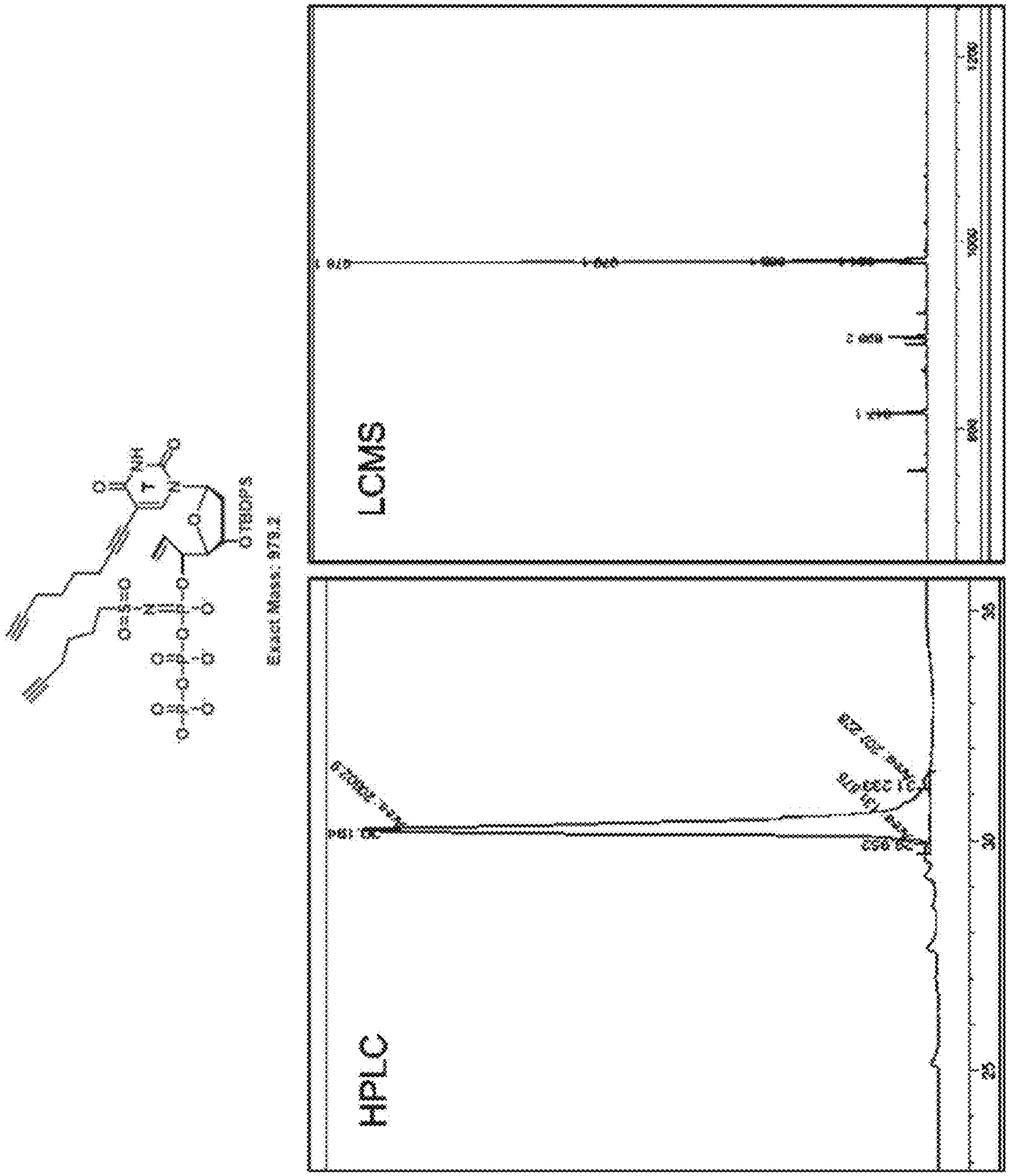
FIG. 65 show HPLC and LCMS characterization of an bifunctional imino-P nucleotide.

FIG. 64 illustrates synthesis of a cyclic loop nucleotide with imino-p substitution according to an embodiment herein. Three stages are illustrated: precursor synthesis (introduction of the allyl cleavable group), imino-P synthesis, and deprotection of the triphosphate nucleotide followed by an exemplary cyclic loop conjugation using a bis-azido PEG20 linker. The imino-P nucleotide was stable in 50 mM $KH_2PO_4$ buffer at pH 5.5 and 7.5 across 2 day time period at 25° C. FIG. 65 illustrates HPLC and LCMS characterization of an imino-P nucleotide.

Example 7: Accessing Imino-P Allyl Bifunctional Triphosphate

Various methods to access the imino-p bifunctional triphosphate were assessed.

Figure 66:
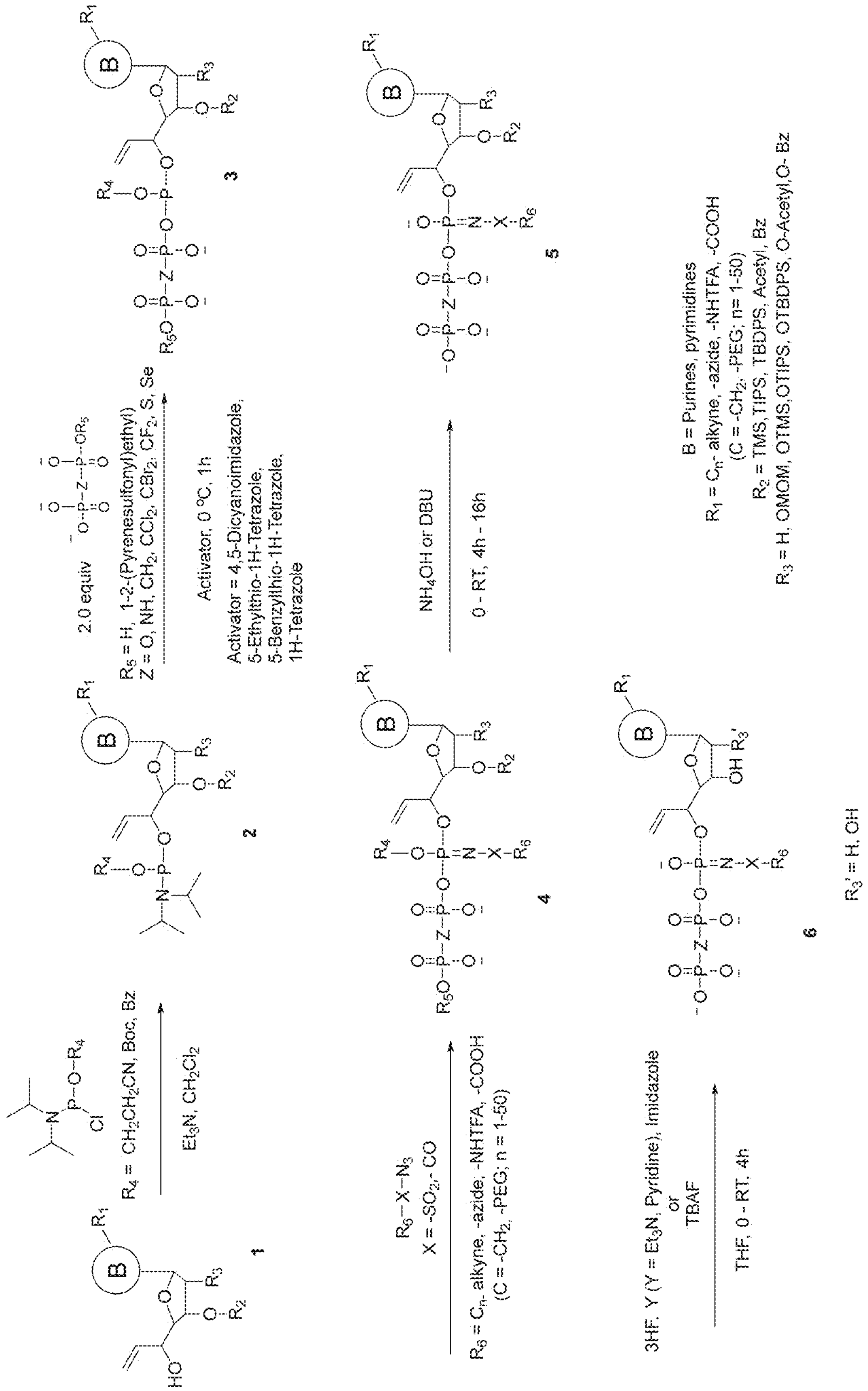
FIG. 66 schematically illustrates one embodiment of a method to synthesize imino-P allyl bifunctional nucleotides.

FIG. 66 schematically illustrates one embodiment of a method to synthesize imino-P allyl bifunctional nucleotides. The 5'-OH allyl nucleoside 1 is activated by a phosphitylating agent to form a first intermediate 2, which is subsequently activated and coupled to a pyrophosphate, forming a second phosphite triester intermediate 3. A Staudinger reaction occurs with an azide moiety to convert the unstable phosphite trimester 3 into a third imino-P phosphotriester intermediate 4. Subsequent deprotection ensues to remove all the orthogonal protecting groups, forming the imino-P allyl bifunctional triphosphate 6.

Figure 67:
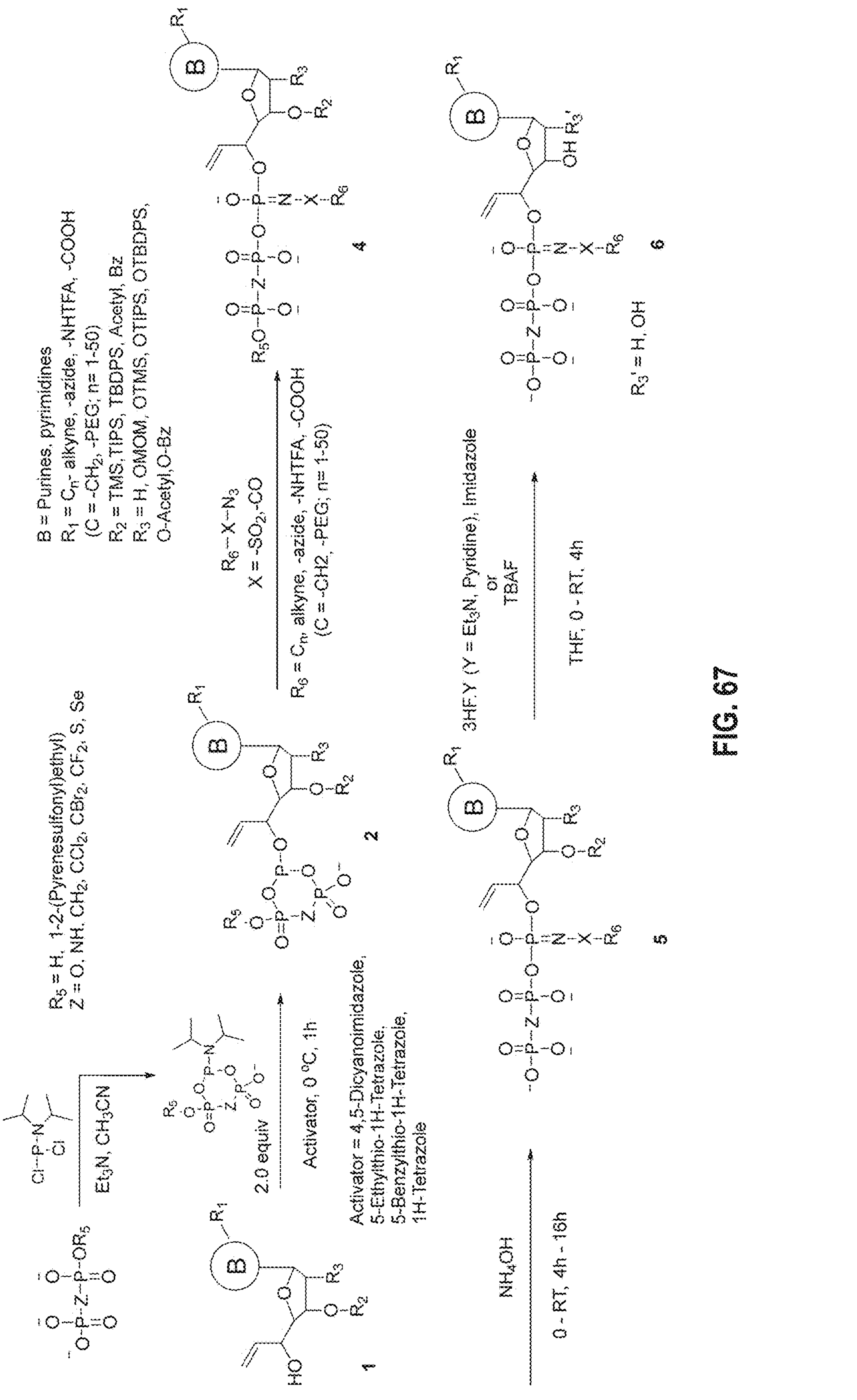
FIG. 67 schematically illustrates another embodiment of a method to synthesize imino-P allyl bifunctional nucleotides.

FIG. 67 schematically illustrates one embodiment of a method to synthesize imino-P allyl bifunctional nucleotides. The 5'-OH allyl nucleoside 1 is coupled to an activated phosphitylating agent to form a first cyclic phosphite triester intermediate 2, followed by Staudinger reaction with an azide functionality to form a second imino-P phosphotriester intermediate 4. Subsequent deprotection ensues to remove all the orthogonal protecting groups, forming the imino-P allyl bifunctional triphosphate 6.

Figure 68:
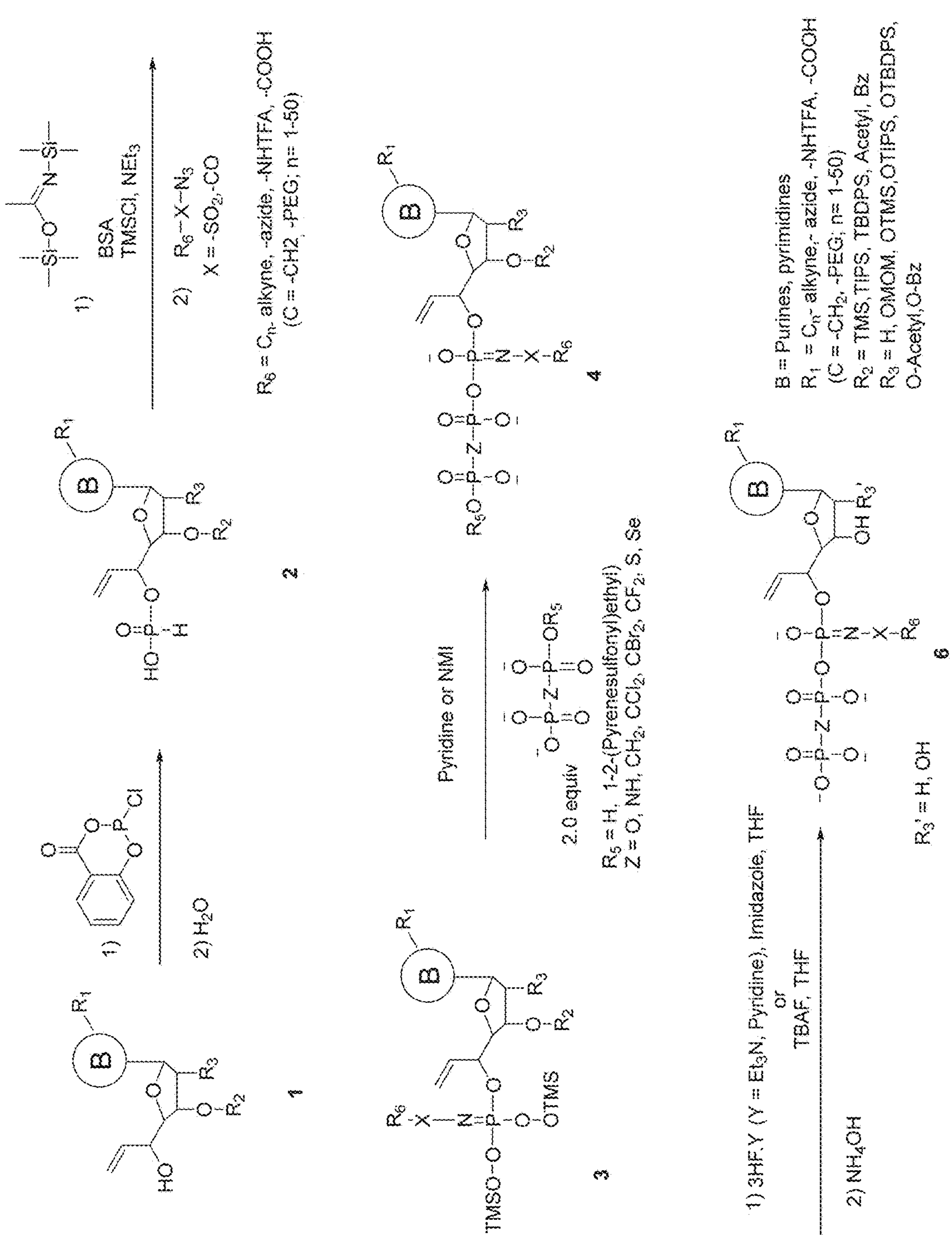
FIG. 68 schematically illustrates another embodiment of a method to synthesize imino-P allyl bifunctional nucleotides.

FIG. 68 schematically illustrates one embodiment of a method to synthesize imino-P allyl bifunctional nucleotides. The 5'-OH allyl nucleoside 1 is coupled to a phosphitylating agent and hydrolyzed to form a first H-phosphonate intermediate 2. It is subjected to sequential BSA treatment and Staudinger reaction with an azide functionality to form a second imino-P phosphotriester intermediate 3. Subsequent coupling with pyrophosphate forms a third intermediate 4. Deprotection ensues to remove all the orthogonal protecting groups, forming the imino-P allyl bifunctional triphosphate 6.

Figure 69:
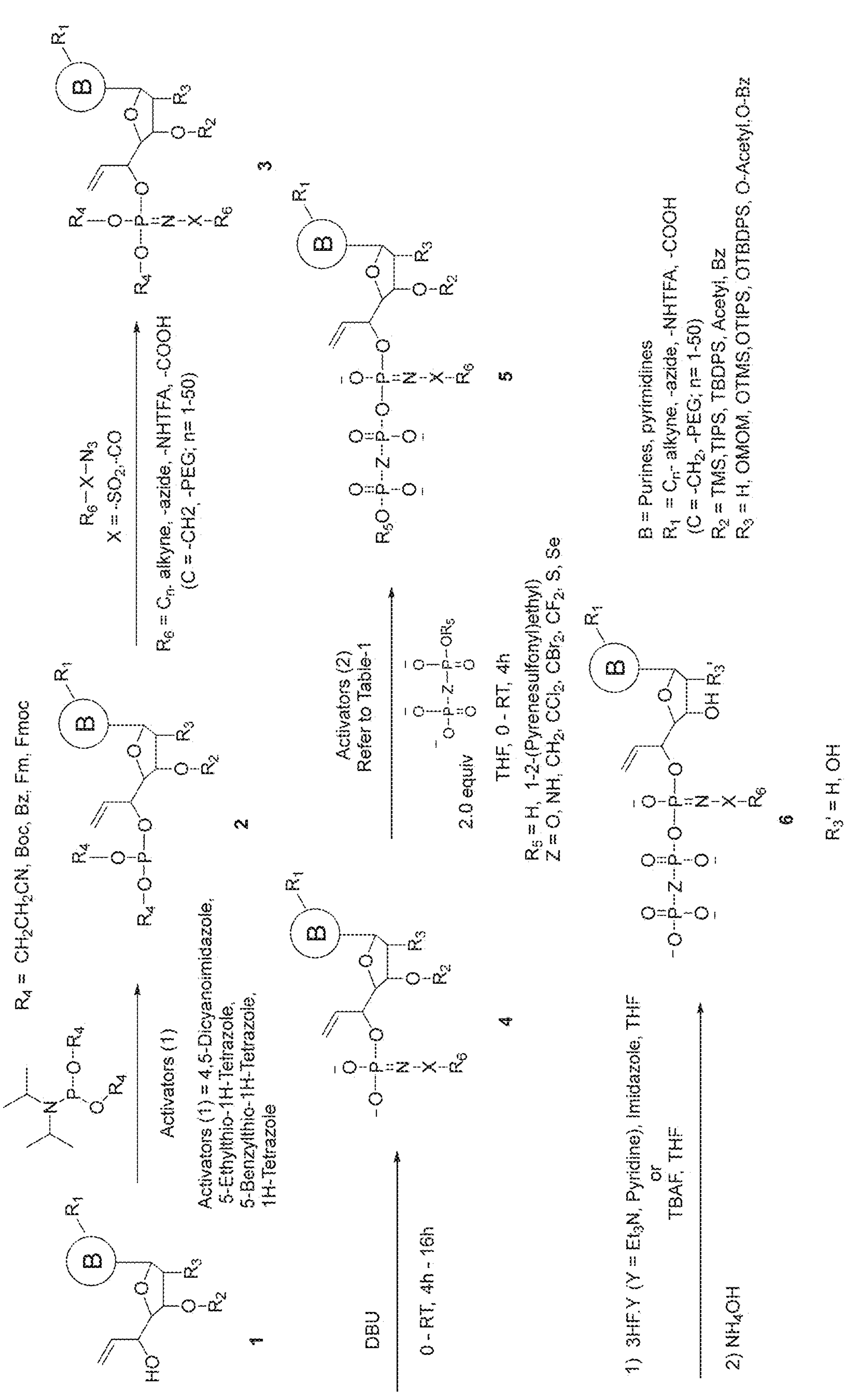
FIG. 69 schematically illustrates another embodiment of a method to synthesize imino-P allyl bifunctional nucleotides.

FIG. 69 schematically illustrates one embodiment of a method to synthesize imino-P allyl bifunctional nucleotides. The 5'-OH allyl nucleoside 1 is activated and coupled to a phosphitylating agent to form a first phosphite triester intermediate 2. It then undergoes a Staudinger reaction with an azide functionality to form a second imino-P phosphotriester intermediate 3. Deprotection is performed to form a third intermediate 4, which is again activated (refer to Table 2) and coupled to a pyrophosphate moiety to form the triphosphate intermediate 5. Deprotection ensues to remove all the orthogonal protecting groups, forming the imino-P allyl bifunctional triphosphate 6.

Figure 70A:
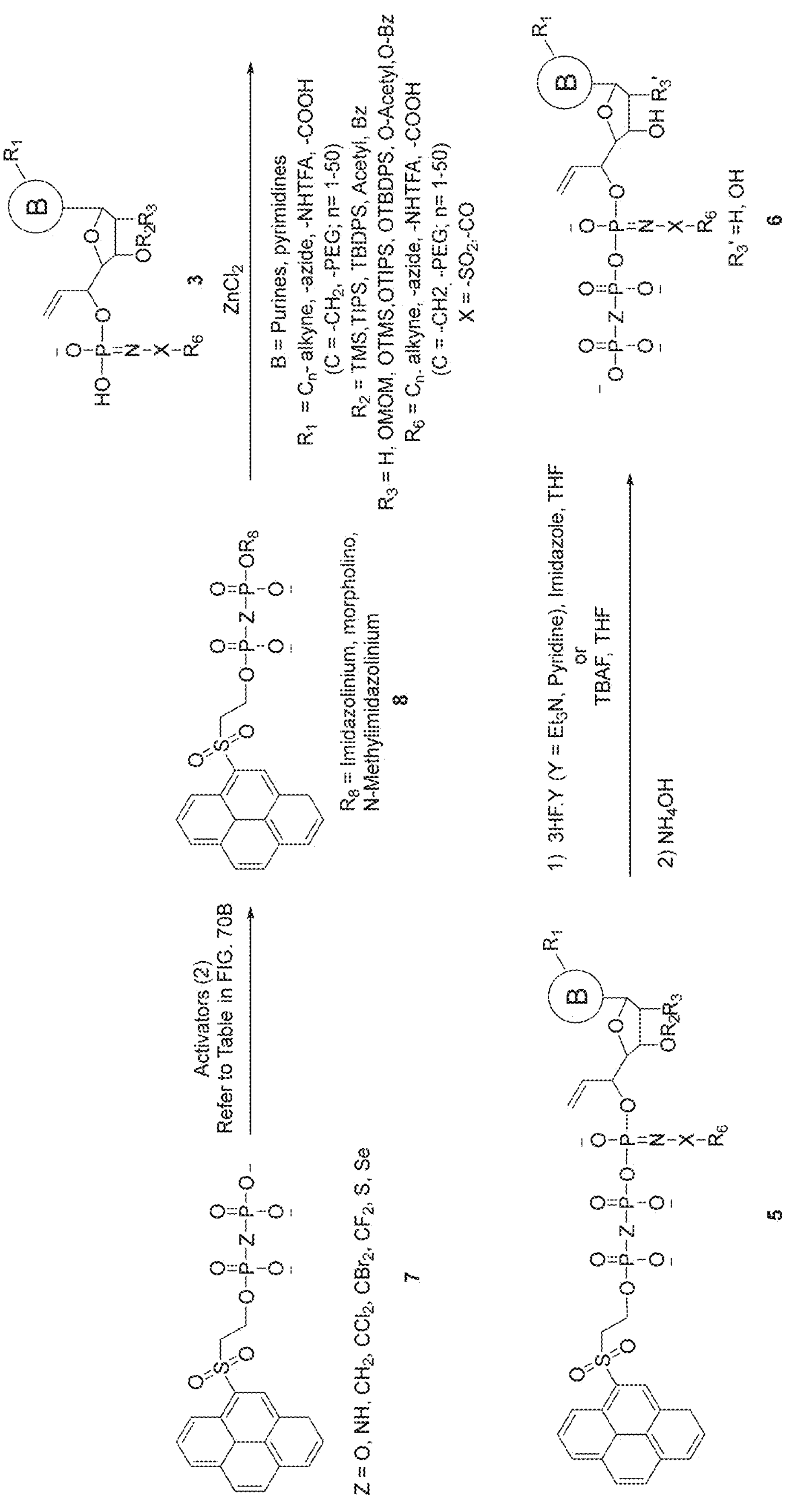
FIG. 70A schematically illustrates one embodiment of a method to synthesize imino-P allyl bifunctional nucleotides.

FIG. 70 schematically illustrates one embodiment of a method to synthesize imino-P allyl bifunctional nucleotides. This method involves the activation of the pyrophosphate moiety (as opposed to the nucleoside monophosphate), thereby swapping the roles of the nucleophile and electrophile. Activation of the pyrophosphate 7 forms the first reactive pyrophosphate intermediate 8, which is then coupled to the nucleoside monophosphate 3, forming a second nucleotide triphosphate intermediate 5. Deprotection ensues to remove all the orthogonal protecting groups, forming the imino-P allyl bifunctional triphosphate 6.

Figure 71:
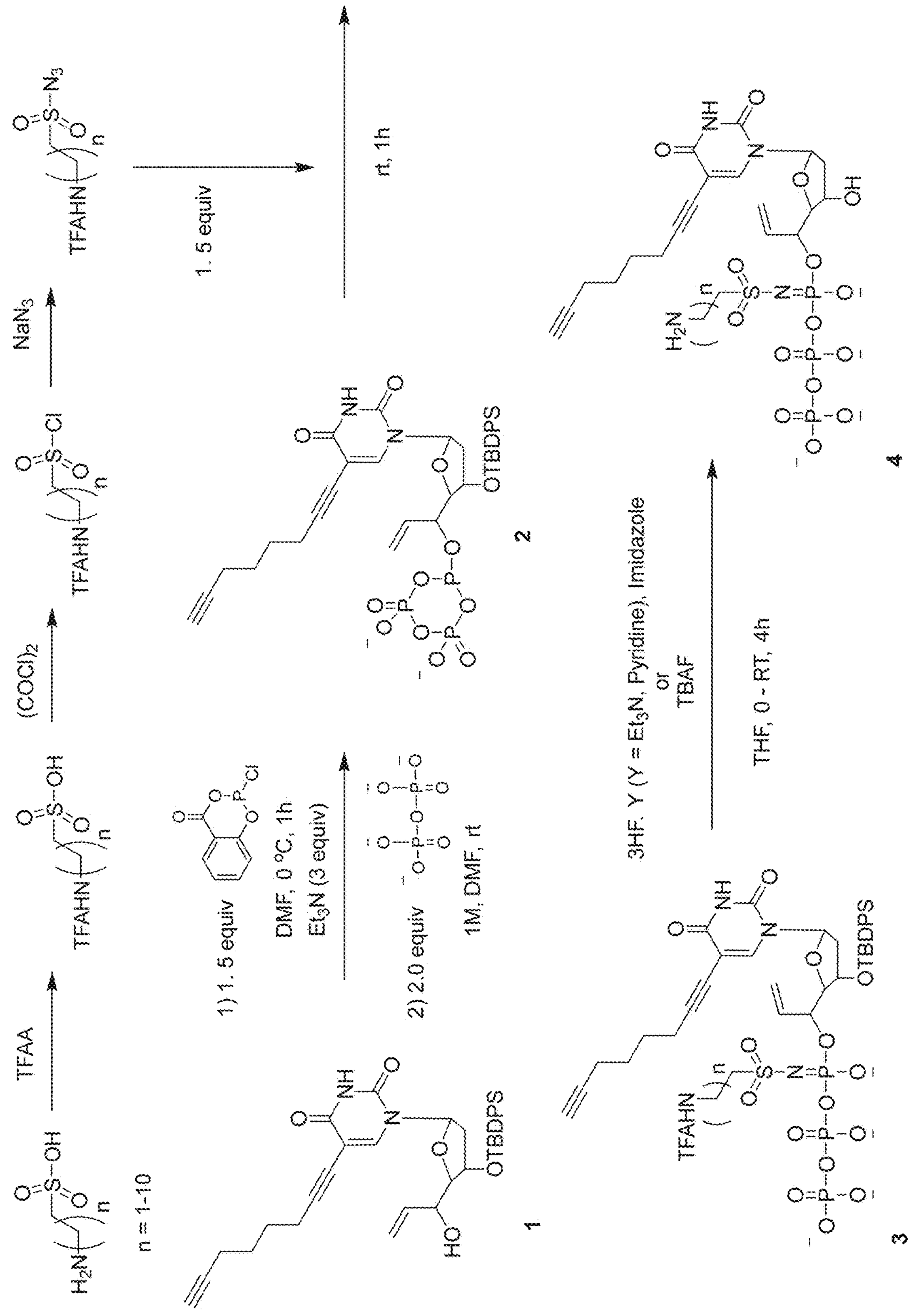
FIG. 71 schematically illustrates an exemplary synthesis of a bifunctional imino-P allyl nucleotide with different reactive groups.

FIG. 71 schematically illustrates an exemplary synthesis of a bifunctional imino-P allyl nucleotide with different reactive groups.

FIG. 72 schematically illustrates deprotection of 3'-OTBDPS group to form 3'-OH, resulting in nucleotide 6. Moreover, deprotection methods may be utilized to deprotect groups such as 3'-OTBDPS, including those selected from the following: HF, TEA, HF-pyridine, TBAF, TAST, DBU, Acetyl Chloride/dry MeOH, selectfluor, or lithium acetate.

Figure 74A:
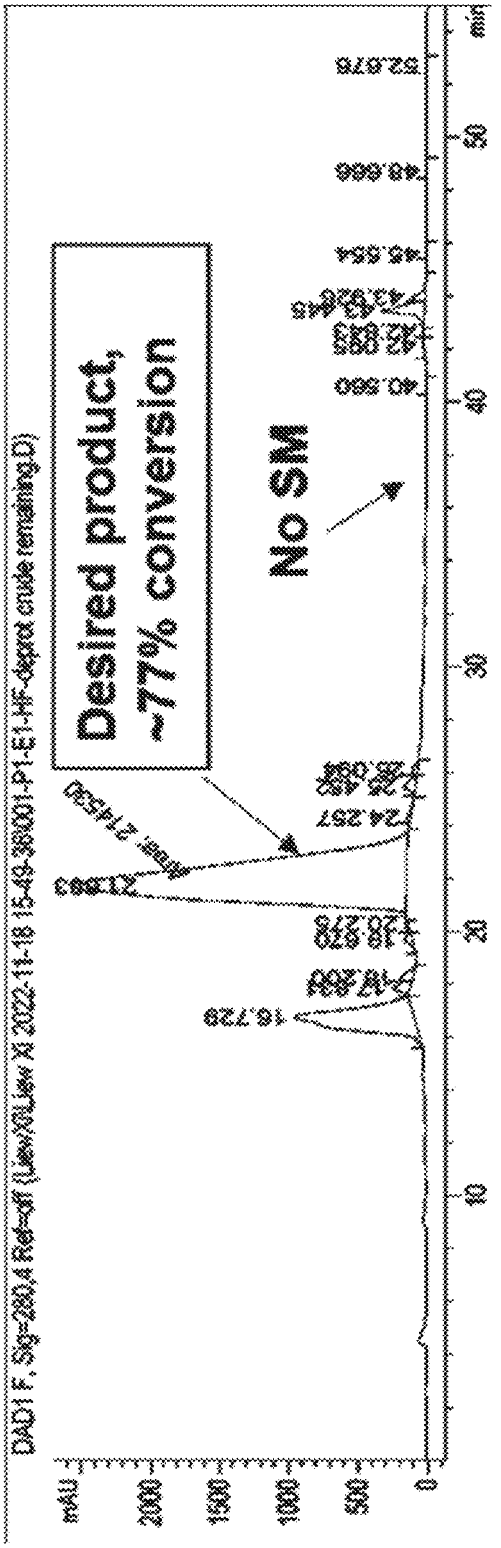
FIGS. 74A-C illustrates crude HPLC, analytical HPLC, and LCMS spectra of a purified nucleotide.
Figure 74B:
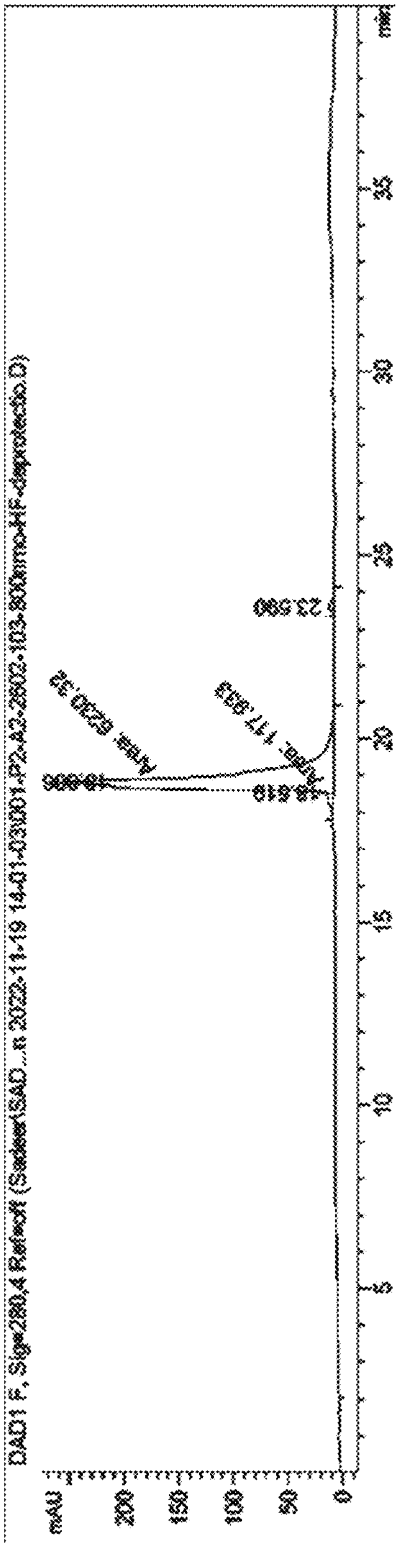
Figure 74C:
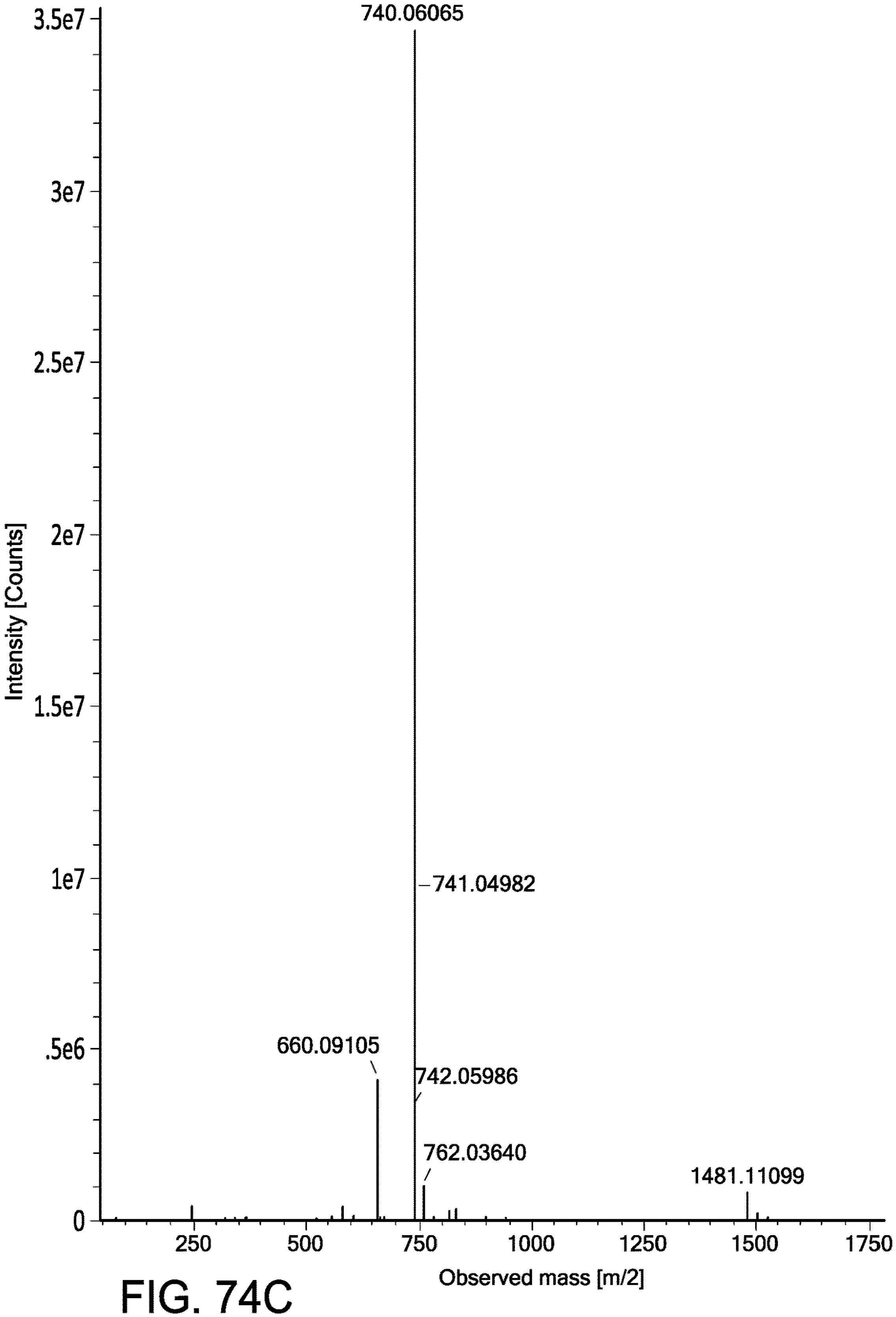

FIG. 73 is a table illustrates HF-TEA and TBAF deprotection methods to assess conversion efficiency and yield of desired triphosphate product. With the optimized HF-TEA deprotection conditions in entry 3, ~77% conversion of 3'-OTBDPS bifunctional nucleotide 5 to the 3'-OH bifunctional nucleotide 6 was achieved. The The crude HPLC, analytical HPLC and LCMS spectra of a purified nucleotide generated using entry 3 of the table in FIG. 73 are shown in FIGS. 74A-C, respectively. The deprotection of 3'-OTBDPS with 1M TBAF at 4° C. for 2 h was also successful. The recovered nucleotide 6 was similarly characterized by LCMS and HPLC to confirm the identity and purity.

Example 8: Selecting Diastereomeric Mixtures

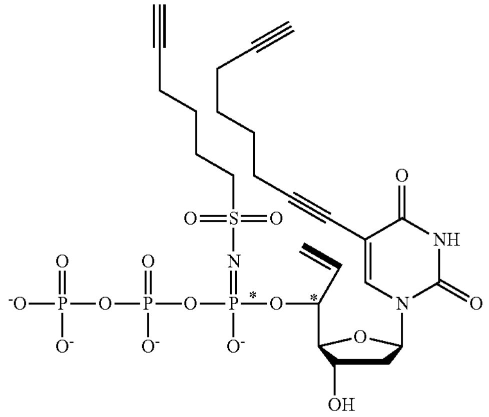

Two new chiral centers at the alpha P and 5'C atoms, indicated by a * symbol, were introduced due to the desymmetrization of the substituents around the alpha phosphorus and 5'-carbon atoms, which results in the possible formation of 4 diastereomers. Herein are described methods to control chirality and select for particular isomers.

Figure 75:
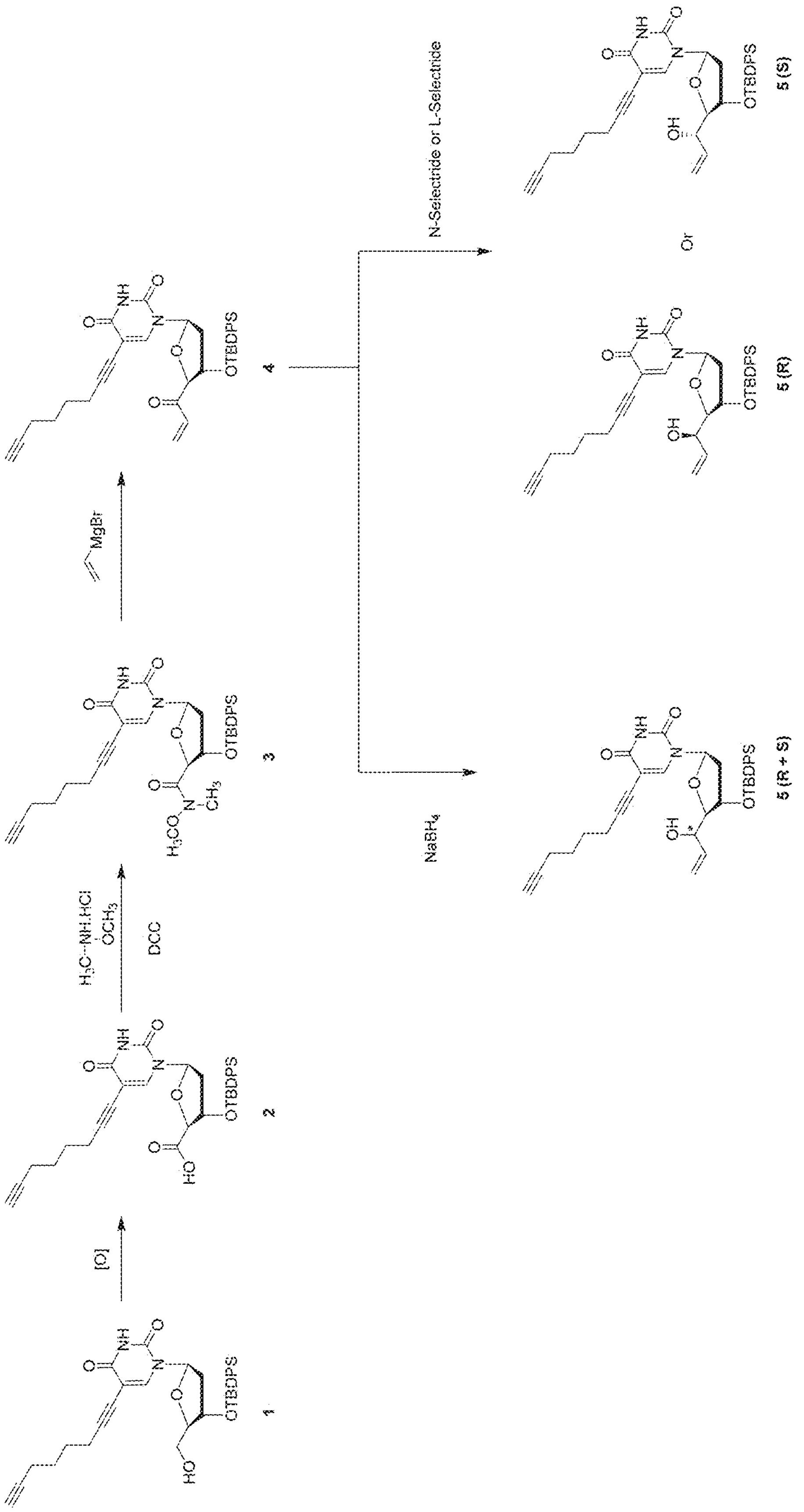
FIG. 75 schematically illustrates a stereoselective reduction of a carbonyl group.

FIG. 75 schematically illustrates a stereoselective reduction of a carbonyl group, therefore controlling chirality at the 5'-carbon atom.

Figure 76:
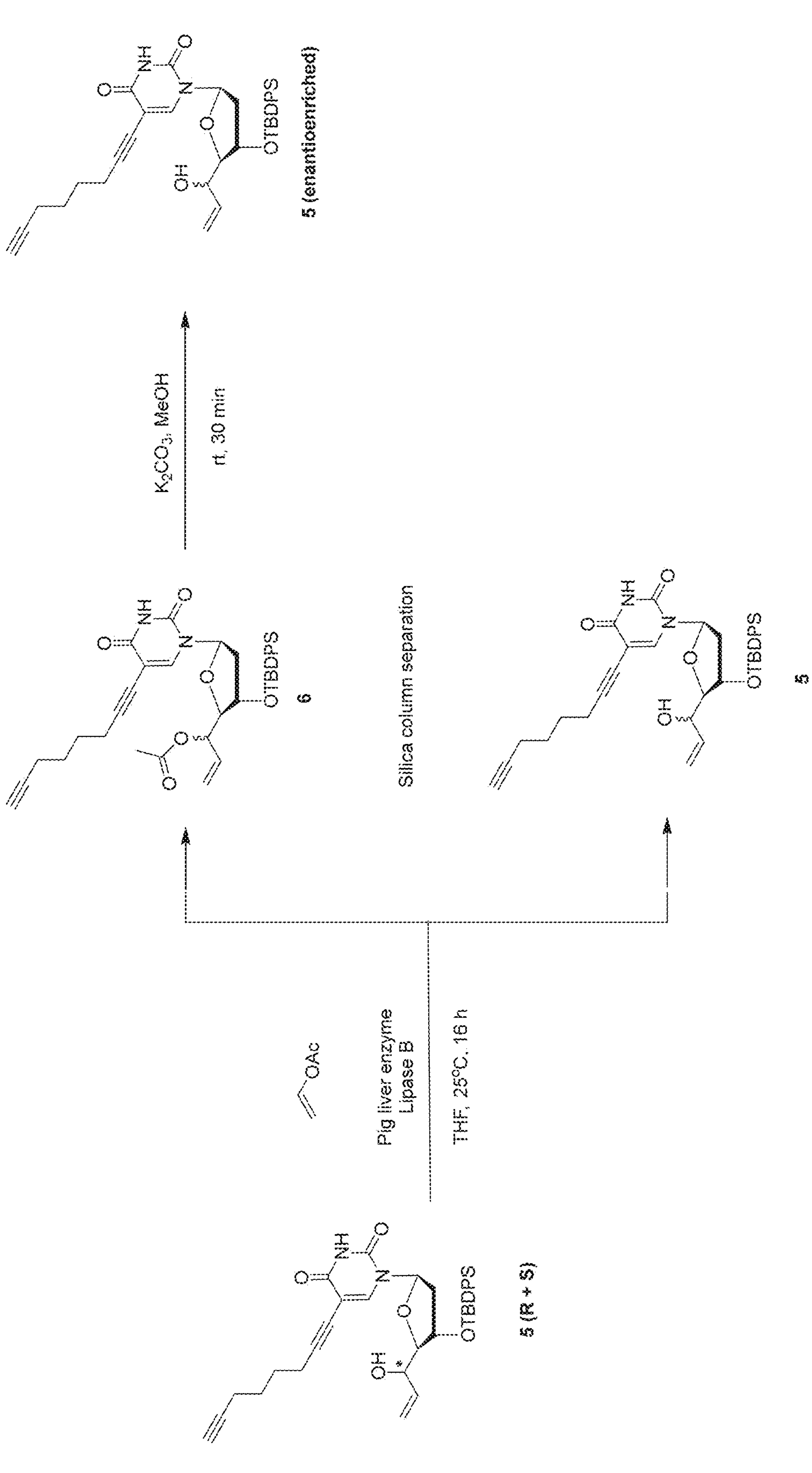
FIG. 76 schematically illustrates a kinetic diastereomeric selection step using enzymes from a racemic precursor.

FIG. 76 schematically illustrates a kinetic diastereomeric selection step using enzymes from a racemic precursor.

Figure 77:
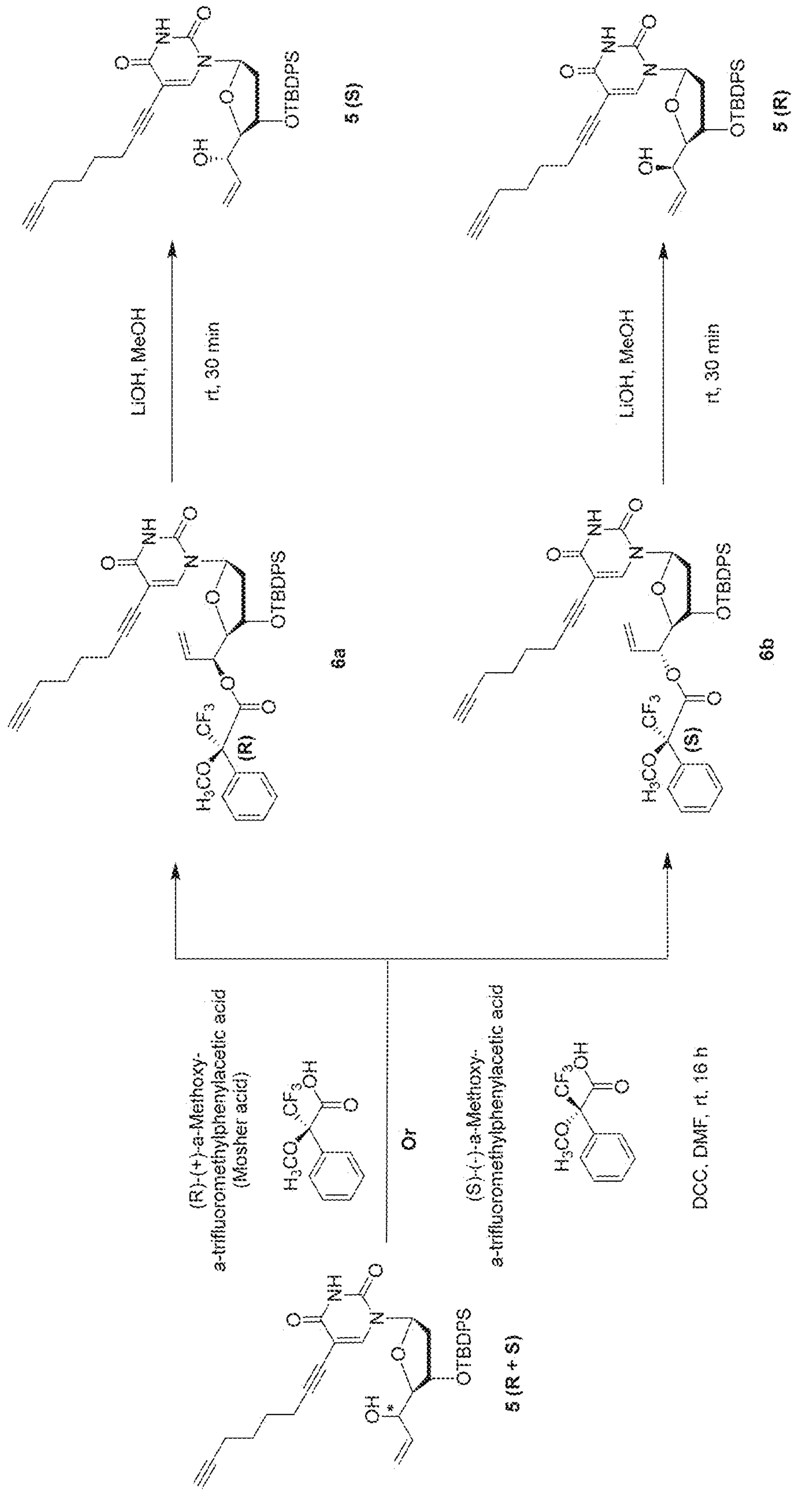
FIG. 77 schematically illustrates a chiral derivatization of isomers to enable eventual column separation.

FIG. 77 schematically illustrates a chiral derivatization of isomers to enable eventual column separation.

Figure 78:
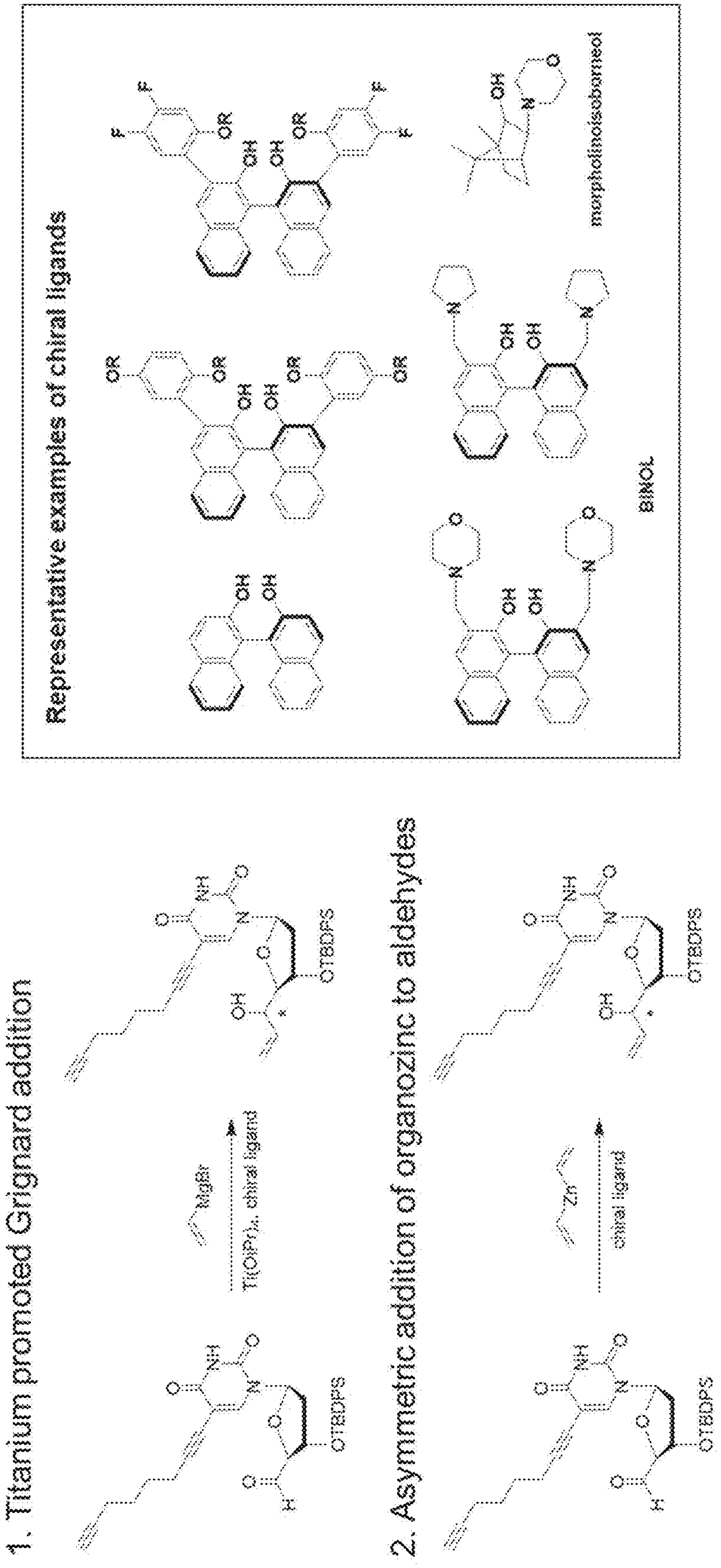
FIG. 78 schematically illustrates a chiral ligand promoted stereoselective alkyl addition.

FIG. 78 schematically illustrates a chiral ligand promoted stereoselective alkyl addition (e.g., nucleophilic addition to an aldehyde group), as well as representative examples of chiral ligands.

Figure 79:
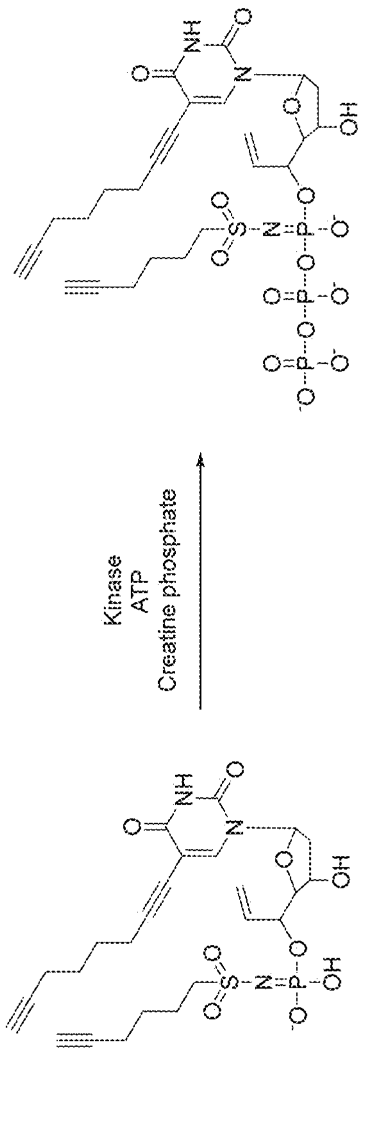
FIG. 79 schematically illustrates a stereoselective enzymatic synthesis of triphosphate.

FIG. 79 schematically illustrates a stereoselective enzymatic synthesis of triphosphate.

Figure 80:
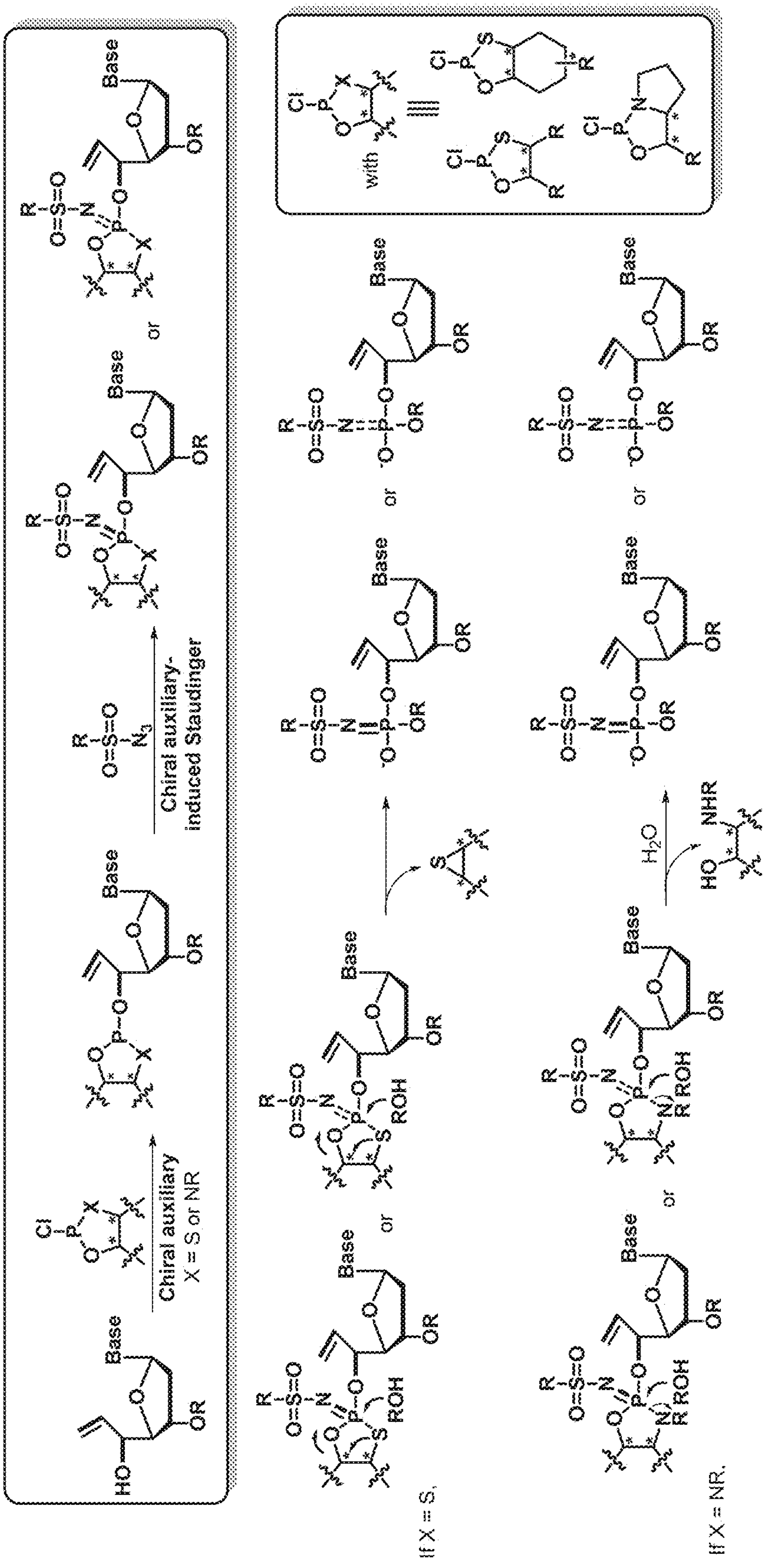
FIG. 80 schematically illustrates a method for controlling chirality at an alpha phosphorous atom.

FIG. 80 schematically illustrates a method for controlling chirality at an alpha phosphorous atom, particularly a stereoselective Staudinger reaction induced by chiral auxiliaries.

Figure 81:
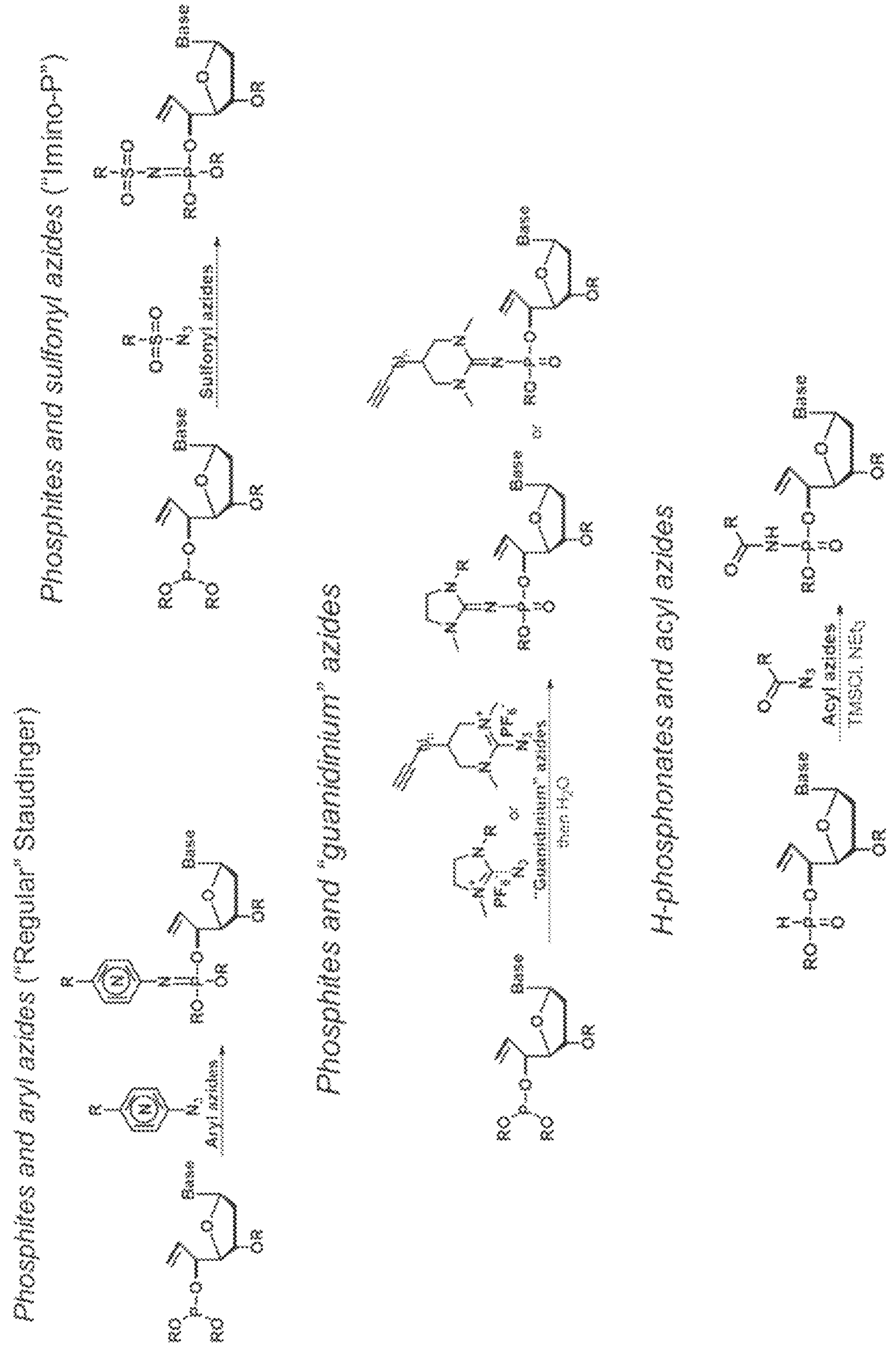
FIG. 81 shows synthesis of exemplary Staudinger variants.

FIG. 81 is an exemplary list of Staudinger variants. Several variants of Staudinger reaction may be considered to modify the substituent at the alpha phosphorus center. One embodiment described herein generates the "imino-P" substitution, which involves a Staudinger reaction between a phosphite and a sulfonyl azide moiety. Those skilled in the art will be able to extend the Staudinger reaction to other variants, such as phosphites with aryl azides, phosphites with guanidinium azide, and H-phosphonates with acyl azides. Additional exemplary synthesis methods to prepare azido variants are provided in FIG. 82.

Example 9: Cyclic Loop Nucleotide Synthesis Pathways

Figure 83A:
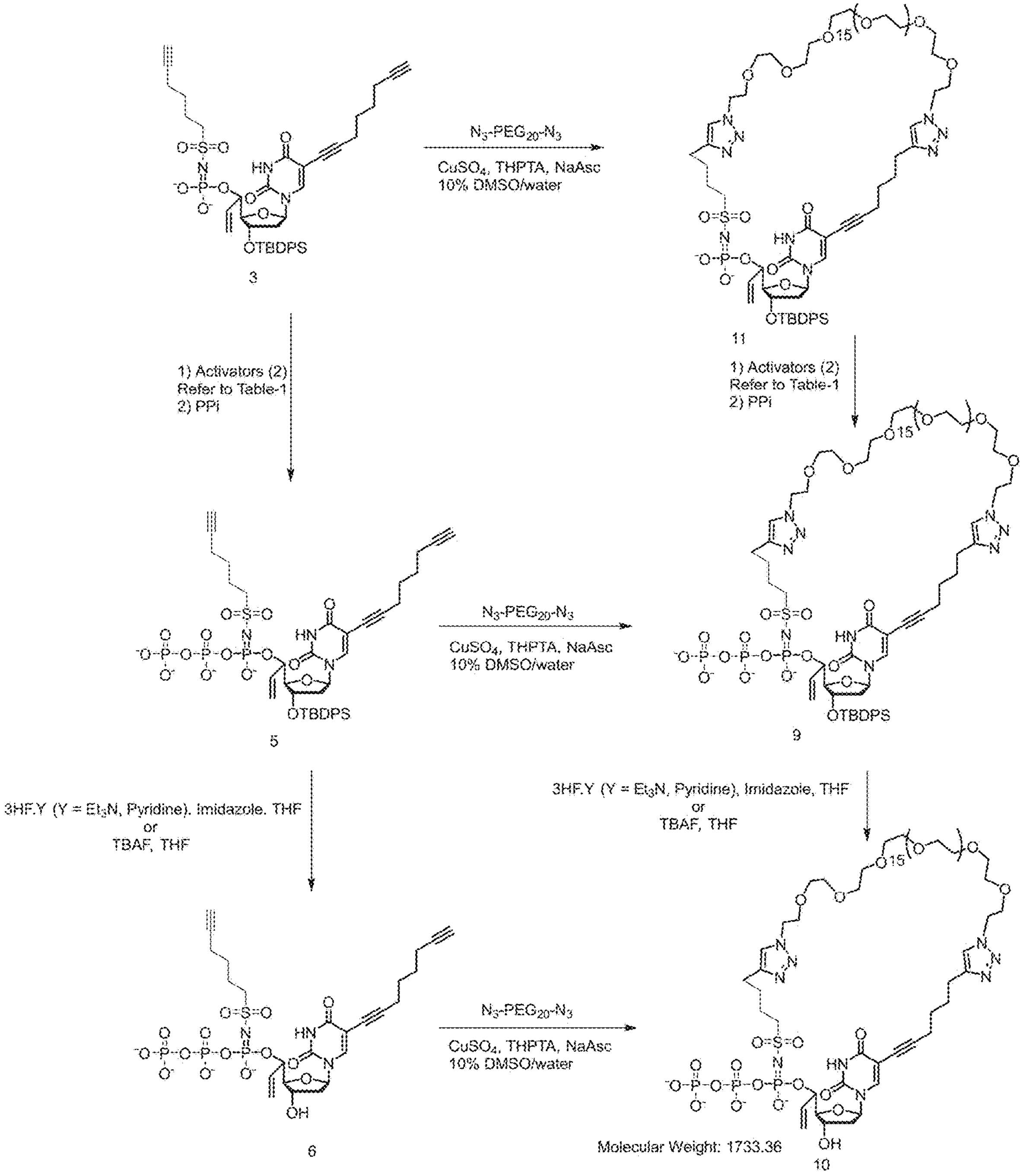
FIGS. 83A-B schematically illustrate embodiments of pathways that result in the formation of an exemplary cyclic loop nucleotide structure.
Figure 83B:
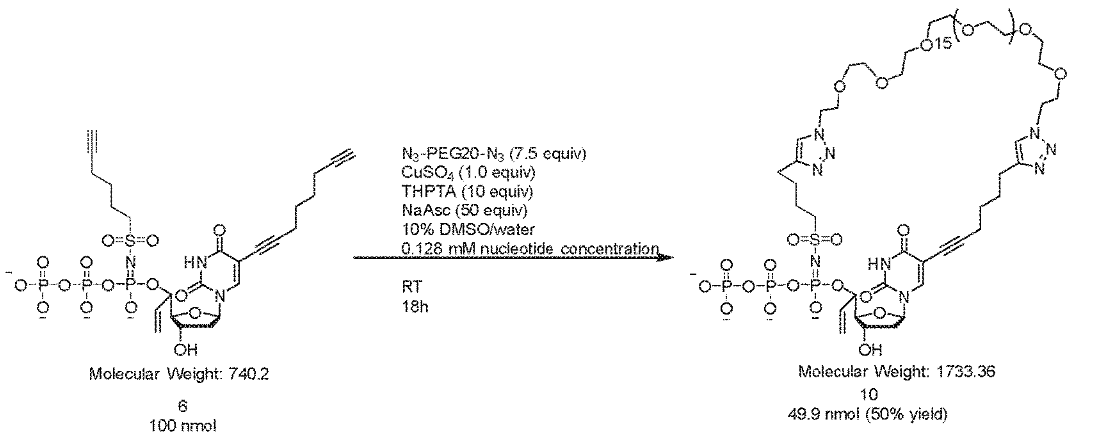
Figure 84A:
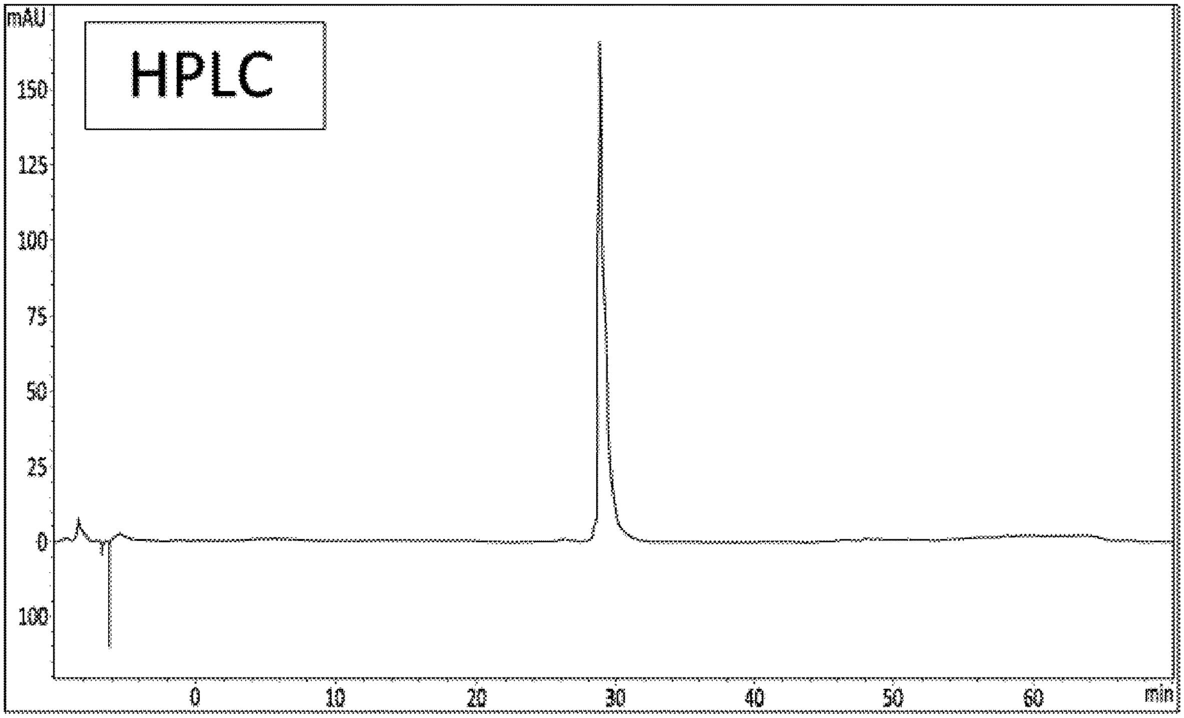
FIGS. 84A-C illustrates HPLC, LCMS, and FTIR characterization of the cyclic loop structure in FIG. 83A.
Figure 84B:
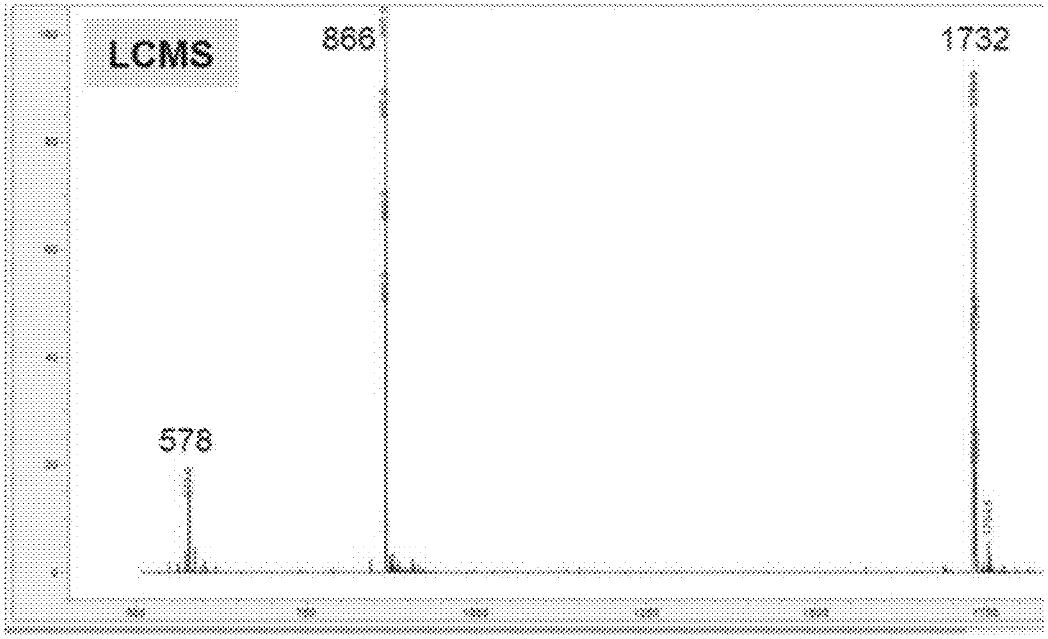
Figure 84C:
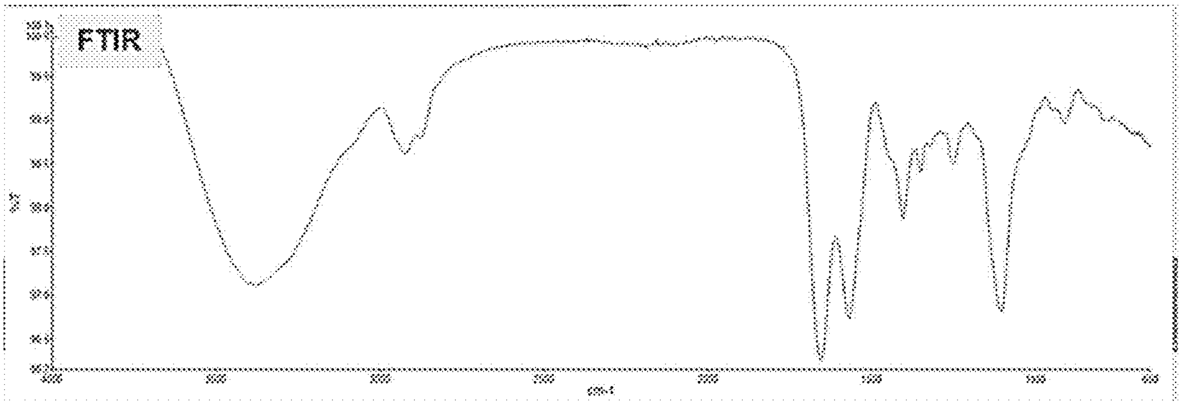

FIGS. 83A and 83B schematically illustrates various pathways that result in the formation of an exemplary looped nucleotide structure 10 using 3 alternative routes. Route A: 3→11→9→10, Route B: 3→5→9→10, and Route C:

3→5→6→10. FIGS. 84A-C demonstrates characterized HPLC, LCMS, and FTIR characterization data for cyclic loop nucleotide structure 10. LCMS confirms the mass of the looped nucleotide 10, the HPLC spectra indicates the purity of the isolated product, and the FTIR confirms the absence of unreacted azide (which would appear at ~2100 cm-1 corresponding to —N═N═N stretching).

Example 10: Preliminary Incorporation Assay of Cyclic Loop Alpha Phosphate Substituted Nucleotides FIG. 85 illustrates results of a bifunctional nucleotide 6 as tested in an incorporation assay using Dpo4 enzyme compared to natural dTTP. The results indicate that the bifunctional nucleotide 6 was incorporated at least twice under the conditions evaluated.

Similarly, the looped nucleotide 10 was assessed as shown in FIG. 86. In comparison to incorporation of nucleotide 6, the incorporation of the sterically bulky looped nucleotide 10 was slower in comparison. By increasing the concentration of looped nucleotide 10 by 5-fold (from 20 μM to 100 μM), concentration of catalytic $Mn^{2+}$ by 5-fold (from 2 mM to 10 mM), concentration of Dpo4 by 2-fold (from 1 μM to 2 μM), and increasing the temperature (from rt to 37° C.), the incorporation of looped nucleotide 10 was visibly improved, as shown in FIG. 87.

Example 11: Preliminary Stability Data of Looped Alpha Phosphate Substituted Nucleotides FIGS. 88-89 illustrate stability assays performed on the bifunctional nucleotide 6 and looped nucleotide 10, which were subjected to stability tests at 25° C. and 60° C. in 50 mM Tris pH 7.5. Both nucleotides 6 and 10 were stable for up to 2 days at 25° C., while ~55% and ~74% of nucleotides 6 and 10 were degraded at 60° C. respectively. ~72% of the alpha P—C modified nucleotide degraded at 25° C. in 50 mM Tris pH 7.5 over 2 days, indicating that the imino-P modification is able to stabilize the alpha phosphate substituted nucleotide triphosphate significantly. This enhanced stability is critical to the manufacturing, scalability and productization of similar nucleotides for sequencing purposes.

ADDITIONAL NOTES

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range, as if such value or sub-range were explicitly recited. For example, a range from about 2 nm to about 20 nm should be interpreted to include not only the explicitly recited limits of from about 2 nm to about 20 nm, but also to include individual values, such as about 3.5 nm, about 8 nm, about 18.2 nm, etc., and sub-ranges, such as from about 5 nm to about 10 nm, etc. Furthermore, when "about" and/or "substantially" are/is utilized to describe a value, this is meant to encompass minor variations (up to +/−10%) from the stated value.

While several examples have been described in detail, it is to be understood that the disclosed examples may be modified. Therefore, the foregoing description is to be considered non-limiting.

While certain examples have been described, these examples have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure.

Features, materials, characteristics, or groups described in conjunction with a particular aspect, or example are to be understood to be applicable to any other aspect or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing examples. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations, one or more features from a claimed combination can, in some cases, be excised from the combination, and the combination may be claimed as a sub-combination or variation of a sub-combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some examples, the actual steps taken in the processes illustrated and/or disclosed may differ from those shown in the figures. Depending on the example, certain of the steps described above may be removed or others may be added. Furthermore, the features and attributes of the specific examples disclosed above may be combined in different ways to form additional examples, all of which fall within the scope of the present disclosure. Also, the separation of various system components in the implementations described above should not be understood as requiring such separation in all implementations, and it should be understood that the described components and systems can generally be integrated together in a single product or packaged into multiple products. For example, any of the components for an energy storage system described herein can be provided separately, or integrated together (e.g., packaged together, or attached together) to form an energy storage system.

For purposes of this disclosure, certain aspects, advantages, and novel features are described herein. Not necessarily all such advantages may be achieved in accordance with any particular example. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain examples include, while other examples do not include, certain features, elements, and/or steps. Thus, such conditional language is not generally intended to imply that features, elements, and/or steps are in any way required for one or more examples or that one or more examples necessarily include logic for deciding, with or without user input or prompting, whether these features, elements, and/or steps are included or are to be performed in any particular example.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain examples require the presence of at least one of X, at least one of Y, and at least one of Z.

Language of degree used herein, such as the terms "approximately," "about," "generally," and "substantially" represent a value, amount, or characteristic close to the stated value, amount, or characteristic that still performs a desired function or achieves a desired result.

The scope of the present disclosure is not intended to be limited by the specific disclosures of preferred examples in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

Although the foregoing invention has been described in terms of certain preferred embodiments, other embodiments will be apparent to those of ordinary skill in the art. Additionally, other combinations, omissions, substitutions and modification will be apparent to the skilled artisan, in view of the disclosure herein. Accordingly, the present invention is not intended to be limited by the recitation of the preferred embodiments, but is instead to be defined by reference to the appended claims. All references cited herein are incorporated by reference in their entirety.

The terminology used in the description presented herein is not intended to be interpreted in any limited or restrictive manner and unless otherwise indicated refers to the ordinary meaning as would be understood by one of ordinary skill in the art in view of the specification. Furthermore, embodiments may comprise, consist of, consist essentially of, several novel features, no single one of which is solely responsible for its desirable attributes or is believed to be essential to practicing the embodiments herein described. As used herein, the section headings are for organizational purposes only and are not to be construed as limiting the described subject matter in any way. All literature and similar materials cited in this application, including but not limited to, patents, patent applications, articles, books, treatises, and Internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc. discussed in the present teachings, such that slight and insubstantial deviations are within the scope of the present teachings herein.

Although this disclosure is in the context of certain embodiments and examples, those of ordinary skill in the art will understand that the present disclosure extends beyond the specifically disclosed embodiments to other alternative embodiments and/or uses of the embodiments and obvious modifications and equivalents thereof. In addition, while several variations of the embodiments have been shown and described in detail, other modifications, which are within the scope of this disclosure, will be readily apparent to those of ordinary skill in the art based upon this disclosure. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes or embodiments of the disclosure. Thus, it is intended that the scope of the present disclosure herein disclosed should not be limited by the particular disclosed embodiments described above.

What is claimed is:

1. A compound having one of the following structures:

(Ia)

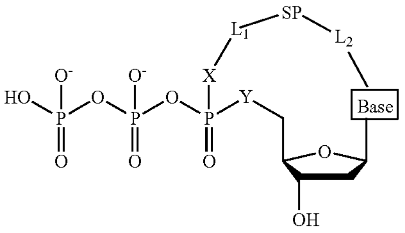

, (IIa)

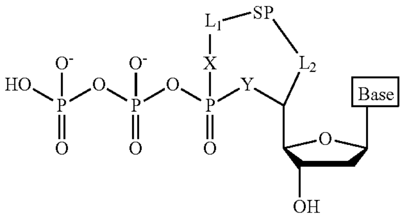

, (IIIa)

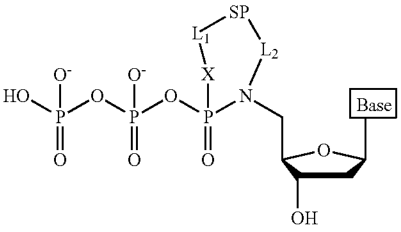

, (IVa)

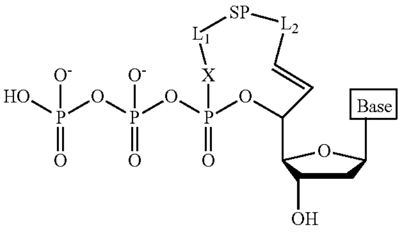

, (Va)

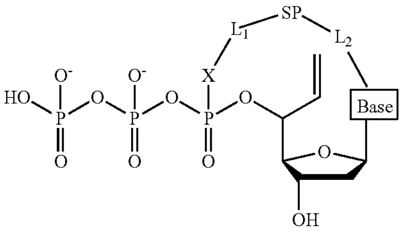

, and

-continued (XIa)

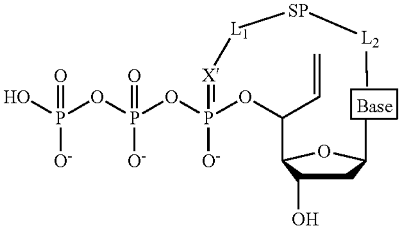

;

wherein

X is —O—, —$CH_2$—, —NH—,

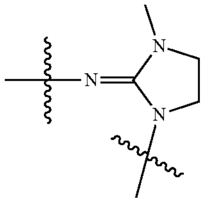

, or

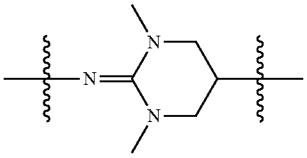

;

X' is =N—$SO_2$—, =NH—CO—, or

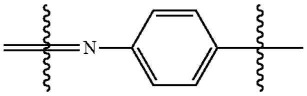

;

Y is —S—, or —Se—;

$L_1$ is a first linking group;

$L_2$ is a second linking group; and

SP is a spacer.

2. The compound of claim 1, wherein SP comprises one or more of the following moieties:

(1) alkyl chains having 5 to 50 carbons, (2) oligonucleotides, modified oligonucleotides or polyphosphates having 1 to 100 repeating units, (3) polypeptides having 1 to 100 repeating units, (4) hydrophilic polymers having 1 to 100 repeating units, and (5) hydrophobic polymers having 1 to 100 repeating units.

3. The compound of claim 2, wherein the hydrophilic polymers are selected from the group consisting of polyethyleneglycol, polyvinyl alcohol, polyacrylamide, polyvinylpyrrolidone, polystyrenesulfonate, and polyethyleneimine.

4. The compound of claim 2, wherein the hydrophobic polymers are selected from the group consisting of polylactic acid, polymethylmethacrylate, and polystyrene.

5. The compound of claim 1, wherein each of $L_1$ and $L_2$ independently comprises a conjugating moiety selected from the group consisting of amine-NHS ester, amine-imidoester, amine-pentafluorophenyl ester, amine-hydroxymethyl phosphine, carboxyl-carbodiimide, thiol-maleimide, thiol-haloacetyl, thiol-pyridyl disulfide, thiol-thiosulfonate, thiol-vinyl sulfone, aldehyde-hydrazide, aldehyde-alkoxyamine, hydroxy-isocyanate, azide-alkyne, azide-phosphine, transcyclooctene-tetrazine, norbornene-tetrazine, azide-cyclooctyne, and azide-norbornene.

6. The compound of claim 5, wherein each of $L_1$ and $L_2$ independently further comprises a first linker between the conjugating moiety and X, and a second linker between the conjugating moiety and SP.

7. The compound of claim 6, wherein the first linker and the second linker are independently selected from the group consisting of polynucleotide having 1 to 100 repeating units, polypeptide having 1 to 100 repeating units, alkyl chains having 5 to 50 carbons, hydrophilic polymers having 1 to 100 repeating units comprising polyethyleneglycol, polyvinyl alcohol, polyacrylamide, polyvinylpyrrolidone, polystyrenesulfonate, or polyethyleneimine, hydrophobic polymers having 1 to 100 repeating units comprising polylactic acid, polymethylmethacrylate, or polystyrene, and combinations thereof.

8. The compound of claim 1, wherein SP or the Base further comprises an arresting construct.

9. The compound of claim 8, wherein the arresting construct is a linear, a branched or a cyclic polymer.

10. The compound of claim 9, wherein the arresting construct comprises a synthetic hydrophobic polymer, a synthetic hydrophilic polymer, an oligonucleotide/polynucleotide, a peptide/polypeptide, or combinations thereof.

11. A kit for determining a sequence of a polynucleotide in a nanopore-based sequencing system, the kit comprising the compound according to claim 1.

* * * * *